US011345970B2

(12) United States Patent
Tanner et al.

(10) Patent No.: US 11,345,970 B2
(45) Date of Patent: May 31, 2022

(54) RAPID DIAGNOSTIC TEST FOR LAMP

(71) Applicant: New England Biolabs, Inc., Ipswich, MA (US)

(72) Inventors: Nathan Tanner, West Newbury, MA (US); Yinhua Zhang, North Reading, MA (US); Eric Hunt, Danvers, MA (US); Gregory Patton, Peabody, MA (US); Guoping Ren, Danvers, MA (US); Zhiru Li, Lexington, MA (US); Andrew Barry, Ipswich, MA (US); Nicole Nichols, Reading, MA (US); Catherine B. Poole, Medford, MA (US); Harriet M. Strimpel, Manchester, MA (US); Ivan R. Correa, Jr., Hamilton, MA (US); Clotilde Carlow, Ipswich, MA (US); Esta Slayton, Epping, NH (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 17/406,959

(22) Filed: Aug. 19, 2021

(65) Prior Publication Data
US 2021/0404024 A1 Dec. 30, 2021

Related U.S. Application Data

(63) Continuation-in-part of application No. 17/221,451, filed on Apr. 2, 2021, now Pat. No. 11,155,887,
(Continued)

(51) Int. Cl.
*G01N 21/78* (2006.01)
*C12Q 1/70* (2006.01)

(52) U.S. Cl.
CPC ............ *C12Q 1/701* (2013.01); *G01N 21/78* (2013.01)

(58) Field of Classification Search
CPC ............................... C12Q 1/701; G01N 21/78
See application file for complete search history.

(56) References Cited

U.S. PATENT DOCUMENTS

| 6,410,278 B1 | 6/2002 | Notomi et al. |
| 8,993,298 B1 | 3/2015 | Ong et al. |
(Continued)

FOREIGN PATENT DOCUMENTS

| WO | 2015195949 A1 | 2/2016 |
| WO | 2018057971 A1 | 3/2018 |
| WO | 2018170340 A1 | 9/2018 |

OTHER PUBLICATIONS

Huang et al. (2020) Lancet, 395, 497-506.
(Continued)

*Primary Examiner* — Jennifer Wecker
*Assistant Examiner* — Michael Paul Shimek
(74) *Attorney, Agent, or Firm* — New England Biolabs, Inc; Harriet M. Strimpel

(57) ABSTRACT

Kits and methods are described that are directed to specific and sensitive methods of target nucleic acid detection and more specifically detecting target nucleic acids directly from biological samples. The kits and methods were developed to be easy to use involving a minimum number of steps and giving rapid and consistent results either at point of care or in high throughput situations. The kits and methods utilize
(Continued)

in various combinations, reversible inhibitors of kit components, thermolabile enzymes, poloxamers, various salts, indicators and one or more Loop-Mediated Isothermal Amplification (LAMP) primer sets for detecting single and/or multiple targets and variants of the targets including SARS-CoV-2 targets and variants thereof in a single reaction. The kits and methods permit detection of the target nucleic with similar sensitivity regardless of the presence of undefined mutations that may enhance the virulence of cells or viruses containing the undefined mutations.

20 Claims, 44 Drawing Sheets
(22 of 44 Drawing Sheet(s) Filed in Color)

Specification includes a Sequence Listing.

Related U.S. Application Data which is a continuation of application No. 17/178,395, filed on Feb. 18, 2021, which is a continuation of application No. 17/122,979, filed on Dec. 15, 2020, now Pat. No. 11,008,629, which is a continuation of application No. 16/938,575, filed on Jul. 24, 2020, now Pat. No. 10,968,493.

(60) Provisional application No. 63/165,465, filed on Mar. 24, 2021, provisional application No. 63/106,120, filed on Oct. 27, 2020, provisional application No. 63/068,564, filed on Aug. 21, 2020, provisional application No. 63/048,556, filed on Jul. 6, 2020, provisional application No. 63/027,216, filed on May 19, 2020, provisional application No. 63/022,303, filed on May 8, 2020, provisional application No. 63/013,442, filed on Apr. 21, 2020, provisional application No. 63/001,909, filed on Mar. 30, 2020, provisional application No. 62/988,696, filed on Mar. 12, 2020.

(56) References Cited

U.S. PATENT DOCUMENTS

| | | |
|---|---|---|
| 9,034,606 B2 | 5/2015 | Tanner et al. |
| 9,074,243 B2 | 7/2015 | Tanner et al. |
| 9,074,249 B2 | 7/2015 | Tanner et al. |
| 9,121,046 B2 | 9/2015 | Tanner et al. |
| 9,127,258 B2 | 9/2015 | Ong et al. |
| 9,157,073 B1 | 10/2015 | Ong et al. |
| 9,546,358 B2 | 1/2017 | Tanner et al. |
| 9,580,698 B1 | 2/2017 | Xu et al. |
| 9,580,748 B2 | 2/2017 | Tanner et al. |
| 9,920,305 B2 | 3/2018 | Zhang et al. |
| 9,920,358 B2 | 3/2018 | Tanner et al. |
| 9,932,567 B1 | 4/2018 | Xu et al. |
| 10,253,357 B2 | 4/2019 | Mitra et al. |
| 10,597,647 B2 | 3/2020 | Zhu et al. |
| 10,968,493 B1 | 4/2021 | Tanner et al. |
| 11,008,629 B1 | 5/2021 | Tanner et al. |
| 11,155,887 B2 | 10/2021 | Tanner et al. |
| 11,162,133 B2 | 11/2021 | Zhang et al. |
| 2015/0247190 A1* | 9/2015 | Ismagilov .......... G01N 21/6428 506/9 |
| 2018/0112195 A1 | 4/2018 | Barnes et al. |
| 2019/0169683 A1 | 6/2019 | Zhang et al. |

OTHER PUBLICATIONS

To, et al., Clinical Infectious Diseases, ciaa149.
Wyllie, et al. MedRxiv Apr. 22, 2020: https://doi.org/10.1101/2020.04.16.20067835.
Notomi, et al. Nucleic Acid Research (2000) 28, E63.
Mori, et al., J. Infect. Chemother. 2009 15: 62-9.
Wastling, et al. (2010) PLoS Negl Trap Dis 4(11): e865. doi: 10.1371/journal.pntd.0000865.
Meredith, et al. Anal. Methods (2017) 9, 534-540.
Tanner, et al. (2015) Biotechniques, 58, 59-68.
Lozano, et al., The Plant Journal, 78, 1073-1083, 2014.
Baek, et al., Emergining Microbes & Infections, 9, 998-1007, 2020.
Breitbach, Milenia Biotec, Mar. 11, 2020.
Kahmann, et al., Human Mutation, 19, 165-172, 2002.

\* cited by examiner

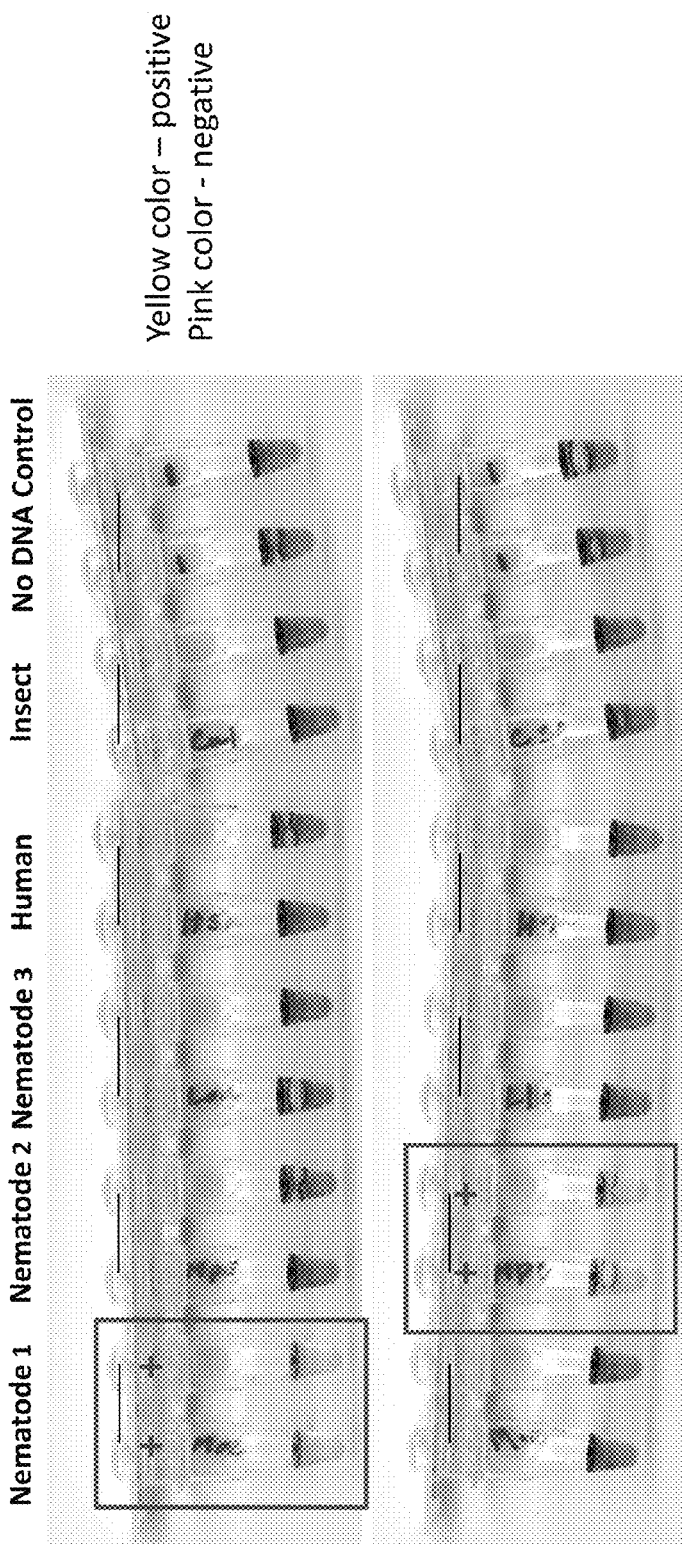
FIG. 4A Nematode 1 LAMP Test
FIG. 4B Nematode 2 LAMP test

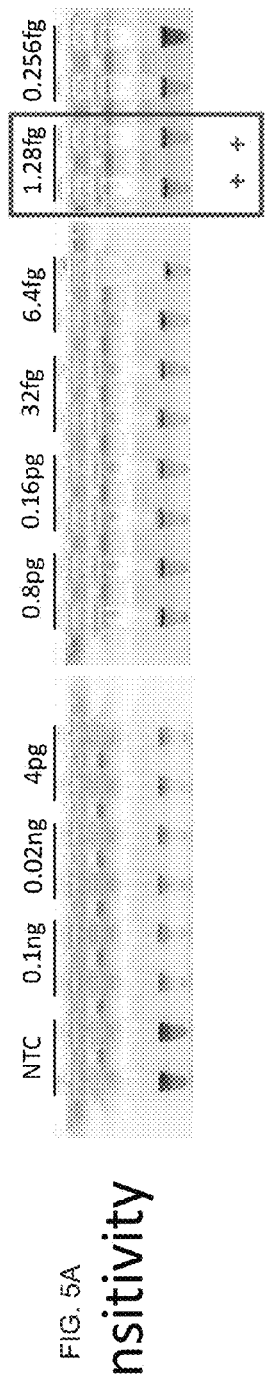

FIG. 5A
Sensitivity

>10X more sensitive than best published qPCR method for pathogen target

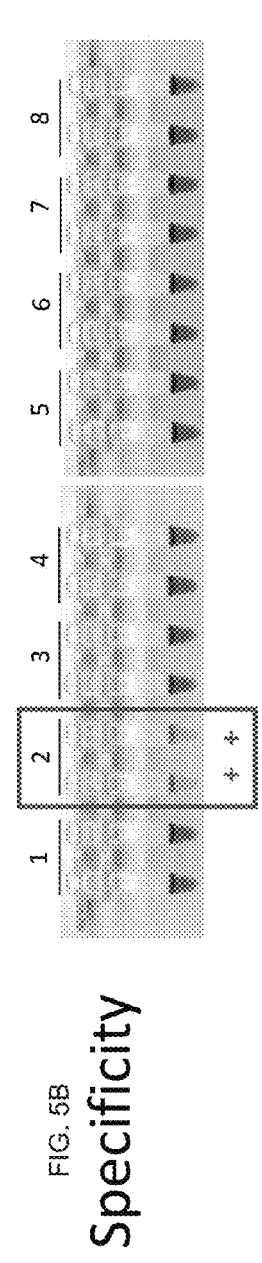

FIG. 5B
Specificity

1: no template DNA control
2: pathogen target DNA
3: DNA from other tick-borne pathogen 1 - negative control
4: DNA from other tick-borne pathogen 2 - negative control
5: DNA from other tick-borne pathogen 3 - negative control
6: Tick DNA
7: Mosquito DNA
8: DNA from other tick-borne pathogen 4

Specific detection of pathogen target DNA

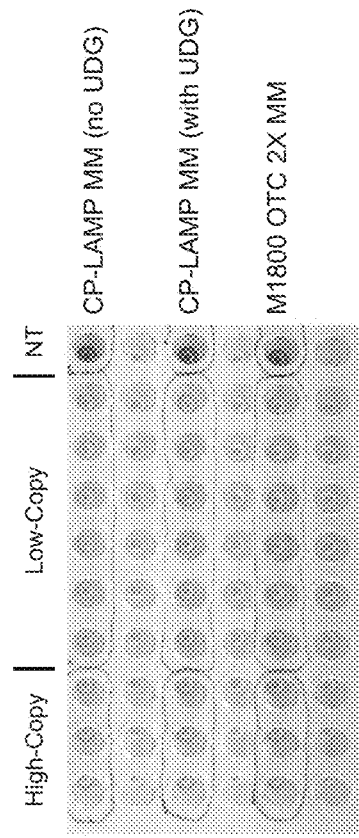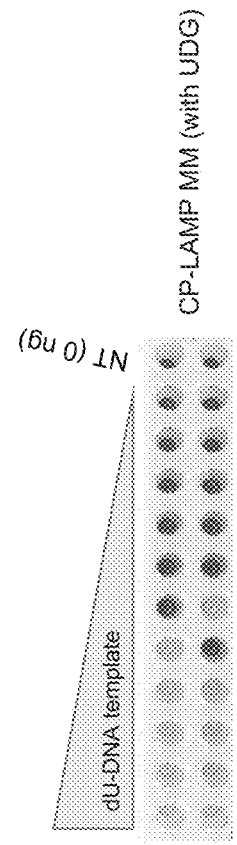
FIG. 6A
FIG. 6B

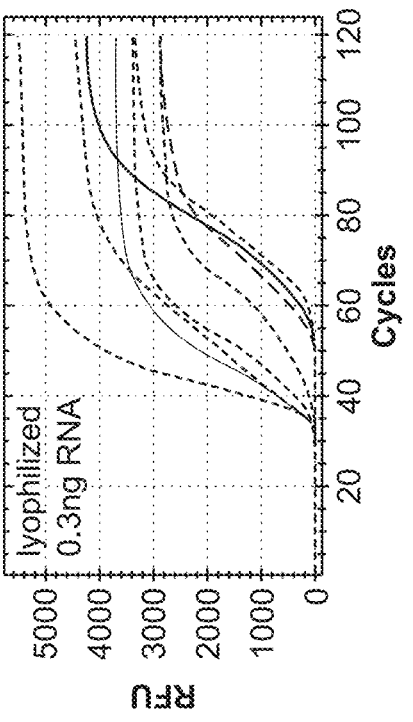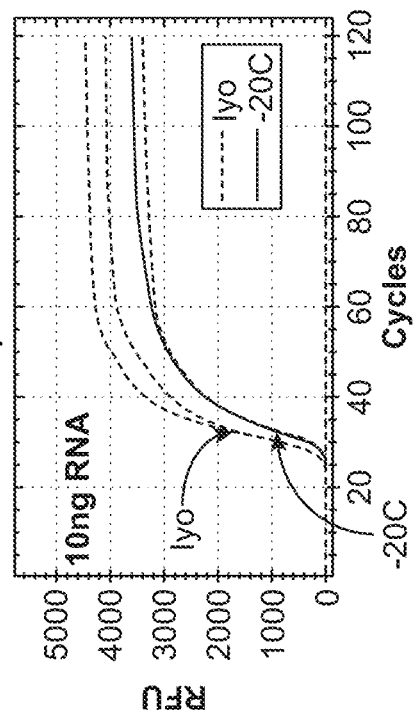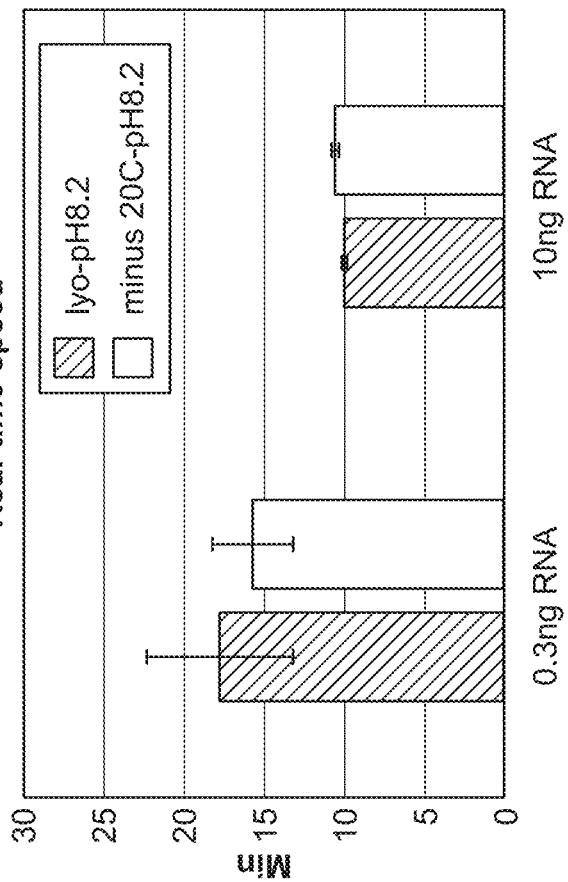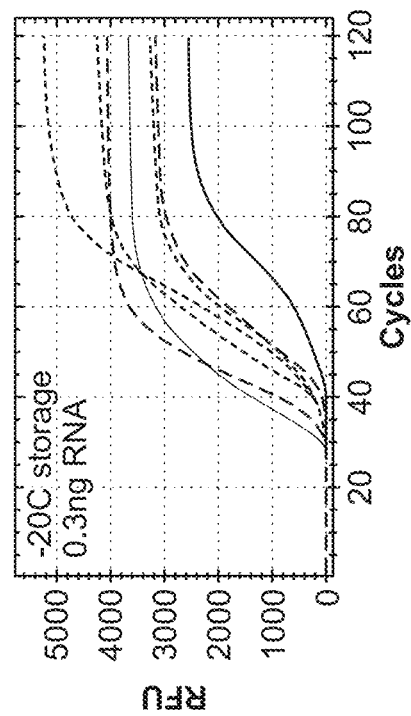
FIG. 8A  FIG. 8B  FIG. 8C

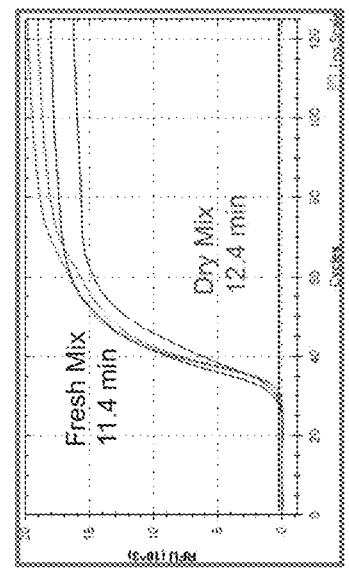
FIG. 9A
WarmStart Colorimetric LAMP 2X Master Mix (DNA & RNA)
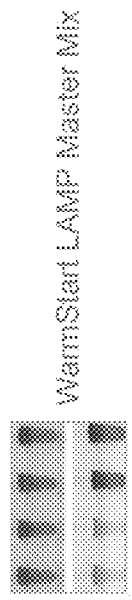
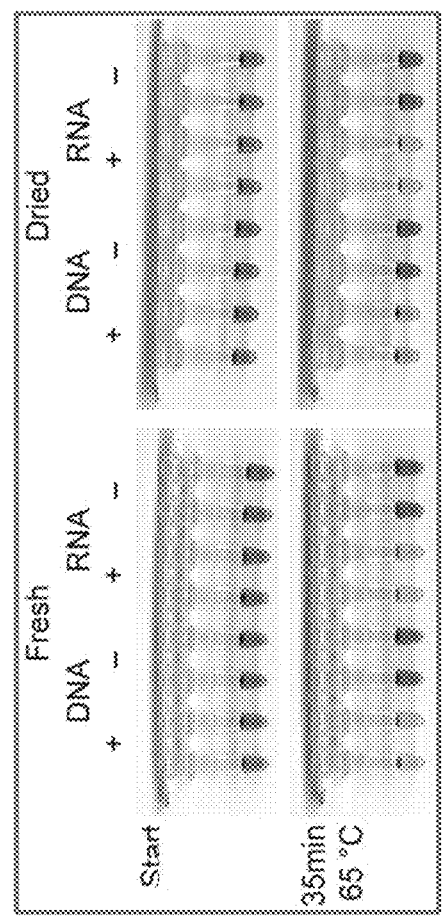
FIG. 9B
FIG. 9C

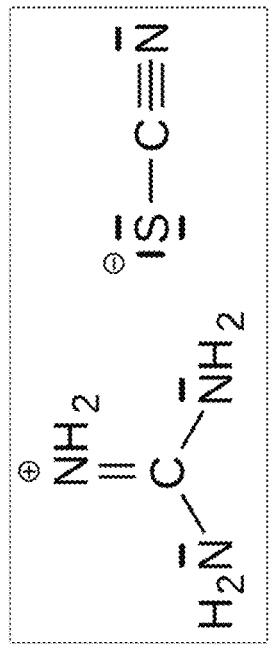
Guanidine hydrochloride (CAS#: 50-01-1)
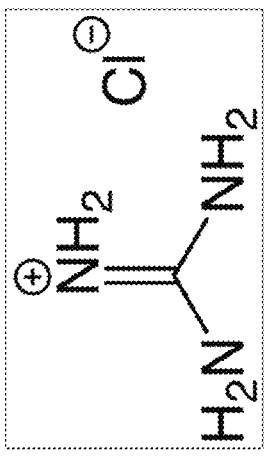
Arginine (CAS#: 7200-25-1)
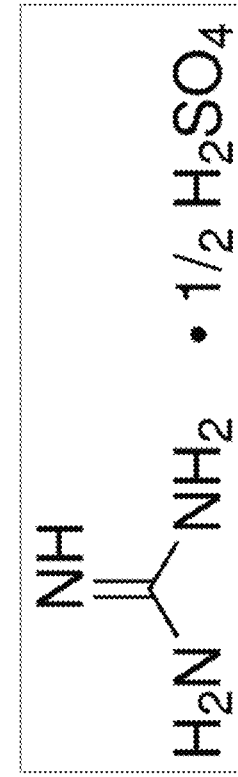
Guanidine thiocyanate (CAS#: 593-84-0)
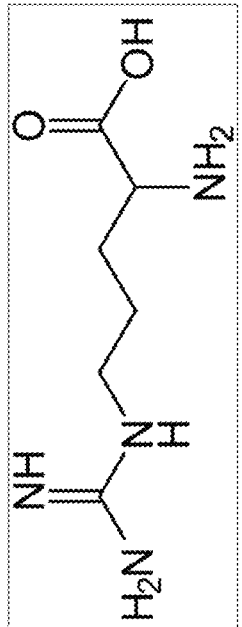
Guanidine sulfate (CAS#: 594-14-9)
FIG. 15

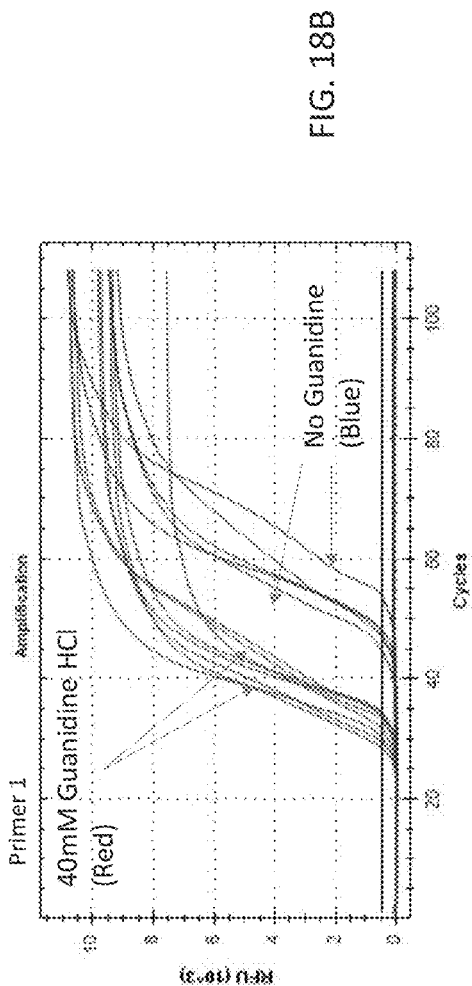
FIG. 18A
FIG. 18B
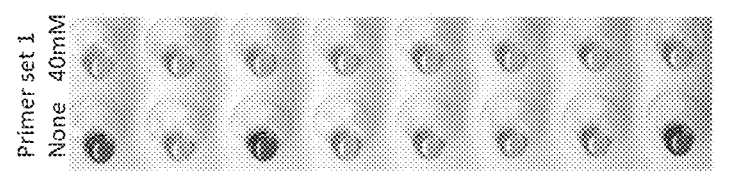
FIG. 18C

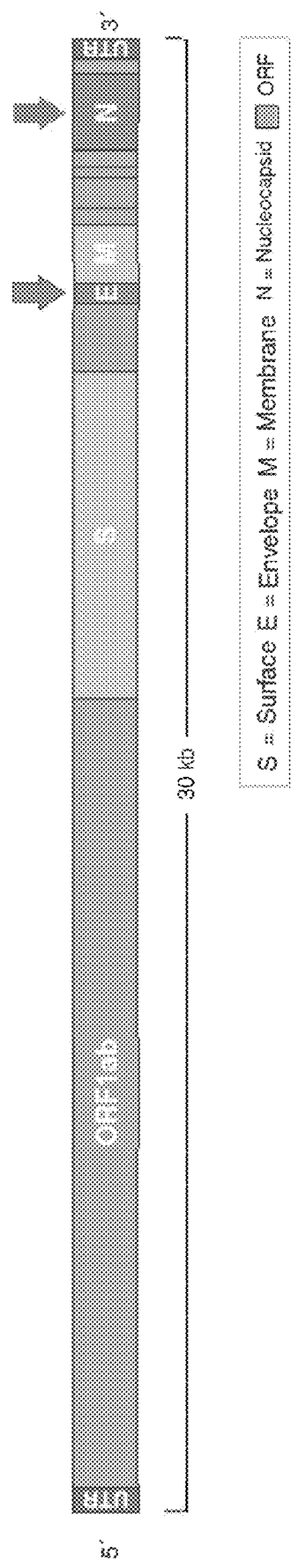

| Primer set | Copy # COVID RNA | None | | | 40mM Guanidine HCl | | |
|---|---|---|---|---|---|---|---|
| | | Positive | Negative | % positive | Positive | Negative | % positive |
| 3 | 50 | 5 | 13 | 28% | 17 | 7 | 70.8% |
| 4 | 50 | | | | 19 | 5 | 79.1% |
| 3+4 | 50 | 17 | 23 | 42.5% | 59 | 5 | 92.2% |
| 3 | 0 | | | | 1 | 7 | 12.5% |
| 4 | 0 | | | | 0 | 8 | 0 |
| 3+4 | 0 | | | | 0 | 8 | 0 |

FIG. 19A

| Primer set | Copy # COVID RNA | 40mM Guanidine HCl | | |
|---|---|---|---|---|
| | | Positive | Negative | % Positive |
| 3 | 12.5 | 21 | 83 | 20% |
| 4 | 12.5 | 28 | 76 | 27% |
| 3+4 | 12.5 | 19 | 21 | 48% |
| 3+5 | 12.5 | 6 | 10 | 38% |
| 4+5 | 12.5 | 25 | 31 | 45% |
| 3+4+5 | 12.5 | 32 | 24 | 57% |
| 3+4 | 0 | 0 | 16 | 0 |
| 3+5 | 0 | 0 | 8 | 0 |
| 4+5 | 0 | 0 | 16 | 0 |
| 3+4+5 | 0 | 0 | 16 | 0 |

| | GnHCl | TCEP [con] | TCEP pH | LiCl | SeraCare |
|---|---|---|---|---|---|
| 1 | 400mM | 1mM | 7.0 | 0 | 20,000 copies/mL |
| 2 | 400mM | 1mM | 7.0 | 75mM | 20,000 copies/mL |
| 3 | 400mM | 1mM | 8.0 | 0 | 20,000 copies/mL |
| 4 | 400mM | 1mM | 8.0 | 75mM | 20,000 copies/mL |
| 5 | 400mM | 4mM | 8.0 | 0 | 20,000 copies/mL |
| 6 | 400mM | 4mM | 8.0 | 75mM | 20,000 copies/mL |

FIG. 21B

| | | | | | | | | | | | | | | | | | |
|---|---|---|---|---|---|---|---|---|---|---|---|---|---|---|---|---|---|
| 1 | N/A | N/A | 79.62 | 43.19 | 34.44 | 36.88 | 42.42 | 35 | 39.25 | 33.67 | 80.38 | 76.32 | N/A | N/A | 35.81 | 71.95 | 8/16 50% |
| 2 | 41.02 | 41.66 | 38.02 | 33.6 | 38.49 | N/A | 34.03 | 35.8 | 46.58 | 39.75 | N/A | N/A | 40.31 | 44.23 | 32.53 | 33.97 | 13/16 81.3% |
| 3 | 34.89 | 34.11 | 45.22 | 32.81 | 61.97 | 35.92 | 80.23 | 34.22 | 33.9 | 46.31 | 32.06 | 33.29 | 39.88 | 43.99 | 32.92 | 36.63 | 14/16 87.5% |
| 4 | 36.86 | 36.32 | 43.02 | 32.49 | 34.5 | 39.41 | 34.94 | 34.45 | 34.3 | 71.84 | 64.73 | 48 | 44.56 | 49.43 | 34.72 | 39.43 | 14/16 87.5% |
| 5 | 35.86 | 37.15 | 38.56 | 43.31 | 61.97 | 33.56 | 89.48 | 49.21 | 36.11 | 43.19 | 50.41 | 39.18 | 39.14 | 37.67 | 37.11 | N/A | 14/15 93.3% |
| 6 | 33.4 | 35.58 | 38.27 | 35.3 | 32.7 | 34.81 | 37.9 | 35.73 | 38.68 | 40.16 | 44.5 | 40.51 | 46.89 | 44.35 | 32.23 | N/A | 15/15 100% |

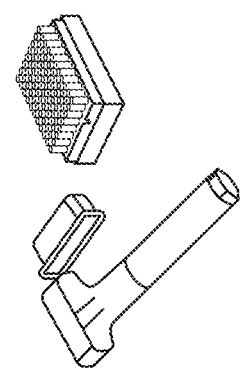
FIG. 28A
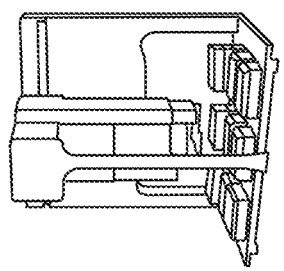
FIG. 28B
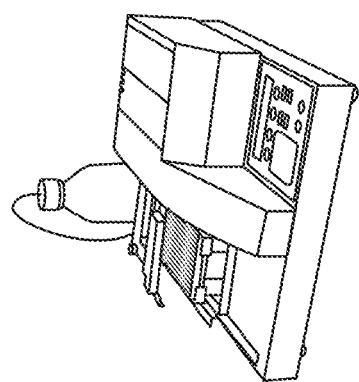
FIG. 28C
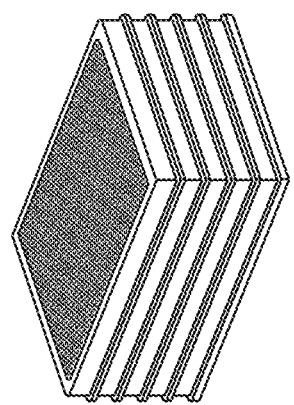
FIG. 28D
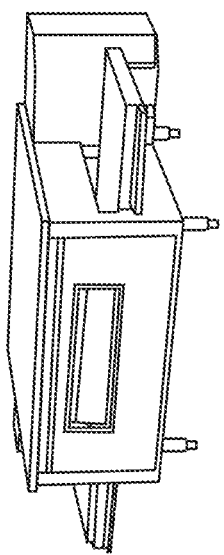
FIG. 28E
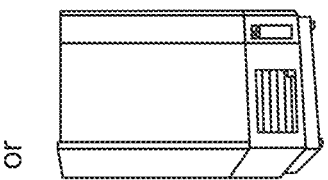
or
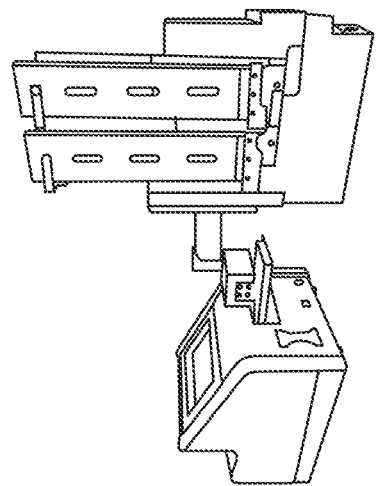
FIG. 28F Multiplexing target primers: E1 in 1+1/2+1/3+1 DARQ LAMP
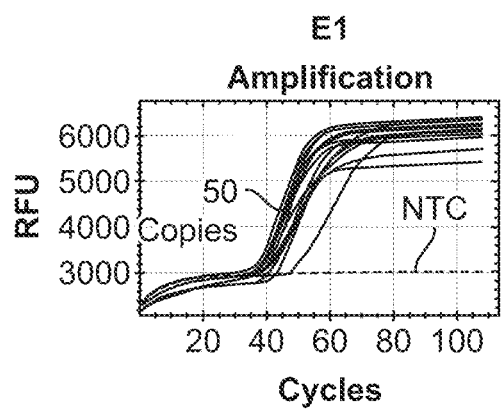
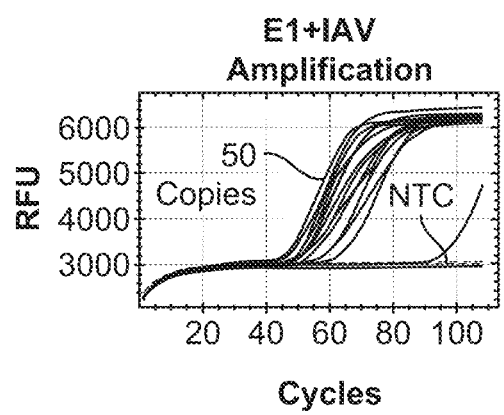
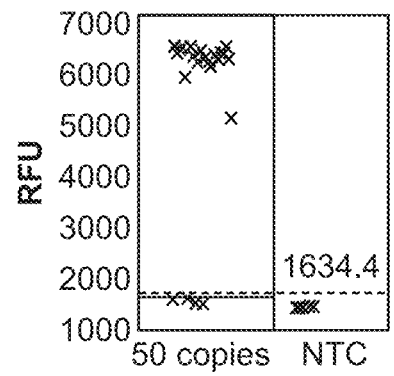
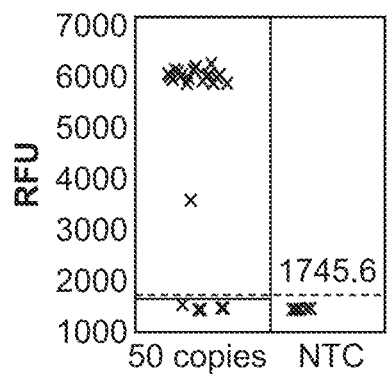
FIG. 31A
FIG. 31B E1700 +1x extra Bst 2.0 +40mM GnCl at 60C LAMP
1x E1, IAV, IBV primers + 220nM QFIP. All with ¼ x ActB primer + 66nM QFIP
24 repeats with ~50 copies of COVID RNA and 8 for NTC; Each cycle =27"
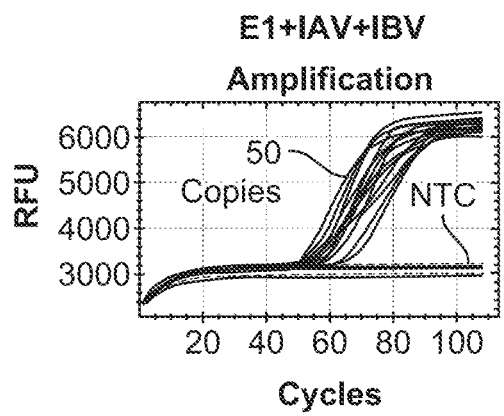
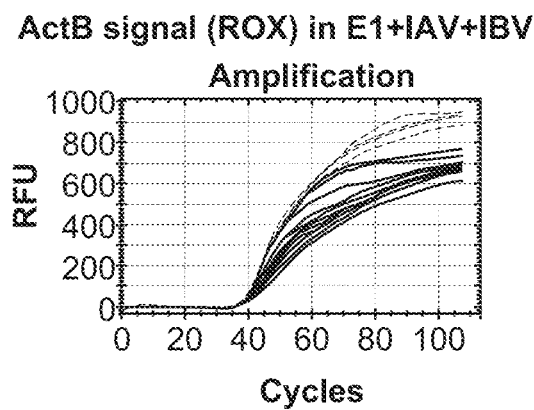
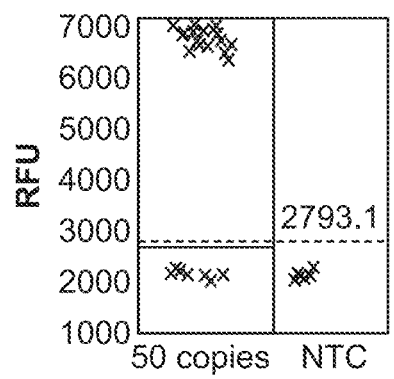
FIG. 31C
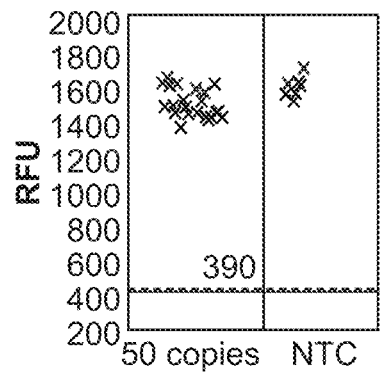
FIG. 31D
| Primer sets | Positives by Real time data | Av.Cq | Std dev | NTC | Positives by endpoint scan | NTC |
|---|---|---|---|---|---|---|
| E1 | 20/24 | 37.53 | 1.927 | 0/8 | 20/24 | 0/8 |
| E1+IAV | 18/24 | 51.82 | 5.029 | 0/8 | 18/24 | 0/8 |
| E1+IAV+IBV | 17/24 | 56.89 | 4.582 | 0/8 | 17/24 | 0/8 |
FIG. 31E

FIG. 33

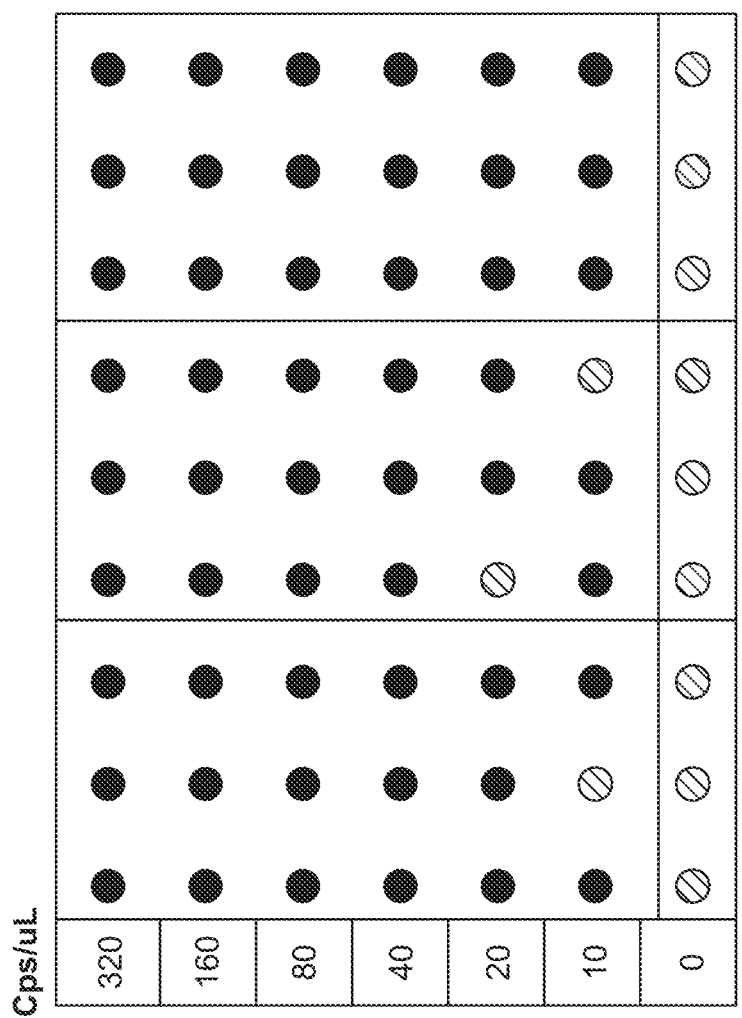
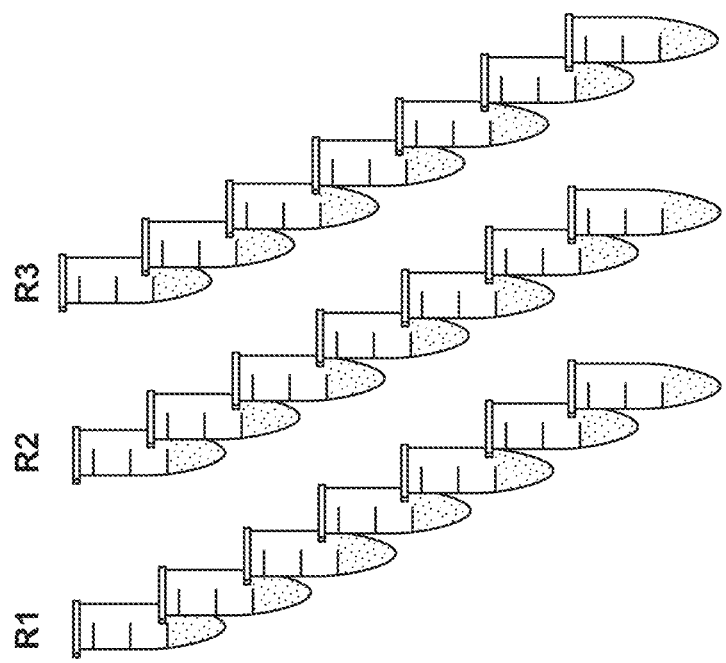
FIG. 34

FIG. 35

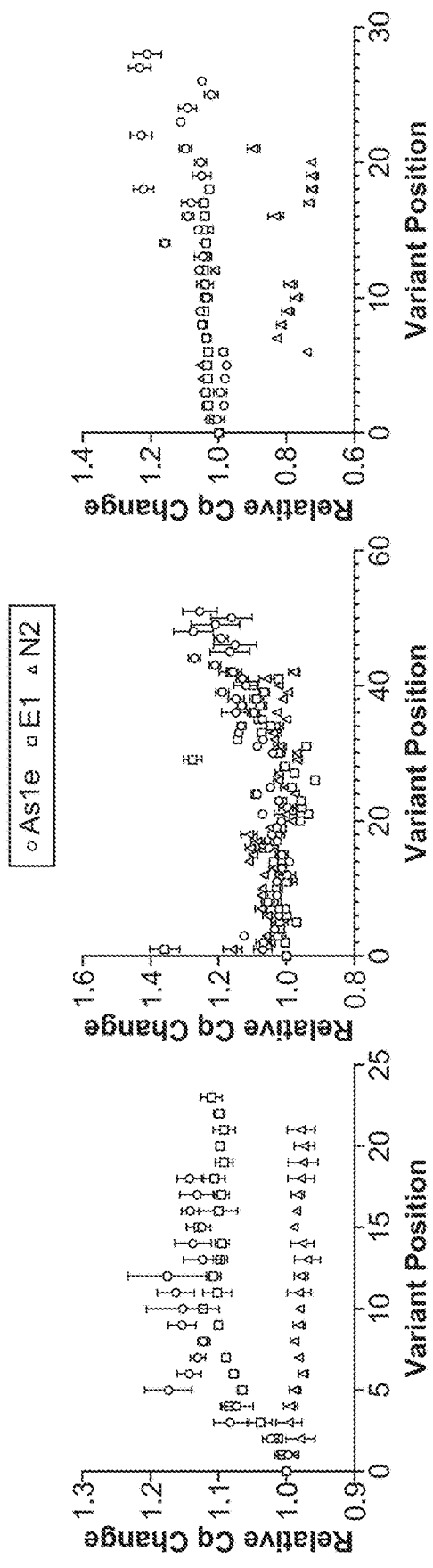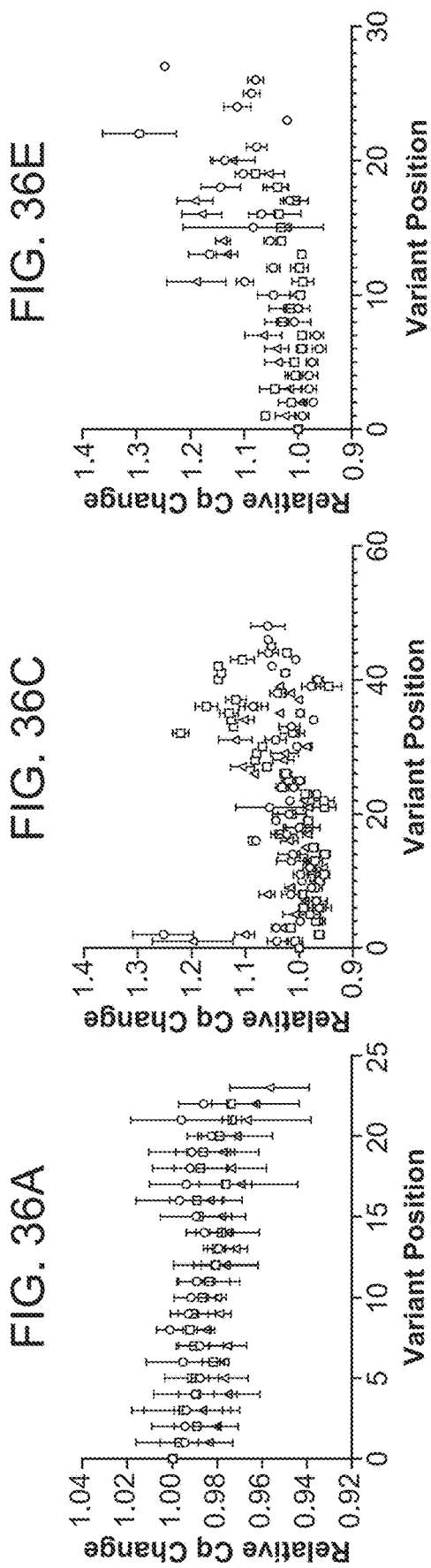
FIG. 36A, FIG. 36B, FIG. 36C, FIG. 36D, FIG. 36E, FIG. 36F

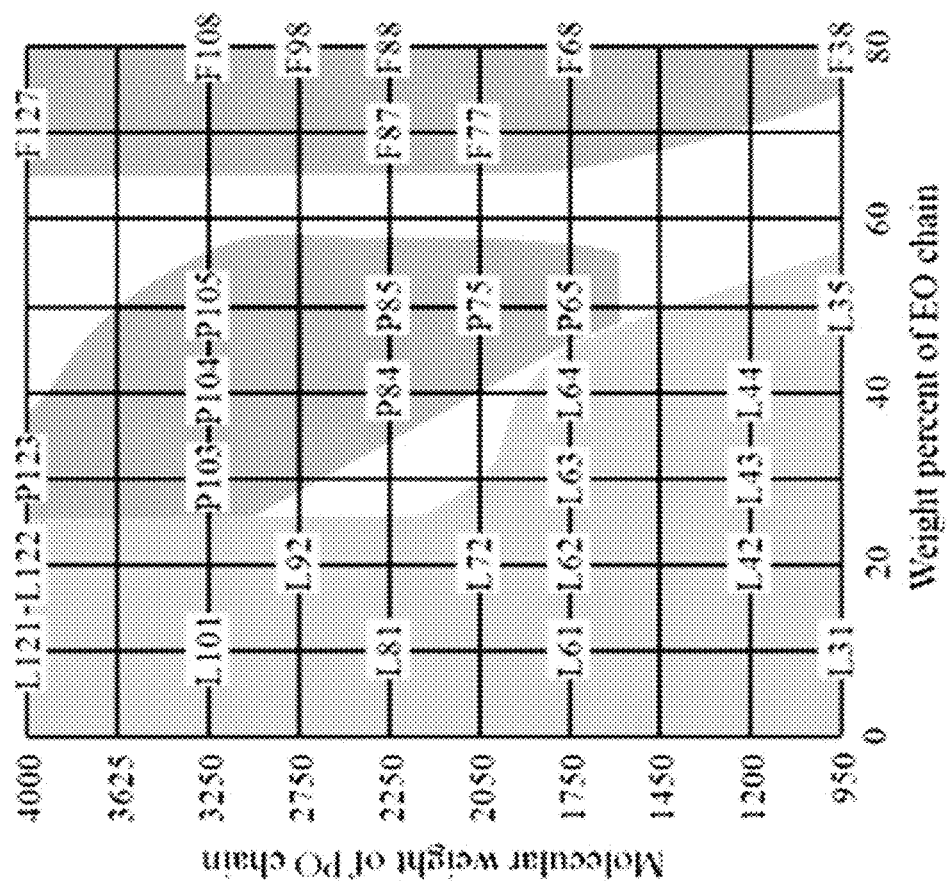
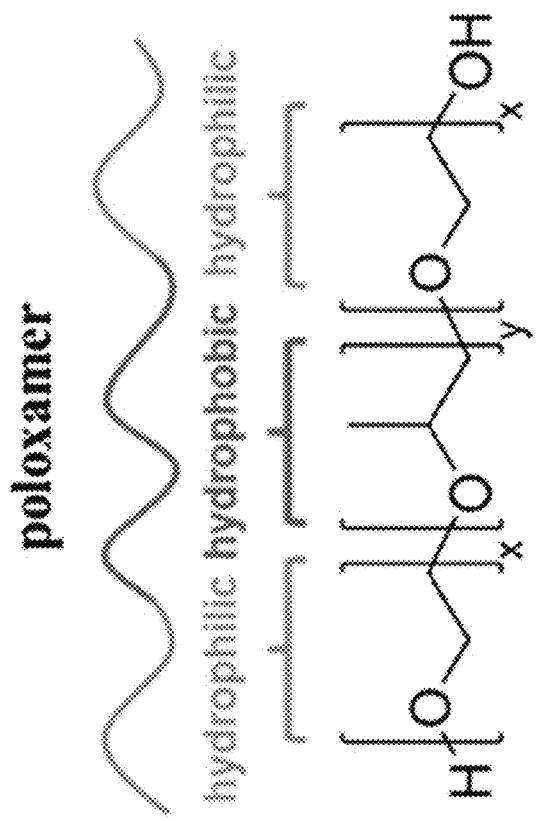
FIG. 38

SEQUENCE LISTING

<160> NUMBER OF SEQ ID NOS: 115

<210> SEQ ID NO 1
<211> LENGTH: 62
<212> TYPE: DNA
<213> ORGANISM: Artificial Sequence
<220> FEATURE:
<223> OTHER INFORMATION: Synthetic construct

<400> SEQUENCE: 1
ccctatgtgt tcatcaaacg ttcggatgct cgaactgcac ctcatggtca tgttatggtt    60
ga                                                                  62

<210> SEQ ID NO 2
<211> LENGTH: 61
<212> TYPE: DNA
<213> ORGANISM: Artificial Sequence
<220> FEATURE:
<223> OTHER INFORMATION: Synthetic construct

<400> SEQUENCE: 2
gctggtagca gaactcgaag gcattcagta cggtcgtagt ggtgagacac ttggtgtcct    60
t                                                                   61

<210> SEQ ID NO 3
<211> LENGTH: 61
<212> TYPE: DNA
<213> ORGANISM: Artificial Sequence
<220> FEATURE:
<223> OTHER INFORMATION: Synthetic construct

<400> SEQUENCE: 3
gtccctcatg tgggcgaaat accagtggct taccgcaagg ttcttcttcg taagaacggt    60
a                                                                   61

<210> SEQ ID NO 4
<211> LENGTH: 61
<212> TYPE: DNA
<213> ORGANISM: Artificial Sequence
<220> FEATURE:
<223> OTHER INFORMATION: Synthetic construct

<400> SEQUENCE: 4
ataaaggagc tggtggccat agttacggcg ccgatctaaa gtcatttgac ttaggcgacg    60
a                                                                   61

<210> SEQ ID NO 5
<211> LENGTH: 24
<212> TYPE: DNA
<213> ORGANISM: Artificial Sequence
<220> FEATURE:
<223> OTHER INFORMATION: Synthetic construct

<400> SEQUENCE: 5
gcttggcact gatccttatg aaga                                          24

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
ctgcacctca tggtcatgtt                                               20

<210> SEQ ID NO 7
<211> LENGTH: 19
<212> TYPE: DNA
<213> ORGANISM: Artificial Sequence
<220> FEATURE:
<223> OTHER INFORMATION: Synthetic construct

<400> SEQUENCE: 7
agctcgtcgc ctaagtcaa                                                19

<210> SEQ ID NO 8
<211> LENGTH: 42
<212> TYPE: DNA
<213> ORGANISM: Artificial Sequence
<220> FEATURE:
<223> OTHER INFORMATION: Synthetic construct

<400> SEQUENCE: 8
gagggacaag gacaccaagt gtatggttga gctggtagca ga                      42

<210> SEQ ID NO 9
<211> LENGTH: 39
<212> TYPE: DNA
<213> ORGANISM: Artificial Sequence
<220> FEATURE:
<223> OTHER INFORMATION: Synthetic construct

<400> SEQUENCE: 9
ccagtggctt accgcaaggt tttagatcgg cgccgtaac                          39

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
ccgtactgaa tgccttcgag t                                             21

<210> SEQ ID NO 11
<211> LENGTH: 25
<212> TYPE: DNA
<213> ORGANISM: Artificial Sequence
<220> FEATURE:
<223> OTHER INFORMATION: Synthetic construct

<400> SEQUENCE: 11
ttcgtaagaa cggtaataaa ggagc                                         25

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
tcatcaaacg ttcggatgct                                               20

<210> SEQ ID NO 13
<211> LENGTH: 18
<212> TYPE: DNA

```
<213> ORGANISM: Artificial Sequence
<220> FEATURE:
<223> OTHER INFORMATION: Synthetic construct

<400> SEQUENCE: 13
tatggccacc agctcctt                                                    18

<210> SEQ ID NO 14
<211> LENGTH: 42
<212> TYPE: DNA
<213> ORGANISM: Artificial Sequence
<220> FEATURE:
<223> OTHER INFORMATION: Synthetic construct

<400> SEQUENCE: 14
cgaccgtact gaatgccttc gagaactgca cctcatggtc at                         42

<210> SEQ ID NO 15
<211> LENGTH: 42
<212> TYPE: DNA
<213> ORGANISM: Artificial Sequence
<220> FEATURE:
<223> OTHER INFORMATION: Synthetic construct

<400> SEQUENCE: 15
agacacttgg tgtccttgtc ccagaagaac cttgcggtaa gc                         42

<210> SEQ ID NO 16
<211> LENGTH: 22
<212> TYPE: DNA
<213> ORGANISM: Artificial Sequence
<220> FEATURE:
<223> OTHER INFORMATION: Synthetic construct

<400> SEQUENCE: 16
ctgctaccag ctcaaccata ac                                               22

<210> SEQ ID NO 17
<211> LENGTH: 21
<212> TYPE: DNA
<213> ORGANISM: Artificial Sequence
<220> FEATURE:
<223> OTHER INFORMATION: Synthetic construct

<400> SEQUENCE: 17
tcatgtgggc gaaataccag t                                                21

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
ctgcacctca tggtcatgtt                                                  20

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
gatcagtgcc aagctcgtc                                                   19
```

<210> SEQ ID NO 20
<211> LENGTH: 41
<212> TYPE: DNA
<213> ORGANISM: Artificial Sequence
<220> FEATURE:
<223> OTHER INFORMATION: Synthetic construct

<400> SEQUENCE: 20
gagggacaag gacaccaagt gtggtagcag aactcgaagg c    41

<210> SEQ ID NO 21
<211> LENGTH: 39
<212> TYPE: DNA
<213> ORGANISM: Artificial Sequence
<220> FEATURE:
<223> OTHER INFORMATION: Synthetic construct

<400> SEQUENCE: 21
ccagtggctt accgcaaggt tttagatcgg cgccgtaac    39

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
accactacga ccgtactgaa t    21

<210> SEQ ID NO 23
<211> LENGTH: 25
<212> TYPE: DNA
<213> ORGANISM: Artificial Sequence
<220> FEATURE:
<223> OTHER INFORMATION: Synthetic construct

<400> SEQUENCE: 23
ttcgtaagaa cggtaataaa ggagc    25

<210> SEQ ID NO 24
<211> LENGTH: 61
<212> TYPE: DNA
<213> ORGANISM: Artificial Sequence
<220> FEATURE:
<223> OTHER INFORMATION: Synthetic construct

<400> SEQUENCE: 24
atgaccaaat tggctactac cgaagagcta ccagacgaat tcgtggtggt gacggtaaaa    60
t    61

<210> SEQ ID NO 25
<211> LENGTH: 61
<212> TYPE: DNA
<213> ORGANISM: Artificial Sequence
<220> FEATURE:
<223> OTHER INFORMATION: Synthetic construct

<400> SEQUENCE: 25
gaaagatctc agtccaagat ggtatttcta ctacctagga actgggccag aagctggact    60
t    61

<210> SEQ ID NO 26

<211> LENGTH: 61
<212> TYPE: DNA
<213> ORGANISM: Artificial Sequence
<220> FEATURE:
<223> OTHER INFORMATION: Synthetic construct

<400> SEQUENCE: 26
ccctatggtg ctaacaaaga cggcatcata tgggttgcaa ctgagggagc cttgaataca    60
c                                                                  61

<210> SEQ ID NO 27
<211> LENGTH: 54
<212> TYPE: DNA
<213> ORGANISM: Artificial Sequence
<220> FEATURE:
<223> OTHER INFORMATION: Synthetic construct

<400> SEQUENCE: 27
caaaagatca cattggcacc cgcaatcctg ctaacaatgc tgcaatcgtg ctac          54

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
tggctactac cgaagagct                                                19

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
tgcagcattg ttagcaggat                                               20

<210> SEQ ID NO 30
<211> LENGTH: 41
<212> TYPE: DNA
<213> ORGANISM: Artificial Sequence
<220> FEATURE:
<223> OTHER INFORMATION: Synthetic construct

<400> SEQUENCE: 30
tctggcccag ttcctaggta gtccagacga attcgtggtg g                       41

<210> SEQ ID NO 31
<211> LENGTH: 40
<212> TYPE: DNA
<213> ORGANISM: Artificial Sequence
<220> FEATURE:
<223> OTHER INFORMATION: Synthetic construct

<400> SEQUENCE: 31
agacggcatc atatgggttg cacgggtgcc aatgtgatct                         40

<210> SEQ ID NO 32
<211> LENGTH: 25
<212> TYPE: DNA
<213> ORGANISM: Artificial Sequence
<220> FEATURE:
<223> OTHER INFORMATION: Synthetic construct

```
<400> SEQUENCE: 32
ggactgagat ctttcatttt accgt                                         25

<210> SEQ ID NO 33
<211> LENGTH: 21
<212> TYPE: DNA
<213> ORGANISM: Artificial Sequence
<220> FEATURE:
<223> OTHER INFORMATION: Synthetic construct

<400> SEQUENCE: 33
actgagggag ccttgaatac a                                             21

<210> SEQ ID NO 34
<211> LENGTH: 19
<212> TYPE: DNA
<213> ORGANISM: Artificial Sequence
<220> FEATURE:
<223> OTHER INFORMATION: Synthetic construct

<400> SEQUENCE: 34
accgaagagc taccagacg                                                19

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
tgcagcattg ttagcaggat                                               20

<210> SEQ ID NO 36
<211> LENGTH: 40
<212> TYPE: DNA
<213> ORGANISM: Artificial Sequence
<220> FEATURE:
<223> OTHER INFORMATION: Synthetic construct

<400> SEQUENCE: 36
tctggcccag ttcctaggta gttcgtggtg gtgacggtaa                         40

<210> SEQ ID NO 37
<211> LENGTH: 40
<212> TYPE: DNA
<213> ORGANISM: Artificial Sequence
<220> FEATURE:
<223> OTHER INFORMATION: Synthetic construct

<400> SEQUENCE: 37
agacggcatc atatgggttg cacgggtgcc aatgtgatct                         40

<210> SEQ ID NO 38
<211> LENGTH: 25
<212> TYPE: DNA
<213> ORGANISM: Artificial Sequence
<220> FEATURE:
<223> OTHER INFORMATION: Synthetic construct

<400> SEQUENCE: 38
ccatcttgga ctgagatctt tcatt                                         25

<210> SEQ ID NO 39
```

```
<211> LENGTH: 21
<212> TYPE: DNA
<213> ORGANISM: Artificial Sequence
<220> FEATURE:
<223> OTHER INFORMATION: Synthetic construct

<400> SEQUENCE: 39
actgagggag ccttgaatac a                                              21

<210> SEQ ID NO 40
<211> LENGTH: 19
<212> TYPE: DNA
<213> ORGANISM: Artificial Sequence
<220> FEATURE:
<223> OTHER INFORMATION: Synthetic construct

<400> SEQUENCE: 40
tccttgaact ttggtctcc                                                 19

<210> SEQ ID NO 41
<211> LENGTH: 23
<212> TYPE: DNA
<213> ORGANISM: Artificial Sequence
<220> FEATURE:
<223> OTHER INFORMATION: Synthetic construct

<400> SEQUENCE: 41
cagttcataa aggaattgat agc                                            23

<210> SEQ ID NO 42
<211> LENGTH: 45
<212> TYPE: DNA
<213> ORGANISM: Artificial Sequence
<220> FEATURE:
<223> OTHER INFORMATION: Synthetic construct

<400> SEQUENCE: 42
atccccagtc tgtgaaattg ggcaaaatgc tgggattata gatgt                    45

<210> SEQ ID NO 43
<211> LENGTH: 47
<212> TYPE: DNA
<213> ORGANISM: Artificial Sequence
<220> FEATURE:
<223> OTHER INFORMATION: Synthetic construct

<400> SEQUENCE: 43
gcagcagaaa gattattaac ttgggcagtt ggtaagtaaa tggaaga                  47

<210> SEQ ID NO 44
<211> LENGTH: 20
<212> TYPE: DNA
<213> ORGANISM: Artificial Sequence
<220> FEATURE:
<223> OTHER INFORMATION: Synthetic construct

<400> SEQUENCE: 44
agaaccagag gccaggcgag                                                20

<210> SEQ ID NO 45
<211> LENGTH: 22
<212> TYPE: DNA
<213> ORGANISM: Artificial Sequence
<220> FEATURE:
<223> OTHER INFORMATION: Synthetic construct

<400> SEQUENCE: 45
```
aggcagatag gcttagactc aa                                              22

<210> SEQ ID NO 46
<211> LENGTH: 18
<212> TYPE: DNA
<213> ORGANISM: Artificial Sequence
<220> FEATURE:
<223> OTHER INFORMATION: Synthetic construct

<400> SEQUENCE: 46
cggtggacaa attgtcac                                                   18

<210> SEQ ID NO 47
<211> LENGTH: 22
<212> TYPE: DNA
<213> ORGANISM: Artificial Sequence
<220> FEATURE:
<223> OTHER INFORMATION: Synthetic construct

<400> SEQUENCE: 47
cttctctgga tttaacacac tt                                              22

<210> SEQ ID NO 48
<211> LENGTH: 28
<212> TYPE: DNA
<213> ORGANISM: Artificial Sequence
<220> FEATURE:
<223> OTHER INFORMATION: Synthetic construct

<400> SEQUENCE: 48
ttacaagctt aaagaatgtc tgaacact                                        28

<210> SEQ ID NO 49
<211> LENGTH: 27
<212> TYPE: DNA
<213> ORGANISM: Artificial Sequence
<220> FEATURE:
<223> OTHER INFORMATION: Synthetic construct

<400> SEQUENCE: 49
ttgaatttag gtgaaacatt tgtcacg                                         27

<210> SEQ ID NO 50
<211> LENGTH: 51
<212> TYPE: DNA
<213> ORGANISM: Artificial Sequence
<220> FEATURE:
<223> OTHER INFORMATION: Synthetic construct

<400> SEQUENCE: 50
tcagcacaca aagccaaaaa tttattttc tgtgcaaagg aaattaagga g               51

<210> SEQ ID NO 51
<211> LENGTH: 49
<212> TYPE: DNA
<213> ORGANISM: Artificial Sequence
<220> FEATURE:
<223> OTHER INFORMATION: Synthetic construct

<400> SEQUENCE: 51
tattggtgga gctaaactta aagccttttc tgtacaatcc ctttgagtg                 49

<210> SEQ ID NO 52
<211> LENGTH: 21
<212> TYPE: DNA

```
<213> ORGANISM: Artificial Sequence
<220> FEATURE:
<223> OTHER INFORMATION: Synthetic construct

<400> SEQUENCE: 52
accaggaact aatcagacaa g                                        21

<210> SEQ ID NO 53
<211> LENGTH: 25
<212> TYPE: DNA
<213> ORGANISM: Artificial Sequence
<220> FEATURE:
<223> OTHER INFORMATION: Synthetic construct

<400> SEQUENCE: 53
gacttgatct ttgaaatttg gatct                                    25

<210> SEQ ID NO 54
<211> LENGTH: 42
<212> TYPE: DNA
<213> ORGANISM: Artificial Sequence
<220> FEATURE:
<223> OTHER INFORMATION: Synthetic construct

<400> SEQUENCE: 54
ttccgaagaa cgctgaagcg gaactgatta caaacattgg cc                 42

<210> SEQ ID NO 55
<211> LENGTH: 40
<212> TYPE: DNA
<213> ORGANISM: Artificial Sequence
<220> FEATURE:
<223> OTHER INFORMATION: Synthetic construct

<400> SEQUENCE: 55
cgcattggca tggaagtcac aatttgatgg cacctgtgta                    40

<210> SEQ ID NO 56
<211> LENGTH: 21
<212> TYPE: DNA
<213> ORGANISM: Artificial Sequence
<220> FEATURE:
<223> OTHER INFORMATION: Synthetic construct

<400> SEQUENCE: 56
gggggcaaat tgtgcaattt g                                        21

<210> SEQ ID NO 57
<211> LENGTH: 20
<212> TYPE: DNA
<213> ORGANISM: Artificial Sequence
<220> FEATURE:
<223> OTHER INFORMATION: Synthetic construct

<400> SEQUENCE: 57
cttcgggaac gtggttgacc                                          20

<210> SEQ ID NO 58
<211> LENGTH: 23
<212> TYPE: DNA
<213> ORGANISM: Artificial Sequence
<220> FEATURE:
<223> OTHER INFORMATION: Synthetic construct

<400> SEQUENCE: 58
tgagtacgaa cttatgtact cat                                      23
```

```
<210> SEQ ID NO 59
<211> LENGTH: 22
<212> TYPE: DNA
<213> ORGANISM: Artificial Sequence
<220> FEATURE:
<223> OTHER INFORMATION: Synthetic construct

<400> SEQUENCE: 59 ttcagattt taacacgaga gt                                              22

<210> SEQ ID NO 60
<211> LENGTH: 42
<212> TYPE: DNA
<213> ORGANISM: Artificial Sequence
<220> FEATURE:
<223> OTHER INFORMATION: Synthetic construct

<400> SEQUENCE: 60
accacgaaag caagaaaaag aagttcgttt cggaagagac ag                       42

<210> SEQ ID NO 61
<211> LENGTH: 44
<212> TYPE: DNA
<213> ORGANISM: Artificial Sequence
<220> FEATURE:
<223> OTHER INFORMATION: Synthetic construct

<400> SEQUENCE: 61
ttgctagtta cactagccat ccttaggttt tacaagactc acgt                     44

<210> SEQ ID NO 62
<211> LENGTH: 19
<212> TYPE: DNA
<213> ORGANISM: Artificial Sequence
<220> FEATURE:
<223> OTHER INFORMATION: Synthetic construct

<400> SEQUENCE: 62
gcgcttcgat tgtgtgcgt                                                 19

<210> SEQ ID NO 63
<211> LENGTH: 18
<212> TYPE: DNA
<213> ORGANISM: Artificial Sequence
<220> FEATURE:
<223> OTHER INFORMATION: Synthetic construct

<400> SEQUENCE: 63
cgctattaac tattaacg                                                  18

<210> SEQ ID NO 64
<211> LENGTH: 18
<212> TYPE: DNA
<213> ORGANISM: Artificial Sequence
<220> FEATURE:
<223> OTHER INFORMATION: Synthetic construct

<400> SEQUENCE: 64
agtaccccat cgagcacg                                                  18

<210> SEQ ID NO 65
<211> LENGTH: 20
<212> TYPE: DNA
<213> ORGANISM: Artificial Sequence
<220> FEATURE:
```

<223> OTHER INFORMATION: Synthetic construct

<400> SEQUENCE: 65
agcctggata gcaacgtaca                                                   20

<210> SEQ ID NO 66
<211> LENGTH: 40
<212> TYPE: DNA
<213> ORGANISM: Artificial Sequence
<220> FEATURE:
<223> OTHER INFORMATION: Synthetic construct

<400> SEQUENCE: 66
gagccacacg cagctcattg tatcaccaac tgggacgaca                              40

<210> SEQ ID NO 67
<211> LENGTH: 38
<212> TYPE: DNA
<213> ORGANISM: Artificial Sequence
<220> FEATURE:
<223> OTHER INFORMATION: Synthetic construct

<400> SEQUENCE: 67
ctgaacccca aggccaaccg gctggggtgt tgaaggtc                                38

<210> SEQ ID NO 68
<211> LENGTH: 21
<212> TYPE: DNA
<213> ORGANISM: Artificial Sequence
<220> FEATURE:
<223> OTHER INFORMATION: Synthetic construct

<400> SEQUENCE: 68
tgtggtgcca gattttctcc a                                                 21

<210> SEQ ID NO 69
<211> LENGTH: 23
<212> TYPE: DNA
<213> ORGANISM: Artificial Sequence
<220> FEATURE:
<223> OTHER INFORMATION: Synthetic construct

<400> SEQUENCE: 69
cgagaagatg acccagatca tgt                                               23

<210> SEQ ID NO 70
<211> LENGTH: 23
<212> TYPE: DNA
<213> ORGANISM: Artificial Sequence
<220> FEATURE:
<223> OTHER INFORMATION: Synthetic construct

<400> SEQUENCE: 70
tgagtacgaa cttatgtact cat                                               23

<210> SEQ ID NO 71
<211> LENGTH: 22
<212> TYPE: DNA
<213> ORGANISM: Artificial Sequence
<220> FEATURE:
<223> OTHER INFORMATION: Synthetic construct

<400> SEQUENCE: 71
ttcagatttt taacacgaga gt                                                22

```
<210> SEQ ID NO 72
<211> LENGTH: 42
<212> TYPE: DNA
<213> ORGANISM: Artificial Sequence
<220> FEATURE:
<223> OTHER INFORMATION: Synthetic construct

<400> SEQUENCE: 72
accacgaaag caagaaaaag aagttcgttt cggaagagac ag         42

<210> SEQ ID NO 73
<211> LENGTH: 44
<212> TYPE: DNA
<213> ORGANISM: Artificial Sequence
<220> FEATURE:
<223> OTHER INFORMATION: Synthetic construct

<400> SEQUENCE: 73
ttgctagtta cactagccat ccttaggttt tacaagactc acgt        44

<210> SEQ ID NO 74
<211> LENGTH: 18
<212> TYPE: DNA
<213> ORGANISM: Artificial Sequence
<220> FEATURE:
<223> OTHER INFORMATION: Synthetic construct

<400> SEQUENCE: 74
cgctattaac tattaacg                                     18

<210> SEQ ID NO 75
<211> LENGTH: 19
<212> TYPE: DNA
<213> ORGANISM: Artificial Sequence
<220> FEATURE:
<223> OTHER INFORMATION: Synthetic construct

<400> SEQUENCE: 75
gcgcttcgat tgtgtgcgt                                    19

<210> SEQ ID NO 76
<211> LENGTH: 42
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: 5IABkFQ

<400> SEQUENCE: 76
accacgaaag caagaaaaag aagttcgttt cggaagagac ag         42

<210> SEQ ID NO 77
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(25)
<223> OTHER INFORMATION: 3Joe_N

<400> SEQUENCE: 77 acttctttt cttgctttcg tggt                              24
```

```
<210> SEQ ID NO 78
<211> LENGTH: 19
<212> TYPE: DNA
<213> ORGANISM: Artificial Sequence
<220> FEATURE:
<223> OTHER INFORMATION: Synthetic construct

<400> SEQUENCE: 78
gacttgaaga tgtctttgc                                                      19

<210> SEQ ID NO 79
<211> LENGTH: 19
<212> TYPE: DNA
<213> ORGANISM: Artificial Sequence
<220> FEATURE:
<223> OTHER INFORMATION: Synthetic construct

<400> SEQUENCE: 79
gactggaaag tgtctttgc                                                      19

<210> SEQ ID NO 80
<211> LENGTH: 19
<212> TYPE: DNA
<213> ORGANISM: Artificial Sequence
<220> FEATURE:
<223> OTHER INFORMATION: Synthetic construct

<400> SEQUENCE: 80
trttatttgg gtctccatt                                                      19

<210> SEQ ID NO 81
<211> LENGTH: 19
<212> TYPE: DNA
<213> ORGANISM: Artificial Sequence
<220> FEATURE:
<223> OTHER INFORMATION: Synthetic construct

<400> SEQUENCE: 81
trttgtttgg gtccccatt                                                      19

<210> SEQ ID NO 82
<211> LENGTH: 39
<212> TYPE: DNA
<213> ORGANISM: Artificial Sequence
<220> FEATURE:
<223> OTHER INFORMATION: Synthetic construct

<400> SEQUENCE: 82
ttagtcagag gtgacarrat tgcagatctt gaggctctc                                39

<210> SEQ ID NO 83
<211> LENGTH: 39
<212> TYPE: DNA
<213> ORGANISM: Artificial Sequence
<220> FEATURE:
<223> OTHER INFORMATION: Synthetic construct

<400> SEQUENCE: 83
ttgtkttcac gctcaccgtg tttggacaaa gcgtctacg                                39

<210> SEQ ID NO 84
<211> LENGTH: 16
<212> TYPE: DNA
<213> ORGANISM: Artificial Sequence
<220> FEATURE:
<223> OTHER INFORMATION: Synthetic construct
```

<400> SEQUENCE: 84
gtcttgtctt tagcca                                                              16

<210> SEQ ID NO 85
<211> LENGTH: 17
<212> TYPE: DNA
<213> ORGANISM: Artificial Sequence
<220> FEATURE:
<223> OTHER INFORMATION: Synthetic construct

<400> SEQUENCE: 85
cmagtgagcg aggactg                                                             17

<210> SEQ ID NO 86
<211> LENGTH: 39
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: 5IAbRQ

<400> SEQUENCE: 86
ttagtcagag gtgacarrat tgcagatctt gaggctctc                                     39

<210> SEQ ID NO 87
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (23)..(23)
<223> OTHER INFORMATION: 3Cy5Sp

<400> SEQUENCE: 87
caatyytgtc acctctgact aa                                                       22

<210> SEQ ID NO 88
<211> LENGTH: 18
<212> TYPE: DNA
<213> ORGANISM: Artificial Sequence
<220> FEATURE:
<223> OTHER INFORMATION: Synthetic construct

<400> SEQUENCE: 88
gcaaccaatg ccaccata                                                            18

<210> SEQ ID NO 89
<211> LENGTH: 20
<212> TYPE: DNA
<213> ORGANISM: Artificial Sequence
<220> FEATURE:
<223> OTHER INFORMATION: Synthetic construct

<400> SEQUENCE: 89
ttctctcttc aagrgacatc                                                          20

<210> SEQ ID NO 90
<211> LENGTH: 41
<212> TYPE: DNA
<213> ORGANISM: Artificial Sequence
<220> FEATURE:

```
<223> OTHER INFORMATION: Synthetic construct

<400> SEQUENCE: 90
tagtcaaggg cyctttgcca ctttgaagca ggaattctgg a                        41

<210> SEQ ID NO 91
<211> LENGTH: 44
<212> TYPE: DNA
<213> ORGANISM: Artificial Sequence
<220> FEATURE:
<223> OTHER INFORMATION: Synthetic construct

<400> SEQUENCE: 91
caagaccgcc taaacagact aaacttttac tttcaggctc actt                    44

<210> SEQ ID NO 92
<211> LENGTH: 19
<212> TYPE: DNA
<213> ORGANISM: Artificial Sequence
<220> FEATURE:
<223> OTHER INFORMATION: Synthetic construct

<400> SEQUENCE: 92
tgaaagyctt tcatagcac                                                19

<210> SEQ ID NO 93
<211> LENGTH: 20
<212> TYPE: DNA
<213> ORGANISM: Artificial Sequence
<220> FEATURE:
<223> OTHER INFORMATION: Synthetic construct

<400> SEQUENCE: 93
caagaataaa gactcacaac                                               20

<210> SEQ ID NO 94
<211> LENGTH: 41
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: 5IAbRQ

<400> SEQUENCE: 94
tagtcaaggg cyctttgcca ctttgaagca ggaattctgg a                       41

<210> SEQ ID NO 95
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: 36-FAM

<400> SEQUENCE: 95
tggcaaagrg cccttgacta                                               20

<210> SEQ ID NO 96
<211> LENGTH: 18
<212> TYPE: DNA
<213> ORGANISM: Artificial Sequence
```

```
<220> FEATURE:
<223> OTHER INFORMATION: Synthetic construct

<400> SEQUENCE: 96 agtacccat cgagcacg                                                    18

<210> SEQ ID NO 97
<211> LENGTH: 20
<212> TYPE: DNA
<213> ORGANISM: Artificial Sequence
<220> FEATURE:
<223> OTHER INFORMATION: Synthetic construct

<400> SEQUENCE: 97
agcctggata gcaacgtaca                                                 20

<210> SEQ ID NO 98
<211> LENGTH: 40
<212> TYPE: DNA
<213> ORGANISM: Artificial Sequence
<220> FEATURE:
<223> OTHER INFORMATION: Synthetic construct

<400> SEQUENCE: 98
gagccacacg cagctcattg tatcaccaac tgggacgaca                           40

<210> SEQ ID NO 99
<211> LENGTH: 38
<212> TYPE: DNA
<213> ORGANISM: Artificial Sequence
<220> FEATURE:
<223> OTHER INFORMATION: Synthetic construct

<400> SEQUENCE: 99
ctgaacccca aggccaaccg gctggggtgt tgaaggtc                             38

<210> SEQ ID NO 100
<211> LENGTH: 21
<212> TYPE: DNA
<213> ORGANISM: Artificial Sequence
<220> FEATURE:
<223> OTHER INFORMATION: Synthetic construct

<400> SEQUENCE: 100
tgtggtgcca gattttctcc a                                               21

<210> SEQ ID NO 101
<211> LENGTH: 23
<212> TYPE: DNA
<213> ORGANISM: Artificial Sequence
<220> FEATURE:
<223> OTHER INFORMATION: Synthetic construct

<400> SEQUENCE: 101
cgagaagatg acccagatca tgt                                             23

<210> SEQ ID NO 102
<211> LENGTH: 23
<212> TYPE: DNA
<213> ORGANISM: Artificial Sequence
<220> FEATURE:
<223> OTHER INFORMATION: Synthetic construct

<400> SEQUENCE: 102
cgagaagatg acccagatca tgt                                             23
```

```
<210> SEQ ID NO 103
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: 5IAbRQ

<400> SEQUENCE: 103
gagccacacg cagctcattg tatcaccaac tgggacgaca                              40

<210> SEQ ID NO 104
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (22)..(22)
<223> OTHER INFORMATION: 3Rox_N

<400> SEQUENCE: 104
tacaatgagc tgcgtgtggc tc                                                22

<210> SEQ ID NO 105
<211> LENGTH: 21
<212> TYPE: DNA
<213> ORGANISM: Artificial Sequence
<220> FEATURE:
<223> OTHER INFORMATION: Synthetic construct

<400> SEQUENCE: 105
gcttttgcaa tgatgtttgt c                                                 21

<210> SEQ ID NO 106
<211> LENGTH: 19
<212> TYPE: DNA
<213> ORGANISM: Artificial Sequence
<220> FEATURE:
<223> OTHER INFORMATION: Synthetic construct

<400> SEQUENCE: 106
agtgtccaca ctctcctag                                                    19

<210> SEQ ID NO 107
<211> LENGTH: 50
<212> TYPE: DNA
<213> ORGANISM: Artificial Sequence
<220> FEATURE:
<223> OTHER INFORMATION: Synthetic construct

<400> SEQUENCE: 107
ccaactagca ggcatataga ccatacattt ctctgtttgt ttttgttacc                  50

<210> SEQ ID NO 108
<211> LENGTH: 43
<212> TYPE: DNA
<213> ORGANISM: Artificial Sequence
<220> FEATURE:
<223> OTHER INFORMATION: Synthetic construct

<400> SEQUENCE: 108
atgacatggt tggatatggt tggttcttgc tgtcataagg att                         43
```

<210> SEQ ID NO 109
<211> LENGTH: 20
<212> TYPE: DNA
<213> ORGANISM: Artificial Sequence
<220> FEATURE:
<223> OTHER INFORMATION: Synthetic construct

<400> SEQUENCE: 109
aagctacagt ggcaagagaa                                         20

<210> SEQ ID NO 110
<211> LENGTH: 22
<212> TYPE: DNA
<213> ORGANISM: Artificial Sequence
<220> FEATURE:
<223> OTHER INFORMATION: Synthetic construct

<400> SEQUENCE: 110
atgcatcagc tgtagtgtta ct                                      22

<210> SEQ ID NO 111
<211> LENGTH: 25
<212> TYPE: DNA
<213> ORGANISM: Artificial Sequence
<220> FEATURE:
<223> OTHER INFORMATION: Synthetic construct

<400> SEQUENCE: 111
ggagctttgt ctggttttaa gctcc                                   25

<210> SEQ ID NO 112
<211> LENGTH: 25
<212> TYPE: DNA
<213> ORGANISM: Artificial Sequence
<220> FEATURE:
<223> OTHER INFORMATION: Synthetic construct

<400> SEQUENCE: 112
cgcagtttga agctaaaaga ctgcg                                   25

<210> SEQ ID NO 113
<211> LENGTH: 260
<212> TYPE: DNA
<213> ORGANISM: Artificial Sequence
<220> FEATURE:
<223> OTHER INFORMATION: Synthetic construct

<400> SEQUENCE: 113
ctgcttttgc aatgatgttt gtcaaacata agcatgcatt tctctgtttg tttttgttac    60
cttctcttgc cactgtagct tatttaata tggtctatat gcctgctagt tgggtgatgc    120
gtattatgac atggttggat atggttgata ctagtttgaa gctaaaagac tgtgttatgt    180
atgcatcagc tgtagtgtta ctaatcctta tgacagcaag aactgtgtat gatgatggtg    240
ctaggagagt gtggacactt                                              260

<210> SEQ ID NO 114
<211> LENGTH: 29
<212> TYPE: DNA
<213> ORGANISM: Artificial Sequence
<220> FEATURE:
<223> OTHER INFORMATION: Synthetic construct

<400> SEQUENCE: 114

```
agtttgtctg gttttaagct aaaagactg                              29

<210> SEQ ID NO 115
<211> LENGTH: 20
<212> TYPE: DNA
<213> ORGANISM: Artificial Sequence
<220> FEATURE:
<223> OTHER INFORMATION: Synthetic construct

<400> SEQUENCE: 115
agtttgaagc taaaagactg                                         20
```

RAPID DIAGNOSTIC TEST FOR LAMP

CROSS REFERENCE

This application is a continuation in part of U.S. application Ser. No. 17/221,451 filed Apr. 2, 2021, which is a continuation of U.S. application Ser. No. 17/122,979, filed Dec. 15, 2020, which claims right of priority to U.S. Provisional Application No. 62/988,696, filed Mar. 12, 2020; U.S. Provisional Application No. 63/001,909, filed Mar. 30, 2020; U.S. Provisional Application No. 63/013,442, filed Apr. 21, 2020; U.S. Provisional Application No. 63/022,303, filed May 8, 2020; U.S. Provisional Application No. 63/027,216, filed May 19, 2020; U.S. Provisional Application No. 63/048,556, filed Jul. 6, 2020; and U.S. application Ser. No. 16/938,575, filed Jul. 24, 2020.

This application also claims right of priority to U.S. Provisional Application No. 63/068,564, filed Aug. 21, 2020; U.S. Provisional Application No. 63/106,120, filed Oct. 27, 2020; and U.S. Provisional Application No. 63/165,465, filed Mar. 24, 2021. The contents of these applications are incorporated herein by reference in their entirety.

BACKGROUND

The ability to detect an infectious agent in a widespread epidemic is a critical aspect of successful quarantine efforts and enables screening of potential cases of infection from patients in a clinical setting. Enabling testing outside of sophisticated laboratories broadens the scope of control and surveillance efforts, but also requires robust and simple methods that can be used without expensive instrumentation.

The emergence of a new coronavirus (2019-nCoV, also called SARS-CoV-2 and COVID-19) has caused a worldwide pandemic for which diagnostic tests play a critical role. The current diagnostic standard combines clinical symptoms and molecular method, where symptoms for some patients range from life threatening to resembling those of common cold and influenza, to no symptoms or widely variable symptoms. Monitoring the spread of infection requires accurate, easy to use, widely available and cost sensitive molecular diagnostic tests. These molecular methods include metagenomics sequencing mNGS and reverse transcriptase-quantitative PCR (RT-qPCR) (Huang, et al. (2020) Lancet, 395, 497-506). mNGS is restricted by throughput, turnover time, high costs and requirement for high technical expertise. RT-qPCR requires multiple steps and expensive laboratory instruments and is difficult to utilize outside of well-equipped facilities. A rapid, specific, and sensitive diagnostic single test for one or several pathogens would be desirable to identify and track infected humans, animals or plants in a widespread epidemic that might threaten health and well-being.

Target pathogens, and particularly RNA viruses, naturally display mutations and changes in their genomic sequences that can impact the sensitivity and accuracy of the molecular diagnostic test when the mutations occur in the regions targeted by the oligonucleotide primers and/or probes. The ongoing SARS-CoV-2 pandemic has seen the emergence of numerous viral variants from different regions of the world, with prominent effects on detection using molecular assays. For example, the B.1.1.7 "alpha" variant features a 6-base deletion (removing 2 amino acids of the spike protein, Δ69-70) which causes a failure of the S Gene assay in the widely used TaqPath™ COVID-19 multiplex RT-qPCR test (Vogels et al. PLoS Biol 19(5), e3001236 (2021)). The other targets in this assay are unaffected, resulting in the ability to provide potential identification of variant RNA during detection, though sequencing is necessary for proper variant identification. In this particular case the other targets can be used for diagnostic detection, but the sensitivity of RT-qPCR to variant mutations is a significant concern to diagnostic testing given the worldwide reliance on the method.

While specific mutations like the alpha Δ69-70 are characterized in great detail, systematic evaluation of potential mutation effects on diagnostic assay performance is lacking. Mutations could be single base changes or deletions that remove a small region of the genome and could result in changes of the amino sequences (missense mutation) or no change (silent mutation). Larger deletions like Δ69-70 likely have more detrimental effects than single base changes, though single base changes located close to the 3' ends of primers might impact more than those located near the 5' ends. The widely-used TaqMan® probes rely on specific hybridization to targeted sequences and may display greater sensitivity to mutations than when they occur in primer binding regions; the Δ69-70 deletion occurs in the TaqPath probe region and completely prevents detection of RNA with that deletion.

SUMMARY

In one aspect, there is provided a master mix comprising: a DNA polymerase suitable for isothermal amplification of DNA; dNTPs (dATP, dGTP, dCTP, and dTTP); and at least one dye that changes color or fluorescence in response to DNA amplification. The master mix may be dried or may be in a weakly buffered solution. In many embodiments, the master mix is a LAMP master mix. However, the parameters tested herein may be applicable to master mixes for non-LAMP isothermal amplification reactions.

The DNA polymerase in the master mix may be any polymerase suitable for use in an isothermal amplification reaction (e.g., in a Loop-Mediated Isothermal Amplification (LAMP) reaction). Suitable DNA polymerases are known in the art and include strand displacing DNA polymerases preferably mesophilic DNA polymerases such as Bst polymerase or variants thereof or Bsu DNA polymerase or variants thereof. A reversible inhibitor of the DNA polymerase may be included in the master mix. For example, the reversible inhibitor may inhibit the polymerase at temperatures below 50° C. Examples of reversible inhibitors include aptamers and antibodies.

The at least one dye may be a colored dye detectable in visible light, or may be a fluorescent dye, so long as the dye provides a change in signal (e.g., a change in color, or a change in color intensity or fluorescence intensity) in response to an amplification reaction.

In one embodiment, the at least one colorimetric or fluorescent dye is or includes a dye that is pH sensitive. When the master mix containing the dye is used in an amplification reaction that alters the pH of the reaction mix, the spectral or fluorescent properties of the dye change (e.g. the dye changes color), which provides confirmation that amplification has occurred. Examples of pH sensitive dyes include colorimetric dyes such as phenol red, cresol red, m-cresol purple, bromocresol purple, neutral red, phenolphthalein, naphtholphthein, and thymol blue; and fluorescent dyes such as 2',7'-Bis-(2-Carboxyethyl)-5-(and-6)-Carboxyfluorescein or a carboxyl seminaphthorhodafluor (e.g. SNARF-1). In one embodiment, the at least one pH sensitive dye is phenol red.

In one embodiment, the at least one dye is or includes a dye that is not pH sensitive, such as a metallochromic indicator. When the master mx containing the metallochromic indicator dye is used in an amplification reaction that alters the availability of one or more metal ions in the reaction mix, the spectral or fluorescent properties of the dye change (e.g. the dye changes color), which provides confirmation that amplification has occurred. In one embodiment, the metallochromic indicator dye is 4-(2-pyridylazo) resorcinol (PAR). If PAR is used, the master mix may additionally comprise manganese ions such that the PAR in the master mix is complexed with Mn ions to form a PAR-Mn complex. Another example of a metallochromic dye is hydroxynaphthol blue (Wastling et al. (2010) PLoS Negl Trop Dis 4(11): e865. doi: 10.1371/journal.pntd.0000865).

In a preferred embodiment, the visually detectable dye in the reaction mix (1× master mix combined with sample) is in the range of 50 µM-200 µM.

The master mix for LAMP may optionally further comprise at least one set of primers (e.g., two, three, four, or five sets of primers) having specificity for a target nucleic acid. If multiple primer sets are used, each primer set may target a different nucleic acid sequence within the target nucleic acid (e.g., two or more different viral gene sequences). For example, the master mix may comprise at least two sets of primers, each specific for a different SARS-CoV-2 target sequence (e.g., in the ORF 1a gene and/or Gene N of SARS-CoV-2). Frequently it is preferred that the primers are provided separately from the master mix.

The master mix may comprise a reverse transcriptase, such as an HIV derived reverse transcriptase, an intron encoded reverse transcriptase, or a reverse transcriptase variant of Moloney murine leukemia virus. The master mix may comprise a reversible inhibitor for the reverse transcriptase that inhibits activity of the enzyme at or below 40° C. Examples of reversible inhibitors include one or more inhibitory oligonucleotides or antibodies. One or more inhibitors of RNase activity that are not reversible may be included in the master mix for inhibiting RNase activity. Examples include inhibitory oligonucleotides such as inhibitory oligonucleotides such as aptamers, or antibodies for inhibiting RNase A and an aptamer for inhibiting RNase I. The master mix may include an RNAse inhibitor that is not an aptamer. The master mix may comprise dUTP and/or a uracil DNA glycosylase (UDG), such as a thermolabile UDG. In one embodiment, the master mix optionally comprises a molecule comprising $C-(NH_2)_2NH$; such as guanidine hydrochloride, guanidine thiocyanate, guanidine chloride, guanidine sulfate, or arginine. In one embodiment, the master mix comprises guanidine hydrochloride. The $C-(NH_2)_2NH$ containing molecule can be present in the master mix at a concentration in the range of up to 60 mM, such as in the range of 20 mM-40 mM (e.g., about 20 mM, 30 mM or 40 mM).

However, in certain embodiments, the master mix does not contain a molecule comprising $C-(NH_2)_2NH$. In these circumstances, a composition comprising $C-(NH_2)_2NH$; such as guanidine hydrochloride, guanidine thiocyanate, guanidine chloride, guanidine sulfate, or arginine is not included in the master mix may be provided separately such as contained in a lysis buffer or in a mixture containing primer sets for adding to a LAMP reaction mixture. In one embodiment, a concentration of guanidine salt in the LAMP reaction mixture is preferably 40 mM guanidine salt. The $C-(NH_2)_2NH$ containing molecule can be present in the composition at a concentration in the range of up to 60 mM, such as in the range of 20 mM-40 mM (e.g., about 20 mM, 30 mM or 40 mM). In certain embodiments, the master mix contains primers that are specific for a target polynucleotide. In other embodiments, the master mix does not contain primers where these are added separately.

In embodiments where the master mix is dried, the master mix may be freeze dried, air dried, or lyophilized. The master mix may be immobilized, for example on paper, or on a natural or synthetic polymer. The dried master mix is reconstituted prior to use in an amplification reaction.

In embodiments where the master mix is in solution (e.g., following reconstitution), the master mix is in a weakly buffered solution, such as in a Tris buffer. The weakly buffered solution preferably has a concentration less than 5 mM, such as less than 5 mM Tris or equivalent buffer. In one embodiment, the weakly buffered solution is in the range of 0.5 mM to 5 mM, such as 0.5 mM to 5 mM Tris or equivalent buffer. The pH of the master mix may be buffered in the range of pH 7.5-pH 9.0; such as in the range of pH 7.8-pH 8.5, or pH 8.1-pH 8.5. The liquid form of the master mix may be in any suitable reaction container.

In one aspect there is provided a kit comprising a master mix as described herein. The kit may optionally further comprise a heating block or water bath suitable for heating a reaction tube, plate, or paper, or a plurality of the same to a temperature suitable for isothermal amplification.

In one aspect there is provided a method for determining whether a target nucleic acid is present in a sample, comprising: bringing an aliquot of the sample into contact with a master mix as described herein to form a reaction mixture wherein the reaction mix additionally includes primers that are specific for the target nucleic acid. In one example, the sample may be in an aqueous solution or absorbed to a test matrix such as paper. The master mix may include additional reagents to enhance sensitivity of the assay such as a guanidine salt, or this could be added separately to the reaction. Additionally, for LAMP, one primer set or a plurality of primer sets may be included in the master mix or added separately to the reaction mix. Not all target specific primer sets work equally well. For improved sensitivity, it is desirable to test a number of primer sets to select one or a combination of primer sets to maximize sensitivity of the LAMP assay. Determination as to whether the target nucleic acid is present in the sample may then proceed by detecting a change in the spectral properties, color, or fluorescence of the reaction mixture.

In one embodiment, the method involves isothermal amplification of the target nucleic acid in a LAMP reaction or a helicase-dependent amplification reaction (HDA). In one embodiment, the method involves colorimetric LAMP, which may be pH sensitive or may be pH insensitive (e.g., using PAR). In one embodiment, the method uses two, three, four, or five sets of target-specific primers in a multiplexed reaction (e.g., multiplexed LAMP); wherein the primers are added to the reaction mixture in the master mix or are added separately.

The sample may be a clinical sample, such as a sample of a body fluid (e.g., blood, sputum, saliva, mucous, lymph, sweat, urine, feces, etc.) or a sample taken from a swab such as a nasal, oral, or buccal swab, which may be from a human or other mammalian subject. The sample may alternatively be an environmental sample. In some embodiments, the method is performed directly on the sample (e.g., crude tissue or cell lysate, or whole blood) without a step of purifying target nucleic acid from the sample. To facilitate this, the sample may be added to a lysis buffer such as exemplified herein for saliva that may nonetheless be suitable for any body fluid. The sample may alternatively be a sample of purified nucleic acid.

Where an aqueous solution is referred to without reference to a body fluid or environmental sample, it may include sterile water or a weak buffer (e.g., 0.5 mM to 5 mM, such as 0.5 mM to 5 mM Tris or equivalent buffer) where the aqueous solution optionally contains a nuclease inhibitor such as an RNase inhibitor or a DNase inhibitors or both.

The target nucleic acid may be any DNA or RNA of interest. For example, the nucleic acid may be associated with a pathogen or a diagnostic target for pathogenesis. In one embodiment, the target nucleic acid is RNA or DNA of a target pathogen. In one embodiment, the target nucleic acid is from a bacterium. In one embodiment, the target nucleic acid is from a multi-cellular parasite, such as a parasitic nematode. In one embodiment, the pathogen is a virus; for example, an RNA virus, such as a coronavirus. For example, the pathogen may be SARS-CoV-2. In one embodiment, the target SARS-CoV-2 RNA sequence is the ORF1a gene and/or Gene N or portion thereof. Thus, there is provided a method for determining whether a SARS-CoV-2 nucleic acid is present in a sample, comprising: bringing an aliquot of the sample in an aqueous solution into contact with a master mix as described herein to form a reaction mixture, wherein the master mix or reaction mixture comprises at least one set of primers specific for a target SARS-CoV-2 nucleic acid; and determining whether the target SARS-CoV-2 nucleic acid is present in the sample by detecting a change in the color or fluorescence of the mixture.

In one embodiment, the nucleic acid is associated with gene expression, or may be an indicator of a metabolic response to a pharmaceutical preparation or allergen. For example, the method may be for determining a gene expression profile in response to an environmental or metabolic event, or in response to a therapeutic treatment. In one embodiment, the target nucleic acid is DNA, and the method is for determining one or more genetic loci correlated to a phenotype. For example, the genetic loci may be selected from the group consisting of a single nucleotide polymorphism (SNP) in a genome, an exon, or a gene in a genome. These methods may be useful in diagnosis of a genetic disease or in personalized medicine.

In one embodiment, the method uses a pH-sensitive dye. During nucleic acid amplification, hydrogen ions accumulate in the reaction mixture so that the mixture becomes increasingly acidic with increasing amplification. pH sensitive dyes change their color, color intensity, or fluorescent intensity, in response to the change in pH in the reaction mixture.

In one embodiment, the method uses PAR as the dye, and the master mix or the reaction mixture further comprises manganese ions (e.g., about 0.4 mM Mn ions per 100 µM PAR). The complex of PAR with manganese ions is in a red-colored state. Pyrophosphate produced during the nucleic acid amplification process, as a byproduct of primer nucleic acid polymerization, sequesters manganese with a higher affinity than does PAR, thereby removing the manganese from solution and returning PAR to a non-complexed, yellow-colored state. In one embodiment, the reaction mixture further comprises a non-ionic detergent such as Triton X-100 (e.g. at about 1%-4%, such as about 1% or 2%), which is shown herein to further enhance the color-change observed when using PAR.

The concentration of the visually detectable dye in the reaction mix may be in the range of 50 µM-250 µM; such as at 50 µM-150 µM, for example at about 50 µM, 75 µM, 100 µM, or 150 µM.

In one embodiment, the reaction mixture further comprises a molecule comprising C—$(NH_2)_2$NH; such as guanidine hydrochloride, guanidine thiocyanate, guanidine chloride, guanidine sulfate, or arginine. In one embodiment, the molecule is guanidine hydrochloride. The C—$(NH_2)_2$NH containing molecule can be added to the reaction at a concentration of up to 60 mM, such as in the range of 20 mM-40 mM (e.g., about 20 mM, 30 mM, or 40 mM). If the method uses a C—$(NH_2)_2$NH containing molecule (e.g., guanidine hydrochloride), the sodium chloride concentration in the reaction mixture is preferably less than 40 mM; for example, the reaction mixture may contain NaCl at a concentration of about 20 mM or about 10 mM. The reaction mixture may alternatively, or additionally, comprise KCl at a concentration of less than 100 mM (e.g., less than 40 mM).

The method may comprise the step of combining one or more RNase inhibitors and/or thermolabile Proteinase K with the sample, prior to combining the sample with the master mix to form the reaction mixture. Alternatively, one or more RNase inhibitors and/or thermolabile Proteinase K can be added to the reaction mixture together with the sample, in which case the thermolabile Proteinase K should be inactivated prior to adding the master mix. The method may comprise adding a reverse transcriptase to the reaction mixture (either via the master mix, or separately) if the target nucleic acid is RNA, such as viral RNA. The reaction mixture may further comprise dUTP and UDG (e.g., thermolabile UDG), which may be added to the reaction mixture from the master mix. Alternatively, the dUTP may be added to the reaction mixture from the master mix, and the UDG may be added separately to the reaction mixture.

In one embodiment, the method comprises analyzing multiple samples. For example, the method may use a reaction container that has multiple compartments each for analyzing a separate sample.

In one embodiment of the method, the master mix is dried and immobilized onto e.g., paper, and an aliquot (e.g., droplet) of the sample is added to the paper, followed by a heating step, resulting in amplification of target nucleic acid in the sample.

The change in the spectral or fluorescent properties of the dye can be detected by eye or using a spectrophotometer or fluorimeter or recorded by means of a camera or other color sensitive recording device. In one embodiment, the method involves comparing the spectral or fluorescent properties of the dye before and after amplification has occurred. In one embodiment, the change in spectral properties or fluorescence of the mixture can be recorded by a spectrophotometer having dual wavelength capabilities, digitized, and stored by a computer.

In one aspect, there is provided a composition, comprising: one or more primer sets suitable for amplification, such as for an isothermal amplification reaction such LAMP, the primer sets having specificity for a single target nucleic acid of interest; and a buffer containing a molecule comprising C—$(NH_2)_2$NH.

In one embodiment, the composition comprises two, three, four, or five primer sets, each having specificity for a single target nucleic acid of interest; such as a viral RNA sequence (e.g., SARS-CoV-2 RNA).

In one embodiment, the composition comprises C—$(NH_2)_2$NH such as selected from guanidine hydrochloride, guanidine thiocyanate, guanidine chloride, guanidine sulfate, or arginine. In one embodiment, the molecule is present in the composition at a concentration in the range of up to 60 mM, such as in the range of 20 mM-40 mM (e.g., about 20 mM, 30 mM, or 40 mM).

The composition may further comprise one or more reagents selected from a DNA polymerase, such as Bst polymerase; a reverse transcriptase; and an RNAse inhibitor. The composition may comprise dNTPs, which may optionally include dUTP; and/or may comprise a thermolabile UDG (also referred to herein as uracil deglycosylase). The composition may further comprise a reporter molecule for detecting amplification in the presence of a target nucleic acid; for example, a colorimetric or fluorescent dye as described herein (e.g., PAR).

In one aspect there is provided a method of isothermal amplification (e.g., LAMP or HDA), comprising: (a) adding any embodiment of the master mix described herein that contains a suitable polymerase, and dNTPs to a sample comprising a target nucleic acid to form a reaction mixture, and in the presence of suitable primers allowing amplification to occur; and (b) detecting whether the target nucleic acid is present in the sample.

The target nucleic acid may be as described above. In one embodiment, the target nucleic acid is a viral nucleic acid such as viral RNA. For example, the target nucleic acid may be a SARS-CoV-2 RNA. In one embodiment, the target SARS-CoV-2 RNA sequence is located within the ORF1a gene and/or Gene N.

In one embodiment, the molecule comprising C—$(NH_2)_2$NH (e.g., guanidine hydrochloride, guanidine thiocyanate, guanidine chloride, guanidine sulfate, or arginine) is present in the reaction mixture at a concentration of up to 60 mM, such as in the range of 20 mM-40 mM (e.g. about 20 mM, 30 mM or 40 mM). In one embodiment, the reaction mixture may further comprise NaCl at a concentration of less than 40 mM; such as at a concentration of about 20 mM. The reaction mixture may alternatively, or additionally, comprise KCl at a concentration of less than 100 mM (e.g., less than 40 mM).

In one aspect there is provided a method for detecting amplification of a target nucleic acid, comprising: providing an amplification reaction mixture containing a target nucleic acid and a master mix or composition as defined herein; and detecting a change in the spectral or fluorescent properties of the dye resulting from amplification of the target nucleic acid. The target nucleic acid may be as described above. In one embodiment, the target nucleic acid is a viral nucleic acid such as viral RNA. For example, the target nucleic acid may be a SARS-CoV-2 RNA.

Embodiments describe the use of immobilized reagent and lyophilized reagents in receiving vessels for saliva and other body fluids to assist in streamlining workflows and improving sensitivity of assays.

Additional embodiments include the following:

A kit is provided for Loop-Mediated Isothermal Amplification (LAMP), that includes either separately or combined in a mixture: (a) a strand displacing polymerase, for example, a Family A DNA polymerase, for example a mesophilic bacterial strand displacing polymerase, for example a *bacillus* family A strand displacing DNA polymerase capable of copying DNA at a temperature in the range of 50° C.-68° C.; (b) a reversible inhibitor of the polymerase, for example, an oligonucleotide reversible inhibitor also referred to as an aptamer that binds and inactivates the polymerase at temperatures at or below 50° C. but is released from the polymerase at temperatures above 50° C., permitting specific amplification with reduced background; (c) a thermolabile UDG that is inactivated at a temperature of above 50° C., a temperature that is preferably lower than the temperature at which the polymerase is active and isothermal amplification occurs where in one example, this is in the range of 60° C.-70° C., for example 64° C., 65° C., 66° C., 67° C. or 68° C.; (d) nucleoside triphosphates comprising dATP, dGTP, dCTP, and dTTP; and dUTP; and (e) at least one indicator reagent such as a metallochromic dye, a pH sensitive colorimetric dye or a fluorescent dye that changes color or provides fluorescence if amplification occurs.

If the kit is intended for use with a target nucleic acid that is RNA, the kit may comprise in addition to the above components, a reverse transcriptase for example a virus derived reverse transcriptase, or an intron expressed reverse transcriptase and a reversible inhibitor of the reverse transcriptase that permits the reverse transcriptase to be active above 50° C. but not below 50° C. so as to reduce background and enhance sensitivity of the LAMP amplification. The reversible inhibitor of the reverse transcriptase and the strand displacing polymerase should not adversely affect either the effectiveness of each inhibitor or the desired activity of either enzyme at the desired temperature. In one example of a combination of reversible inhibitory oligonucleotides or aptamer these were obtained individually as WarmStart® (New England Biolabs, Ipswich, Mass.) and RTX (New England Biolabs, Ipswich, Mass.) and combined and tested as shown herein to provide the desired sensitivity for detecting as few as 50 viral genomes (SARS-CoV-2) in a saliva sample spiked with virus.

The kit may additionally contain a receiving container for a biological sample. For example, the receiving container may be a vessel with a lid or a paper, a microfluidic device or a polymer surface to which the reagents and/or sample are attached and suitable for absorbing reagents or sample in a liquid form. The receiving container may be a vessel for combining reagents in a liquid form with samples in a liquid form. The kit may also contain lysis reagents for combining with the biological sample prior to performing LAMP with the kit reagents. These lysis reagents are for adding to or contained in the receiving container for lysing a biological sample to release any target nucleic acids therein for amplification by LAMP. The lysis reagents may include a reducing agent such as Tris (2-carboxyethyl) phosphine hydrochloride (TCEP) and a metal chelator such as EDTA. The lysis mixture may further include a salt of C—$(NH_2)_2NH^+$. The lysis mixture may further include a poloxamer. Additionally, the kit may contain at least one set of LAMP primers. The kit may contain a plurality of primer sets for amplifying a plurality of target nucleic acids in the biological sample such as for example different respiratory RNA viruses. The kit may contain a plurality of primer sets for amplifying a single nucleic acid target such as a viral genome such as Gene N and Gene E in SARS-CoV-2 in the biological sample. The kit may contain a plurality of primer sets for amplifying a single or multiple target nucleic acids from single or multiple samples. Pooling samples is one form of high throughput analysis of populations having a low infection rate with a pathogen.

Any of the amplification reagents or the reagents in the lysis mix may be freeze dried or lyophilized preferably excluding salts of C—$(NH_2)_2NH^+$. In addition, or alternatively, any of the specified enzyme and/or oligonucleotide reagents may be immobilized or incorporated on a matrix. If any of the reagents are supplied in a buffer for use with pH dependent colorimetric LAMP, then the buffering capacity should be no greater than equivalent to 5 mM Tris.

The kit provided herein may include instructions for use with a biological sample where the biological sample is selected from a body fluid or tissue, an agricultural sample, a food sample, a waste product, and a pathogen for example, the biological sample is a body fluid or tissue selected from the group consisting of mucous, urine, lymph, blood, saliva, feces, sputum, sweat, semen and biopsy, for example a saliva or a nasal swab. The instructions provide how to test for a target RNA genome in a single viral strain or in multiple viral strains or from multiple samples from a population of subjects.

The kit may contain a receiving container for a biological sample, that includes a vessel with a lid, the lid containing a solution of indicator reagent for release into the reaction vessel after lysis of the biological sample or after LAMP. Instructions for use of the kit may include a method for high sample throughput workflow enabled by the kit that is partially or completely automated and further comprises a recording device for storing and/or reporting positive sample data after detection of a change in color or fluorescence of the indicator resulting from amplification of the target nucleic acid.

In one aspect, a reaction mixture, is provided that includes a thermolabile UDG, a strand displacing polymerase, a reversible inhibitor of the polymerase, and a salt of $C-(NH_2)_2NH^+$.

In another aspect, a lysis mixture is provided for releasing an RNA from a biological sample for detection by amplification and/or sequencing, comprising a poloxamer, a reducing agent and a metal chelating agent.

The lysis mixture may further include a salt of $C-(NH_2)_2NH^+$.

In another aspect, a master mix is provided that includes a thermolabile UDG, a strand displacing polymerase, a reversible inhibitor of the polymerase, a reverse transcriptase and a reversible inhibitor of the reverse transcriptase.

In another aspect, a method is provided for amplifying any target nucleic acid in a biological sample by LAMP, that includes: (a) combining the biological sample with a lysis reagent to form a lysis mix; (b) incubating the lysis mix at a temperature of at least 60° C. for a period of time in the range of 3 minutes to 45 minutes; (c) combining an aliquot of the heat treated mix after step (b) with amplification reagents that include a strand displacing polymerase, a reversible inhibitor of the polymerase, a thermolabile UDG, nucleoside triphosphates, and at least one set of LAMP primers that hybridize to the target nucleic acid, to produce a reaction mix; and (d) incubating the reaction mix under amplification conditions for LAMP to permit inactivation of the thermolabile UDG and amplification of the target nucleic acid. The amplification reagents may further include a reverse transcriptase and a reversible inhibitor of the reverse transcriptase.

The lysis reagent in (a) may include at least one of a salt of $C-(NH_2)_2NH^+$ and a poloxamer to produce a lysis mix. The lysis reagent may also include a reducing agent and a metal chelating reagent. When the biological sample is combined with the lysis reagent to form a lysis mix, the lysis mix may be incubated at 95° C. for 5 minutes to break open the sample and release target nucleic acid.

In the method, any of the reagents in the lysis mix may be immobilized and/or lyophilized or freeze dried. Prior to the addition of the biological sample. The method may comprise a further step of determining if amplification has occurred by measuring fluorescence and/or color changes of one or more indicators in the amplification reagent mix.

In examples of the method, the biological sample may be saliva, the target nucleic acid may be an RNA virus such as a coronavirus and the amplification reagents may include a reverse transcriptase and a reverse transcriptase reversible inhibitor single or multiple sets of LAMP primers for amplifying at least two sequences in a target DNA or a cDNA of an RNA target such as Gene E and Gene N sequences in SARS-CoV-2, and/or for amplifying multiple target nucleic acids from different viruses and/or for amplifying target nucleic acids from different biological samples or from different animal subjects.

In one embodiment, a method is provided for analyzing a biological sample to determine the presence of a target nucleic acid, that includes: (a) combining the biological sample with a lysis reagent comprising a reducing agent, a metal chelator and at least one of a guanidine salt and a poloxamer to produce a lysis mix; and (b) determining the presence of the target nucleic acid by selectively amplifying, by means of, for example, LAMP, the target nucleic acid in a reaction mix that comprises an aliquot of the lysis mix. The reaction mix in (b) may include an indicator reagent that changes color or provides fluorescence if amplification occurs, and the method may include the additional step of determining whether the reaction mix contains the target nucleic acid based on a change in color or fluorescence.

In one embodiment, a method is provided for detecting an RNA virus in saliva or a nasal swab of a subject, that includes (a) collecting saliva in a receiving container that comprises: (i) substrate immobilized oligonucleotides for binding viral RNA and a lysis reagent mix comprising two or more reagents (for example, 3 or more reagents) selected from a guanidinium salt, a poloxamer, a reducing agent, a DNase inhibitor, an RNase inhibitor, a detergent, a metal chelator and a proteolytic agent; or (ii) lyophilized substrate immobilized oligonucleotides for binding viral RNA, and/or one or more lyophilized reagents contained in a lysis reagent mix, wherein the lysis reagent mix comprises two or more reagents (for example, 3 or more reagents) selected from a poloxamer, a reducing agent, DNase inhibitor, an RNase inhibitor, a detergent, a metal chelator and a proteolytic agent, wherein the lyophilized reagents become rehydrated when contacted by the collected saliva; (b) incubating the receiving container after step (a) at an effective temperature and time to release nucleic acid from any coronaviruses in the saliva for binding to the immobilized oligonucleotides; (c) removing the lysis reagent mix from the receiving vessel leaving the coronavirus genome bound to the immobilized oligonucleotides on the substrate; (d) adding amplification reagents to the substrate after step (c), wherein amplification reagents comprise reverse transcription reagents and DNA amplification reagents, to make a reaction mix; and (e) incubating the reaction mix under amplification conditions to amplify a cDNA copy of at least a portion of the coronavirus genome. In this embodiment, the receiving container may be selected from a paper substrate, a microfluidic device or a polymer surface. The reaction mix of (d) in this method may further include an indicator reagent that changes color or provides fluorescence if amplification occurs, and wherein the method further comprises detecting a change in a signal that indicates the presence of coronavirus in the saliva of the subject.

The method may include amplification reagents for LAMP as specified in the kit above and single or multiple primer sets as specified above also. For example, the amplification reagents may include LAMP primer sets targeting a second viral genome that is not a coronavirus wherein the LAMP primer sets are combined in a single reaction mix and wherein the LAMP primer set for the coronavirus is linked to a colorimetric indicator that changes color after amplification that is detectable at one wavelength and a second LAMP primer set for amplifying a second non coronavirus nucleic acid, having a colorimetric or fluorescent indicator that changes color after amplification that is detectable at a second wavelength.

Although the above examples of methods may include a sequencing step after the amplifying step.

One embodiment, provides for a method for amplifying a target nucleic acid by LAMP, that includes: (a) combining in a mixture, a biological sample from a mammalian subject with a buffer comprising a poloxamer; (b) heating the mixture to a temperature of at least 65° C. for an effective time to denature proteins in the biological sample; (c) allowing the sample to cool; and (d) amplifying one or more nucleic acids from the mix by LAMP where the biological sample may be saliva, a nasal swab or a buccal swab.

In one embodiment, a kit is provided for use in diagnostic detection of a target nucleic acid and variants thereof having undefined mutations, obtained from a cell or virus in a biological sample. The kit may include (a) a lyophilized mixture of a strand displacing polymerase and an indicator reagent and optionally a lyophilized reverse transcriptase, wherein (i) the indicator reagent is characterized by its ability to change color or provide fluorescence in a nucleic acid amplification reaction; and (ii) the strand displacing polymerase when rehydrated is capable of amplifying DNA at a temperature in the range of 50° C.-68° C.; and (b) a universal primer set suitable for loop mediated amplification (LAMP) of the target nucleic acids and variants thereof containing undefined mutations within one or more of the primer binding sites. Any of the reagents in the kit may be combined in a mixture in a single container or provided in separate containers.

The universal primer set as defined below is preferably suitable for LAMP and is capable of hybridizing to the target DNA in the presence of a plurality of undefined mutations to provide a positive result for the target DNA in a predetermined assay time period otherwise determined for a positive sample of a target nucleic acid having a known sequence. For example, the universal primer set may be similarly diagnostic for the target nucleic acids and variants thereof where deletions and additions in the BIF and FIP primer binding sites of the variants do not exceed 6-9 nucleotides. In one example, the target DNA is the reverse transcription product of an RNA virus, for example, a coronavirus. In one example, the indicator reagent is a molecular beacon.

The kit may include (c) lysis reagent in a container for receiving the biological sample, wherein the lysis reagents comprise a reducing agent and a metal chelator. The lysis reagent may include the reducing agent is Tris (2-carboxyethyl) phosphine hydrochloride (TCEP). The lysis reagents may include at least one of a salt of C—$(NH_2)_2NH^+$ and a poloxamer.

The kit may include one or more of components in (a)-(b) are immobilized on a substrate.

The lyophilized indicator reagent may be a metallochromic dye or a molecular beacon. If a reverse transcriptase is included in the kit, the reverse transcriptase may be a virus encoded reverse transcriptase, or a bacteria encoded intron II reverse transcriptase.

In one embodiment, a method is provided for detecting a target nucleic acid or unknown variant thereof in a biological sample by LAMP, that includes combining the biological sample with a lysis reagent to form a lysis mix; incubating the lysis mix at a temperature of at least 60° C. for a period of time in the range of 2 minutes to 45 minutes; combining in a reaction mix, an aliquot of the heat treated lysis mix with amplification reagents comprising a strand displacing polymerase, a reversible inhibitor of the polymerase, nucleoside triphosphates, and at least one set of LAMP primers that is capable of hybridizing to the target nucleic acid and to undefined variants of the target nucleic acid; and incubating the reaction mix for a reaction positive period of time under amplification conditions for LAMP to detect the presence of the target nucleic acid or undefined variants thereof in the sample. An additional step may be included of sequencing the target nucleic acid detected in the method to determine whether it is a variant of the target nucleic acid and characterizing any mutations.

The lysis reagent in the method may include a reducing agent and a metal chelating reagent. Once combined with the biological sample, the lysis mix may be heated to 95° C. for 5 minutes.

The method may include a reverse transcriptase and a reversible inhibitor of the reverse transcriptase in the amplification reagents. Any of the amplification reagents and/or lysis reagents may be lyophilized prior to combining with the biological sample. Any of the amplification reagents and/or lysis reagents may be immobilized on a matrix prior to or during the method.

An example of a biological sample is saliva for detecting a target nucleic acid such as an RNA virus for example, a coronavirus is saliva.

BRIEF DESCRIPTION OF THE FIGURES

The patent or application file contains at least one drawing executed in color. Copies of this patent or patent application publication with color drawings will be provided by the office upon request and payment of the necessary fee.

Figures that show results from pH dependent colorimetric LAMP rely on a color change from red/pink (negative) to yellow (positive). These colors are represented in the figures by replacing yellow (positive) in the tubes and on plates by black and by replacing red/pink (negative) with hash lines against a white background. FIGS. 11A, 13A-13D, and 14 describe color changes from metallochromic dyes where colors change from brown/orange to yellow. These colors are represented by dots that vary in density according to whether the reaction is positive (high density) or negative (1 or 2 dots) or somewhere in between.

A comparison of RNA and gBlock double-stranded DNA (dsDNA) templates in LAMP amplification is shown using real time amplification curves. Two primer sets (ORF1a-A in FIG. 2A and Gene N-A in FIG. 2B) were used to amplify either RNA (green curves, dilutions from $120 \times 10^6$ to 120 copies) or gDNA (blue curves, $60 \times 10^6$ to 60 copies). For ORF1a-A primer set, the gBlock is faster than RNA template; for Gene N-A primer set, the RNA is slightly faster. Each "cycle" represents 20 seconds, with 30 minute timepoint noted by dashed line.

Figure 3A:
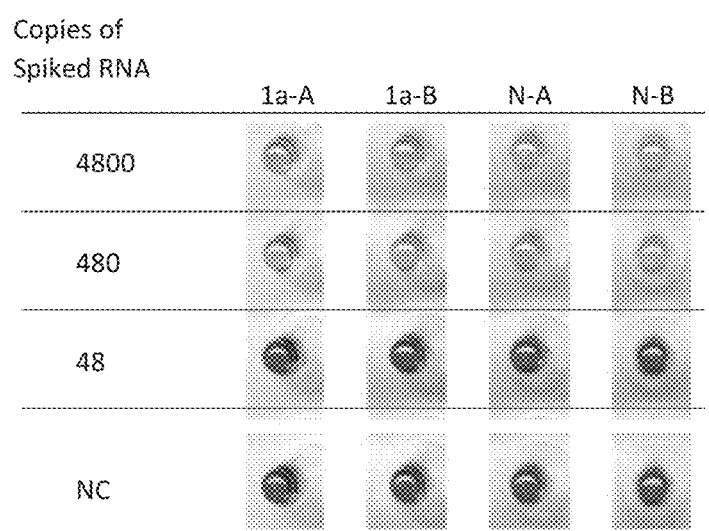
Figure 3B:
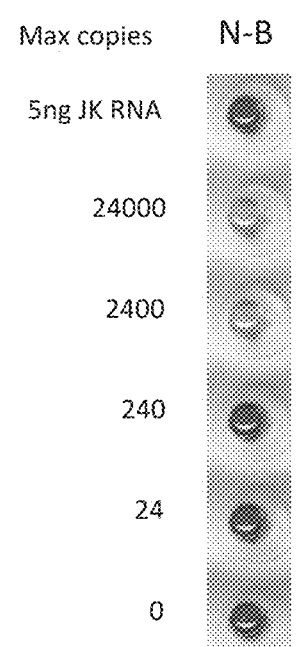

FIG. 3A and FIG. 3B shows that pH dependent colorimetric LAMP can detect viral genomes in total cell lysates and whole blood without requiring a purification step to remove total RNA. The primer sets described in Example 1 were used here. Lysis was performed using a cell lysis reagent (Luna® Cell Ready (New England Biolabs, Ipswich, Mass.)).

FIG. 3A shows direct RNA LAMP detection using total cell lysate. The approximate maximum number of copies of synthetic RNA added to each LAMP reaction is shown. The viral RNA was spiked into a Hela cell lysate. For 4800 copies of viral RNA, there were about 200 Hela cells present. NC, no cell, and no template control.

FIG. 3B shows colorimetric LAMP detection of various amounts of target RNA spiked in whole blood. The number of copies of the target RNA that could be detected are shown. In a control, 5 ng of Jurkat total RNA was added, which is similar to the total RNA present in the reaction with blood samples.

FIG. 4A-FIG. 4B shows the detection of various closely related nematode parasites was achieved for as little as 0.01 pg of nematode DNA in an environmental sample using the colorimetric LAMP described in Example 1. The control was a reagent mix absent nematode sample. Although Example 1 describes the test for an RNA virus, the same methodology applies to detecting the DNA from the various nematodes using an appropriate set of primers. As indicated in the figure, the assay could detect 0.01 pg-0.1 pg of nematode parasite DNA.

FIG. 5A-FIG. 5B shows that pH colorimetric LAMP is a useful diagnostic tool for detecting tick borne pathogens as it is both sensitive and specific for the target.

FIG. 5A shows detection of 1.28 fg target DNA from a specific target tick borne pathogen, with negative results (pink) from samples of non-target tick borne pathogens and hosts.

FIG. 5B shows specificity for the target DNA with negative (pink) results for non-target DNA. 1) no template DNA control; 2) pathogen target DNA; 3) DNA from other tick-borne pathogen 1 (negative control); 4) DNA from other tick-borne pathogen 2 (negative control); 5) DNA from other tick-borne pathogen 3 (negative control); 6) tick DNA; 7) mosquito DNA; 8) DNA from other tick-borne pathogen 4 (negative control).

FIG. 6A shows that pH-dependent colorimetric LAMP sensitivity is unaffected by the presence of dUTP and UDG. The endpoint color change with target nucleic acid in two Carryover Prevention WarmStart® Colorimetric LAMP 2× master mixes (abbreviated CP-LAMP MM) (New England Biolabs, Ipswich, Mass.). Two CP-LAMP MM contained a 50/50 mixture of dUTP/dTTP replacing dTTP. One CP-LAMP MM did not contain UDG (no UDG). One CP-LAMP MM (with UDG) includes 0.02 U/μL thermolabile uracil DNA glycosylase (UDG) (New England Biolabs, Ipswich, Mass.). A third LAMP MM contained neither UDG nor dUTP. In all other respects the same protocols were followed as described in Example 1 and in the figures above.

FIG. 6B shows that carryover of polynucleotide substrate is effectively prevented by including dUTP in the LAMP reaction prevented over 10 fold dilutions of the dU template from a first sample to a second master mix that does not contain any target nucleic acid. Each sample from left to right is a 10 fold dilution of the previous sample. At 50 fold-60 fold dilution, the carryover material was destroyed by the thermolabile UDG (0.02 U/μl). Carryover prevention (CP) was determined in CP-LAMP MM.

Figure 7:
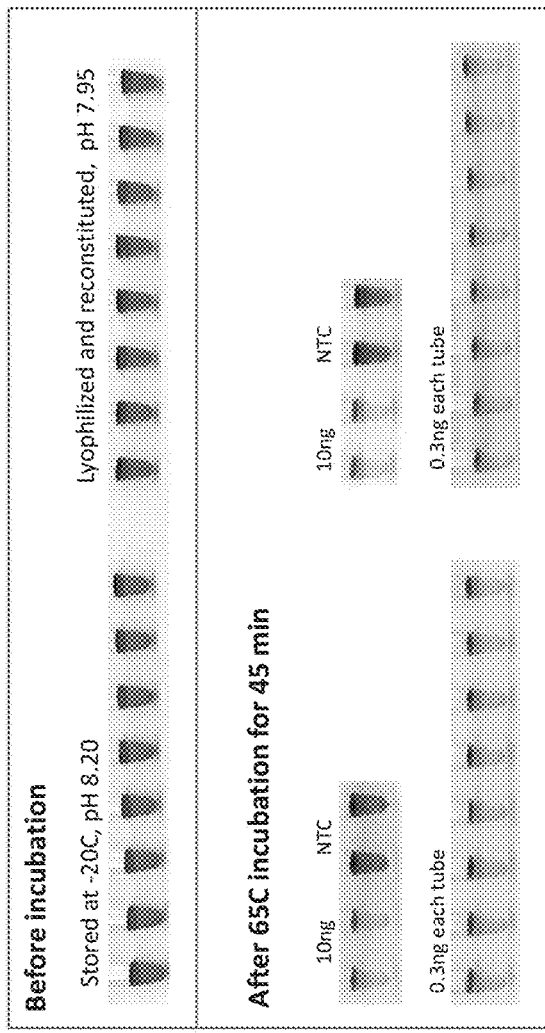

FIG. 7 shows that lyophilized pH-dependent LAMP MM is equally effective when compared to non-lyophilized LAMP MM stored at −20° C. The starting pH of the lyophilized LAMP when reconstituted was reduced by 0.25 units in this example.

FIG. 8A-FIG. 8C shows real time detection of target RNA (Jurkat total RNA) using a lyophilized LAMP MM and an HMBS2 primer set and a −20° C. storage preparation of LAMP MM. The LAMP MM contained the fluorescent dye (Syto-9) for following amplification. FIG. 8D provides a comparison of the rate of LAMP using a previously lyophilized LAMP MM or a MM stored at −20° C.

FIG. 9A-FIG. 9C shows that no difference in sensitivity of the LAMP reaction was observed using a LAMP MM versus −20° C. stored LAMP MM for DNA and RNA analyses, where RNA analysis additionally required a reverse transcriptase in the MM. FIGS. 9A and 9B showed a color change with phenol red while FIG. 9C used a fluorescent dye to detect amplification. WarmStart® LAMP Kit (DNA & RNA) is provided New England Biolabs.

Figure 10:
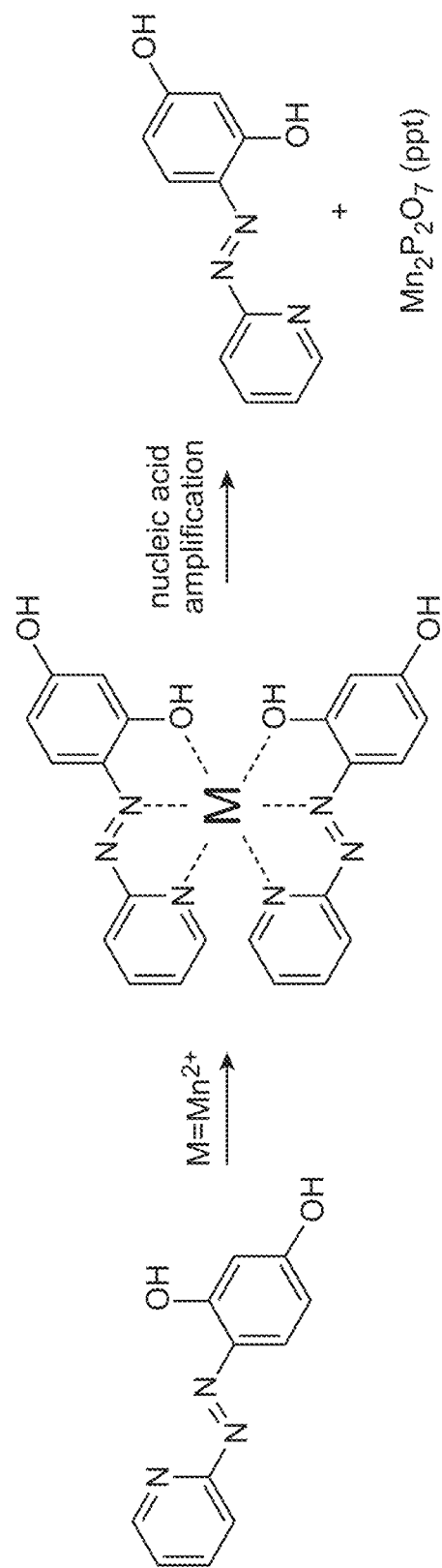

FIG. 10 shows the mechanism of the colorimetric response for 4-(2-pyridylazo) resorcinol (PAR). PAR is a known metallochromic indicator which, in the absence of metals in solution, exhibits a yellow color. When complexed with manganese in solution PAR produces a red color. During the nucleic acid amplification process, pyrophosphate is produced as a by-product of primer nucleic acid polymerization. By including a small amount of manganese ions in an amplification reaction, PAR is initially complexed with the metal and therefore in a red-colored state. The pyrophosphate by-product sequesters manganese with a higher affinity than does PAR, resulting in the dissociation of Mn from PAR and thereby returning PAR to a yellow-colored state.

Figures 11A, 11B:
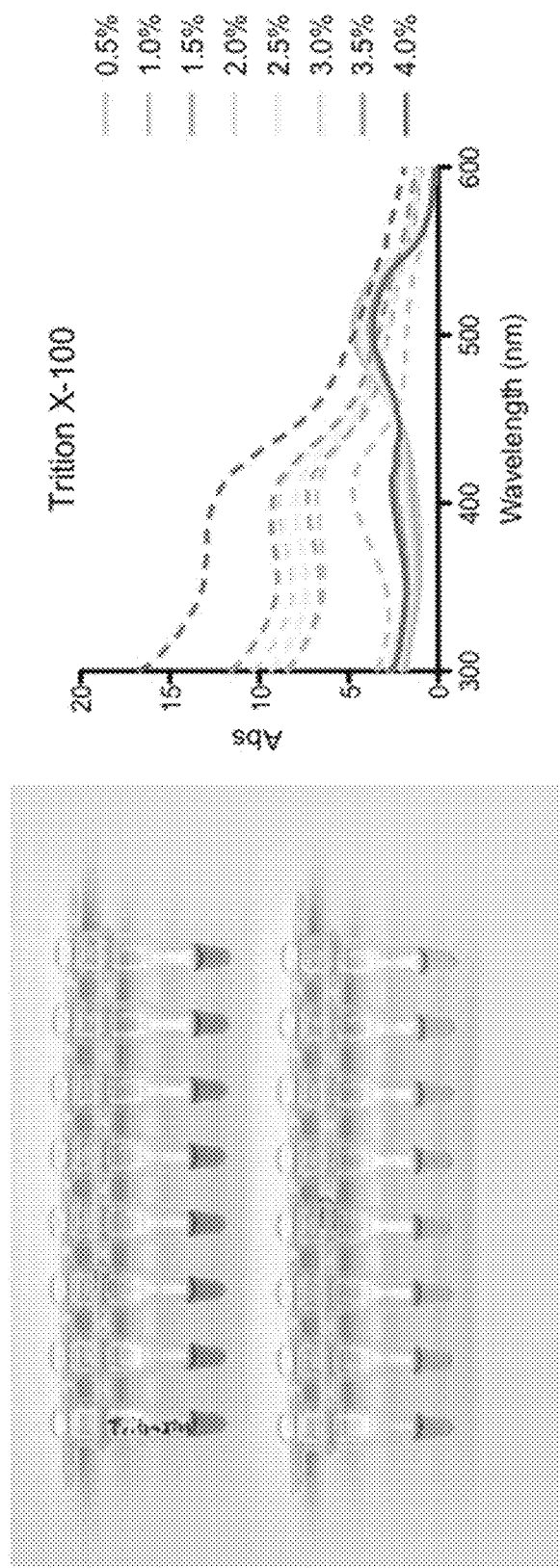

FIG. 11A and FIG. 11B shows that because pyrophosphate exhibits a higher affinity for manganese ions than PAR, this property can be used to detect amplification of nucleic acids using LAMP. Pyrophosphate generated during nucleic acid polymerization precipitates manganese from solution, thus disrupting the PAR:Mn complex and restoring the yellow color. This is demonstrated spectroscopically by spiking in pyrophosphate to restore the yellow color (bottom row) (FIG. 11A).

The color change can be further enhanced by the addition of Triton X-100 (FIG. 11B).

Figures 12A, 12B:
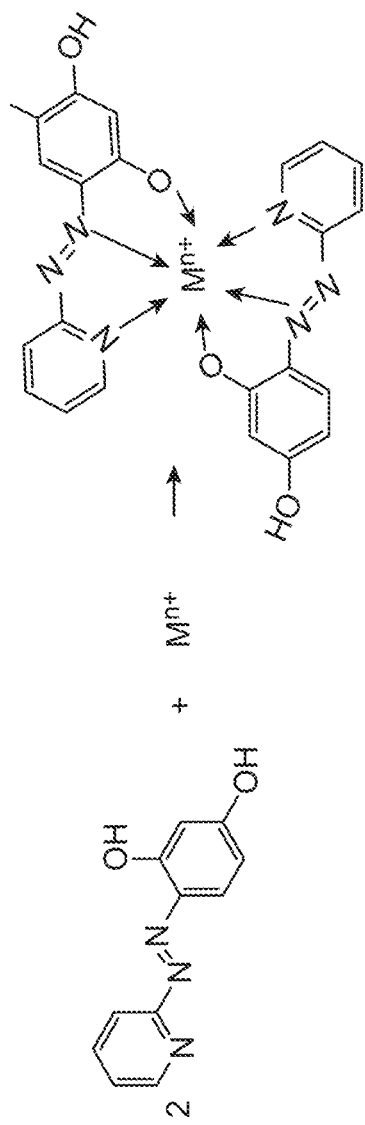

FIG. 12A shows that PAR has been demonstrated to be compatible with use in microfluidic paper-based analytical devices (μPADs) (Meredith, et al. Anal. Methods (2017) 9, 534-540). FIG. 12B shows the results of a paper-based spot test showing metal-PAR reactivity (orange and red color formation) for a number of transition, alkali, and alkaline earth metals.

Figure 13A:
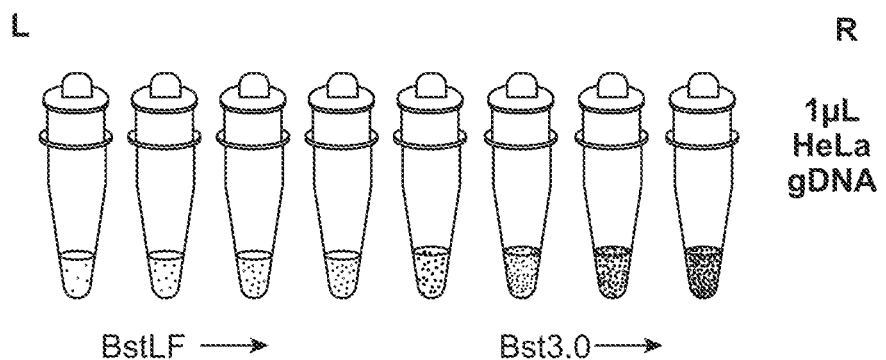
Figure 13B:
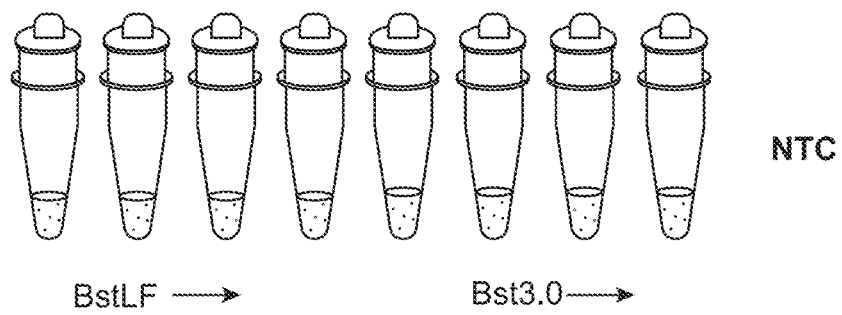
Figure 13C:
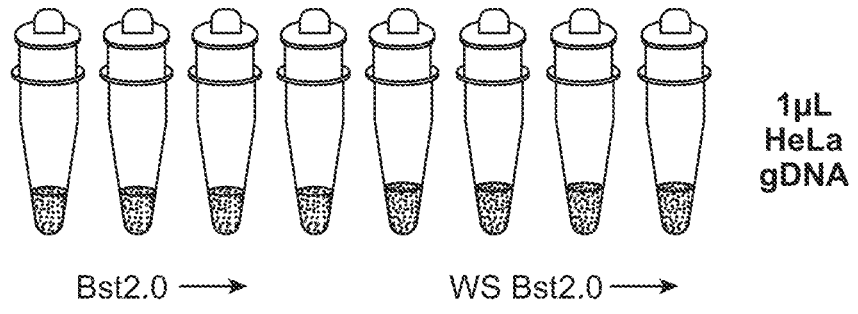
Figure 13D:
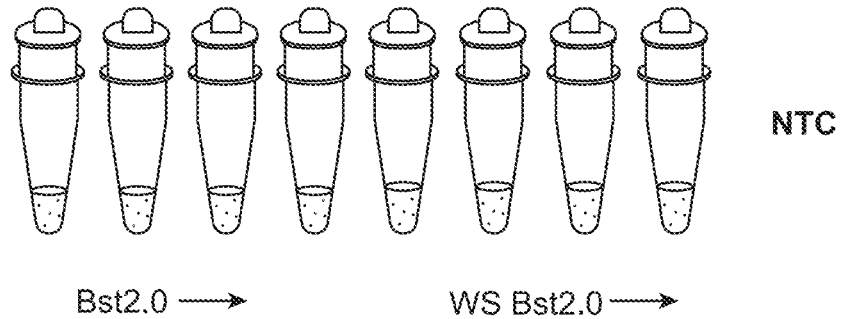

FIG. 13A-13D shows that PAR provides the means of a colorimetric endpoint for LAMP in a LAMP MM. A color change is observed when precipitation of manganese occurs that is caused by the release of pyrophosphates in a LAMP reaction. The enzymes added to perform LAMP in the presence of resorcinol and conditions of the reaction are as follows:

FIG. 13A: DNA polymerase Bst LF: (M0275) in 1× ThermoPol® added to 1 ul of Hela Cell gDNA; FIG. 13B: Bst 3.0: (M0374) in 1× Isothermal Amplification Buffer II absent gDNA; FIG. 13C: Bst 2.0: (M0537) in 1× Isothermal Amplification Buffer plus 1 ug gDNA; and FIG. 13D: WarmStart Bst 2.0: (M0538) in 1× Isothermal Amplification Buffer (New England Biolabs, Ipswich, Mass.);

PAR concentrations left to right: 150 µM, 100 µM, 75 µM, 50 µM;

$Mn^{2+}$ concentration: 0.5 mM $MnCl_2$;

LAMP Reaction Incubation: 65° C. for 1 hour;

LAMP Primer Set: BRCA2b FIP/BIP/F3/B3/LF/LB.

Target polynucleotide is the BRCA gene in Hela cell genomic DNA.

The non-template control retains the red color of PAR bound to manganese ions while the positive sample turned yellow corresponding to the reaction of manganese with pyrophosphate.

Figure 14:
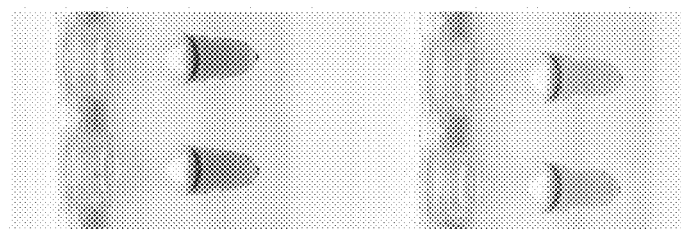

FIG. 14 shows the strong color reaction of a PAR-based LAMP in the presence of 2% Triton X-100 and 0.5 mM $MnCl_2$, Bst 2.0 polymerase, 1× Isothermal Amplification Buffer, 200 µM PAR and the BRCA2b primer set using 1 µl Hela cells. The non-template control retains the red color of PAR bound to manganese ions while the positive sample turned yellow corresponding to the reaction of manganese with pyrophosphate.

FIG. 15 shows examples of 4 different guanidine salts (also called guanidinium salts) for enhancing the LAMP reaction.

Figure 16:
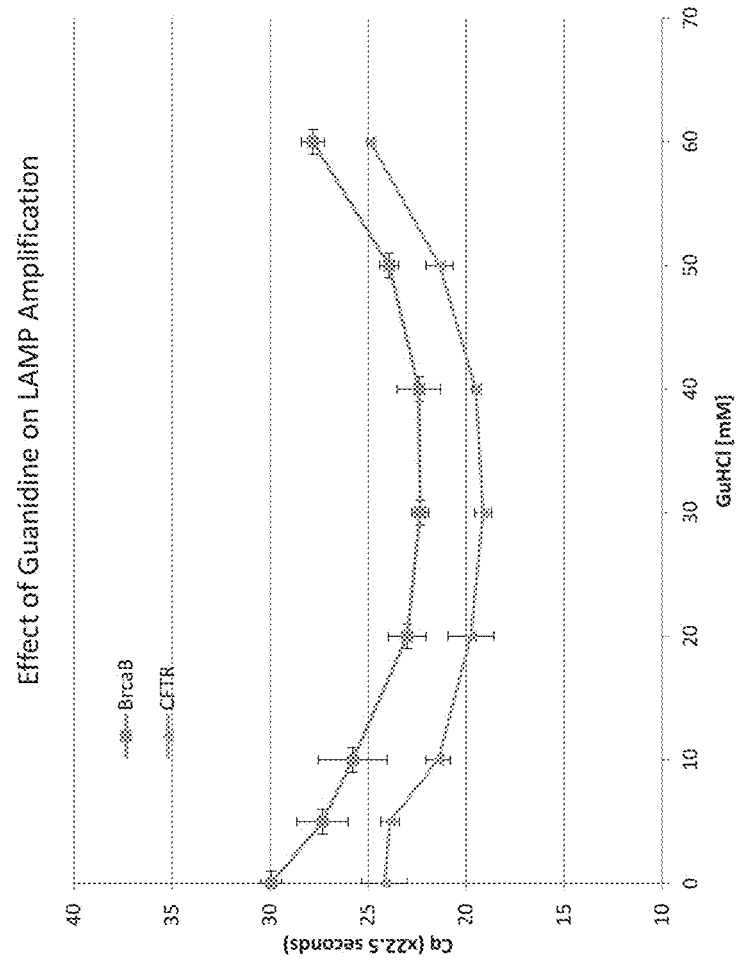

FIG. 16 shows that guanidine hydrochloride (GuCl) increases the reaction speed of a LAMP amplification reaction. Detection of two different genes-BRACA and CFTR were achieved using LAMP MM and increasing concentrations of GuCl.

Figure 17A:
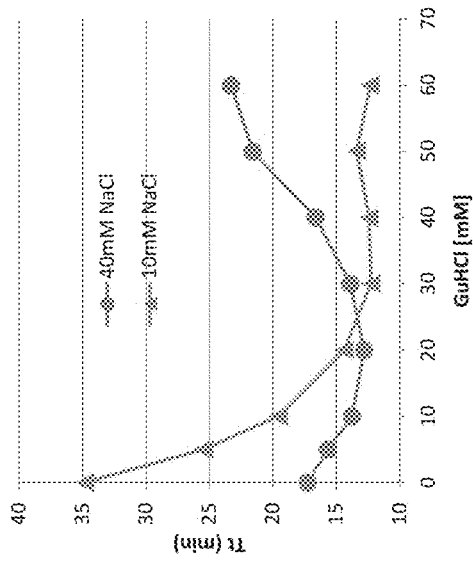
Figure 17B:
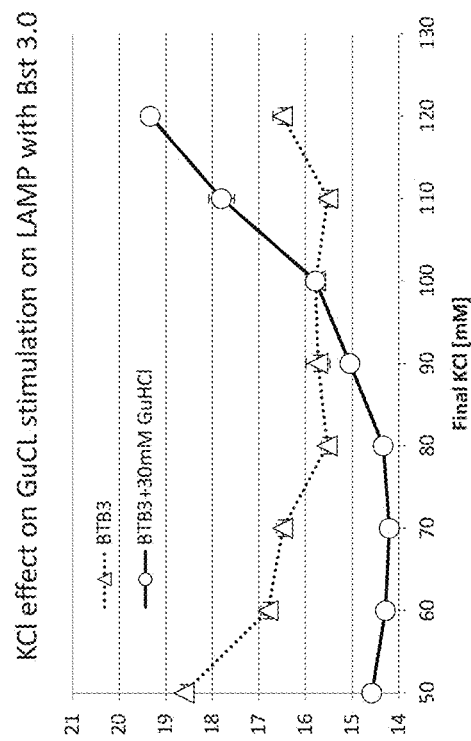
Figure 17C:
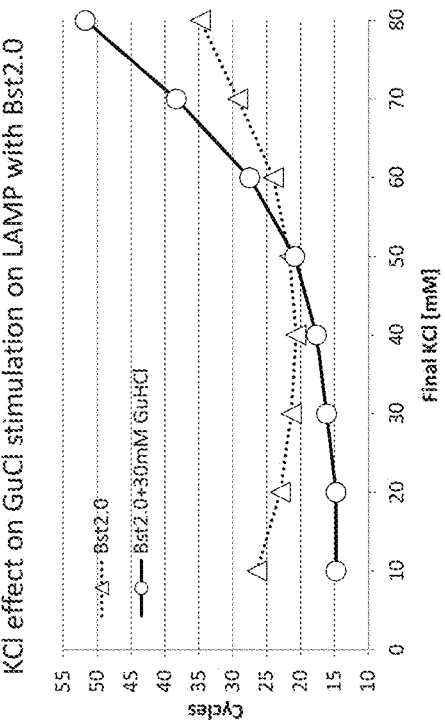

FIG. 17A-17C shows that GuHcl was effective in increasing the rate of isothermal amplification reactions and this effect was enhanced by selecting a range of concentrations for NaCl or KCl in the reaction buffer.

FIG. 17A shows the results of standard HDA reactions in IsoAmp II kit (H0110) and 0.1 ng plasmid, with 10 mM NaCl versus 40 mM NaCl, in which guanidinium hydrochloride was added at a final concentration of 0 mM-60 mM. The reactions were performed at 65° C. and EvaGreen® dye (Biotium, Inc., Hayward, Calif.) was included to monitor the progression of amplification. The effect of reducing NaCl concentrations was most noticeable at higher concentrations of GuCl (30 mM-60 mM guanidine hydrochloride) resulting in a reduction of Time to threshold (Tt) of 35 minutes (40 mM NaCl) to 12.3 minutes (10 mM NaCl).

FIG. 17B shows an increase in the rate of amplification using the LAMP assay described in Example 1 and Bst 2.0 DNA polymerase with a lambda1 primer set and 0.5 ng lambda DNA in ThermoPol buffer containing 10 mM KCl plus or minus 30 mM guanidine hydrochloride. The addition of guanidine stimulated the LAMP amplification rate significantly at the lower end of the KCl concentration (less than 40 mM KCl).

FIG. 17C shows an increase in the rate of amplification using the LAMP assay described in Example 1 and Bst 3.0 DNA polymerase (also referred to as BTB3) with a lambda1 primer set and 0.5 ng lambda DNA in an isothermal amplification buffer containing 50 mM KCL plus or minus 30 mM guanidine hydrochloride. The addition of guanidine stimulated the LAMP amplification rate significantly at the lower end of the KCl concentration (less than 100 mM KCl).

FIG. 18A-18D shows that guanidine hydrochloride not only increases LAMP reaction speed but also improves the limit of detection sensitivity.

FIG. 18A shows that colorimetric LAMP could detect 100 copies of synthetic SARS-CoV-2 RNA with 40 mM guanidine hydrochloride using primer set 1. The color change from pink to yellow indicates a positive detection. "None" denotes no guanidine hydrochloride. In the presence of 40 mM guanidine hydrochloride, 8/8 positive reactions were detected, whereas 5/8 positive reactions were detected without it.

FIG. 18B shows the results of real time colorimetric LAMP using primer set 1 in the presence and absence of 40 mM Guanidine HCl. The reaction also contains 1 µM dsDNA binding dye Syto-9 for monitoring the real time progression of the amplification.

FIG. 18C shows the results with 4 different primer sets. In all cases, sensitivity was increased in the presence of guanidine hydrochloride. The percentage of positive reactions for detecting 100 copies of SARS-CoV-2 RNA is shown in the table. The table shows that guanidine improves the detection sensitivity of all primer sets.

FIG. 18D shows a diagram of SARS-CoV-2 with the location of 2 template sequences (E and N) in the target nucleic acid.

Figure 19C:
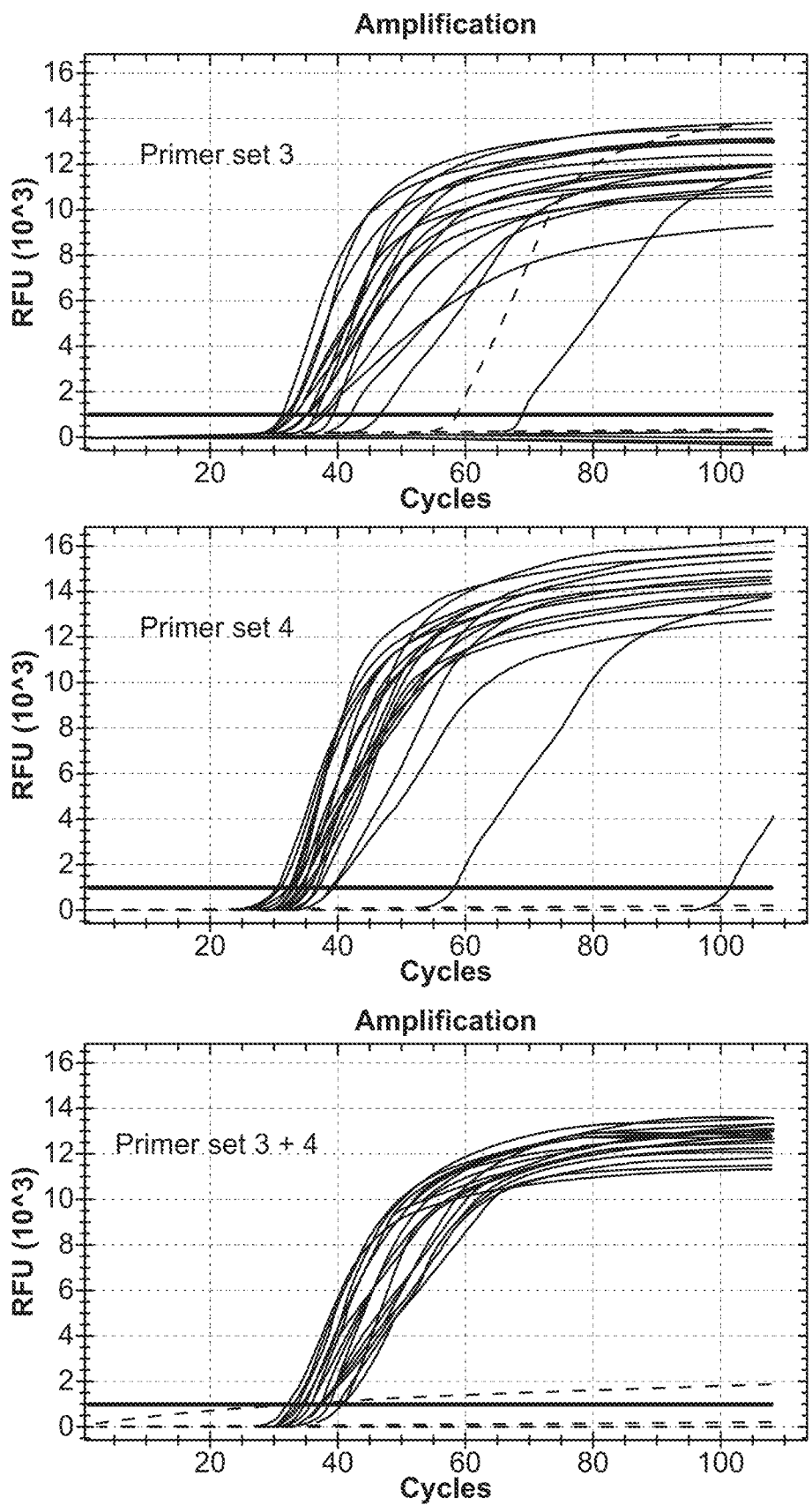

FIG. 19A-19C shows that guanidine allows efficient multiplexing of LAMP amplifications with multiple LAMP primer sets in the same reaction without adverse effects on the rate of amplification while significant improvements in sensitivity were observed.

FIG. 19A shows sensitivity of pH colorimetric LAMP by the percentage of positive samples detected using single sets of primers (identified as sets 3 and 4) and when sets 3 and 4 are combined in the presence or absence of 40 mM guanidine hydrochloride in a 40 minute incubation. The tables shows that 92.2% positives were detected for known test samples containing 50 copies synthetic SARS-CoV-2 RNA using a combined set of primers 3 and 4 with guanidine, compared with 28% for single sets of primers in the absence of guanidine.

FIG. 19B shows the sensitivity of pH colorimetric LAMP for detecting 12.5 copies of synthetic SARS-CoV-2 RNA in the presence of guanidinium hydrochloride and a plurality of primer sets. The results shows an increase of detection rate with any combinations of 2 primer sets (3+4, 3+5, 4+5). The reactions including all 3 primer sets (3+4+5) also showed further increase of detection rate over any 2 primer sets, providing detection of 57% of all positives in a 40 minute incubation. The reactions without template remained negative and showed no sign of amplification signal, indicating robust specific amplification.

FIG. 19C shows that real time amplification with guanidine hydrochloride resulted in an expected rate of amplification with a combination of primer sets 3 and 4 and 50 copies of template CV-19 RNA where the combination of primer sets did not adversely affect the rate of amplification.

Figure 20:
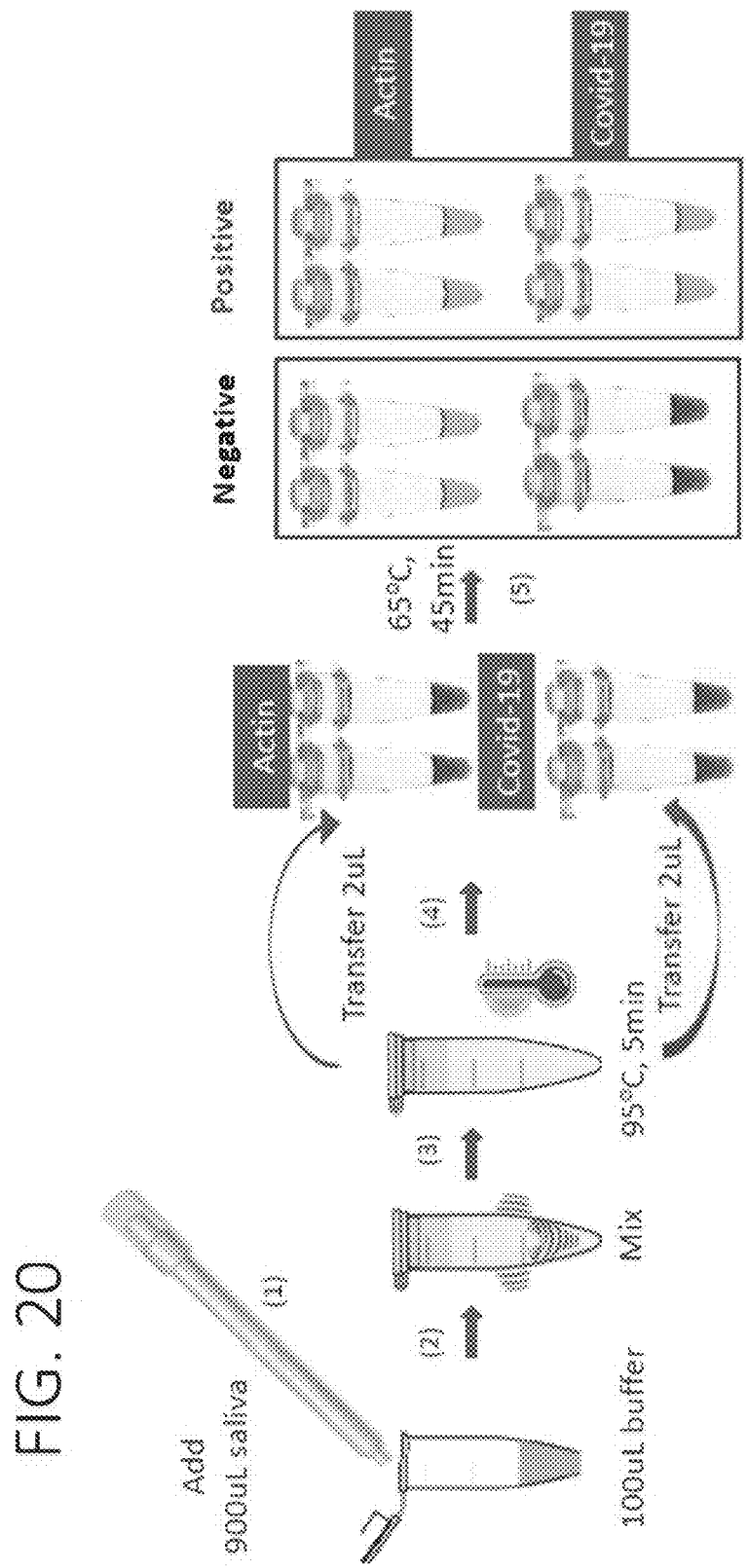

FIG. 20 shows an example of the use of lysis buffer for SARS-CoV-2 detection in saliva where 900 µl of saliva from a patient is added to 100 µl of 10× lysis buffer (1), mixed (2) and then heated to 95° C. for 5 minutes (3). 2 µl of the sample is then added to 18 µl of pH colorimetric LAMP Master mix either containing primers to SARS-CoV-2 (target) or primers for actin (control) (4). After an incubation for 45 minutes at 65° C., the test tubes were examined for a color change from pink to yellow indicative of the presence of SARS-CoV-2 (5).

FIG. 21A-21B shows that various ratios of the reagents in the lysis buffer spiked with synthetic SARS-CoV-2 RNA were tested to determine which combination if any interfered with pH colorimetric LAMP and if not which conditions provided the greatest sensitivity for detecting 40 copies of the virus genome. The results did not suggest any interference and the saliva lysis mixture containing 4 mM TCEP (reducing agent) and 75 mM LiCl at pH 8.0 with 400 mM guanidine hydrochloride (GnHCL) gave the best results.

FIG. 21A shows 6 different conditions for the saliva lysis buffer.

FIG. 21B shows the color changes indicative of a positive result under the 6 different test conditions where 4 mM TCEP (reducing agent) and 75 mM LiCl at pH 8.0 with 400 mM guanidine hydrochloride (GnHCL) resulted in 100% detection of 40 copies of viral genome.

Figure 22:
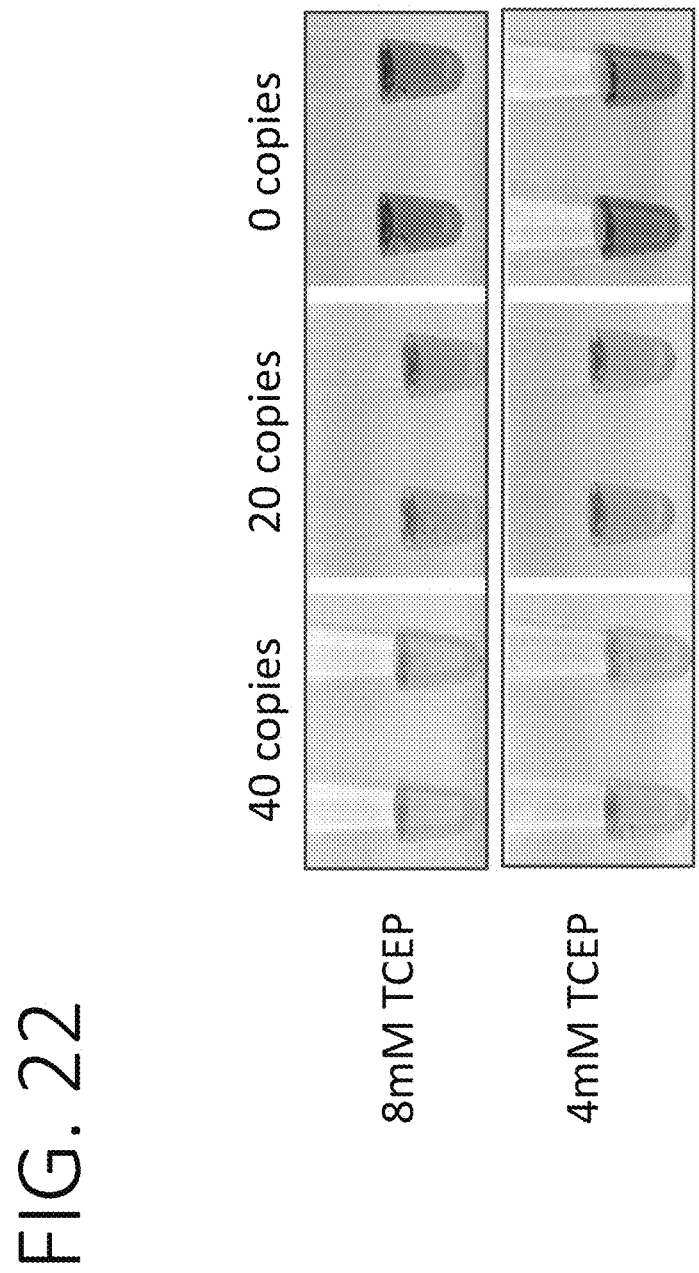

FIG. 22 shows that 8 mM TCEP in addition to 75 mM LiCl and 400 mM GnHCL performed similarly to 4 mM TCEP in the saliva lysis buffer when 5 μl 10× lysis buffer was added to 45 μl saliva sample containing inactive virus particles (SeraCare) and heated for 5 minutes at 95° C. 2 μl of this sample was then added to 18 μl LAMP master mix and incubated for 35 minutes at 65° C.

Figures 23A, 23B, 23C, 23D:
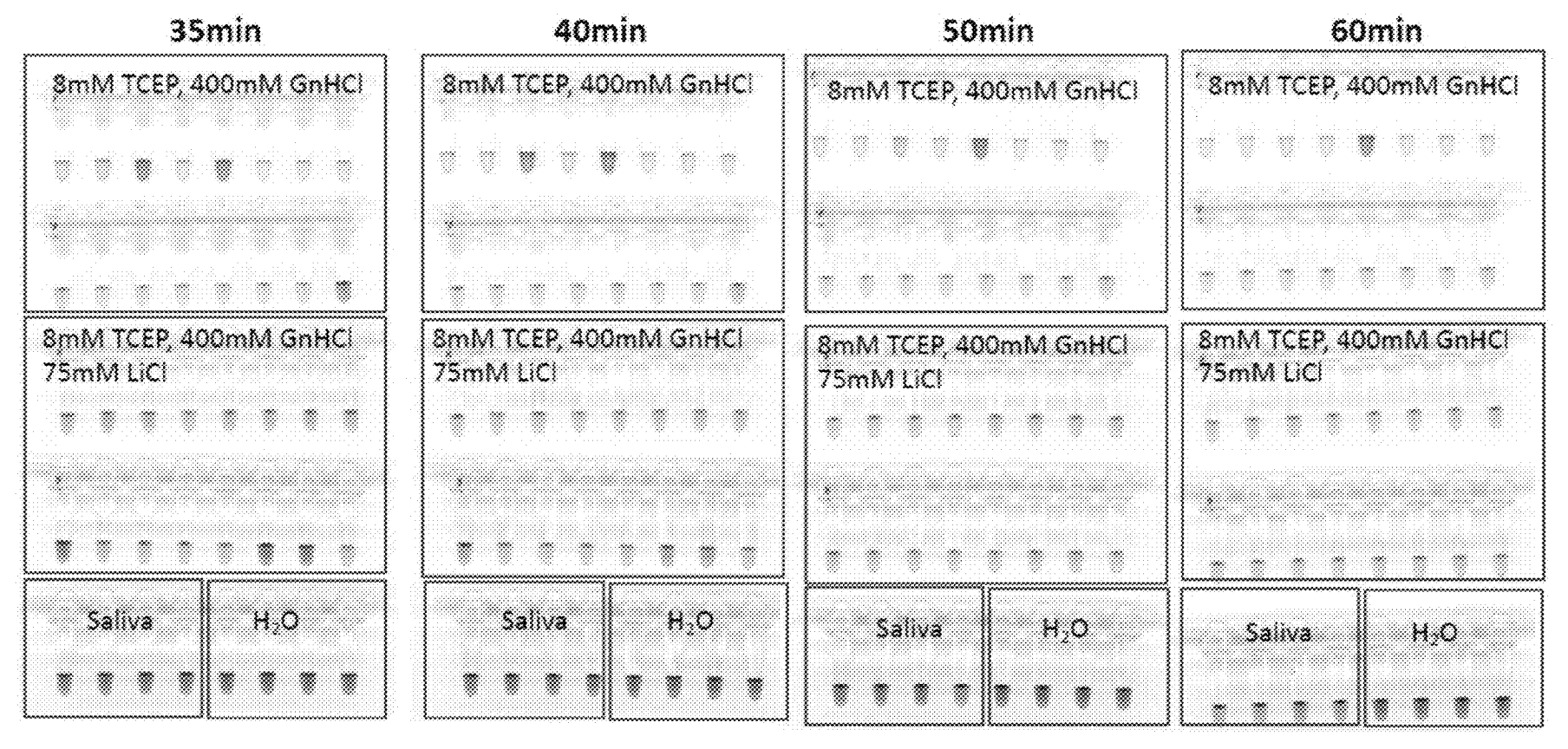

FIG. 23A-23D shows the effect of varying the LAMP assay time after the 5 minute saliva lysis reactions on saliva spiked with 10,000 cps/ml synthetic SARS-CoV-2 RNA (20 copies/2 μl) using a saliva lysis buffer containing 8 mM TCEP, 0 mM LiCl/75 mM LiCl and 400 mM GnCL. Increased sensitivity was observed over time with the presence of LiCl consistently contributing to increased sensitivity as the time of incubation increased beyond 35 minutes. Saliva not containing RNA and $H_2O$ were used as negative controls.

Figure 24:
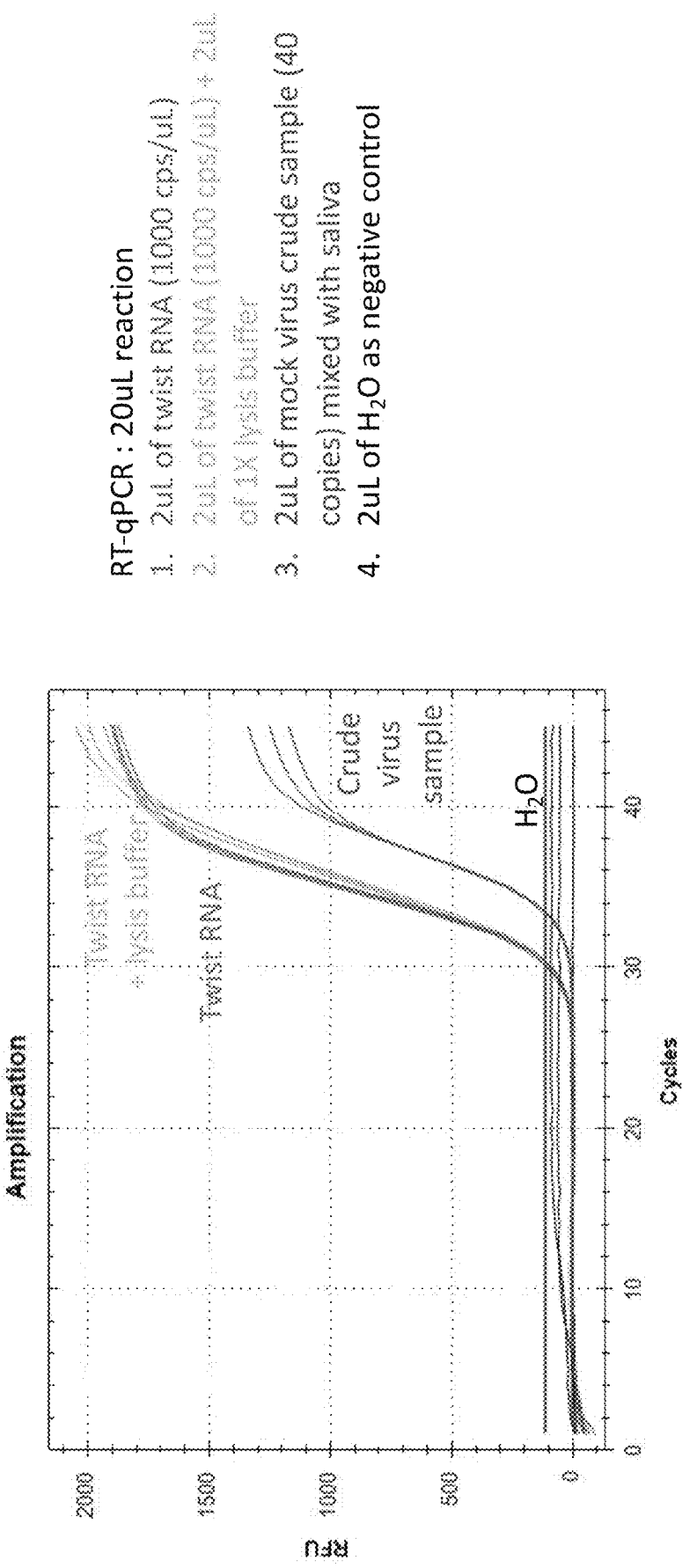

FIG. 24 shows that when a saliva sample spiked with a known copy number of synthetic SARS-CoV-2 input (Twist) is treated with saliva lysis buffer (8 mM TCEP, 75 mM LiCl and 400 mM GnCl), followed by RT-qPCR, the lysis buffer was shown to have minimal or no adverse effect on the RT-qPCR reaction.

Figure 25:
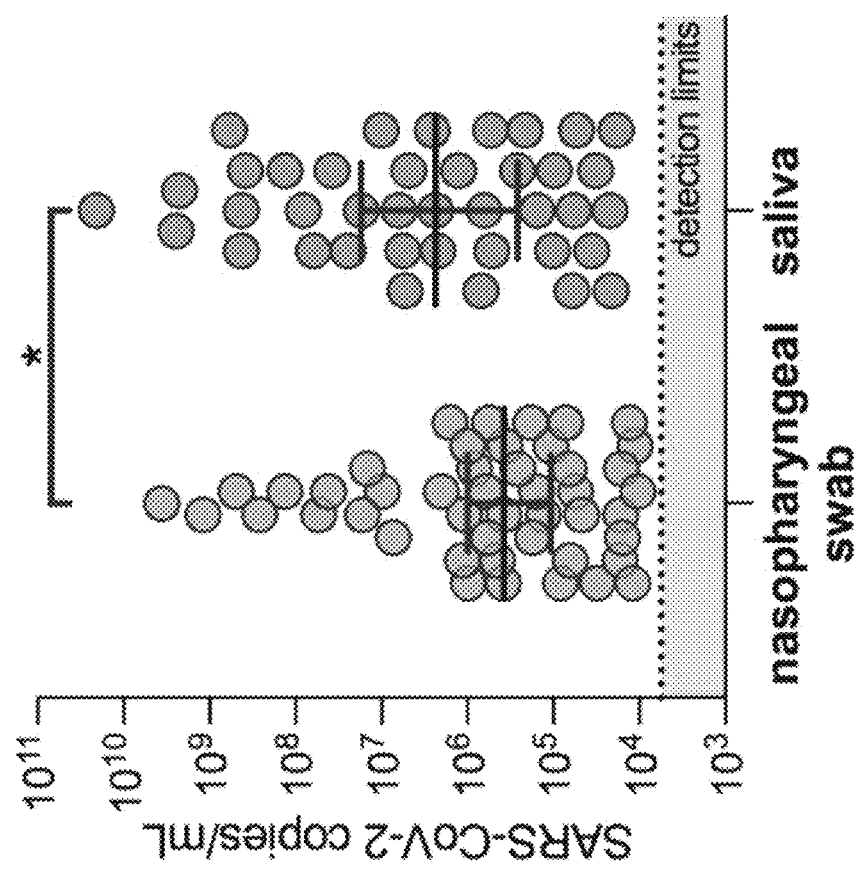

FIG. 25 shows that the lysis buffer described in FIGS. 23A-23D and FIG. 24 can provide similar sensitivity of virus detection as that reported by others after purification of the viral RNA from nasopharyngeal swabs and saliva (Wyllie et al. MedRxiv Apr. 22, 2020: https://doi.org/10.1101/2020.04.16.20067835).

All positive nasopharyngeal swabs (n=46) and saliva samples (n=39) were compared by a Mann-Whitney test (p<0.05). Bars represent the median and 95% Cl. Our assay detection limits for SARS-CoV-2 using the US CDC "N1" assay is at cycle threshold 38, which corresponds to 5,610 virus copies/mL of sample (shown as dotted line and grey area).

Figure 26:
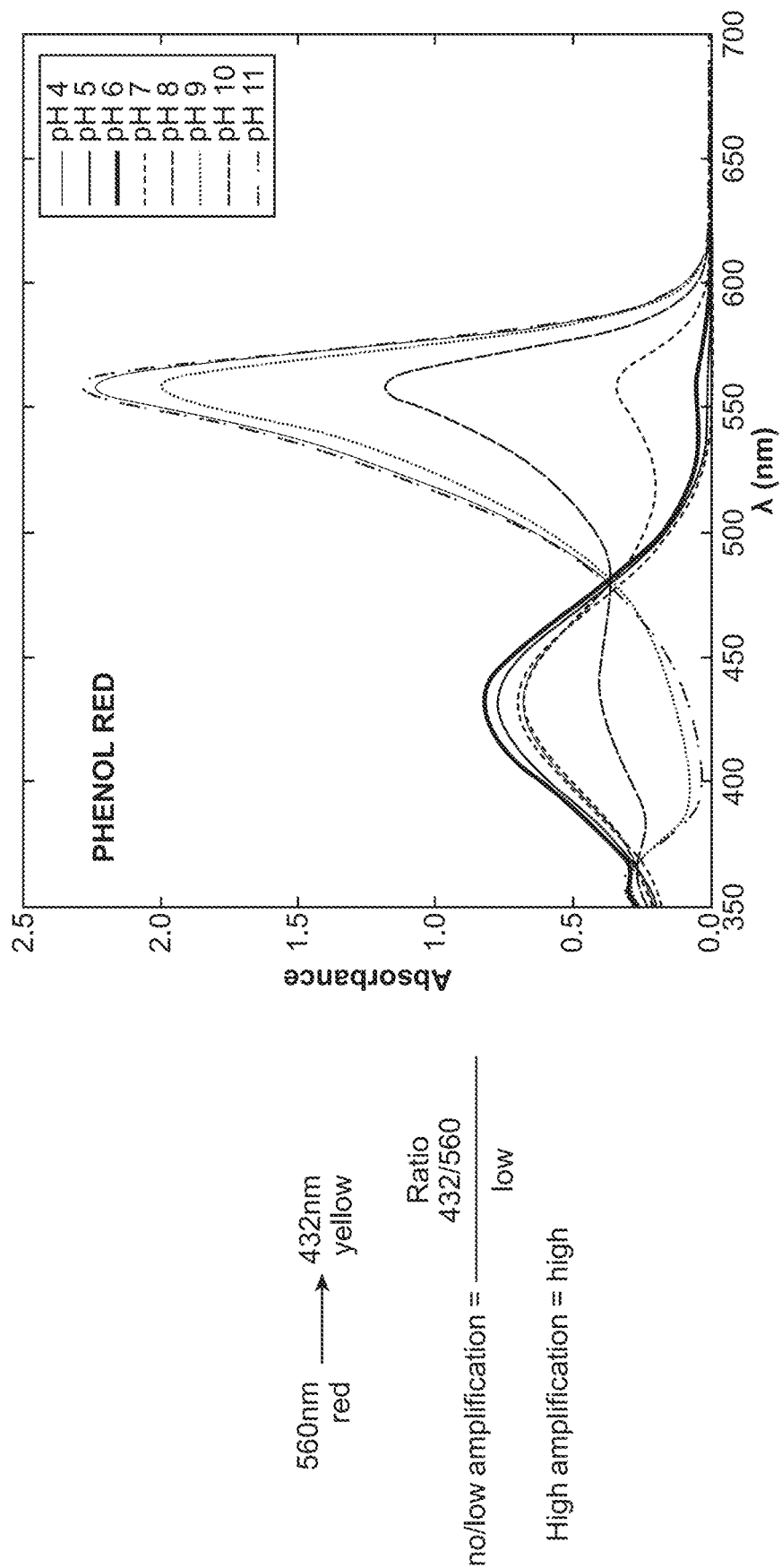

FIG. 26 shows that endpoint absorbance ratio (432 nm/560 nm wavelengths) at a range of pH from pH 4-pH 11 can be measured by a colorimeter. The highest positive signal at 560 nm is between pH 9-pH 11 and the highest negative signals at 432 nm occurs at pH 4-pH 6. The 432/560 nm signal ratio can be used to determine positive and negative samples in pH-dependent colorimetric LAMP.

Figure 27:
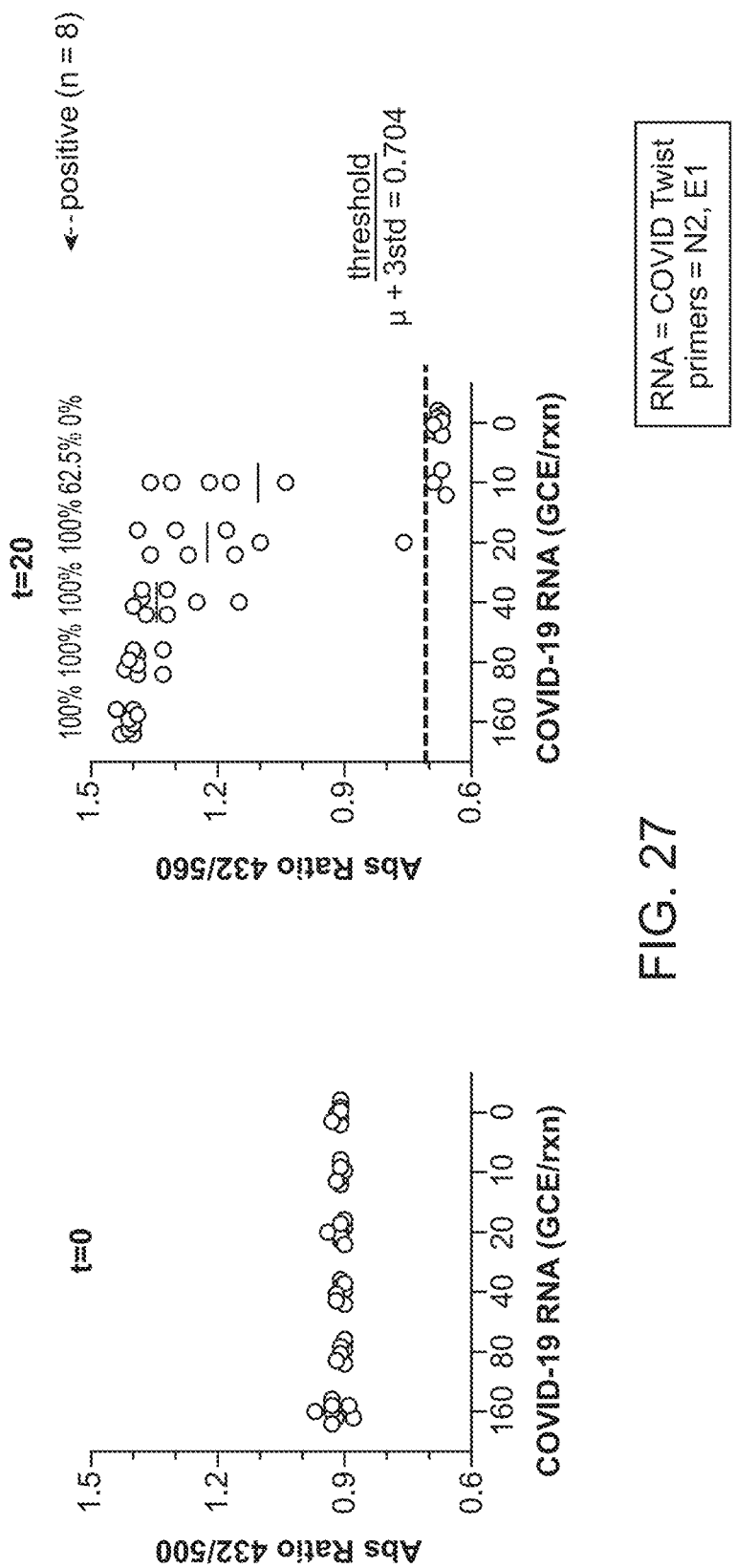

FIG. 27 shows the absorbance results after pH dependent colorimetric LAMP was performed on samples containing synthetic SARS-CoV-2 RNA using dual primer sets of N2 and E1 after no incubation at 65° C. and after 20 minutes incubation at 65° C. The samples were allowed to cool to room temperature before the color was measured in the SpectraMax® (Molecular Devices, San Jose, Calif.). Data is provided from a SpectraMax readout that provided 100% detection of 20 copies of SARS-CoV-2 RNA and 62% detection of 10 copies of SARS-CoV-2 RNA using a sample spiked with 20 copies of SARS-CoV-2 RNA.

FIG. 28A-28F shows an example of an automated workflow that permits 100,000 reactions in about 20 hours. This is calculated from a batch size of 5,760 reactions (15×384 well plates or 60×96 tube racks) with a process time of 40 minutes/sample and 100 minutes/batch.

FIG. 28A shows how an individual saliva sample from a collection tube might be placed in a tube containing saliva lysis buffer in a 96 tube rack.

FIG. 28B shows a robot that can transfer samples (for example 3 μl) from individually 2D barcoded sample collection tubes or batches of 4×96 tube racks to 384 well plates with a linear barcode to associate each sample to a discrete well location in 4 minutes.

FIG. 28C shows a robot liquid handler that can add for example 17 μl of reaction mix (e.g. 2 μL 10× primer mix, 10 μL WarmStart Colorimetric Lamp 2× Master Mix (M1800), 5 μL of DNAse, RNAse free H2O) into the 384 well plate within about 1 minute.

FIG. 28D shows a stack of plates each with plastic seal ready for the LAMP reaction.

FIG. 28E shows two devices for performing LAMP that requires incubation at 65° C. for a period of time such as 30 minutes. This may be achieved by means of a horizontal conveyor belt that sends each plate through a heated chamber so that the residence time in the chamber is the desired incubation time. Alternatively, this may be achieved by stacking plates in a tower incubator where heating occurs for the programmed time.

FIG. 28F shows a robotic plate handler that takes the 384 plates from the incubator and places them in sequence in a SpectraMax or other spectrophotometer (absorbance reader) that records the 2D barcode on the plate and the color of each well at specific wavelengths.

Figure 29:
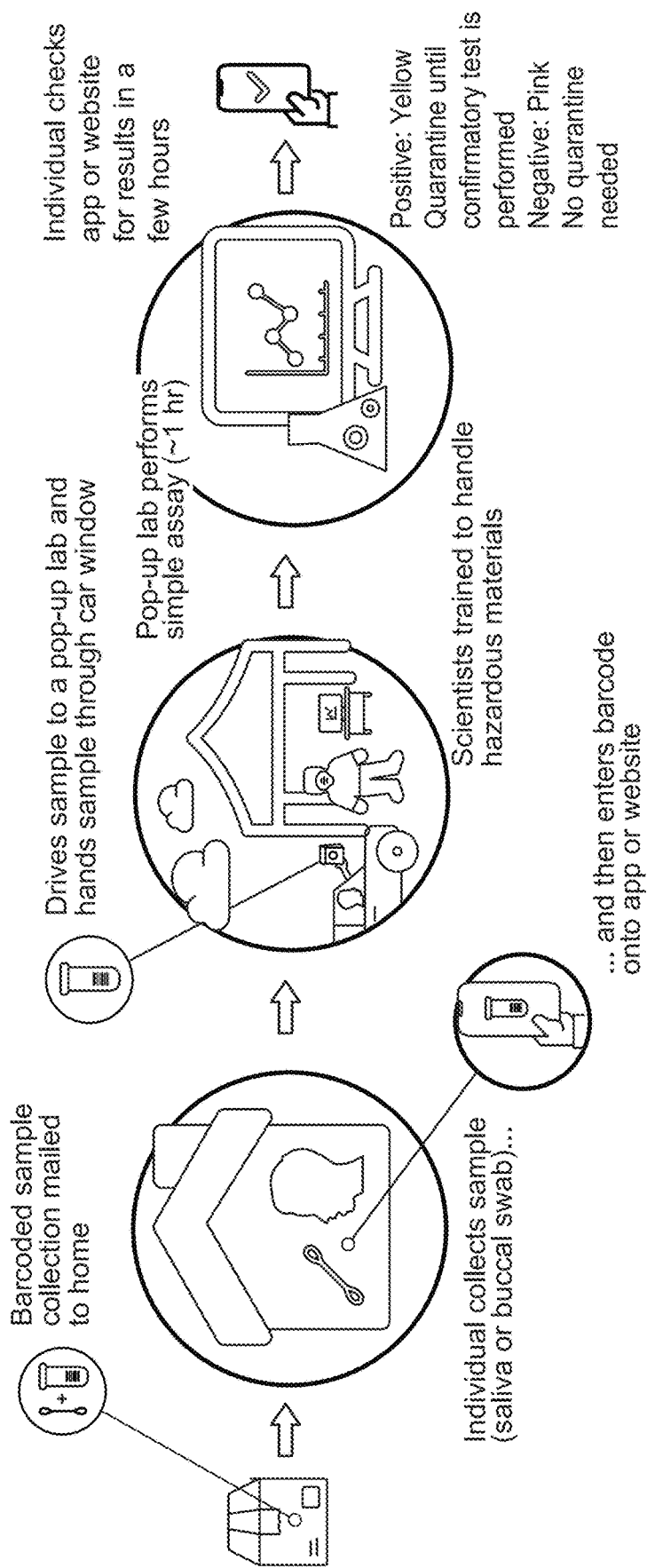

FIG. 29 shows a schematic for handling large numbers of patients at a pop-up laboratory using embodiments of the rapid LAMP method for detecting SARS-CoV-2.

Figure 30:
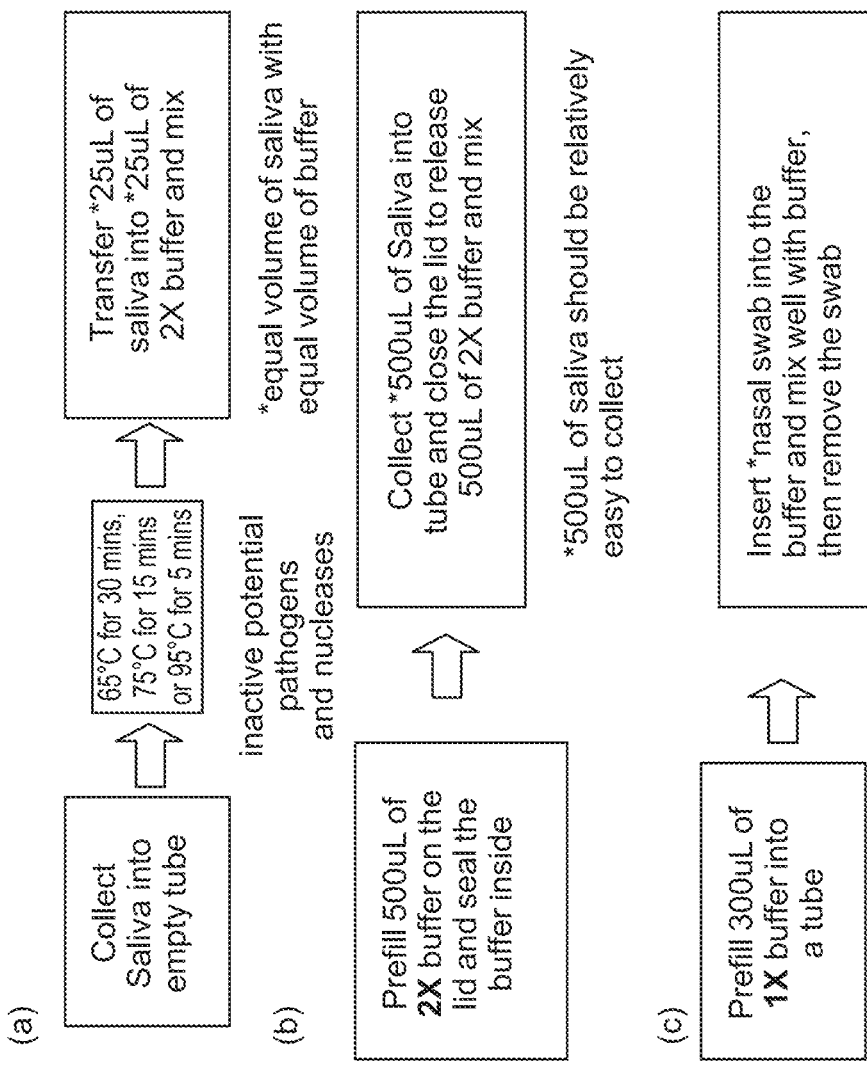
Figure 30:
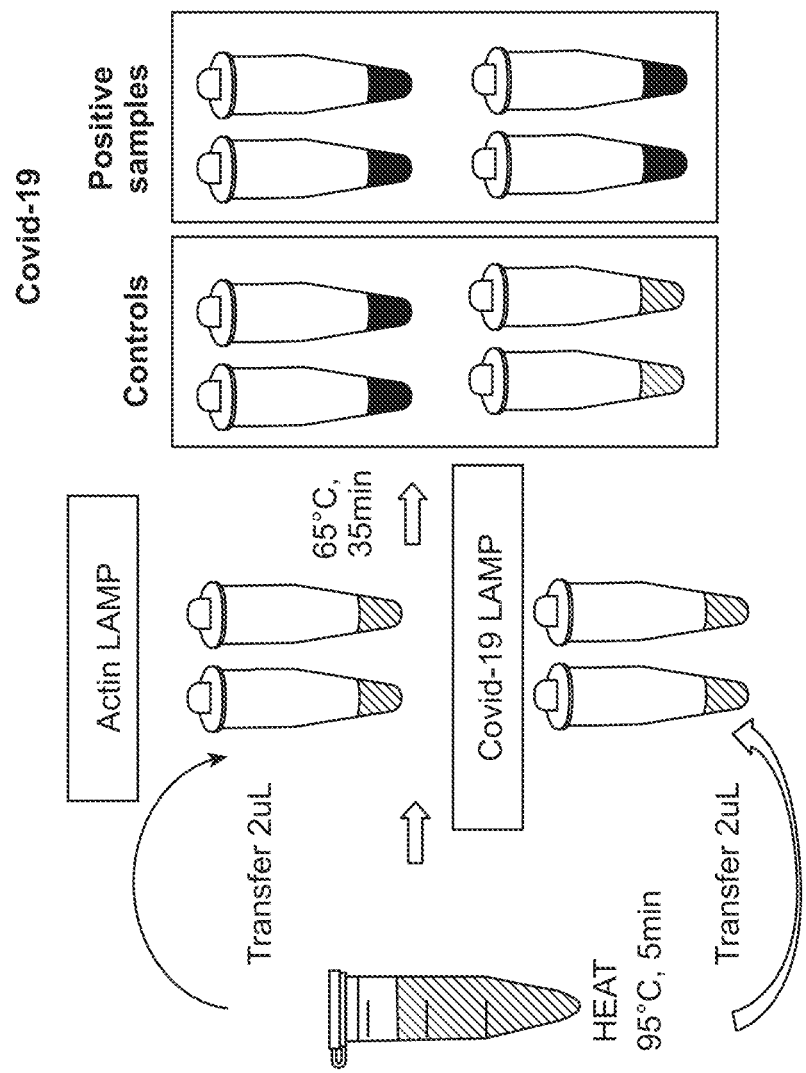

FIG. 30 (a)-(c) shows a workflow for a LAMP reaction using each of 3 different types of sample collection. These are:

FIG. 30 (a) collect patient saliva sample into an empty tube, inactivation of any infectious virus in the absence of a buffer using a temperature of 65° C. for 30 minutes, 75° C. for 15 minutes or 95° C. for 5 minutes and then transfer for example, 1 volume of the sample into 1 volume of 2× buffer or an equivalent ratio using 4× buffer or 10× buffer resulting in a 1× mixture;

FIG. 30 (b) incorporating a volume of a concentrated viral inactivation buffer (for example 2×, 5× or 10×) into a compartment of a saliva collection tube prior to collection of saliva from the patient in the same tube. After collecting the saliva and closing the lid of the tube, the sample is mixed with viral inactivation buffer released from the compartment;

FIG. 30 (c) a volume of viral inactivation buffer is present in a sample tube for receiving a nasal or oral swab from a patient where the contents of the swab are directly released into the buffer. In all cases in this example, the viral inactivation buffer contains a poloxamer surfactant such as PF68 suitable for reducing RNase activity in addition to a reducing agent (e.g., TCEP) and a metal chelator (e.g., EDTA). Also, in all three types of sample collection (a)-(c), a heating step at 95° C. for 5 minutes is performed that is generally expected to break up the cells and any viruses releasing RNA while inactivating nucleases. An aliquot of the patient sample is then transferred into standard LAMP master mix containing a DNA polymerase, and reversible inhibitor, a reverse transcriptase with reversible inhibitor, primer sets and nucleoside triphosphates for fluorescent LAMP (e.g., fluorescent LAMP using an intercalating dye or DARQ LAMP for multiplexing) or colorimetric LAMP. The sensitivity of the colorimetric LAMP is improved by the additional presence of guanidium salt. Alternatively, though not shown, an aliquot can be used for RT-qPCR or for any other diagnostic assay including sequencing.

FIG. 31A-31E show minimal interference between primer sets in a multiplex reaction. The duplex of the 5'-modified version of the FIP primer (Q-FIP) annealed to Fd complementary sequence on the SARS-CoV-2 target genome (50 copies) and the actin control in the presence of 1, 2, 3 and 4 primer sets. 24 samples were tested for SARS-CoV-2 and 8 samples were tested for the actin control. Rox (Integrated DNA technologies (IDT) Wisconsin) was used for the fluorescent label for ACTB while JOE (IDT) was used for E1.

FIG. 31A shows DARQ LAMP with E1 and ACTB primer sets in the presence of SARS-CoV-2 target RNA and ACTB target RNA. SARS-CoV-2 signal.

FIG. 31B shows DARQ LAMP with E1, ACTB and EIA primer sets (all with Q-FIP:Fd) in the presence of SARS-CoV-2 target RNA and ACTB RNA.

FIG. 31C shows DARQ LAMP with E1, ACTB, EIA and EIB primer sets (all with Q-FIP:Fd) in the presence of SARS-CoV-2 target RNA and ACTB RNA.

FIG. 31D shows DARQ LAMP with E1, ACTB, EIA and EIB primer sets (all with Q-FIP:Fd) in the presence of ACTB RNA.

FIG. 31E provides a summary table of results provided by 31A-31D.

Figures 32A, 32B, 32C:
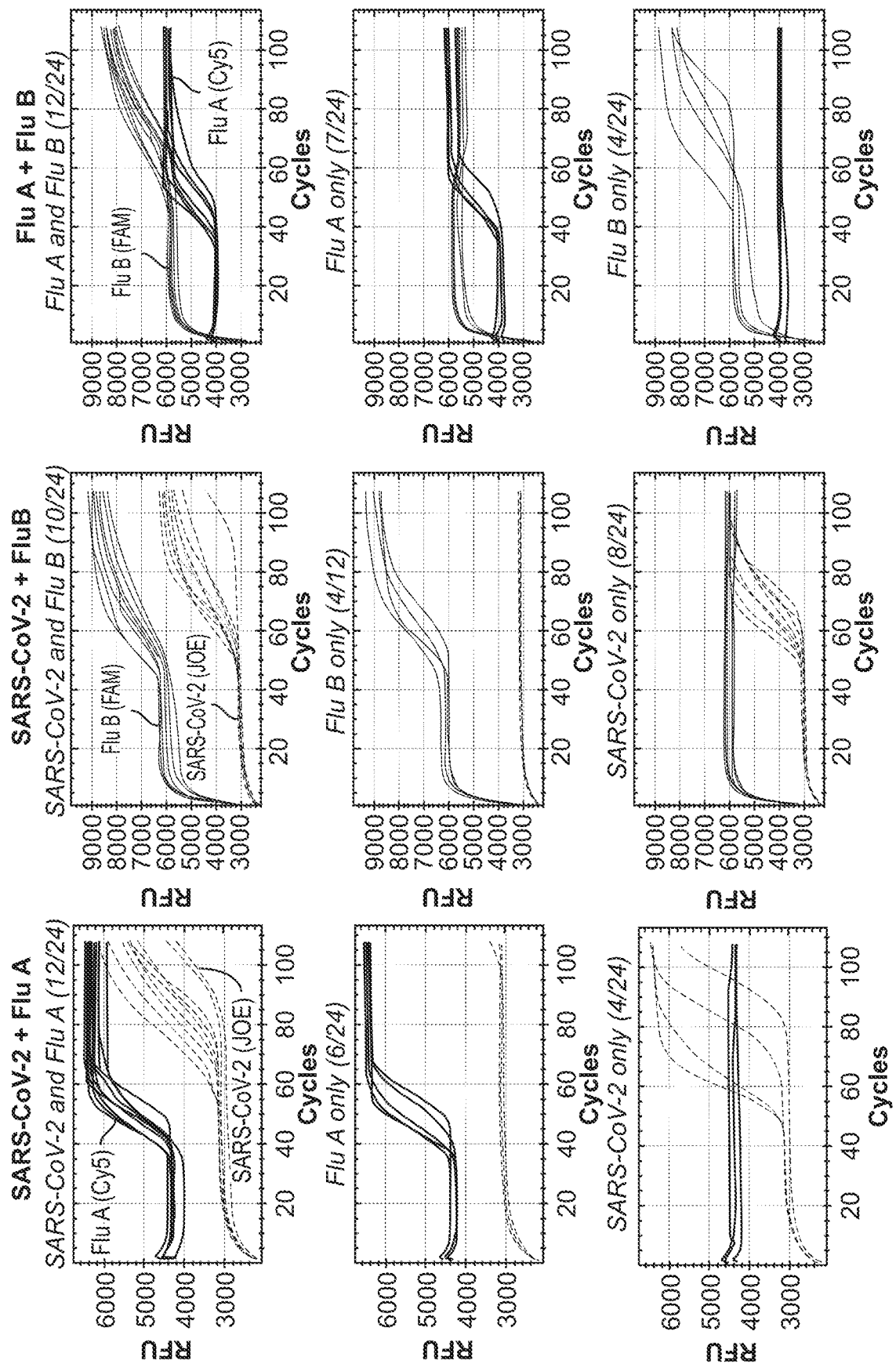

FIG. 32A-32C shows that SARS-CoV-2 and Influenza strain A or B can be detected in a single sample in a multiplex reaction.

FIG. 32A DARQ LAMP detection of SARS-CoV-2 (labeled with JOE) and Flu A (labeled with Cy5) provides similar results to the detection of Flu A and SARS-CoV-2 alone.

FIG. 32B DARQ LAMP detection of SARS-CoV-2 (labeled with JOE) and Flu B (labeled with FAM) provides similar results to the detection of Flu B and SARS-CoV-2 alone.

FIG. 32C DARQ LAMP detection of Flu A (Cy5) and Flu B (FAM) provides similar results to the detection of Flu A and Flu B alone.

Figure 33:
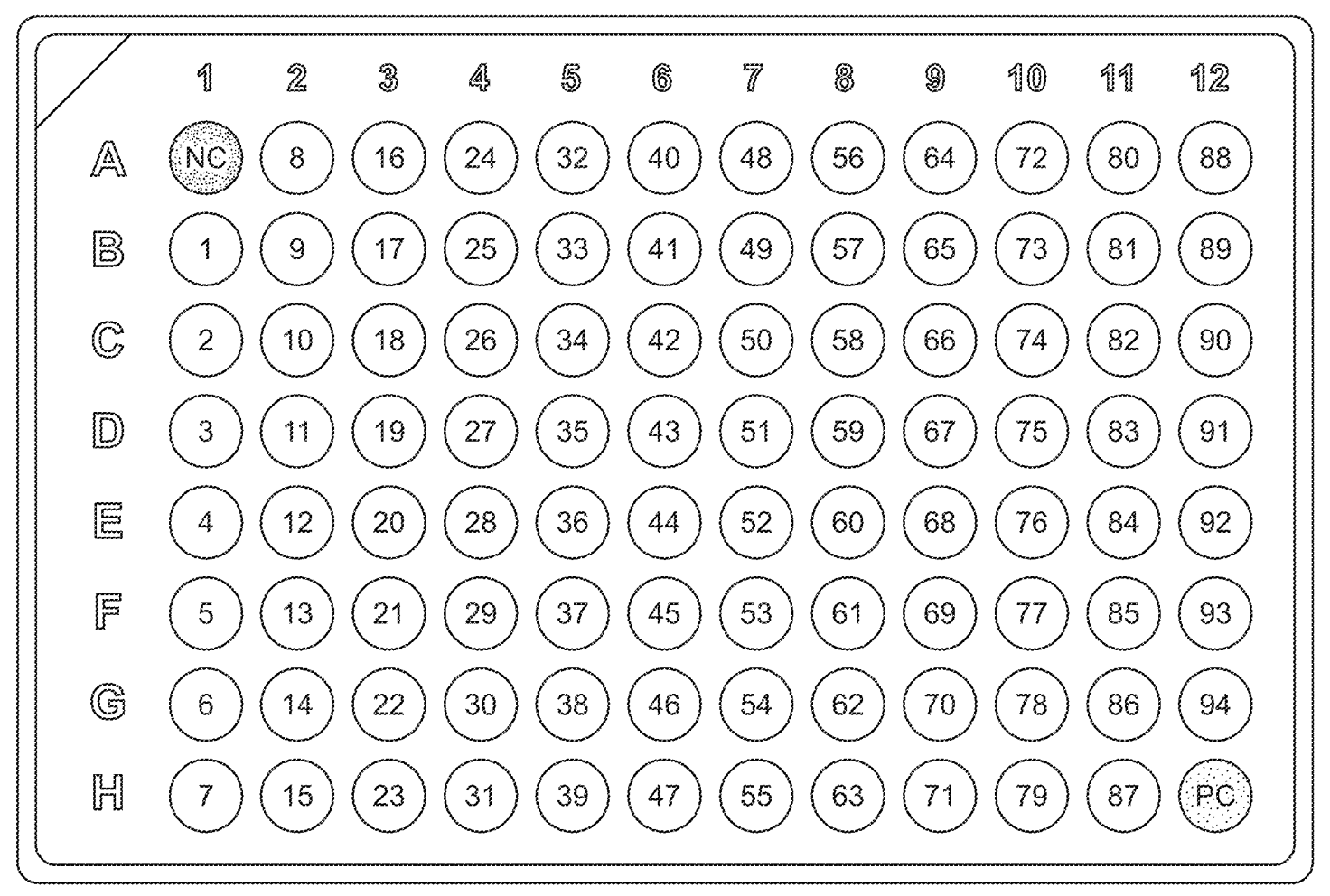

FIG. 33 shows a supported lipid bilayer (SLB) 96 well plate with numbered wells containing serial dilutions of virus spiked into negative saliva samples.

FIG. 34. shows the results of a colorimetric LAMP assay using inactivated SARS-Cov-2 virus spiked negative saliva. The dilution series shows samples where the limit of detection (LOD) is 40 cps/uL.

Figure 35:
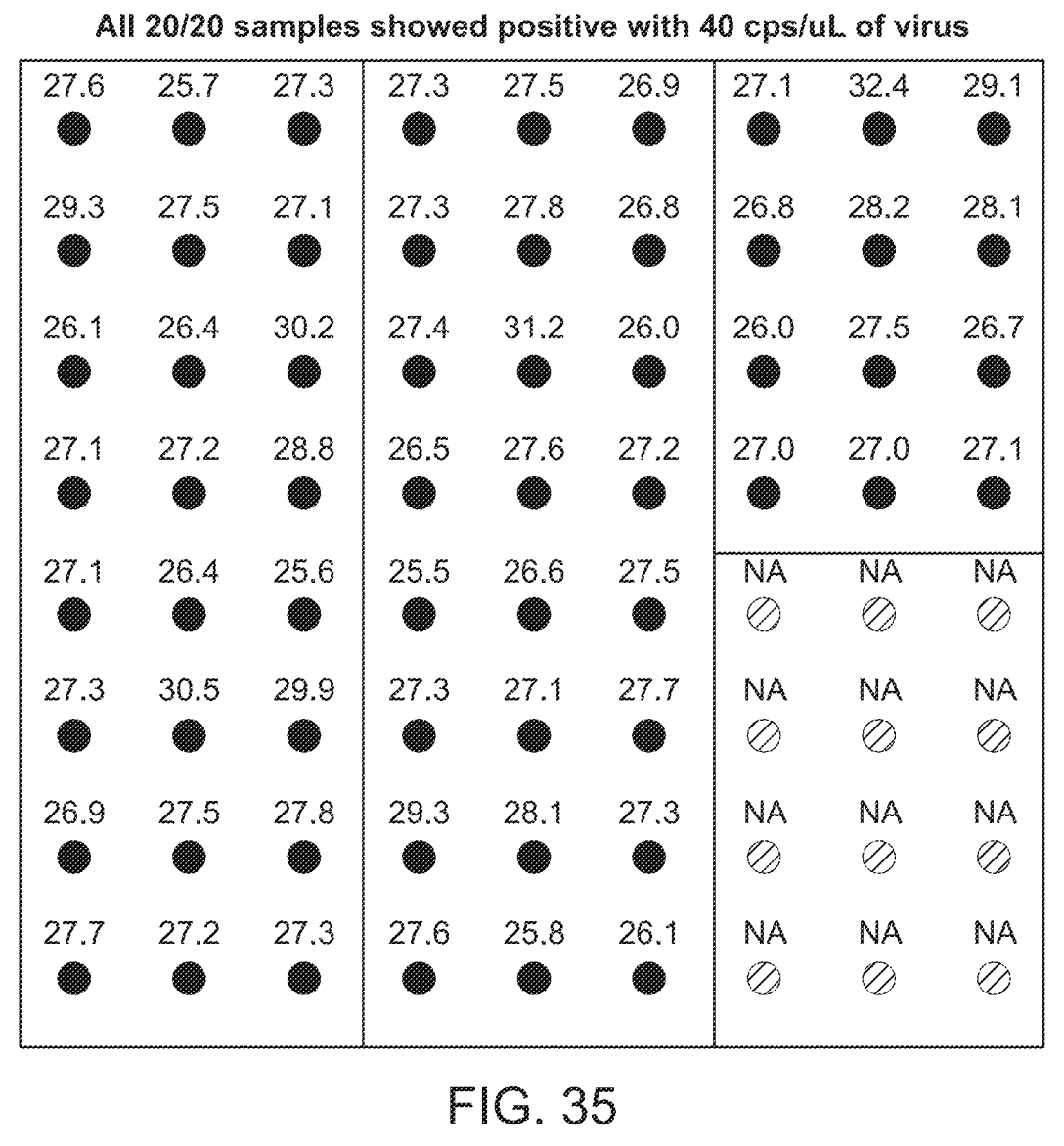

FIG. 35 shows that all samples were positive that contained 40 copies of inactivated virus into saliva with LAMP reactions for each sample.

FIG. 36A-36F shows that mutation position effects on RT-LAMP amplification does not affect sensitivity but can make small changes in time to endpoint. Plots of the effects of change relative to the WT primer set for three genes from SARS Covid 2-As1e (circle), E1 (square), N2 (triangle) are provided for each primer.

FIG. 36A—F3 primer; FIG. 36B—B3 primer; FIG. 36C—FIP primer; FIG. 36D—BIP primer; FIG. 36E-Loop F primer; and FIG. 36F—Loop B primer.

Figure 37A:
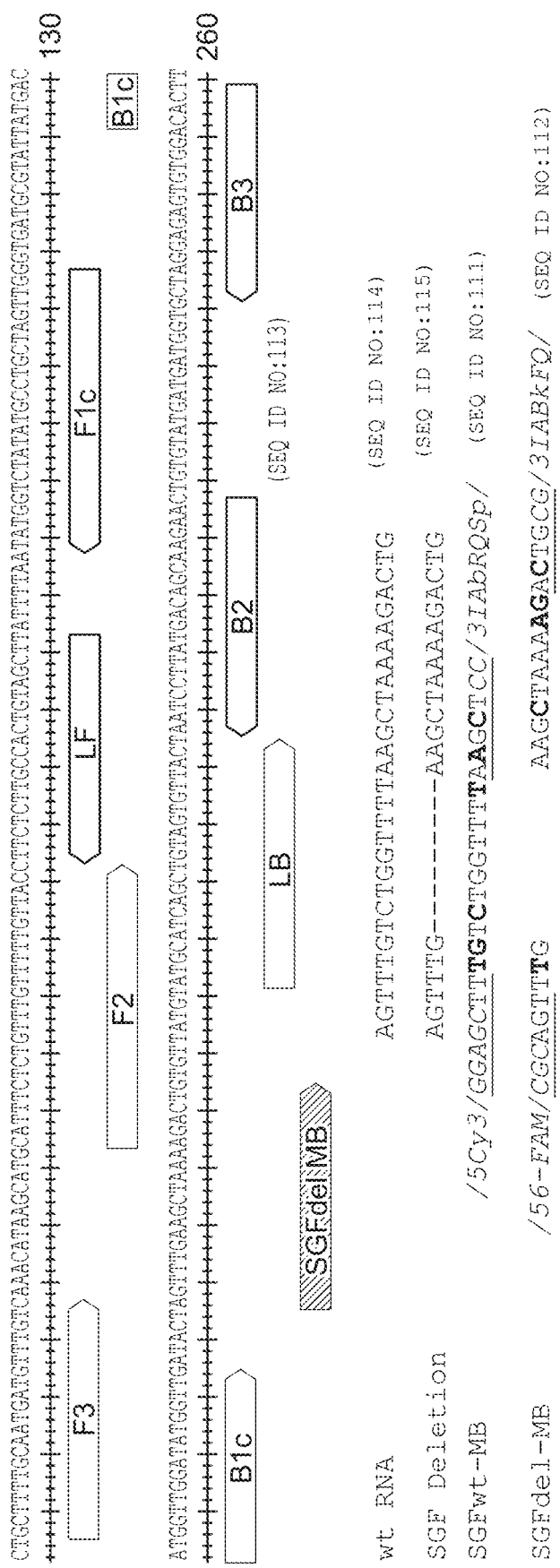
Figure 37B:
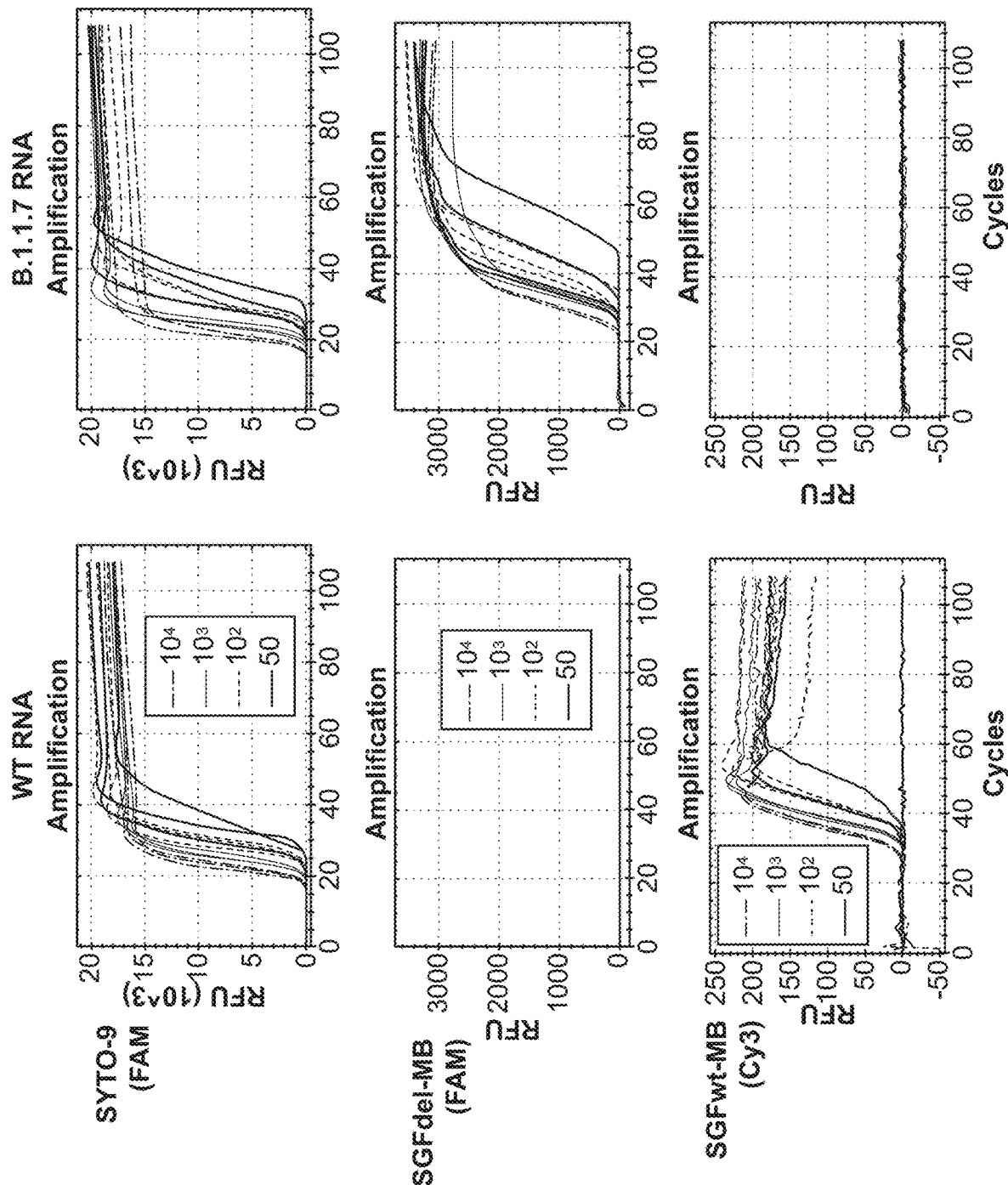

FIG. 37A-37B shows that a molecular beacon assay is an effective end point for a universal LAMP assay.

FIG. 37A describes the design of SGF LAMP primers and beacons. Upper panel shows the locations of various LAMP primers and molecular beacons. The lower panel compares the sequences for wt, SGF deletion, SGFwt-MB and SGFdel-M B. Dashes: bases deleted in SGF deletion; Bold: LNA base; Underlined: stem region; Italics, non-target sequence, attached fluorophores and quenchers.

FIG. 37B shows comparable sensitivity of detection of SARS-CoV-2 sequences including wild type (SGFwt) and variant RNA (SGFdel) by LAMP using molecular beacons. Results of LAMP reactions with either WT RNA (left panels) or B.1.1.7 RNA (right) in the presence of SYTO-9, SGFdel-MB, or SGFwt-MB are shown. The primer set amplifies both the wt and B.1.1.7 RNA with similar efficiency as detected with SYTO-9 (top). When MB beacon was added as a reporter, both SGFdel-MB (middle) and SGFwt-MB (lower) showed only with their intended template RNAs from 50-10,000 copies.

FIG. 38 shows the structure of a poloxamer.

DESCRIPTION OF EMBODIMENTS

Embodiments utilize isothermal amplification, such as LAMP, and simple visual detection of amplification in a liquid or on a reaction matrix for potential use in rapid, field applications. LAMP is an isothermal amplification protocol first developed by the Eiken Chemical Co. in Japan (see for example, Notomi, et al. Nucleic Acid Research (2000) 28, E63). LAMP is also described in detail in U.S. Pat. No. 6,410,278 and Mori, et al. (J. Infect. Chemother. 2009 15: 62-9). In LAMP, four primers recognize six unique target sequences on the template strand. Two of the primers are designated as "inner primers" (FIP and BIP) and two are designated "outer primers" (F3 and B3). In addition to containing a sequence that is complementary to a target sequence at their 3' ends, the inner primers also contain a tail that comprises a sequence that is downstream of the 3' end of primers in the template. Thus, extension of an inner primer results in a product that has a self-complementary sequence at the 5' end. Displacement of this product by an outer primer generates a product that has a loop at the 5' end. Thus, the primer sets used in LAMP typically contain four, five or six template-complementary sequences, where four sequences are found at the 3' ends of the primers and two of the sequences are found at the 5' ends of two of the primers. The initial reaction in LAMP results in a DNA product that has a dumbbell-like structure. In this product, the ends form stem loops and the single stranded region in between the stem loops is copied from the template. This product self-primes its own amplification to amplify the template sequence. LAMP uses a strand-displacing polymerase, and is isothermal, that is it does not require heating and cooling cycles.

Primer sets for LAMP as used herein refer to four to six primers that includes optionally loop forward and/or backward primers (LF and LB) in addition to forward internal primers (FIP) and backward internal primers (BIP) and forward primer (F3) and backward primer (B3).

LAMP assays are described herein that enable rapid and sensitive detection of target nucleic acids; such as a nucleic acid of or associated with a pathogen, such as a virus, in a human or animal population. These assays are simple and portable while retaining sensitivity and minimizing false positives and negatives. The LAMP assays described herein rely on detection of a change in some aspect, such as fluorescence, or color of a dye in a reaction mix due to a change in pH or metal ions. Turbidity may also be used as an end point in some LAMP assays.

The LAMP assays described herein were tested for their ability to detect not only the target nucleic acid but also variants thereof. The test sample was SARS-Cov-2 which has been able to evolve by mutating its RNA to escape the host immune system and to be more infectious. For example, SARS-CoV-2 variant strains B.1.1.7 (alpha), B.1.351 (beta), P.1 (gamma), B.1.617.2 (delta) and C.37 (lambda) emerged in different regions of the world, and rapidly became the most frequently isolated strains worldwide. They have numerous and distinctive missense mutations, most prominently located in the spike protein. While only alpha carries the Δ69-70 deletion, all but delta carry a 9-base, 3-amino acid deletion at positions 3675-3677 in the Orf1a sequence (termed the "SGF" deletion).

Here we established the first comprehensive screen of LAMP primer tolerance to mutation, investigating a single base mutation at every position of every primer in three prominent SARS-CoV-2 RT-LAMP assays. Remarkably, we find very little impact of the single base changes, with only marginal effect on speed in most positions. The robustness of RT-LAMP to sequence variation is a significant benefit to its adoption, with reduced worry about deleterious effects from the commonly emerging single-base changes that could occur with some frequency in the regions targeted by the LAMP primers. Additionally, many RT-LAMP assays combine primer sets for added speed and sensitivity (Zhang et al. *Biotechniques* 69(3), 178-185 (2020)) adding an additional layer of protection against possible sequence variation.

It is desirable to detect unknown variants in order to make an assessment of the change in the virus population and to monitor its spread. Once a positive result is obtained, the virus can be sequenced and the mutations defined. After the mutations have been discovered, new primer pairs can be used to detect viral infections with confidence by means of RT-PCR amplification tests.

This relatively large deletion provides a reliable means for designing molecular diagnostics specific for these strains.

The effect of SARS-CoV-2 sequence mutations on RT-LAMP amplification was analyzed by creating 572 single point mutation "variants" covering every position of the LAMP primers in 3 SARS-CoV-2 assays and analyzing their effects with over 4,500 RT-LAMP reactions. With this evaluation we remarkably observed only moderate effects on amplification speed and no effect on detection sensitivity, highlighting RT-LAMP as an extremely robust technique for viral RNA detection. Additionally we describe the use of molecular beacons to sensitively distinguish variant RNA sequence.

All abbreviated references herein to embodiments that relate to "colorimetric tests" refer to detection of a target nucleic acid (e.g., a target pathogen nucleic acid) by a change in color of a dye in a reaction mix due to a change in pH or metal ion binding or dissociation.

The "target nucleic acid" as used herein refers to any nucleic acid that is targeted by primers to determine its presence in a biological sample.

The diagnostic LAMP methods described herein may be used for detecting pathogens, including any of: prokaryotes such as bacteria, eukaryotic pathogens such as multicellular parasites, fungi, single cell pathogens such as trypanosomes or yeasts, and *mycoplasma*; as well as for use in genetic tests, such as for genetic diseases, and in personalized medicine, which may require SNP detection or gene analysis of the genome of a subject or RNA analysis to determine gene expression profiles in response to an environmental or metabolic event. Other diagnostic uses include testing food for undesirable biological entities and monitoring environmental samples which may include biological material and are here referred to as biological samples also. Many of the examples provided herein are directed to the SARS-CoV-2 RNA virus because of a sensitive diagnostic test is of paramount importance. However, the improvements in sensitivity described here may be applied to any colorimetric or fluorescent LAMP based assay to detect a target nucleic acid and indeed may find applications in non-LAMP assays also.

Described herein are modifications to isothermal amplification diagnostic assays (e.g. LAMP) to improve their sensitivity. Such modifications and improvements may include one or more of:

(a) sample collection in water or weak buffer;

(b) sensitive detection of a pathogen such as a virus from a sample body fluid such as saliva;

(c) avoiding nucleic acid purification for assaying for the target nucleic acid in the sample;

(d) addition of one or more nuclease inhibitors (e.g., RNase and/or DNase inhibitors) to the sample (e.g., into a sample receiving tube) to prevent loss of sample and thereby to increase overall sensitivity of the assay;

(e) addition of thermolabile Proteinase K to the sample (e.g., into the sample tube) to facilitate the efficiency of the LAMP reaction by removing unwanted protein, followed by heat inactivation of the Proteinase K prior to subsequent isothermal amplification (e.g., LAMP or RT-LAMP) reactions;

(f) inactivating pathogens and nucleases in a sample by heat treatment prior to or at the same time as the addition of lysis buffer;

(g) addition of dUTP and UDG (e.g., thermolabile UDG) into the reaction mix to prevent sample carryover when large numbers of samples are being handled where the thermolabile UDG is inactivated at the temperature of the LAMP reaction that is further coordinated with the release of inhibition of the strand displacing polymerase to allow amplification of the target to occur while at the same time permitting incorporation of dUTP into the amplified target DNA;

(h) addition of various components to the reaction mix to reduce background and enhance signal, such as a helicase (see for example, U.S. Pat. No. 9,920,358), or a carboxamide (see for example, U.S. Pat. No. 9,546,358);

(i) other adjustments to reduce background and enhance signal, such as optimizing the ratio of probes (see for example, U.S. Pat. No. 9,074,249); design of primers or probes (see for example, U.S. Pat. No. 9,074,243), improvements in the strand displacing polymerase for use in LAMP (see for example, U.S. Pat. Nos. 9,157,073 and 9,127,258) addition of guanidine salts, use of reversible inhibitors of the DNA polymerase and reverse transcriptase in the and/or in reverse transcriptases for use in LAMP (see for example, U.S. Pat. Nos. 9,920,305, 9,580,698 and 9,932,567);

(j) storage of concentrated master mix at room temperature in a lyophilized form for uses that include ease of transport and storage at the test site;

(k) substituting a pH sensitive dye and associated amplification buffer (of no greater than 5 mM Tris) with a metallochromic dye such as resorcinol (PAR), manganese ions, a detergent such as a non-ionic detergent and a standard isothermal reaction buffer;

(l) storing lyophilized master mix with probes and metallochromic dye or fluorescent dye on a paper, microfluidic device, or polymer surface for use in a target specific strip test where a liquid sample is added to the paper, microfluidic device or polymer surface containing the lyophilized reagents and a readout is obtained;

(m) adding a guanidine salt to increase the rate of the isothermal amplification (e.g., LAMP) reaction and increase sensitivity;

(n) using multiple sets of LAMP primers for use in amplifying a single template to enhance sensitivity;

(o) using multiple sets of LAMP primers for amplifying multiple target nucleic acids (p) reducing the concentration of NaCl or KCl in the buffer in the presence of guanidine salts to enhance the rate of reaction and/or improve sensitivity of the LAMP assay;

(q) using a sample lysis buffer for direct analysis of nucleic acids from a sample without purification where the lysis buffer contains a guanidine salt and a reducing agent such as TCEP and optionally LiCl and optionally a detergent or a poloxamer;

(r) use of a dual wavelength spectrophotometer to distinguish positive from negative samples rapidly in high throughput workflows and/or real time analysis;

(s) use of a high throughput automated workflow from sample collection to recording of results to achieve at least 100,000 samples in 20 hours;

(t) a point of care kit that provides a positive/negative result concerning the presence of a nucleic acid within 45 minutes of receiving a sample and without instrumentation outside a source of time- and/or thermostat-regulated heat;

(u) Improving sensitivity of the diagnostic test for target nucleic acids contained in biological samples without requiring isolation or purification of the nucleic acid;

(v) Endpoint detection of a positive results using visual color change (colorimetric) that may be pH dependent or a change in the color of a transition metal or by means of fluorescence such as DARQ (Zhang et al. *Biotechniques* 70(3), 167-174 (2021)); molecular beacons (Sherrill-Mix et al. *Genome Biol* 22(1), 169 (2021)) or coupled to secondary molecular analysis platforms such as CRISPR (Broughton et al. Nat Biotechnol 38(7), 870-874 (2020); and Joung et al. N Engl J Med 383(15), 1492-1494 (2020); next generation sequencing (LamPORE and LAMP-Seq) (Ludwig et al. Nat Biotechnol doi:10.1038/s41587-021-00966-9 (2021)); Peto et al. J Clin Microbiol 59(6), (2021).

The combination of a quick sample preparation method with an easy detection process provides portable, field detection in addition to a rapid screening for point-of-need testing applications. The use of this diagnostic methodology for a virus that represents an emerging significant public health concern provides applications outside of traditional laboratories that will enable greater prevention and surveillance approaches. These embodiments provide the basis for a model for inevitable future outbreaks of viral pathogens and indeed any infectious agent to dramatically expand the reach of testing capabilities for better healthcare outcomes.

The term "Bst polymerase" refers to any of Bst large fragment or mutant of the Bst polymerase or Bst large fragment. Examples of mutants of Bst polymerase are described in U.S. Pat. Nos. 9,157,073, 9,993,298, and 9,127,258.

The term "master mix" refers to a combination of reagents which can be added to a sample to execute a reaction in an assay where the combination enhances the efficiency and speed of performing the assay. The master mixes described herein include a mesophilic strand displacing DNA polymerase and may additionally include other enzymes such as a reverse transcriptase, uracil deglycosylase (also referred to herein as uracil DNA glycosylase) for example, a thermo-labile UDG which becomes inactivated in the temperature range of 50° C.-60° C. or at 65° C.; and a thermolabile Proteinase K such as a thermolabile Proteinase K. The master mix may also include a reversible inhibitor of DNA polymerase activity. An example of a reversible inhibitor is an oligonucleotide known as an aptamer that binds to the DNA polymerase and blocks its activity below a selected temperature (for example 50° C., 55° C. or 60° C.) but above that temperature, the oligonucleotide is disassociated from the enzyme, permitting the reverse transcriptase to become active. In some embodiments, the master mix includes a reverse transcriptase and a reversible inhibitor of reverse transcriptase activity for inhibiting the activity of these enzymes below 40° C. or below 45° C. or below 50° C. An example of a reversible inhibitor is an oligonucleotide known as an aptamer that binds to the reverse transcriptase and blocks its activity below a selected temperature (for example 40° C.) but above that temperature, the oligonucleotide is disassociated from the enzyme, permitting the reverse transcriptase to become active. This permits setting up a reaction at room temperature while avoiding nonspecific amplification. The master mix may also contain inhibitors of nucleases such as RNase inhibitors and/or DNAse inhibitors. These inhibitors may be chemical reagents such as poloxamers, and/or aptamers. However, nucleases may also be inactivated by submitting the sample combined with a lysis buffer to a high temperature for an effective time such as The master mixed may also include dNTPs such as dTTP, dATP, dGTP and dCTP as well as dUTP for carryover prevention. For example, a 2× master mix may contain the dNTPs in equal quantities except the dUTP at 50% concentration of the other dNTPs. The master mix may include single strand binding proteins and/or helicases to reduce nonspecific amplification. The master mix may include a pH-sensitive dye or a metallochromic dye. The master mix may be lyophilized or freeze dried. It may be preserved for storage in a suitable buffer that may contain at least one reducing agent and at least one detergent and capable of storage at −20° C. for an extended period of time (for example months). The inclusion of a reducing agent is desirable if RNA is the template nucleic acid. It is not required for DNA. The master mix for use in pH colorimetric LAMP may have a low buffer concentration such as 5 mM Tris or less. A low buffer concentration is not required if a metallochromic dye of fluorescent dye is used to detect amplification. The master mix may be prepared in a 2×, 3×, 4×, 5×, 10× or any suitable concentration. The master mix once diluted by the sample will result in a 1× concentration. The master mix may contain primers or primers are not contained in the master mix.

Kits refer to a combination of materials that are needed to perform a reaction. A kit may contain multiple tubes or a single tube. The kit may include a mixture of lyophilized reagents and reagents in a storage buffer. In one embodiment, the kits described herein contain multiple tubes wherein the master mix is contained in one tube, guanidine salt in a second tube and oligonucleotide primers in a third tube. In embodiments of the kit, unless the primers are lyophilized together with the master mix, the oligonucleotide primers in the third tube comprise a plurality of sets of LAMP primers, for example two sets of primers consisting of 8-12 primers where each set has 4-6 primers and wherein both sets of primers target different sequences in a single nucleic acid or different nucleic acid targets. The third tube may contain more than 2 sets of LAMP primers where a plurality of sets may target a single nucleic acid or multiple different nucleic acid sequences. For example, a plurality of sets of LAMP primers in the third tube may target the genome of SARS-CoV-2 and a different set or plurality of sets of LAMP primers in the third tube may target the genome of influenza virus. The plurality of LAMP primers in the third tube may additionally contain a sample identification sequence if multiple samples are pooled for combining with the kit. In one embodiment, the kit contains a 2× master mix, a 5×-25× guanidinium salts, and 5×-25× of LAMP primer sets.

Sampling to Obtain Target Nucleic Acid

In embodiments, purified nucleic acid such as RNA or DNA, or direct tissue or cell lysate can be analyzed in a colorimetric LAMP such as a pH dependent colorimetric LAMP assay, a fluorescent LAMP assay or a metallochromic based LAMP assay. Either purified or lysate can be used in a simple, rapid method for SARS-CoV-2 RNA detection.

In one embodiment, a sample is obtained from the nasal passages of a patient (human or mammal) by nasal swab or from the buccal cavity. The biological sample may be one or more of the following body fluids: saliva, sputum, mucous, blood, semen, urine, sweat, lymph fluid, feces. The biological sample may alternatively be a tissue sample. The biological sample may include pathogens such as parasites such as viruses, bacteria, archaea, worms, ticks, single cell organisms, and fungi, Samples may also be obtained from an environmental source such as a food, plant, sewage, water, dust, or surface swab of an object. Samples can be placed into a small volume of water saline, TE, or suitable transport medium (for example, a universal transport medium for viruses) or directly into a lysis buffer that inactivates and breaks open the pathogen if that is the diagnostic target while protecting the released target nucleic acids from nuclease digestion. The samples may be further purified from lysis buffer or added without further purification to a LAMP amplification master mix for testing for the presence of a pathogen, gene, SNP, mutation or other nucleic acid target.

The pH of the sample may determine the type of assay detection that is preferably used. For example, urine has an acid pH so a metallochromic based assay that is not pH sensitive might be used, instead of a pH endpoint.

Saliva

The nucleic acids in saliva may come from cheek cells and tongue cells as well as any typical oral microbial species. Saliva can be collected from a human subject using a commercial collection device such as provided by for example any of Boca Scientific Inc. (Westwood, Mass.), Salimetrics LLC (Carlsbad, Calif.), Mantacc (Shenzhen, China), Greiner Bio-One BD Sputum Collection (Monroe, N.C.). Saliva has some challenges as a body fluid for nucleic acid analysis. Its pH and composition may vary according to the biology of the individual and also according to the recent intake of food and/or liquid into the mouth. For example, it is well known that a glass of water containing the juice of a squeezed lemon will cause the saliva to become acidic for a short time after intake. Where the saliva based diagnostic test relies on an amplification procedure that is pH dependent such as pH dependent colorimetric LAMP, the pH can be normalized to the extent necessary with respect to subsequent dilution before initiation of the amplification reaction so that the concentration of buffer in the final reaction mixture is less than a corresponding amount of 5 mM Tris while optimizing the pH to be preferably within the range of pH 7.9-pH 8.3. Alternatively, the subject providing the saliva might avoid ingestion of a particular food or drink for a predetermined number of minutes (such as 30 minutes) before providing the saliva sample.

Where saliva is tested for a pathogenic virus, it may be desirable to immediately inactivate the virus in the receiving tube. In these circumstances, a detergent may be added to the collection tube if storage before analysis is intended. For example, Triton X-100 in relatively high concentrations has been shown not to interfere with a subsequent colorimetric LAMP reaction (see for example, FIG. 11B). The lysis buffer as described below will inactivate the virus and release nucleic acid for amplification or for sequencing. The lysis buffer described in Example 9 is suited for amplification generally as illustrated for RT-QPCR and for LAMP. The saliva lysis buffer may also be applied to other body fluids for a similar purpose. The lysis buffer may be used for obtaining nucleic acid samples suitable for direct sequencing such as by Oxford Nanopore.

In one embodiment, the sensitivity of the methods described herein was tested in samples of human SARS-CoV-2 negative saliva spiked with either SARS-CoV-2 viral RNA (Twist Synthetic SARS-CoV-2 RNA Control 2 (MN908947.3) (Twist Biosciences, San Francisco, Calif.) or virus particles provided by SeraCare (Milford, Mass.). An aliquot of the spiked saliva samples was added to the lysis buffer that was then analyzed using a pH colorimetric LAMP assay as shown in FIG. 20. Using the methods described herein it was possible to detect less than a 100 copies of viral RNA (80 copies of virus) derived from a saliva sample, more particularly less than 80 particles, more particularly, 40 particles or less with up to 100% efficacy. This corresponded to less than 50,000/ml virus particles in the original sample where less than 100 copies of virus were detected, less than 40,000/ml copies of virus in the sample (80 copies), 20,000 copies/ml or less in the sample (40 particles) with 10,000 copies/ml corresponding to detection of 20 particles.

Reaction Platform

In one embodiment, a microfuge tube receives the sample, for example a swab, in a suitable buffer. Alternatively, a reaction platform such as a 96 well dish, 384 well dish or other multi-well dish may be used for multiple sample analysis. Alternatively, the sample may be spotted onto a paper, plastic, or glass surface. The sample may also be introduced into a microfluidic device, such as a lab-on-a-chip. In this context, an Echo® Liquid Handler (Labcyte Inc., San Jose, Calif.) may be used to handle fluid samples. Because the one tube reaction is simple, any automated liquid handler of device may be used for analysis of multiple samples. Because the endpoint is a color change, a computerized analysis of a photographic image of the sampling platform or insertion of the reaction platform into a light reader connected to a computer is enabled for digitizing the reaction platform itself or image thereof. Further details are described in FIG. 26-FIG. 28F and Example 12.

Preparation of a Master Mix for Use in a LAMP Assay on or in a Reaction Platform or Reaction Vessel A master mix can include or be combined with oligonucleotide probes or primers. A master mix can be added directly to the sample, or alternatively, a portion of the sample can be added to the master mix. The primers and/or probes can be added to the master mix prior to adding the mixture to the sample or the primers and/or probes can be added to the sample prior to or after addition of the master mix. Where large-scale analysis of multiple samples is desired, the LAMP primers and/or probes may be incorporated into the LAMP master mix so that all that is required is to add an aliquot of sample (purified nucleic acid or lysed cell or fluid sample) to the master mix and to raise the temperature to 60° C.-65° C. for a 15 minute, 30 minute, 45 minute or 60 minute incubation time for amplification to occur, to detect a change in color or fluorescence that defines the presence of the target nucleic acid.

The master mix will contain a DNA polymerase dNTPs and a suitable buffer or water. The master mix may additionally include one or more of the following: probes or primers, a plurality of sets of primers, reverse transcriptase, dUTP and UDG, a helicase, a single strand binding protein, a carboxamide, an RNase inhibitor (e.g., murine RNase inhibitor or an aptamer), a pH-sensitive dye or a metallochromic dye such as PAR, and/or manganese ions, and/or guanidine salts. The master mix may have been previously stored at −20° C., prepared in a liquid formulation that is stable at room temperature or lyophilized.

Prevention of Carryover of Contaminating Nucleic Acid Between Samples

Even a very small amount of carryover of previously amplified nucleic acid from a positive sample into a tube that might be negative for the target nucleic acid would be very undesirable. For this reason, including dUTP in the dNTPs in a primary amplification reaction results in incorporation of UMP into the amplified nucleic acid. If this previously amplified DNA then strays into a subsequent sample tube, UDG that is present will cleave the incoming contaminant DNA. The established method has been to include dUTP with dATP, dCTP, dTTP and dGTP so that a fraction of dT is replaced by a dU in the amplified DNA of the first sample. The second sample is then exposed to UDG prior to amplification and this enzyme creates an abasic site at the incorporated uracil. Consequently, it is not possible to amplify sample 1 amplified DNA in sample 2 which would result in a false positive. However, before sample 2 is amplified, the UDG is temperature inactivated or it would adversely affect the desired amplification. It is desirable that the diagnostic test described herein is simple to perform, and also rapid and sensitive. Hence a thermolabile UDG is incorporated into the master mix along with dUTP so that once the temperature is raised to the temperature required for amplification, namely 55° C.-75° C., the UDG is inactivated.

A preferred feature of embodiments of the diagnostic test described herein is inhibition of carryover contamination. In order to confirm that pH-dependent colorimetric LAMP is not adversely affected by dUTP and thermolabile UDG, a 2×LAMP master mix containing a buffer concentration of less than 8 mM TRIS buffer and the pH sensitive dye was tested with and without dUTP and Antarctic UDG. It was found that master mixes containing dUTP and Antarctic UDG yielded substantially the same speed, sensitivity and specificity observed in the absence of UDG (see Examples 3 and 4 and FIG. 6A-FIG. 6B). Because prevention of carryover is important for high throughput screening, preferably, UDG and dUTP should be included in master mixes for pH colorimetric LAMP detection of pathogens.

Degradation or Inhibition of Unwanted Proteins in Samples Containing Nucleic Acids in the Absence of the Step of Purifying the Nucleic Acid Prior to LAMP Thermolabile Proteinase K (see for example, U.S. patent application Ser. No. 16/719,097) and/or a proteinase inhibitor such as murine proteinase K inhibitor and/or an RNase inhibitor (see for example U.S. provisional application Ser. No. 62/992,921) and/or a DNase inhibitor can be added to the sample or the reaction tube into which the sample is added. Where thermolabile Proteinase K is used, it may be inactivated before addition of the master mix. Thermolabile Proteinase K is available from New England Biolabs, Inc, Ipswich, Mass.

Storage of the Master Mix: Dried or Liquid

LAMP master mix containing enzymes, dNTPs, buffer, and pH sensitive dyes (e.g. colorimetric or fluorometric dyes), and/or other dyes that bind metals (e.g. PAR), may be freeze dried or lyophilized and stored at room temperature as a master mix, for example a 2× master mix or 5× master mix or a 10× master mix until needed. The master mix may then be added to a solution containing primers and/or sample to be tested for target nucleic acid in a reaction container, a microfluidic device, a lab on a chip device or a matrix such as paper, plastic, or glass.

If the reagents in the master mix are stored in a dried or lyophilized form, then the pH and buffer concentration of the master mix is not relevant until the dried master mix is added to the sample or the master mix is rehydrated. It was here shown that the pH of the buffer of rehydrated master mix is slightly changed when the master mix is rehydrated so this is taken into account during formulation.

Use of Color or Fluorescence Changes in a Diagnostic Test pH dependent colorimetric LAMP is shown here to be quick, easy, reliable, and suitable for scale-up in molecular diagnosis of viruses and multicellular parasites and their pathogens. In certain point of care formats, it may be desirable to utilize a colorimetric LAMP diagnostic test in which a color change occurs as a side product of amplification that does not rely on staining amplified DNA. A desirable format for measuring a color change is a strip test such as routinely used for pregnancy tests that rely on antibodies (CVS) or the Quickvue® in-line StrepA test (Quidel Corporation, San Diego, Calif.) or equivalent. Alternatively, a liquid test may be convenient in which the sample is added to a first solution (e.g., a lysis buffer) from which an aliquot is removed to a second solution containing the master mix that is then heated on a small pad provided with the test kit (this could be an equivalent of an activated handwarmer or directions for heating a small amount of water in a kettle or a heat block). In these circumstances a pH change will result in a color change denoting a positive result. Alternatively, in place of a pH dependent colorimetric LAMP assay, a metallochromic dye such as PAR has been found to be useful in a colorimetric LAMP assay and provides an alternative should body fluid to be tested be acidic such as urine. The PAR based assay is described in the figures and examples. Manganese used in the PAR colorimetric endpoint LAMP assay is a suitable ion as it does not negatively affect the activity of the polymerase or the reverse transcriptase in a LAMP reaction. Because PAR it is not pH sensitive, it has advantages in a variety of situations in which pH colorimetric LAMP is not best suited as enumerated herein. Either pH colorimetric LAMP or PAR may be used in conjunction with Calcein which also binds to manganese to give a fluorescent signal and/or with the fluorescent dye, Syto-9. Guanidine salts may also be used in conjunction with colorimetric LAMP to enhance the sensitivity of the assay.

Master Mix

In embodiments, a master mix may contain a pH sensitive dye, fluorescent dye or PAR, a polymerase, plus optionally a reverse transcriptase for RNA detection (such as for an RNA virus), reversible inhibitors for the polymerase and reverse transcriptase to reduce unwanted background noise and increase sensitivity, primers and dNTPs form a reaction mix when combined with a sample for determining the presence of a target nucleic acid. The master mix is preferably in a concentrated form, for example a 2×, 3×, 5×, 7× or 10× master mix where the final amount of master mix after combination with a sample is 1×.

Some of the considerations in forming the master mix beyond those established in commercial master mixes (see M1800 from New England Biolabs, Ipswich, Mass.) may include one or more of the following parameters: (1) the concentration of dye; and (2) the amount of buffer; (3) the pH; (4) dilution of the master mix in the sample; and (5) the proposed incubation time of the reaction mix to which the master mix is added.

(1) In an example of pH dependent colorimetric LAMP, the concentration of dye in the master mix should be sufficient such that when diluted with sample, it enables unambiguous visual detection of a positive sample. However, the concentration of dye must not be so high as to adversely affect the activity of the polymerase and/or reverse transcriptase. In a preferred embodiment, the visually detectable dye in the reaction mix (1× master mix plus sample) is in the range of 50 µM-200 µM.

(2) The amount of buffer in a liquid concentrated master mix should be sufficient to maintain the enzymes and other reagents in a stable condition but suitable for dilution to detect a color change if amplification of a target nucleic acid has occurred. It is desirable therefore not to exceed 5 mM buffer in the reaction mix-sample combination for pH dependent colorimetric LAMP where buffer concentrations of greater than 5 mM (e.g., 5 mM Tris) in the reaction mix designed to detect amplification via a pH-based color change were found to substantially reduce any visually detectable signal for identifying a positive sample. The buffer concentration was formulated to meet the 1× amount of master mix to have an equivalence to 0.5 mM Tris-5 mM Tris. However, PAR or fluorescence based LAMP do not require this limit on buffer concentration.

(3) A pH 8.1-pH 8.5 in the master mix was tested and found to be suitable for phenol red, a pH sensitive dye used in the examples. This pH could be increased up to a preferred maximum of pH 9 while retaining a visually detectable signal change of pH for a positive sample. The pH could also be reduced to below pH 8.1 in the master mix to provide a change in color by the dye according to the established pH range of pink/red phenol red. Lower pH for a detectable color change is undesirable in the event of exposure to atmospheric $CO_2$ that may acidify the solution since the master mix is weakly buffered. As the pH is increased between pH 8.1 and pH 9.0, the color of the negative control becomes more pink. Different pH sensitive dyes have different ranges of pH optima. The pH range is well known in the art (see for example, Tanner et al. (2015) Biotechniques, 58, 59-68).

(4) As described above, LAMP master mixes may be prepared as 2×, 3×, 5×, 7× or 10× although 2×, 5× or 10× are the usually preferred concentrations for easy dilution into a sample. For biological material containing enzyme inhibitors such as blood, sputum, and urine but not necessarily nasal or buccal swabs, it may be desirable to dilute the sample at least two fold before adding to the appropriately concentrated master mix. In addition to this strategy, adjustment of the acidic pH of urine or the alkali pH of sodium hydroxide treated sputum may be desirable to ensure that the pH of the sample does not inhibit the detection of the amplified target nucleic acid in the sample. Buccal and nasal swabs can be placed in water or transport media and added in a 1:1 ratio to a volume of master mix resulting in a pH and buffer concentration as described above. In some circumstances, it may be desirable to extract the nucleic acid, for example, using Monarch® (New England Biolabs, Ipswich, Mass.), Qiagen or Roche purification kit prior to testing. In these circumstances, the samples can be used in higher volumes especially if eluted from extraction matrices in diluted buffer or water. Lysis buffers are discussed below.

Figure 1:
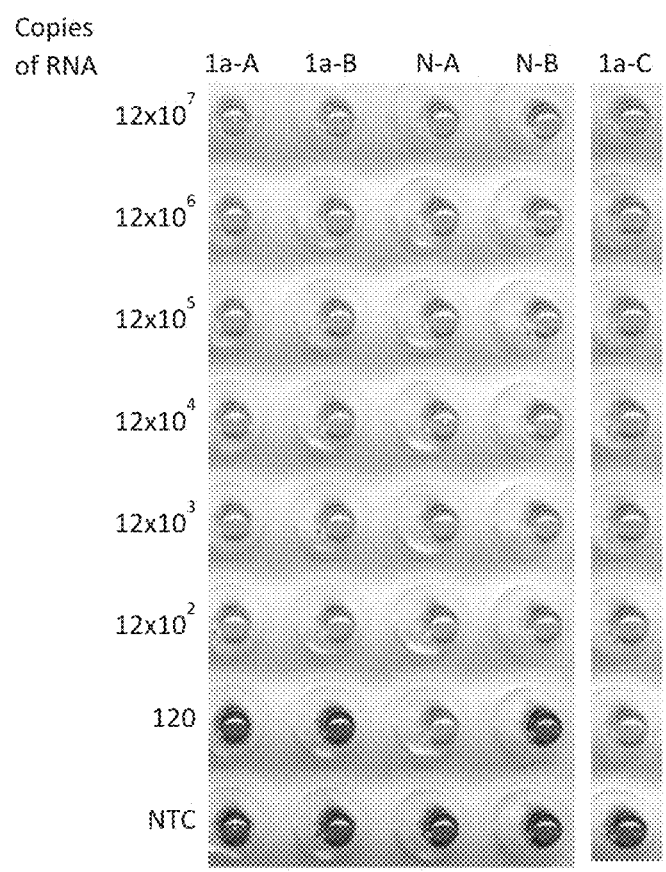
FIG. 1 shows detection sensitivity of synthetic SARS-CoV-2 RNA amplicons by a pH dependent colorimetric LAMP assay using phenol red as the indicator that changed color from red to yellow when amplification of a target nucleic acid occurred, causing the pH of the reaction mixture to decrease. 5 sets of LAMP primers (1a-A, 1a-B, N-A, N-B, and 1a-C) were tested with templates ranging from $120 \times 10^6$ to 120 copies of viral RNA (Twist Biosciences), or a no-template control (NTC). Yellow, positive amplification; pink, no amplification.
Figure 2A:
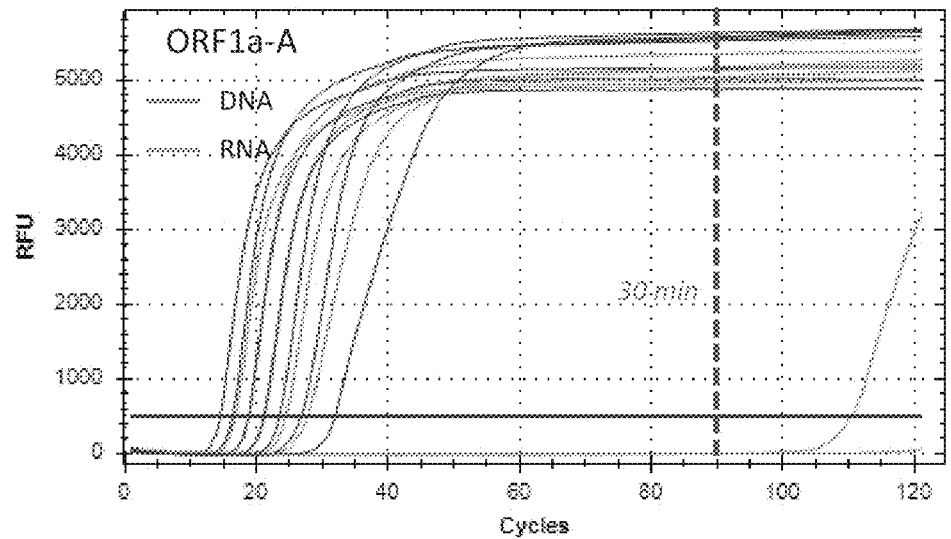
FIG. 2A-FIG. 2B shows that RNA can be detected as efficiently as DNA using pH dependent colorimetric LAMP (New England Biolabs, Ipswich, Mass. (M1800)) using the primers described in Example 1 that targeted two different SARS-CoV-2 sequences.
Figure 2B:
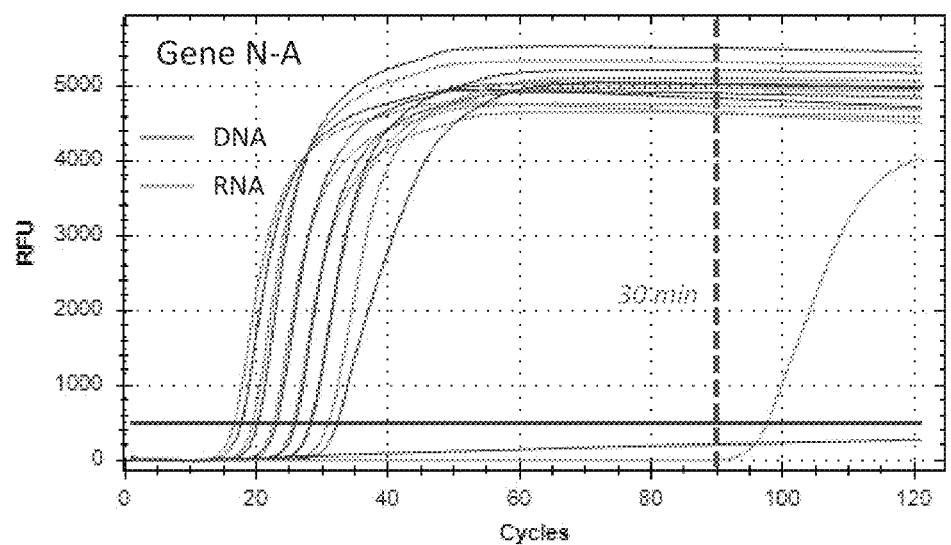

(5) For a rapid test for an infectious agent, it is desirable to analyze a sample directly from a swab or sample matrix containing test nucleic acid without requiring a purification step. Previously, it was shown that LAMP can detect 2-3 copies of a purified target DNA in a genome in under 30 minutes and 10 copies under 15 minutes (Tanner, et al. (2015) Biotechniques, 58, 59-68). FIG. 2A-FIG. 2B shows the sensitivity of assays described herein for nematode parasites as little as 0.01-0.1 picograms nematode DNA can be detected. FIG. 3A-FIG. 3B shows detection of 1.28 femtograms of DNA of a tick-borne pathogen from whole ticks. Embodiments of the test described herein for a target RNA of a virus in a nasal or oral swab can be performed within 15 minutes. Example 1 provides an example of pH dependent colorimetric LAMP as used for detection of viral pathogens such as RNA or DNA viruses for example, SARS-CoV-2 RNA. The results for SARS-CoV-2 RNA in FIG. 21-FIG. 27 show that the virus can be reliably detected at between 10-40 copies in under 60 minutes.

Preparation of Samples for Analysis

Biological material that may contain one or more pathogens can be sampled for one or more target nucleic acids in parallel to obtain distinctive results for each or together for purposes of efficiency initially but that might result in secondary tests. For example, where a sample is taken from a subject to test for SARS-CoV-2 and influenza, it might be desirable to perform tests in parallel using one or more primer sets that are specific for each target nucleic acid. Samples may be obtained from any biological source. For example, samples may be derived from blood (e.g., from a venous draw), serum, plasma, urine, feces, sputum, hair follicles, lavage, nasal, oral or buccal swabs, and/or saliva may be used for detecting the pathogen using pH dependent color LAMP or PAR dependent color LAMP that is not pH dependent. The samples may be dried, placed in an aqueous solution that may be selected from water or stored in a transport medium, for example saline, TE or a transport medium available from Copan (Murrieta, Calif.). Such products include Sputum Dipper™, SnotBuster™, UriSponge™ and UTM® Universal Transport System™.

Different types of samples contain variable amounts of RNases that might be contained in the biological material. These RNAses are particular concern if they are released when a diagnostic test requires testing for RNA such as the viral RNA diagnostics for SARS-CoV-2 are performed. The RNases that are released from the sample can digest the viral RNA from disrupted virus of interest reducing the sensitivity of the test.

Detergents are routinely used to disrupt biological material. Examples of such detergents include Tween and Triton X. These detergents appear to contribute to the observed loss of viral RNA (within 5 minutes at room temperature) once the biological sample is exposed to these detergents. Not wishing to be limited by theory, it is hypothesized either that these detergents either activate cell RNases or cause the viruses to break open releasing the viral RNA that is quickly enzymatically digested by RNases. One way to prevent RNase digestion is to heat the sample to 95° C. for at least 5 minutes immediately after adding buffer containing Tween or Triton X to the samples. This heat inactivates the majority of RNAses. However, without some alternative intervention, the availability of intact sample RNA can be significantly reduced. Moreover, when handling large numbers of samples, it is problematic to administer immediate heat treatment (95° C.) within minutes of adding buffer to avoid loss of RNA. Taking the caps of tubes alone can slow the heat treatment of large numbers of samples. Although storage on ice might help a little, it does not solve the problem of RNA loss.

We have identified a family of surfactants also called an antifoaming agents specifically poloxamers, that can inactivate the virus particles and either inhibit RNases or do not break open the virus particles, so that substantially all or a significant portion of the RNA remains intact for at least 2 hours, 3 hours, 4 hours, 5 hours and up to at least 6 hours at room temperature after addition of the surfactant prior to a heat step at 95° C. to release viral RNA from virus particles and inactivate the RNase. The observed advantage of the poloxamer PF68 is described in Examples 13-15. It is expected that other related poloxamer surfactants will be similarly effective. Examples of other members of this group of surfactants are provided below.

Since the improvement observed relates to the preparation of RNA from a sample, it is believed that this group of surfactants can be effective in the purification of RNA and in improving the sensitivity of colorimetric and fluorescent LAMP reactions as well as RT-qPCR reactions and also in the preparation of samples for nucleic acid sequencing. The improvements relate to obtaining RNA from any biological source including any diagnostic test known in the art for a virus from any biological material.

The workflow that utilizes these surfactants in a buffer for a sensitive diagnostic assay for an RNA virus is described in FIG. 30 in 3 different initial workflows where saliva or other body fluid or buccal or nasal swab is collected in a tube, or in a microwell in a 96 well dish or a 384 well dish that may be empty or may contain a buffer with the foaming agent or may contain buffer in a compartment in the tube or well that is released on introduction of sample. If the collection tube receives the sample in the absence of buffer, an aliquot can then be transferred to receiving compartment (tube or a multi-sample microwell dish) where each well or tube contains buffer. The tubes or wells containing sample in buffer containing the poloxamer is then heated to 95° C. for 5 minutes and an aliquot transferred into a fluorescent LAMP, DARQ LAMP, colorimetric LAMP (cLAMP) or RT-qPCR reaction tube to determine the presence of the virus or viruses. Because of the sensitivity of RNA to RNases, the poloxamer foaming agent may be best suited for adding to the sample at the earliest convenience. It may also be used for DNA viruses or other samples. There was no adverse effect of the carryover of the poloxamer from sample tubes to the amplification reaction.

Where DARQ (see for example, U.S. Pat. No. 9,074,243) or fluorescent (intercalating dye) LAMP is used to detect target RNA, the poloxamer agent is important for improved results while the buffer used along with the poloxamer does not appear to be of critical importance. For example, a buffer containing TCEP and EDTA may be adequate (for example, 100× buffer containing 0.5 MTCEP (2.5 ml)) 0.5 M EDTA (1 ml) and 1.1 N NaoH (1.5 mls) described in Rabe and Cepko (2020) PNAS vol 117, pp 24450-24458) can be used without LiCl. Moreover, while Guanidinium chloride has proved useful for colorimetric LAMP, it is not required in a fluorescent or DARQ LAMP reaction.

Another factor found to be significant is the volume of buffer in the tubes or wells. The volume in a 96 well dish (e.g., 25 µl) is preferably 2× the volume in a 364 well dish (12.5µ).

SARS-CoV-2 LAMP tests were analyzed using a Cq value for real time analysis to detect virus and also endpoint +/− analysis. As more is understood about SARS-CoV-2, it is important to understand the amount of virus in a patient as determined by a nasal or buccal swab or saliva that corresponds to active infection. It has been observed that titers of the order of $2 \times 10^4$ virus particles/ml (20 virus particles/µl) may be detected at the onset of infection or at the end of a recovery phase of infection whereby virus titers in the region of $10^9$-$10^{11}$ signal an infectious dose. Therefore, it would be desirable to be able to test individuals over several days, for example, three times over a single week to get a more accurate picture of whether they are spreaders or are about to be spreaders versus non spreaders. Cost, speed and ease of use of the tests become even more significant in this context. The present colorimetric tests (either using pH dependent dyes or fluorescent dyes) described herein meet these criteria where the time to perform a test is less than 1 hour (e.g., 5 minutes to heat a sample to 95° C. and 35-40 minutes to perform the LAMP reaction with an immediate endpoint color readout). Moreover, the colorimetric LAMP test can readily be performed on multiple samples simultaneously as needed, for example in 96 well or 384 well plates with instantaneous detection of positive samples by eye or by spectrophotometer to detect a color change. Moreover, colorimetric LAMP can consistently detect 100% of samples containing 50-80 particles/µl ($5$-$8 \times 10^4$ particles/ml) and is described herein, can detect RNA corresponding to as few as 25 viruses with 90% success rate. These detection ranges of 25-50 virus particles are below the concentration required to detect virus load of an active spreader using saliva, nasal or buccal swabs.

Embodiments are provided for lysis buffers suitable for LAMP. The lysis buffer was prepared as a 2× mix but could also be prepared as a 4×, 5× or 10× mix or indeed any concentrated form limited only by possible undesirable precipitation of individual reagents at high concentrations. In one example, the 2× lysis mix described herein comprises 800 mM guanidine HCl, 4% Triton X-100, 80 mM TCEP and 150 mM LiCl at pH 8.0. This 2× lysis mix can be combined with an equal volume of saliva resulting in a final concentration of 400 mM guanidine HCl, 2% Triton X-100, 40 mM TCEP and 75 mM LiCl at pH 8.0. In one embodiment, it was shown that allowing the saliva-lysis mixture to stand at room temperature for 30 minutes increased the sensitivity and reliability of the subsequent LAMP reaction. Subsequent to incubation for 30 minutes at room temperature, the temperature of the mix was raised to 95° C. for 5 minutes or 75° C. for 20 minutes or 65° C. for 60 minutes. 2 µl of the saliva-lysis mix was then added to the standard master mix for LAMP along with primers.

In a further improvement, it was found that Triton X or Tween could be replaced with a non-ionic detergent having improved properties with respect to RNases in saliva. Whereas Triton X and Tween 20 were very effective at lysing virus particles at room temperature, these detergents appeared to have the effect of exacerbating RNAse activity with an adverse effect on the sensitivity of an isothermal amplification performed on saliva. It was found here that an alkoxylated alcohol which is an amphiphilic water soluble polymorphic block copolymer of poly(ethylene oxide) (PEO) and poly(propylene oxide) (PPO), did not have the undesirable effect on RNAse activity observed for the other detergents. A preferable composition would be an ABA triblock copolymer, wherein A is the hydrophilic block PEO and B is the hydrophobic block PPO. Preferable copolymers have molar mass ratio between the PEO and PPO blocks from 1:9 to 8:2. Examples of such block copolymers are Pluronic detergents and poloxamers. The class of ABA triblock copolymers commercially available as Pluronic® (non-proprietary name "poloxamers") offers a pool of more than 50 amphiphilic, water-soluble and polymorphic materials (A=hydrophilic block poly(ethylene oxide) (PEO) and B=hydrophobic block poly(propylene oxide) (PPO). Example 13 describes the use of Pluronic F68 (CAS [691397-13-4]) (Thermo Fisher, Waltham Mass.). The structure is provided in FIG. 38.

Detergents of this class may also be referred as Epoxyethane-epoxypropane copolymer, Ethoxylated propoxylated propylene glycol, Ethylene glycol-propylene glycol copolymer, Ethylene glycol-propylene glycol polymer, Ethylene oxide-1,2-propylene oxide copolymer, Ethylene oxide-propylene oxide copolymer, Ethylene oxide-propylene oxide copolymer ethylene glycol ether, Ethylene oxide-propylene oxide copolymer, Ethylene-propylene glycol copolymer, Methyloxirane-oxirane copolymer, Oxirane-methyloxirane copolymer, Oxirane-propylene oxide copolymer, Oxyethylene-oxypropylene copolymer, Oxypropylene-oxyethylene copolymer, Oxypropylene-oxypropylene copolymer, Poly(oxyethylene) poly(oxypropylene) glycol, Poly(oxyethylene)-poly(oxypropylene) polymer, Poly(oxyethylene-oxypropylene) ether, Poly(propylene oxide-ethylene oxide), Polyethylene oxide-polypropylene oxide, Polyethylene oxide-polypropylene oxide copolymer, Polyethylene-polypropylene glycol, Polyethylene-propylene glycol diethylene glycol ether, Polyoxyethylenated poly(oxypropylene), Polyoxyethylene oxypropylene, Polyoxyethylene-polyoxypropylene, Polyoxyethylene-polyoxypropylene copolymer, Polyoxyethylenepropylene glycol ether, Polyoxypropylene polyoxyethylene propylene glycol ether, Polyoxypropylene-polyoxyethylene copolymer, Polypropylene glycol-ethylene oxide copolymer, Propylene glycol-ethylene glycol copolymer, Propylene oxide, polymer with ethylene oxide, Propylene oxide-ethylene oxide copolymer, Propylene oxide-ethylene oxide polymer, Propylene oxide-oxirane copolymer, or Propylene oxide-propylene glycol-ethylene oxide copolymer.

PEO-PPO-PEO triblock copolymers are also referred as Ethene oxide-propene oxide triblock copolymer, Ethylene glycol-propylene glycol copolymer triblock, Ethylene glycol-propylene glycol triblock copolymer, Ethylene oxide-Excenol 1020-propylene oxide triblock copolymer, Ethylene oxide-propylene oxide triblock copolymer, Ethylene oxide-propylene oxide-ethylene oxide triblock copolymer, Oxirane-methyloxirane triblock copolymer, Oxirane-oxypropylene triblock copolymer, Oxirane-propylene oxide triblock copolymer, Poly(ethylene oxide)-block-poly(propylene oxide)-block-poly(ethylene oxide), Polyethylene oxide polypropylene oxide polyethylene oxide triblock copolymer, Polypropylene-polyethylene-polypropylene triblock copolymer, Propylene glycol-ethylene glycol triblock copolymer, Propylene oxide-ethylene oxide triblock copolymer, or Propylene oxide-oxirane triblock copolymer.

Most preferable detergents are Pluronic F68 and Poloxamer 188. Other detergents of interest are Pluronic L31, Pluronic L61, Pluronic L81, Pluronic L101, Pluronic L121, Pluronic L42, Pluronic L62, Pluronic L72, Pluronic L92, Pluronic L122, Pluronic L43, Pluronic L63, Pluronic L44, Pluronic L64, Pluronic P84, Pluronic P103, Pluronic P123, Pluronic P65, Pluronic P75, Pluronic P85, Pluronic P105, Pluronic F77, Pluronic F87, Pluronic F127, Pluronic F38, Pluronic F88, Pluronic F98, and Pluronic F108. Further detergents of interest are Poloxamer 10R5, Poloxamer 1100, Poloxamer 122, Poloxamer 123, Poloxamer 127, Poloxamer 17R4, Poloxamer 181, Poloxamer 183, Poloxamer 202, Poloxamer 237, Poloxamer 272, Poloxamer 317, Poloxamer 333, Poloxamer 334, Poloxamer 407, Poloxamer 68, Poloxamer F 98, Poloxamer P 188, and Poloxamer P 407.

Further detergents of interest are Acclaim 2220N, Acclaim 4220N, Acclaim Polyol PPO 2220N, Acclaim Polyol PPO 4220N, Aclube 517, Adeka CM 294, Adeka L 61, Adeka Nol 17R2, Adeka Polyether CM 294, Adekanol 25R1, Adekanol F 68, Adekanol L 61, Adekanol L 64, Aduxol VP 11115, Antarox 17R4, Antarox 31R1, Antarox L 61, Antarox L 62, Antarox L 64, Antarox SC 138, Arlatone F 127G, BASF PE 6800, Basorol 150R1, Basorol PE 6100, Basorol RPE 3110, BL 10500, BL 6400, Blaunon P 0840, Blaunon P 106, Blaunon P 124, Blaunon P 1461, Blaunon P 174, Blaunon P 304, Chemax BP 261, Chemex BP 261, CM 294, CRL 1005, Daltocel F 460, EO 106P070E0106, EO 20P070E020, EP 1900, Epan 410, Epan P 45, Epan U 105, EPE 2900, Ethox 17R2, Ethox L 122, Ethox L 62, Ethox L 64, EXL 540, EXL 552, EXL 902, ExpertGel 56, ExpertGel EG 56SEC, F 108, F 123, F 126, F 127, F 38, F 61, F 68, F 77, F 87, F 88, F 98, H 1000, Hiflex 211, HLB 0.80, Hydropalat WE 3161, Hydropalat WE 3162, Hydropalat WE 3164, Hydropalat WE 3966, Kolliphor 188, Kolliphor 407, Kolliphor P 188, Kolliphor P 188 Micro, Kolliphor P 237, Kolliphor P 407, Kolliphor P 407 Micro, L 101, L 103, L 121, L 123, L 180, L 31, L 35, L 350, L 43, L 44, L 45, L 61, L 62, L 62D, L 62LF, L 63, L 64, L 81, LeGoo-endo, Lutrol 127, Lutrol 68, Lutrol F 126, Lutrol F 68, Lutrol F 68NF, Lutrol F 77, Lutrol F 87, Lutrol FC 127, Lutrol L 42, Lutrol L 61, Lutrol L 63, Lutrol L 72, Lutrol L 92, Lutrol, Micro 68, Meroxapol 108, Meroxapol 172, Meroxapol 174, Meroxapol 252, Meroxapol 258, Meroxapol 311, Newpol PE 108, Newpol PE 61, Newpol PE 75, Newpol PE 78, Nissan Plonon 104, Nissan Plonon 188P, Nissan Plonon 202B, Nissan Plonon 204, Nissan Plonon 208, Nissan Plonon 235P, Nissan Plonon 407, Novanik 600/20, Novanik 600/40, Novanik 600/50, P 103, P 104, P 105, P 108, P 123, P 123 surfactant), P 31R1, P 407, P 450, P 65, P 68, P 75, P 84, P 85, PE 103, PE 10500, PE 3100, PE 3500, PE 300, PE 61, PE 6100, PE 6120, PE 6800, PE 8100, PE 9400, PEG 100P6, PEP 400-6, Pionin P 1310R, Pionin 2015R, Pionin P 2535, Plonon 104, Plonon 188P, Plonon 202B, Plonon 204, Plonon 208, Plonon 235P, Plonon 407, Pluriol PE, Pluriol PE 10100, Pluriol PE 10500, Pluriol PE 1600, Pluriol PE 3100, Pluriol PE 6100, Pluriol PE 6400, Pluriol PE 6810, Pluriol PE 9200, Pluriol PE 9400, Proxanol P 268, PS 137-25, RA 20, RPE 1720, RPE 1740, RPE 2520, Slovanik 310, Slovanik S 3040, Slovanik S 3070, Surfactant P 123, Surfonic POA 25R2, Synperonic 85, Synperonic F 108, Synperonic F 127, Synperonic F 68, Synperonic F 87, Synperonic L 64, Synperonic P 85, Synperonic P 94, Synperonic PE-F 103, Synperonic PE-F 108, Synperonic PE-F 127, Synperonic PE-F 88, Synperonic PE-P 85, Synperonic PE/L 121, Synperonic PE/L 61, Synperonic PE/L 64, Synperonic PE/P 65, Tergitol L 61PU, Voranol 222-056N, Voranol 223-060LM, and Voranol EP 1900.

Even further detergents of interest are 333E, 50 MB-26X, 75H380000, 75HB1440, 80DE40U, Acclaim 2200N, Actcol ED 36, Actcol ED 56, Actcol MF 12, Actcol MF 18, Actcol NF 04, Actinol P 3035, Adeka Carpol MH 150, Adeka Carpol MH 500, Adeka Carpol PH 2000, Adeka L 31, Adeka Polyether PR 5007, Adeka PR 2008, Adeka PR 3007, Adeka PR 5007, Adekanol L 34, Adekanol L 62, Adekanol NP 1200, Agnique ED 0001, Alcox EP 10, Alcox EP 20, Alkan 416, Alkox EP 10, Alkox EP 1010N, Alkox EP 10X, Alkox EP 20, Alkox EP 20X, Antifoam P 21, Atlas SF 131, Balab 615, Berol 370, Berol 374, Berol TVM 370, Blaunon EP 1461, Blaunon P 172, Blaunon P 201, Bloatguard, BPE 1500, Breox 50A1000, Breox 50A225, Breox 50A50, Breox 75W270, Breox 75W55000, Breox PAG 50A1000, BSP 5000, C 310B, Caradol ED 52-03, Carpol 2040, Carpol 2050, CE, CF 0802, Clerol PLB 847, CMC 252, CP 1000, CP 1000 (polyoxyalkylene), CP 1000L, CP 2000, CP 2000 (glycol), CP 2000L, CS-DF 900, D 10, D 21/700, Daltocel F 3001, DDL 400, DE 1, DE 1 (demulsifier), DEP 4000E, Desmophen 7100, Desmophen L 2830, Dezemulsionat E 96, Disfoam CC 222, DP 4002E, DP 6000E, DR 4500, ED 36, EL 551, Emkalyx EP 64, Emkalyx L 101, Emkarox VG 1051W, Emkarox VG 217W, Emkarox VG 379W, Emkarox VG 650W, Emulgen PP, Emulgen PP 150, Emulgen PP 250, Emulgen PP 290, EP 1660, EP 20, Epan 70, Epan 742, Epan U 102, Epan U 180, EPO 61, EPOB 15F, EPOB 20F, EPOB 30E, EPOB 50E, EPOB 80E, Ethox P 104, Excenol 2026T, Excenol 3040, Exocorpol, FT 257, Genapol PF, Genapol PF 10, Genapol PF 20, Genapol PFIO, GPE 2035, Gran Up US 30, HB 126, Hiflex 604, Hiflex D 300, Hiflex DR 4500, Hilube D 550, Hilube TB 1120, IBY 2, Industrol N 3, Jeffol PPG 3706, Jeffox FF 200, Jeffox PPG 2000, K-HN 8200, KE 220, Konion DR 802, Koremul LX 94, KRE 15, KWC-Q, L 5050, Laprol 1502-2-70, Laprol 1601, Laprol 2402C, Laprol 4202-2630, Laprol 5002-2630, Laprol D 10, LF 40, LF 40 (polyether), LF 62, LF 62 (polyether), Lupranol 2020, Lupranol 2022, Lupranol VP 9243, M 90/20, M-RPE 1293, MAG 540-90DT, Magcyl, Mazu DF 204, MM 8750, Monolan 12000E80, Monolan PB, MST 188, Multranol 9111, Multranol 9182, N 480, Nalco PP 10-3340, Nalco SPF-WTB 33, ND 8, Newcol 3280, Newpol PE 34, Nissan Disfoam CC 222, Nissan Nonion A 10R, Nissan Unilube 25DE, Nissan Unilube 30DP3B, Nissan Unilube 50DE25, Nissan Unilube 50MB168X, Nissan Unilube 50MB26X, Nissan Unilube 50TG32U, Nissan Unilube 60DP5B, Nissan Unilube 60MB161, Nissan Unilube 750DE2620, Nissan Unilube 75DE170, Nissan Unilube 75DE5000, Nissan Unilube 80DE120U, Nissan Unilube 80DE40E, Nissan Unilube 80DE40U, Nissan Unilube DE 60, Nixolen, Nixolen NS 4, Nixolen SL 19, Nixolen SL 2, Nixolen SL 8, Nixolen VS 13, Nixolen VS 2600, Nixolen VS 40, Nonion A 10R, Novanik 3010, NSC 63908, Nutek 7C, OHV 112, OHV 168.2, OHV 56.1, OHV 84.1, Oligoether L 1502-2-30, Oxalgon, Oxilube 50/150, Oxilube 50000, PAG, PAG 1, PAG 1 (polyglycol), PAG 2, PEG 600PR, PEG-PPG copolymer, PEP 101, PEPB 2080, PEPB 4555, Pepol AS 053X, PEPP 6040, PEPP 8020, PF 10, PF 20, PF 732, PF 80, Pluracare L 4370, Pluracol 686, Pluracol V, Pluradyne FL 11, Plurasafe WT 9000H, Pluriol A 2600PE, Pluriol A 4000PE, Pluriol L 64, Pluriol SC 9361, Polosham 188, Poloxalcol, Poloxalene, Poloxalene 2930, Poloxalene L 64, Poloxalkol, Poly-G 55NTP, Poly-G WT 90000, Poly-G WT 9150, Polyglycol D 21/150, Polyglycol EP 530, Polyglycol SD 301, Polyglykol D 21/700, Polyglykol PR 600, Polylon 13-5, PPG Diol 3000EO, PPPB 1585, PPPB 3070, Pr 168, PR 3007, PR 5007, PR 600, Prevocell EO, PRO 21, Proksanol, Proxanol, Proxanol 158, Proxanol 168, Proxanol 186, Proxanol 224, Proxanol 228, Proxanol P 168, Proxanol TsL 3, PS 072, PY 1002, RC 102, Regulaid, Rokopol 30P9, Rokopol D 1012E, Rokopol PE 40, Sannix PE 75, SBU 0319, SC 2204, SDT 06E, Separol 29, Separol WF 34, Separol WF 41, Sinoponic P-PE 64, Sipol L 61, SKF 18667, Slovanik, Slovanik 1070/7, Slovanik 610, Slovanik 630, Slovanik 660, Slovanik M, Slovanik M 340, Slovanik PV 670, Slovanik T 310, Slovanik T 320, Slovanik T 630, Supronic B 50, Supronic B 75, Supronic E 400, Supronic E 800, Surflo HS 1, Surfonic D 500, Synalox 40D100, Synalox 40D300, Synalox 40D700, Synthionic 80-20, Systol T 154, T 320, Takelac XLR 51, Tdiol 1000, Tdiol 2000, Teric PE, Teric PE 40, Teric PE 60, Teric PE 61, Teric PE 62, Teric PE 68, Teric PE 70, TPE 1000, TsL 431, TVM 370, Ucon 25H, Ucon 75H, Ucon 75H1400, Ucon 75H450, Ucon 75H90000, Unilube 50DE25, Unilube 50MB168X, Unilube 50MB26X, Unilube 60MB161, Unilube 75DE5000, Unilube 80DE120U, Unilube 80DE40U, Upol U, Velvetol OE 2NT1, Vepoloxamer, Voranol 222-056, Voranol 5287, Voranol P 2001, Wanefoam RCB 6, WL 1590, Woopol U, WS 661, Wyandotte 7135, X 423, X 427, XD 8379, XUS 15176, Yukol 4813, Z 4, Z 4 (demulsifier), Zeospan 8100L, ZS 2185, ZSN 8100, and ZSP 8100L.

Other amphiphilic block copolymers of interest include combination of one or more of the selected polymers polyethylene glycol (PEG), poly(D,L-lactide-co-glycolide) (PLGA), poly(lactic acid) (PLA), poly(glutamic acid) (PGA), poly(caprolactone) (PCL), N-(2-hydroxypropyl)-methacrylate (HPMA) copolymers, and poly(amino acids).

Improved Efficiencies in Workflow Design for Diagnosing Samples from Patients Infected with a Pathogen Immobilized reagents can improve a diagnostic workflow. Examples of immobilized reagents that may be used for enrichment of a target nucleic acid such as a target RNA contained in a target pathogen or exosome in a sample (see description above) may include one or more of: an oligonucleotide for hybridizing to the target nucleic acid, a poly-dT oligonucleotide, an oligonucleotide that serves as primer or probe for reverse transcription and/or replication of a target nucleic acid; a nucleic acid binding protein such as p19 (see for example U.S. Pat. No. 8,753,809), and where the target nucleic acid is DNA, an oligonucleotide reagent that hybridizes top the target DNA, a transcriptional activator protein that is sequence specific for the target DNA such as described in (see for example U.S. Pat. No. 9,963,687), or a nonspecific DNA binding protein such as a repair protein moiety or a polymerase moiety (such as SSO7); a methyl binding domain for binding methylated DNA; or for a pathogen containing a target DNA or RNA, a protein specific for binding a pathogen such as a virion (ACE 2 or GRP78 for SARS-CoV-2 spike protein), or an antibody for binding a specific antigen prior lysis of the pathogen or exosome so that extraneous material can be removed and the nucleic acid protected before lysis occurs. Immobilized reagents may include a combination so that the pathogen or exosome may be immobilized and on release of the nucleic acid from pathogen and exosome possibly in the same receiving tube, immobilized oligonucleotides can bind target nucleic acid for further characterization involving amplification to generate a detectable signal with high sensitivity. Reagents for LAMP may be immobilized on a substrate instead of the primers or target nucleic acid. Immobilization of LAMP reagents such as any or all of the strand displacing polymerase, reverse transcriptase, uracil deglycosylase, nuclease inhibitors and stabilizing reagents may be immobilized through the use of linkers and/or tags as discussed below.

In one embodiment, a mixture of immobilized reagents may be utilized in a composition where a portion of the immobilized reagents bind to and enrich for one or more pathogens or exosomes or their nucleic acids in a sample where the one or more pathogens and/or exosomes may be different targets from a single subject (for example, SARS-CoV-2 and Influenza viruses) or the same or different targets from multiple subjects. In the latter case, it is desirable to integrate a sample barcode into the reagent oligonucleotide used to capture the target nucleic acids.

Embodiments of the method described herein include washing and replacement of the biological fluid with a suitable RNAse or DNAse free buffer containing a lysis reagent, where a second portion of immobilized reagents captures and enriches the nucleic acid from the lysed particles.

For example, a nucleic acid from a biological sample including environmental samples can be detected after enrichment in a workflow that involves a minimum number of steps to produce a sensitive and specific result. In one example, a reagent is added to an environmental sample or a body fluid or a solution containing the contents of a swab (see above) to releases nucleic acid from a pathogen or exosome contained in the sample. The target nucleic acid hybridizes to an immobilized oligonucleotide on a substrate, such as a bead, so that separation of the immobilized nucleic acid from the rest of the solution can occur and a new solution can be added that has the necessary reagents for reverse transcription if the nucleic acid is RNA and for amplification, for example, using a polymerase chain reaction (PCR) or by isothermal amplification, for example, LAMP. The amplification event can then be detected using fluorescence or color by eye or by means of a simple device. Example 14 describes this approach for a coronavirus. The hybridized target nucleic acid can be released from the substrate after enrichment or the immobilized oligonucleotide can act as a primer or probe so as to function both to enrich the target nucleic acid and to initiate cDNA synthesis and/or replication.

The use of an immobilized reagent is intended to enhance efficiency of the workflow and potentially also enhance sensitivity of an assay for detecting the pathogen. Others have used immobilization for enrichment of exons in a genomic DNA sample (see for example U.S. Pat. Nos. 9,708,658, 9,567,632, 10,087,481 and 10,246,702). Embodiments described herein differ from the approaches described in these references because they are applicable to detecting a pathogen in a biological fluid and because the immobilized reagents may preferably serve as primers or probes to enrich and reverse transcribe and/or amplify the nucleic acid obtained from the biological sample in a single step.

In present embodiments, immobilized reagents may be provided in a lyophilized state and hydrated by the addition of a body fluid sample or sample containing a swab. The rehydrated reagent may include RNase inhibitors, DNase inhibitors, a detergent and/or surfactant, salts, reducing agents such as DTT or TCEP and proteolytic agents such as Proteinase K (such as a heat labile Proteinase K) and salts at a suitable concentration for aiding hybridization that is well understood in the art and/or destabilizing protein. Examples of a detergent such as a non-ionic detergent includes an amphiphilic water soluble polymorphic block copolymer of poly(ethylene oxide) (PEO) and poly(propylene oxide) (PPO), Tween 80 or Triton X suitable for disrupting a virus or exosome to release the nucleic acid. The type of detergent and/or surfactant may be selected depending on what proteolytic agents and reducing agents are included to aid in the release of nucleic acid from pathogens or exosomes. If the target nucleic acid is RNA, the use of reducing agents such as DTT, TCEP are desirable for stabilizing the RNA. The receiving tube may include in addition to lyophilized reagents or buffer containing reagents, a concentration of chaotropic salts for denaturing proteins. A heating step may be included where heat can cause denaturing of both proteins and nucleic acids and can be used to (a) inactive proteins (e.g., DNases and RNases) in the absence of proteinase K and (b) to melt nucleic acid secondary and/or intermolecular hybridization structures. However, a heat-denaturing step can be damaging to nucleic acids, particularly in the presence of divalent metals, Features of the Substrate for Immobilizing Oligonucleotide Reagents Unless specified otherwise, substrates as used with reference to enrichment refer to immobilization substrates. Substrates may be biological, non-biological, organic, inorganic or a combination thereof, and may be in the form of solid or porous particles, strands, precipitates, gels, sheets, tubings, spheres, containers, capillaries, pads, slices, films, plates such as microplates, slides, and have any convenient shape, including flat, disc, sphere, circle, etc. A substrate as used herein is meant to comprise any material (porous or non-porous, flexible or rigid) material onto which it is desired to capture and immobilize a reagent oligonucleotide. The substrate may form a colloidal solution from microbeads. The substrate may be beads that sediment in a solution. The substrate may be magnetic beads that can be concentrated in one part of a tube in response to an external magnet. The substrate may have any desired shape. A spherical shape is convenient because of the maximal surface area to volume. The substrate may include any desirable material known in the art suitable for binding oligonucleotides including magnetic, paramagnetic or non-magnetic beads.

The substrate for immobilizing reagents may be beads. Examples of suitable beads include magnetic or paramagnetic beads are coated with negatively charged molecules (e.g., carboxyl-containing molecules) which reversibly bind viral nucleic acids in the presence of a crowding agent (e.g., polyethylene glycol, such as 10-50% PEG) and salt (e.g., NaCl, such as 1-4 M NaCl). Examples of such beads are SPRI® and AM Pure® beads (Beckman Coulter, Brea, Calif.). Electrostatic reversible binding of nucleic acids to magnetic or paramagnetic beads may be improved in the presence of chaotropic salts (e.g., guanidine hydrochloride, guanidinium thiocyanate, etc.). In some other embodiments, magnetic or paramagnetic beads are coated with positively charged molecules (e.g., amino-containing molecules) which reversibly bind viral nucleic acids. In some further embodiments, magnetic or paramagnetic beads are coated with silica and reversibly binds nucleic acids based on salt concentration.

Substrate may be modified with secondary molecules to provide surfaces that facilitate coating of the substrate with a reagent. Examples are provided below.

The surface of the substrate may be composed of a variety of materials, for example, polymers, plastics, resins, polysaccharides, silica or silica-based materials, carbon, metals, inorganic glasses, membranes, etc., provided that the surface may support functional groups. Convenient substrates include: glass such as glass slides or glass beads; plastic such as in microtiter plates; functionalized polymers such as polymer beads. The surface of the substrates may be chemically modified for example by oxides such as silicon dioxide, tantalum pentoxide or titanium dioxide, or by metals, such as noble metal surfaces such as gold or silver, copper or aluminum surfaces. The substrate surface may be magnetized for example by Fe, Mn, Ni, Co, and their oxides. The substrate may be nanoparticles made of III-V semiconductor material (quantum dots) using for example GaN, GaP, GaAs, InP, or InAs) or II-VI semiconductor material using for example ZnO, ZnS, CdS, CdSe, or CdT or Ln-doped fluoride nanocrystals, rare earth-doped oxidic nanomaterials.

The surface of the substrate may inherently contain a linker, cross linker or spacer, a binder, a functional group, or electrostatic charge to prepare the substrate for a coating with oligonucleotide reagent. The substrate surface for binding an oligonucleotide can be added or activated in a coating (such as a polymer coating) of the substrate using a suitable material. Activation as used herein means a modification of a functional group on the surface of the substrate to enable coupling of a binding agent to the surface. Examples of polymer coatings include any suitable class of compounds, for example, polyethylene glycols, polyethylene imides, polysaccharides, polypeptides, or polynucleotides. Attachment of the polymers to the substrate surface may be achieved by a variety of methods which are readily apparent to a person skilled in the art. For example, polymers having trichlorosilyl or trisalkoxy groups may be reacted with hydroxyl groups on the substrate surface to form siloxane bonds. Attachment to a gold or silver surface may take place via thiol groups on the polymer. Alternatively, the polymer may be attached via an intermediate species, such as a self-assembled monolayer of alkanethiols. The type of polymers selected, and the method selected for attaching the polymers to the surface, will thus depend on the polymer having suitable reactivity for being attached to the substrate surface, and on the properties of the polymers regarding non-specific adsorption to, especially, DNA and RNA. The functional groups may be present on the polymer or may be added to the polymer by the addition of single or multiple functional groups. Optionally, a spacer arm can be used to provide flexibility to the binding oligonucleotide allowing it to interact with its environment in a way which minimizes steric hindrance with the solid support. The substrate can be modified with a binder, e.g., an antibody (or antibody fragment) or another affinity binder, e.g. streptavidin suitable for binding an oligonucleotide molecule that has been modified with the corresponding affinity ligand, e.g. biotin, and another affinity binder, e.g. an antibody recognizing part of the sequence of a biomolecule.

A binder as used herein means any agent that is a member of a specific binding pair. Examples of binders include agonists and antagonists for cell membranes, toxins and venoms, antigenic determinants, hormones and hormone receptors, steroids, peptides, enzymes, substrates, cofactors, drugs, lectins, sugars, oligonucleotides, oligosaccharides, proteins, glycoproteins, cells, cellular membranes, organelles, cellular receptors, vitamins, viral epitopes, and immunoglobulins, e.g., monoclonal and polyclonal antibodies. Examples of binding pairs include biotin-steptavidin/avidin, hapten/antigen-antibody, carbohydrate-lectin, or others known to those skilled in the art.

Additional examples of specific binding pairs allowing covalent binding of oligonucleotides to a solid support are e.g. SNAP-tag/AGT and benzylguanine derivatives (U.S. Pat. Nos. 7,939,284; 8,367,361; 7,799,524; 7,888,090; and 8,163,479) or pyrimidine derivatives (U.S. Pat. No. 8,178,314), CLIP-tag/ACT and benzylcytosine derivatives (U.S. Pat. No. 8,227,602), HaloTag and chloroalkane derivatives (Los, et al. Methods Mol Biol., 356:195-208 (2007)), serine-beta-lactamases and beta-lactam derivatives (International Patent Application Publication No. WO 2004/072232). In such as examples, oligonucleotides can be functionalized with benzylguanine, pyrimidine, benzylcytosine, chloroalkane, or beta-lactam derivatives respectively, and subsequently be captured in a solid support modified with SNAP-tag/AGT, CLIP-tag/ACT, HaloTag or serine-beta-lactamases.

Coating of the surface of the substrate with an oligonucleotide reagent by means of a binder may be achieved using an affinity binding pair such as biotinylated oligonucleotides for binding streptavidin-functionalized beads. Other affinity groups on oligonucleotide reagents include desthiobiotin, avidin, NeutrAvidin, protein A, protein B, maltose-binding protein, chitin, poly-histidine, HA-tag, c-myc tag, FLAG-tag, SNAP-tag, S-tag and glutathione-S-transferase (GST). In one example, magnetic or paramagnetic beads are coated with a poly dT sequence (e.g., 10-25 dT oligonucleotide) which is then used as for the direct binding of poly(A)+ viral RNA. Cap-binding protein attached to an immobilization substrate (an example of such a protein is the translation initiation factor 4E, eIF4E) can serve as reagents to directly bind target nucleic acid such as m7G(5')ppp(5')N (where N is any canonical nucleotide, including nucleotides with 2' O-methylation) capped viral RNA (see for example PCT/US2020/031653 for modified caps).

Properties of Oligonucleotides for Use in Immobilizing Target Nucleic Acid

The oligonucleotide for hybridizing target nucleic acid should be at least 6 nucleotides long and may include one or more modified nucleotides. The oligonucleotide may be designed to function as a probe or primer for reverse transcription and/or amplification. The oligonucleotide may be any of an RNA, DNA, peptide nucleic acid (PNA), a lock nucleic acid (LNA), an unlock nucleic acid (UNA), a triazole nucleic acid, a phosphorothioate oligonucleotide, or a combination thereof.

Modified nucleotides may improve oligonucleotide chemical stability (e.g., resistance to degradation at basic or acidic pH, at high temperatures, upon UV radiation, etc.), mechanical stability (e.g., resistance to degradation following mechanical manipulation such as sonication, acoustic shearing, etc.), and/or enzymatic stability (e.g., resistance to degradation in the presence of a nuclease such as a restriction enzyme, a DNase, a RNase, etc.). Modified nucleotides may also improve oligonucleotide ability to hybridize (e.g., through base pairing) with a fully or partially complementary nucleic acid targeted sequence.

Examples of base modifications include 2-aminopurine, 2,6-diaminopurine, 5-iodouracil, 5-bromouracil, 5-fluorouracil, 5-hydroxyuracil, 5-hydroxymethyluracil, 5-formyluracil, 5-proprynyluracil, 5-methylcytosine, 5-hydromethylcytosine, 5-formylcytosine, 5-carboxycytosine, 5-iodocytosine, 5-bromocytosine, 5-fluorocytosine, 5-proprynylcytosine, 4-ethylcytosine, 5-methylisocytosine, 5-hydroxycytosine, 4-methylthymine, thymine glycol, ferrocene thymine, pyrrolo cytosine, inosine, 1-methyl-inosine, 2-methylinosine, 5-hydroxybutynl-2'-deoxyuracil (Super T), 8-aza-7-deazaguanine (Super G), 5-nitroindole, formylindole, isothymine, isoguanine, isocytosine, pseudouracil, 1-methyl-pseudouracil, 5,6-dihydrouracil, 5,6-dihydrothymine, 7-methylguanine, 2-methylguanine, 2,2-dimethylguanine, 2,2,7-trimethylguanine, 1-methylguanine, hypoxanthine, xanthine, 2-amino-6-(2-thienyl)purine, pyrrole-2-carbaldehyde, 4-thiouracil, 4-thiothymine, 2-thiothymine, 5-(3-aminoallyl)-uracil, 5-(carboxy)vinyl-uracil, 5-(1-pyrenylethynyl)-uracil, 5-fluoro-4-O-TMP-uracil, 5-(C2-EDTA)-uracil, C4-(1,2,4-triazol-1-yl)-uracil, 1-methyladenine, 6-methyladenine, 6-thioguanine, thienoguanine, thienouracil, thienocytosine, 7-deaza-guanine or adenine, 8-amino-guanine or adenine, 8-oxo-guanine or adenine, 8-bromo-guanine or adenine, ethenoadenine, 6-methylguanine, 6-phenylguanine, nebularine, pyrrolidine, and puromycin. Examples of sugar modifications include but are not limited to those found in dideoxynucleotides (e.g., ddGTP, ddATP, ddTTP, and ddCTP), 2'- or 3'-O-alkyl-nucleotides (e.g., 2'-O-methyl-nucleotides and 3'-O-methyl-nucleotides), 2'- or 3'-O-methoxyethyl-nucleotides (MOE), 2'- or 3'-fluoro-nucleotides, 2'- or 3'-O-allyl-nucleotides, 2'- or 3'-O-propargyl-nucleotides, 2'- or 3'-amine-nucleotides (e.g., 3'-deoxy-3'-amine-nucleotides), 2'- or 3'-O-alkylamine-nucleotides (e.g., 2'-O-ethylamine-nucleotides), 2'- or 3'-O-cyanoethyl-nucleotides, 2'- or 3'-O-acetalester-nucleotides, 4'-C-aminomethyl-2'-O-methyl-nucleotides, and 2'- or 3'-azido-nucleotides (e.g., 3'-deoxy-3'-azide-nucleotides). Further examples of sugar modifications include those found in the monomers that comprise the backbone of synthetic nucleic acids such as 2'-O,4'-C-methylene-β-D-ribonucleic acids or locked nucleic acids (LNAs), methylene-cLNA, 2',4'-(N-methoxy)aminomethylene bridged nucleic acids (N-MeO-amino BNA), 2',4'-aminooxymethylene bridged nucleic acids (N-Me-aminooxy BNA), 2'-O,4'-C-aminomethylene bridged nucleic acids (2',4'-BNA(NC)), 2'4'-C—(N-methylaminomethylene) bridged nucleic acids (2',4'-BNA(NC)[NMe]), peptide nucleic acids (PNA), triazole nucleic acids, morpholine nucleic acids, amide-linked nucleic acids, 1,5-anhydrohexitol nucleic acids (HNA), cyclohexenyl nucleic acids (CeNA), arabinose nucleic acids (ANA), 2'-fluoro-arabinose nucleic acids (FANA), α-L-threofuranosyl nucleic acids (TNA), 4'-thioribose nucleic acids (4'S-RNA), 2'-fluoro-4'-thioarabinose nucleic acids (4'S-FANA), 4'-selenoribose nucleic acids (4'Se-RNA), oxepane nucleic acids (ONA), and methanocarba nucleic acids (MC).

Attachment of Oligonucleotides to the Substrate

Oligonucleotides as described herein may be attached to a substrate via a linker, a functional group, by cross linking, or by electrostatic charge that enables coating of the substrate with the reagent oligonucleotide but avoids non-specific binding of the target oligonucleotide. To immobilize the oligonucleotide on the solid support surface, the activated functional groups on the surface may be present on the predefined regions only, or alternatively on the entire surface, are reacted selectively with the functional groups present in the oligonucleotide molecules. The necessary reaction conditions, including time, temperature, pH, solvent(s), additives, etc. will depend on inter alia the particular species used and appropriate conditions for each particular situation will readily be apparent to the skilled person.

(a) Linker: The oligonucleotide reagent may be attached to the substrate through the oligonucleotide 5' end, 3' end or through an internal nucleotide. The oligonucleotide may be attached to the solid support through a linear or branched linker. The linker separating the oligonucleotide from the substrate may serve as steric spacer and does not necessarily have to be of defined length. Examples of suitable linkers may be selected from any of the hetero-bifunctional cross-linking molecules described by Hermanson, Bioconjugate Techniques, 2nd Ed; Academic Press: London, Bioconjugate Reagents, pp 276-335 (2008), incorporated by reference. The linker may be a flexible linker connecting the solid support to one or a plurality of same or different oligonucleotides.

(b) Functional Group or Cross Linking: A variety of methods are known for attaching an oligonucleotide to a substrate, including covalent bonding to the support surface and non-covalent interaction (binding by adsorption, e.g. cationic surfaces) of the oligonucleotide with the surface. Typically, covalent immobilization involves the reaction of an active functional group on the oligonucleotide with an activated functional group on the solid surface. Examples of reactive functional groups include amines, hydroxylamines, hydrazines, hydrazides, thiols, phosphines, isothiocyanates, isocyanates, N-hydroxysuccinimide (NHS) esters, carbodiimides, thioesters, haloacetyl derivatives, sulfonyl chlorides, nitro- and dinitrophenyl esters, tosylates, mesylates, triflates, maleimides, disulfides, carboxyl groups, hydroxyl groups, carbonyldiimidazoles, epoxides, aldehydes, acyl-aldehydes, ketones, azides, alkynes, alkenes, nitrones, tetrazines, isonitriles, tetrazoles, and boronates. Examples of such reactions include the reaction between an amine and an activated carboxy group forming an amide, between a thiol and a maleimide forming a thioether bond, between an azide and an alkyne derivative undergoing a 1,3-dipolar cycloaddition reaction, between an amine and an epoxy group, between an amine and another amine functional group reacting with an added bifunctional linker reagent of the type of activated bis-dicarboxylic acid derivative giving rise to two amide bonds, or other combinations known in the art. Other reactions, such as UV-mediated cross-linking can be used for covalent attachment of oligonucleotide to solid supports. Functionalization of surfaces with biological materials can also be used for attaching oligonucleotides to solid supports.

Alternatively, oligonucleotides can be specifically or non-specifically attached to SNAP-tag/AGT, CLIP-tag/ACT, HaloTag or serine-beta-lactamases and subsequently be captured in a solid support functionalized with benzylguanine, pyrimidine, benzylcytosine, chloroalkane, or beta-lactam derivatives, respectively.

To immobilize the oligonucleotide reagent on the surface of a substrate, the activated surface functional groups may be present in predefined regions of the substrate only, or alternatively on the entire surface of the substrate, and can be reacted selectively with functional groups present in the oligonucleotide molecules. The necessary reaction conditions, including time, temperature, pH, solvent(s), additives, etc. will depend on inter alia the particular species used and appropriate conditions for each particular situation will readily be apparent to the skilled person.

Reagent Oligonucleotides

Oligonucleotides can be synthesized to incorporate a desired functional group. Individual nucleotides can be modified either chemically or enzymatically with any type of functional group in order to provide the desired reactivity. This chemical or enzymatic functionalization can be extended to DNA and RNA molecules.

For example, oligonucleotides can be specifically or non-specifically attached to SNAP-tag/AGT, CLIP-tag/ACT, HaloTag or serine-beta-lactamases and subsequently be captured on a substrate functionalized with benzylguanine, pyrimidine, benzylcytosine, chloroalkane, or beta-lactam derivatives, respectively. Further examples of specific binding pairs allowing covalent binding of oligonucleotides to a solid support are acyl carrier proteins and modifications thereof (binder proteins), which are coupled to a phosphopantetheine subunit from Coenzyme A (binder substrate) by a synthase protein (see for example, U.S. Pat. No. 7,666,612).

Examples of proteins or fragments thereof allowing convenient binding of DNA to a solid support are e.g. chitin binding domain (CBD) (see for example, U.S. Pat. Nos. 584,247 and 7,732,565 and New England Biolabs) maltose binding protein (MBP) (See for example U.S. Pat. Nos. 5,643,758 and 8,623,615 and NEBExpress® MBP Fusion system (New England Biolabs, Ipswich, Mass.) omitting TEV cleavage), glycoproteins, transglutaminases, dihydrofolate reductases, glutathione-S-transferase a1 (GST), FLAG tags, S-tags, His-tags, and others known to those skilled in the art. Typically, an oligonucleotide is modified with a molecule which is one part of a specific binding pair and capable of specifically binding to a partner covalently or noncovalently attached to a solid support.

Coating of magnetic or paramagnetic beads with oligonucleotide primers may be achieved using an affinity binding pair, such as in streptavidin-functionalized beads and biotinylated oligonucleotides. Other preferred affinity groups include desthiobiotin, avidin, NeutrAvidin, protein A, protein B, maltose-binding protein, chitin, poly-histidine, HA-tag, c-myc tag, FLAG-tag, SNAP-tag, S-tag and glutathione-S-transferase (GST). In some other preferred embodiments, magnetic or paramagnetic beads are coated with a poly dT sequence (e.g. 10-25 dT oligonucleotide) which can then be used as for the direct binding of a target nucleic acid having a poly A tail such as a poly(A)+ viral RNA. Further preferred embodiments include magnetic or paramagnetic beads coated with a cap-binding protein (an example of such a protein is the translation initiation factor 4E, elF4E) which can be used for the direct binding of m7G(5')ppp(5')N (where N is any canonical nucleotide, including nucleotides with 2' O-methylation) capped viral nucleic acid (see for example PCT/US2020/031653).

Reactors for Analyzing Saliva.

A further consideration is the use of immobilized enzymes to improve a coronavirus testing workflow that utilizes saliva (or other bodily fluid) as a starting material to test for the presence of virus and uses LAMP to amplify nucleic acids derived from any SARS-CoV-2 virus present in the saliva to determine whether an individual is infected. In such embodiments, the enzymes involved in reverse transcription and LAMP are stably and efficiently immobilized on a microchip or any column reactor or fluid channel network (including low-cost polymers, such as elastomer, and paper). The enzymes may be irreversibly adsorbed or covalently linked to the solid surface using any one of the methods described in this invention. The saliva sample and any other buffers and reagents are flowed through the microreactor by a peristaltic pump. Any unwanted biological material may be separated from the desired viral genome by means of an integrated in-line microchannel containing an appropriate separation material. The separation material may be irreversibly adsorbed or covalently linked to channel to permit separation through one or more of the following techniques: size-selection, ion exchange, size-exclusion, affinity selection, hybridization, and liquid chromatography. The saliva nucleic acid is then flowed through one or more channel(s) where the enzymes involved in reverse transcription and LAMP are immobilized. A readout of the LAMP reaction will indicate or not the presence of viral genome.

Analysis of Assay Endpoints for Individual or Multiple Samples

Individual samples were tested herein in strip well tubes or 96 well plates with positive and negative outcomes observed by eye, and also with a spectrophotometer (SpectraMax) using dual wavelengths that captured signal from 560 nm (red) to 432 nm (yellow) from each 384 well plate. The data was then presented on a computer readout. The results particularly with a cooling step between the LAMP reaction and the reading of plates resulted in increased sensitivity in detecting as few as 20 copies of viral RNA/ well in 100% of samples tested.

An example of an automated workflow from sample to collection to output was envisaged in FIG. 28A-FIG. 28F. Although there are many possibilities in the uses of robotic devices for individual steps, the exemplified workflow is predicted to have a capability to perform 100,000 reactions in 20 hours.

There is some flexibility based on the parameters described herein that will be apparent to a person of ordinary skill in the art as to one or more modifications selected from: the source of a sample from a patient; sample storage; sample lysis containing for example, guanidine salts, reducing agent and optionally detergent to provide RNA or DNA that may then be directly amplified or sequenced; the type of sequencing platform selected as to whether it is a single molecule sequencer such as Oxford Nanopore or a sequencer of libraries with adapters such as required by an Illumina sequencing platform; the type of amplification reaction selected according to a high through put time and cost efficient LAMP based reaction using appropriately selected single or multiple primer sets or an RT-qPCR real time slightly more sensitive but less time and cost efficient than LAMP; carry over prevention; the optimization of the amplification reactions with respect to pH, buffer content including guanidine salts, and concentration, of reagents; end point color change be it pH dependent or dependent on a chemical reaction or fluorescence; and a suitable reader for distinguishing positives from negative samples in a binary determination and a rapid read out.

LAMP sensitivity has been improved by reducing background and enhancing signal and these improvements can be followed through to the present assay. See for example: U.S. Pat. Nos. 9,121,046, 9,546,358, 9,074,249, 9,074,243, 9,157,073, and 9,127,258 in addition to U.S. Pat. Nos. 9,580,748, 9,034,606, and 10,597,647 all incorporated in entirety by reference. These modifications can be incorporated into the colorimetric LAMP assay described herein to improve the detection of pathogens even further. U.S. Pat. No. 10,253,357 is also incorporated by reference.

The diagnostic test of whether a pathogen is present in a sample can be scaled up without any difficulty so that any of 1-1000s of reactions can be performed at the same time. If the reactions are performed in 96 well dishes or in 1000 well dishes, a robot liquid handler can add master mix to each well and then the swab sample and a computer system can record the color changes and the location of the well testing positive. For individual or small numbers of samples, the reactions might be performed in microfuge or PCR tubes. The entire diagnostic test can be completed within 4 hours, for example in less than 3 hours, for example less than 2 hours, for example less than 1 hour from the time of taking the sample to obtaining a result. The diagnostic test can be performed in a doctor's office or even at home.

In certain embodiments the master mix including enzymes, dyes, primers and nucleotides may be dried onto a solid matrix such as paper so that addition of a measured droplet of the sample onto the paper and a heating step even on a surface heated by a homemade water bath, or small heating block that can be transported in a backpack for environmental use results in a color change to indicate a result. Alternatively, the master mix may be freeze dried or lyophilized and contained in a tube ready for addition of a sample in the home or clinic.

Embodiments include incorporating amplification reagents in a facemask possibly immobilized on beads such that when droplets of saliva containing virus contact the beads, fluorescence results from an isothermal amplification reaction. Whereas LAMP as described in embodiments herein requires a 65° C. temperature step, this requirement may be circumvented in the future for LAMP or by use of other isothermal amplification methods. Alternatively, the combination of a saliva droplet containing a virus particle interacting with immobilized regent on a bead might trigger an exothermic chemical reaction. The higher the virus load, the stronger the signal that would result from amplification. Alternatively, the signal from the production of hydrogen ions or change in flow of electrons (that result from amplification as pyrophosphates are released when dNTPs are incorporated during amplification reaction) that generates a visual signal might in turn trigger a sound wave that is amplified resulting in an audible sound. Such microelectronic technology already exists in a different formats and could be constructed using synthetic biology constructed circuits. An audible sound could alert the wearer of the mask of $3^{rd}$ party released virus without the need to remove the mask while a visual signal would alert others of the wearer of the mask being infected.

In one embodiment, a discrete portion of a face mask may contain a chamber containing lysis reagent in a dried or liquid form so that incoming saliva droplets will be lysed and the polynucleotides released.

Embodiments describing improvements in the LAMP reaction that include carryover prevention, RNase inhibition, enhancement of sensitivity and rate of the LAMP reaction by the use of guanidine salts and/or reduced NaCl or KCl in the buffer, selecting primer sets and multiplexing primer sets, lyophilization of reagents can be combined in any combination for purposes of automation of large numbers of assays for genomic studies, gene expression studies or epidemiology analysis as well as point of care and miniaturization of tests to act as environmental sensors of pathogens.

Multiplexing as discussed herein can be achieved by pooling patient samples or purified nucleic acids from different sources and testing for the presence of a single species of target sequence such as contained in a single infectious agent such as SARS-CoV-2. The samples in the pool can be differentiated by the use of random sequence identifiers referred to in the art as "unique identifiers" (UIDs), "unique molecular identifiers" (UMIs) or "degenerate base regions" (DBRs) etc. pH or fluorescent colorimetric LAMP as discussed herein is well suited for analyzing pooled samples.

Multiplexing may also be used on a single vertebrate subject sample, to determine the presence any one of several different target nucleic agents such as genes, or infectious agents such as viruses, bacterial or fungi such as respiratory viruses such a coronavirus, a rhinovirus, a respiratory syncytial virus, an Influenza virus, a parainfluenza virus, a metapneumovirus, an adenovirus and a bocavirus. One example of a multiplex test would include Influenza A and B and SARS-CoV-2 that may occur together or separately in humans in winter seasons in northern and temperate zones. Other vertebrates may include mammals such as wild or domestic mammals such as bats, pigs or birds that are carriers of viruses that are pathogenic for humans.

Multiplex LAMP for multiple targets is preferably performed using fluorescent colorimetric LAMP for example using "Detection of Amplification by Releasing of Quenching" (DARQ) that supplements a standard LAMP primer set with a pair of oligonucleotides in duplex form for detection (see for example, U.S. Pat. No. 9,074,243). The DARQ oligonucleotide duplex consists of a 5'-modified version of the FIP primer (Q-FIP) annealed to a 3'-modified oligonucleotide represent the F1 region (Fd), complementary to the FIP in its 5' section. The fluorescent dye and quencher can be present either on the 5' or complementary 3' oligonucleotide of the duplex. The two modifications are selected to be dark quencher-fluorophore pairs, and when the quenched FIP is incorporated into the LAMP product, subsequent amplification displaces the Fd oligo, releasing quenching and producing fluorescent signal specific to the label and target of interest. A list of some fluorescent dyes and quenchers are provided in U.S. Pat. No. 9,074,243.

Other versions of this approach for single targets have been used, moving the quencher and fluorophore to a Loop primer or incorporated into the amplification products and detected after the reaction (see for example, Tanner, et al. Biotechniques 53(2), 81-89 (2012), Curtis, et al. J. Virol Methods 255 91-97 (2018) and Yaren, et al. medRxiv doi:10.1101/2020.09.29. 20204131 2020.2009.2029.20204131 (2020)).

As the SARS-CoV-2 pandemic continues into flu season, the ability to distinguish which causative agent is responsible for what can manifest as very similar symptoms will be of great importance for diagnostics and disease surveillance. A patient presenting with respiratory symptoms may have SARS-CoV-2, Influenza A or B, RSV, a rhinovirus, etc. and using one test to identify multiple infectious agents in the same procedure will save time and cost. Most importantly, it gives a more definitive diagnostic identification. Example 17 describe a diagnostic assay in which multiple LAMP primer sets were used in a single tube and together were capable of detecting the two most common influenza strains and SARS-CoV-2 (SARS-CoV-2, Influenza A, Influenza B, and an internal control). The diagnostic assay also conformed to the useful properties of speed, sensitivity and non-interference thereby expanding the utility of the widely-used LAMP chemistry to a multiplex diagnostic setting (see for example, FIGS. 31A-31E and 32A-32C).

The selection of appropriate targets, confirmation of minimum interference between primer sets, and choice of a suitable internal control to verify LAMP was achieved to enable a successful multiplex reaction to be performed. It was found that an internal control (a cellular RNA such as actin (ACTB)) could be effectively incorporated into a multiplex DARQ LAMP reaction without interference providing that the concentration of the primer set for detecting the control was lower than the concentration used to detect respiratory pathogens in the sample. It was found that the concentration of the control primer set should preferably be between 25% and 80% of the concentration of the primer sets for pathogen targets. For example, the preferred range was 50%-80% or 50%-75%.

Criteria were identified to establish the number and type of fluorescent dyes including wavelength emission spectrum, sensitivity of emitted signal from the unquenched sample and suitable multichannel devices for reading endpoint or continuous signals from multiple different fluorescent labels from a single reaction vessel.

It was confirmed that multiplex DARQ LAMP using primer sets for multiple virus targets and an internal control had advantageous properties including:
  (a) The rate of the DARQ LAMP showed a target dosage response that was approximately equivalent to the conventional LAMP monitored by the intercalating dye-SYTO-9. SARS-CoV-2 RNA was used at various concentrations with the E1 primer set and ACTB (actin) control primer set.
  (b) The detection sensitivity of multiplex DARQ LAMP was determined to be similar to standard single target LAMP and DARQ LAMP under the same conditions as in (a). The addition of a second primer set did not significantly alter the detection sensitivity.
  (c) End point fluorescence measurements could be reliably used to distinguish between positive and negative samples using a threshold value that was set based on negative (background) values. Positives were matched to those called during real time monitoring. The end point result demonstrates compatibility of endpoint, plate-reader measurements with multiplex DARQ LAMP, enabling use on a wider range of instrument types and increasing potential test throughput compared with real time detection. A limitation of real time detection is that it relies on certain detection instruments that are tied up during the entire incubation time of samples thereby negatively impacting sample throughput.

(d) DARQ LAMP could be used for detecting 5 different targets using 5 different sets of LAMP.
  primers. The limitation of 5 was set by the number of channels in a BioTek reader (BioTek, Winooski, Vt.). BioTek Synergy Neo2 microplate reader was used detecting a fluorescence signal for 5-FAM (Excitation, 484/20, Emission 530/25, Signal Gain 75), HEX (524/20, 565/20, 75), 5-ROX (569/20, 615/25, 85) and Cy5 (640/20, 682/20, 75). Indeed, there are as many as a hundred different fluorescent dyes that have different wavelengths across the 480 nm-640 nm spectrum. Providing there is at least 20 nm-40 nm of wavelength between individual fluorescence peaks, a reader might accommodate primer sets and targets that exceed 5 targets in a single multiplex reaction. Primer sets against two different Influenza RNA targets and one SARS-CoV-2 RNA target and a single internal control were used to establish the feasibility of multiplexing.

Unless otherwise defined, all technical and scientific terms used herein have the same meaning as commonly understood by one of ordinary skill in the art to which this disclosure belongs. Still, certain elements may be defined for the sake of clarity and ease of reference. It is also to be understood that the terminology used herein is for the purpose of describing particular embodiments only, and is not intended to be limiting, since the scope of the present teachings will be limited only by the appended claims.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular Biology, 2nd ed., John Wiley and Sons, New York (1994), and Hale & Markham, the Harper Collins Dictionary of Biology, Harper Perennial, N.Y. (1991) and the like.

As used herein and in the appended claims, the singular forms "a", "an", and "the" include plural referents unless the context clearly dictates otherwise. For example, the term "a protein" refers to one or more protein, i.e., a single protein and multiple proteins. It is further noted that the claims can be drafted to exclude any optional element.

Aspects of the present disclosure can be further understood in light of the embodiments, section headings, figures, descriptions, and examples, none of which should be construed as limiting the scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Numeric ranges are inclusive of the numbers defining the range. All numbers should be understood to encompass the midpoint of the integer above and below the integer i.e. the number 2 encompasses 1.5-2.5. The number 2.5 encompasses 2.45-2.55 etc. When sample numerical values are provided, they may represent, unless specified otherwise, an intermediate value in a range of values. If specified, an individual numerical value may represent an extreme point in a range. Where a plurality of numerical values are provided these may represent the extremes of a range unless specified. If specified, these values may represent intermediate values in a range.

The term "non-naturally occurring" as used herein refers to a composition that does not exist in nature. A "non-naturally occurring" protein may have an amino acid sequence that is different from a naturally occurring amino acid sequence for example, one or more amino acid substitutions, deletions or insertions at the N-terminus, the C-terminus and/or between the N- and C-termini of the protein. Hence the non-naturally occurring protein may have less than 100% sequence identity to the amino acid sequence of a naturally occurring protein although it may have at least 80%, at least 85%, at least 90%, at least 95%, at least 97%, at least 98%, at least 98.5% or at least 99% identity to the naturally occurring amino acid sequence. In certain cases, a non-naturally occurring protein may include a protein that has a post-translational modification pattern that is different from the protein in its natural state for example, an N-terminal methionine or may lack one or more post-translational modifications (e.g., glycosylation, 5 phosphorylation, etc.) if it is produced by a different (e.g., bacterial) cell.

In the context of a nucleic acid, the term "non-naturally occurring" refers to a nucleic acid that contains: a) a sequence of nucleotides that is different from a nucleic acid in its natural state (i.e., having less than 100% sequence identity to a naturally occurring nucleic acid sequence); b) one or more non-naturally occurring nucleotide monomers (which may result in a non-natural backbone or sugar that is not G, A, T or C); and/or c) may contain one or more other modifications (e.g., an added label or other moiety) to the 5'-end, the 3' end, and/or between the 5'- and 3'-ends of the nucleic acid.

In the context of a composition, the term "non-naturally occurring" refers to: (a) a combination of components that are not combined by nature, e.g., because they are at different locations, in different cells or different cell compartments; (b) a combination of components that have relative concentrations that are not found in nature; (c) a combination that lacks something that is usually associated with one of the components in nature; (d) a combination that is in a form that is not found in nature, e.g., dried, freeze dried, crystalline, aqueous; and/or (e) a combination that contains a component that is not found in nature. For example, a composition may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature. The non-naturally occurring polymerase may be purified so that it does not contain DNases, RNases or other proteins with undesirable enzyme activity or undesirable small molecules that could adversely affect the sample substrate or reaction kinetics.

All publications, patents, and patent applications mentioned in this specification are herein incorporated by reference to the same extent as if each individual publication, patent, or patent application was specifically and individually indicated to be incorporated by reference including: U.S. Provisional Ser. Nos. 62/988,696, 63/001,909, 63/013,422, 63/022,303, 63/027,216, 63/048,556, 63/059,891, 63/068,564, 63/106,120 and 63/165,465 and U.S. Ser. Nos. 16/938,575, 17/122,979, 17/178,395 and 17/221,541.

Certain embodiments of the invention are summarized below:

1. A master mix comprising: a strand displacing polymerase suitable for Loop-Mediated Isothermal Amplification (LAMP) of DNA; dATP, dGTP, dCTP, and dTTP; at least one reagent that changes color or provides fluorescence if amplification occurs; wherein the master mix is either dried or in a weakly buffered solution at a starting pH which is measurably altered during amplification.
2. The master mix according to 1, immediately above, further comprising a reverse transcriptase.
3. The master mix according to 2, immediately above, wherein the reverse transcriptase is selected from an HIV derived reverse transcriptase, an intron expressed reverse transcriptase and a reverse transcriptase variant of mouse murine virus.
4. The master mix according to any of 1 through 3 above, wherein the starting pH is in the range of pH 7.5-pH 9.0.
5. The master mix according to 4, wherein the starting pH is preferably in the range of pH 7.8-pH 8.5.
6. The master mix according to any of 1 through 5, wherein the master mix is in a weakly buffered solution of 5 mM Tris or less.
7. The master mix according to any of 1 through 6, wherein the master mix further comprises an aptamer for regulating the activity of the strand displacing polymerase.
8. The master mix according to any of 1 through 7, wherein the master mix further comprises one or more RNase inhibitors.
9. The master mix according to 8, wherein the RNase inhibitors comprise an aptamer for inhibiting RNase A, an aptamer for inhibiting RNase I and/or a protein inhibitor of RNAse.
10. The master mix according to 1 through 9, further comprising at least one set of primers having specificity for a target nucleic acid.
11. The master mix according to 1 through 10, further comprising a plurality of sets of primers having specificity for a target nucleic acid.
12. The master mix according to 1 through 11, wherein the at least one reagent includes a dye that is pH sensitive and changes color after an amplification reaction in which the pH is altered.
13. The master mix according to 1 through 12 further comprising dUTP.
14. The master mix according to 1 through 13, wherein the at least one reagent includes a dye that is a metallochromic indicator.
15. The master mix according to 1 through 14, wherein the at least one reagent comprises a metallochromic dye and a fluorescent dye.
16. The master mix according to 1 through 15, wherein the metallochromic indicator is 4-(2-pyridylazo) resorcinol (PAR).
17. The master mix according to 1 through 16, wherein the master mix is freeze dried, air dried, or lyophilized.
18. The master mix according to 1 through 17, wherein the master mix is immobilized; such as wherein the master mix is immobilized on paper, or on a natural or synthetic polymer.
19. The master mix according to any of 1 through 16, wherein the master mix is in liquid form in a reaction container.
20. The master mix according to any of 1 through 19, further comprising dUTP.
21. A method for determining whether a target nucleic acid is present in a sample, comprising:
    (a) placing the sample into an aqueous solution in a container;
    (b) bringing an aliquot of the sample into contact with a master mix according to any of claims 1 through 20 to form a reaction mixture; and
    (c) determining whether the target nucleic acid is present in the sample by a change in the color or fluorescence of the mixture.
22. The method according to 21, wherein the sample is a clinical sample, such as a sample of a body fluid or a sample taken from a swab, an environmental sample, or a sample of purified nucleic acid.
23. The method of 21 or 22, wherein the target nucleic acid is: associated with a pathogen or is a diagnostic target for pathogenesis; associated with gene expression; or an indicator of a metabolic response to a pharmaceutical preparation or allergen.
24. The method of 23, wherein the target nucleic acid is an RNA.
25. The method according to 23 or 24, wherein the target nucleic acid is associated with a pathogen.
26. The method according to 25, wherein the pathogen is a virus.
27. The method according to 26, wherein the virus is an RNA virus.
28. The method of 21 or 22, wherein the target nucleic acid is DNA, and the method is for determining genetic loci correlated to a phenotype.
29. The method of 28, wherein the genetic loci are selected from the group consisting of a single nucleotide polymorphism (SNP) in a genome, an exon, or gene in the genome.
30. The method according to any of 21 through 29, wherein the container contains multiple compartments each for analyzing a separate sample.
31. The method according to any of 21 through 30, wherein the change in color or fluorescence of the mixture can be digitized and recorded by a computer.
32. A composition, comprising: one or more primer sets suitable for amplification, the primer sets having specificity for a single template nucleic acid of interest; and a buffer containing a molecule comprising C—$(NH_2)_2NH^+$.
33. The composition according to 32, wherein the molecule comprising C—$(NH_2)_2NH^+$ is selected from guanidine hydrochloride, guanidine thiocyanate, arginine, and guanidine sulfate.
34. The composition according to 32 or 33, wherein the one or more primer sets are primer sets for Loop-Mediated Isothermal Amplification (LAMP).
35. The composition according to any of 32 through 34, wherein the one or more primer sets are two or three or four primer sets having specificity for a single template nucleic acid.

36. The composition according to any of 32 through 36, further comprising one or more reagents selected from an RNAse inhibitor, a reverse transcriptase, a thermolabile Proteinase K, and a polymerase.
37. The composition according to any of 32 through 37, further comprising dNTPs; and optionally further comprising a reporter molecule for detecting amplification in the presence of a target nucleic acid.
38. The composition according to 37, wherein the reporter molecule comprises a metallochromic dye.
39. The composition according to 38, wherein the metallochromic indicator is 4-(2-pyridylazo) resorcinol (PAR).
40. A method of isothermal amplification (e.g., LAMP), comprising: (a) adding the composition according to any of 1 through 20, and 32 through 38, to a sample comprising a target nucleic acid; and (b) detecting whether the target nucleic acid is present in the sample.
41. A method for detecting a target nucleic acid in a biological sample, comprising:
   (a) treating the biological sample with a lysis mixture comprising a C—(NH$_2$)$_2$NH$^+$ salt, and a reducing agent; at an elevated temperature for an effective period of time;
   (b) adding an aliquot of the sample from (a) into a master mix according to any of 1 through 20;
   (c) incubating the mixture under conditions for Loop mediated amplification (LAMP) to permit a color change in the presence of a detectable amount of a target nucleic acid; and
   (d) determining whether the sample contains the target nucleic acid.
42. The method according to 41, wherein the detectable amount is less than 100 copies of the target nucleic acid.
43. The method according to 41 or 42, wherein the C—(NH$_2$)$_2$NH$^+$ salt in the lysis mixture is a guanidine salt.
44. The method according to any of 41 through 43, wherein the guanidine salt is present in a 10× lysis buffer.
45. The method according to any of 41 through 44, further comprising increasing the sensitivity of detection by determining whether the sample contains the target nucleic acid using a dual wavelength spectrophotometer.
46. The method according to any of 41 through 45, wherein the elevated temperature in (a) is 95° C. and the effective time is 5 minutes.
47. The method according to any of 41 through 46, wherein (a) further comprises allowing the sample in the lysis mixture to incubate at room temperature before treating with an elevated temperature.
48. The method according to 47, wherein if the incubation time at room temperature is at least 30 minutes then the elevated temperature may be 75° C. or less, for a period of time that is 60 minutes or less.
49. The method according to any of 41 through 48, wherein the lysis mixture further comprises a detergent.
50. The method according to 49, wherein the detergent is Triton X.
51. A composition comprising: a guanidine salt, a reducing agent and detergent.
52. The composition according to 51, further comprising LiCl.
53. The composition according to 51 or 52, wherein the guanidine salt is guanidine hydrochloride (Guanidine HCl).
54. The composition according to any of 51 through 53, wherein the reducing agent is Triton X.
55. The composition according to any of 51 through 54, wherein the reducing agent is Tris(2-carboxyethyl) phosphine hydrochloride (TCEP).
56. The composition according to any of 51 through 55, further comprising a biological sample.
57. The composition according to any of 51 through 56, wherein the biological sample is saliva.
58. The composition according to any of 51 through 57, wherein the composition further comprises a master mix according to any of 1 through 20.
59. The composition according to any of 51 through 58, comprising at least one LAMP primer set.
60. The composition according to any of 51 through 59, wherein the at least one LAMP primer set is at least two different LAMP primer sets for detecting a single target.
61. The composition according to any of 51 through 60, wherein the composition further comprises a target polynucleotide.
62. The composition according to any of 51 through 61, wherein the target polynucleotide is a coronavirus RNA.
63. A method for preparing a biological sample for an amplification reaction; comprising:
   (a) obtaining a lysis mixture comprising guanidine salt, a reducing agent, and a detergent;
   (b) combining the lysis mixture in (a) with a biological sample containing a target polynucleotide to form a diagnostic sample; and
   (c) analyzing an aliquot of the diagnostic sample for identifying if the template polynucleotide is present and optionally the sequence of the template polynucleotide, wherein the step of analyzing is selected from one or more of (i) amplifying the target polynucleotide to detect the presence of a template polynucleotide by a change in color or fluorescence; (ii) amplifying the target polynucleotide and sequencing the amplified polynucleotides; and (iii) direct sequencing of an aliquot of the diagnostic sample.
64. A method according to 63, wherein a 2× lysis mixture comprises guanidine salt in the range of 300 mM-1.5 M guanidine hydrochloride, TritonX in the range of 1%-6%, and TCEP in the range of 40 mM-120 mM.
65. The method of 64, wherein the 2× lysis mixture further comprises LiCl.
66. The method of 65, wherein the LiCl is in the range of 50 mM-100 mM.
67. The method of any of 64 through 66, wherein the 2× lysis mixture comprises 800 mM guanidine hydrochloride, 4% Triton X and 80 mM TCEP.
68. The method of 67, wherein the 2× lysis mixture further comprises 150 mM LiCl.
69. The method of any of 63 through 68, wherein (b) further comprises increasing the temperature of the diagnostic sample to release the polynucleotides from biological material in the sample.
70. The method of 69, wherein the step of increasing the temperature further comprises raising the temperature in the range of 65° C.-95° C. wherein the time of incubation at the raised temperature is inversely proportional to the temperature.

71. The method of 69, wherein increasing the temperature further comprises raising the temperature to 75° C. for 20 minutes.

72. The method of 70, further comprises incubating the sample at room temperature for 30 minutes prior to increasing the temperature.

73. The method according to any of 63 through 72, wherein the step of amplifying further comprises amplifying the target polynucleotide by LAMP.

74. The method according to 73, wherein the LAMP is pH-dependent colorimetric LAMP.

75. The method according to 74, wherein the pH of the lysis mixture is at least pH 7.9 if the biological sample is saliva.

76. The method according to 63, wherein sequencing further comprises adding sample barcodes for large scale multiplexing of samples, wherein the bar code is added in the primer where amplification precedes sequencing or by ligation when the target polynucleotides are sequenced directly.

77. The method according to any of 40 through 48, and 63 through 75, further comprising a high throughput automated workflow for performing the steps of the method.

78. A kit comprising the master mix of any of 1 through 20, and/or the compositions of 32 through 39, and 51 through 62, wherein the kit optionally further comprises a heating block suitable for heating a reaction tube, plate, or paper, or a plurality of the same.

79. A kit for performing multiplex loop mediated amplification (LAMP) reaction, comprising:
   (a) a plurality of sets of oligonucleotide primers, wherein the different sets of primers hybridize to different template sequences in the same target nucleic acid and are suitable for amplifying the different template sequences of the target nucleic acid by LAMP;
   (b) a strand-displacing DNA polymerase; and
   (c) a guanidinium salt;
   wherein the reagents of (a)-(c) are in separate containers.

80. The kit according to 79, wherein the stand-displacing DNA polymerase of (b) is contained in a master mix that further comprises:
   deoxynucleotide triphosphates including dUTP;
   a reversible inhibitor of polymerase activity that blocks polymerase activity at a temperature below 40° C.; and
   at least one dye or fluorescent indicator for detecting an amplification product by a change in color or fluorescence.

81. The kit according to 80, further comprising instructions to combine the reagents of (a)-(c) with a target DNA in order to amplify the different template sequences by LAMP.

82. The kit according to 81, further comprising a reducing agent.

83. The kit according to 82, wherein the reducing agent is Tris(2-carboxyethyl)phosphine hydrochloride (TCEP).

84. The kit according to 79, wherein the guanidinium salt is guanidine hydrochloride.

85. The kit according to 80, wherein the indicator is a metallo-chromatic dye.

86. The kit according to 85, wherein the metallo-chromatic dye is hydroxynaphthol blue.

87. The kit according to 80, wherein the indicator is phenol red.

88. The kit according to 80, wherein the master mix further comprises a reverse transcriptase.

89. The kit of 79, wherein each set of oligonucleotide primers comprises 4, 5 or 6 primers.

90. The kit according to 79, wherein the target nucleic acid is derived from a coronavirus RNA and each set of primers hybridizes to a different template sequence in the coronavirus RNA genome, or cDNA copy thereof.

91. The kit according to 79, wherein the plurality of sets of oligonucleotide primers comprise a mixture of 12 different primers.

92. The kit according to 79, wherein the oligonucleotide primers target multiple target nucleic acids with a plurality of sets of oligonucleotide primers for each target.

93. A method comprising:
   (a) combining the kit of 79 with a target nucleic acid to produce a reaction mix; and
   (b) incubating the reaction mix to produce an amplification product.

94. The method according to 93, wherein the composition further comprises a reverse transcriptase if the target nucleic acid is RNA, and the method comprises reverse transcribing the RNA into DNA.

95. The method according to claim 94, wherein the composition of claim 79 further comprises at least one additional reagent selected from the group consisting of: reverse transcriptase, UDG, dUTP, dATP, dTTP, dGTP, dCTP, a color or fluorescent indicator that changes color or fluorescence when amplification has occurred, a reducing agent and a detergent.

96. The method according to 93, wherein the target nucleic acid is from an infectious agent.

97. The method according to 96, wherein the infectious agent is a coronavirus.

98. The method according to 93, wherein each set of oligonucleotide primers comprises 4 or 6 primers.

99. The method of claim 93, wherein the plurality of sets of primers for the target nucleic acid comprise at least 2 sets of primers, each set of primers hybridizing to a different target sequence in the coronavirus genome, or cDNA copy thereof.

100. The method of 93, wherein the plurality of sets of primers for the target nucleic acid comprise at least 2 sets of primers and (a) further comprises including multiple different target nucleic acids wherein a plurality of sets of primers hybridize to a different target sequence in each target nucleic acid.

101. A method for detecting SARS-CoV-2 virions in saliva of a subject, comprising:
   (a) collecting saliva in a receiving vessel containing reagents comprising (i) oligonucleotides immobilized on a substrate in a diluting volume of buffer containing DNase inhibitors, RNase inhibitors and proteolytic agents or (ii) lyophilized oligonucleotide immobilized on a substrate, DNase inhibitors, RNase inhibitors and one or more proteolytic agents for rehydration in contact with the saliva;
   (b) permitting virions in contact with the reagents to be disrupted, releasing viral RNA for binding to the immobilized oligonucleotides;
   (c) removing the non-bound material from the receiving tube;

(d) adding a master mix containing primers specific for SARS-CoV-2 RNA and/or cDNA for reverse transcribing the RNA and amplifying the cDNA; and
(e) detecting a change in a signal resulting from amplifying cDNA.

102. The method according to 101, wherein the oligonucleotides are immobilized on beads or on the surface of the receiving vessel.

103. The method according to 101 or 102, wherein the oligonucleotides are characterized by a single sequence capable of binding to either end of the virion RNA or to an internal sequence in the virion RNA.

104. The method according to 101 or 102, wherein the oligonucleotides are characterized by a plurality of different sequences wherein each sequence targets a different region of the viral genome.

105. The method according to 101 or 102, wherein the oligonucleotides are characterized by one or a plurality of sequences capable of acting as a primer to initiate reverse transcription.

106. The method according to 101 or 102, wherein the oligonucleotides are characterized by a plurality of sequences capable of targeting different viral RNA genomes such as SARS-CoV-2 and Influenza.

107. The method according to any of 101 through 106, wherein the one or more proteolytic reagents are selected from Proteinase K, thermolabile Proteinase K, salt, detergent, and reducing agent.

108. The method according to any of 101 through 107, wherein the receiving vessel further contains a guanidinium salt.

109. The method according to any of 101 through 108, wherein amplifying cDNA is achieved by isothermal amplification.

110. The method according to 109 wherein the isothermal amplification is LAMP.

111. The method according to any of 101 through 107, wherein the amplification is achieved by a polymerase chain reaction.

112. The method according to any of 101 through 111, wherein the change in signal is a change in color or fluorescence.

113. The method according to 112, further comprising, detecting the change in color or fluorescence by eye.

114. The method according to 112, further comprising, detecting the change in color or fluorescence by a device.

115. The method according to any of 101 through 114, wherein the RNAse inhibitors are aptamers or antibodies.

116. The method according to any of 101 through 115, wherein the buffered reagents or the lyophilized reagents contain reagents for facilitating hybridization of complementary single strand nucleic acids.

117. The method according to any of 101 through 116, wherein the one or more oligonucleotides contains a sample bar code.

118. The method according to 117, further comprising a pooling step between (c) and (d) wherein multiple samples may be pooled prior to reverse transcription or after reverse transcription and prior to amplification of the cDNA.

119. A composition comprising a receiving vessel containing reagents comprising (i) oligonucleotides immobilized on a substrate in a diluting volume of buffer containing DNase inhibitors, RNase inhibitors and proteolytic agents or (ii) lyophilized oligonucleotide immobilized on a substrate, DNase inhibitors, RNase inhibitors and one or more proteolytic agents for rehydration in contact with the saliva; wherein the oligonucleotides are characterized by one or more sequences, wherein at least one sequence is complementary to a portion of SARS-CoV-2 RNA.

120. The composition according to 119, wherein the oligonucleotides are capable of hybridizing to at least one of the polyA tail of the viral RNA, the capped end of the RNA or to an internal target sequence.

121. The composition according to 119 or 120, wherein the oligonucleotide is a primer for reverse transcription of the hybridized virion RNA.

122. The composition according to any of 119 through 121, wherein the one or more oligonucleotide contains modified nucleotides.

123. The composition according to any of 119 through 122, wherein the one or more oligonucleotides contain a sample barcode.

124. The composition according to any of 119 through 123, wherein the reagents further comprise one or more of the following: Proteinase K, thermolabile Proteinase K, aptamer inhibitors of RNAses and/or DNases, antibody inhibitors of RNAses and/or DNases, salts to facilitate hybridization and/or protein denaturation, detergents, surfactants and/or reducing agents.

125. A kit comprising the compositions of 119 through 124.

126. A composition, comprising a mixture of LAMP primer sets wherein each of a plurality of different primer sets in the mixture have a specificity for a different respiratory virus.

127. A composition according to 126, further comprising a primer set in the mixture having a specificity for a cellular non-viral target.

128. The composition according to any of 126 or 127, wherein the plurality of primer sets in the mixture are specific for one or more target pathogens selected from a coronavirus, a rhinovirus, a respiratory syncytial virus, an influenza virus, a parainfluenza virus, a metapneumovirus, an adenovirus and a bocavirus.

129. The composition according to any of 126 through 128, wherein the mixture further comprises a plurality of duplex oligonucleotides, wherein (i) each duplex is formed from a 5'-modified version of an FIP primer (Q-FIP) annealed to a complementary oligonucleotide; (ii) the Q-FIP contains a quenching molecule or a fluorescent label such that the fluorescent label is quenched until one strand of the duplex hybridizes to a target; and (iii) the fluorescent label for each primer set can be differentiated by wavelength emission when unquenched.

130. The composition according to any of 126 through 129, wherein the concentration-of the primer sets in the mixture are similar except for the primer set in the mixture that is specific for the cellular non-viral target.

131. The composition according to any of 126 through 130, wherein the concentration of the primer set in the mixture that is specific for the cellular non-viral target has a concentration in the range of 25%-80% for example 50-75% of the primer sets for respiratory viruses.

132. A kit, comprising:
(a) a sample collection container;
(b) a mixture of primer sets according to any of 126 through 131, wherein the mixture may be in the sample collection container or separate from the sample collection container;

(c) a polymerase and optionally a reverse transcriptase in the same container as (a) or separate container; and (d) instructions for performing multiplex loop mediated amplification using a fluorescent probe and quencher.

133. A kit according to 132, wherein the sample collection container contains a poloxamer surfactant.

134. A composition, comprising a biological sample combined with a buffer containing an antifoaming agent, wherein the antifoaming agent is a poloxamer.

135. A composition according to 134, further comprising one or more LAMP primer sets.

136. A composition according to 134 or 135, wherein the poloxamer is PF68.

137. A composition according to any of 134 through 136, wherein the buffer further comprises TCEP and EDTA.

138. A kit comprising, a reaction container for receiving a swab containing a biological sample or a liquid biological fluid, the reaction container optionally containing a buffer containing a poloxamer or wherein the buffer containing the poloxamer is contained in a distinct compartment in the reaction container or is provided in a separate tube for receiving an aliquot of the biological sample.

139. A method, comprising:
(a) combining a biological sample from a nasal or buccal swab or from saliva from a vertebrate subject, with a buffer containing a poloxamer in a container;
(b) heating the biological sample in the container from (a) to 95° C.; and
(c) allowing the sample to cool and adding one or more LAMP primer sets.

140. The method according to claim 139, wherein the poloxamer is PF68.

141. The method according to 139 or 140, further comprising:
(d) combining a plurality of LAMP primer sets with an aliquot of the cooled sample in a LAMP reaction buffer where each primer set comprises a quenched fluorescent dye in a duplex oligonucleotide.

142. The method according to 141, wherein the plurality of LAMP primer sets are specific for one or more virus nucleic acids selected from the group consisting of a coronavirus, a rhinovirus, a respiratory syncytial virus, an influenza virus, a parainfluenza virus, a metapneumovirus, an adenovirus and a bocavirus.

143. The method according to any of 139 through 142, wherein the vertebrate subject is a mammal.

144. The method according to 143, further comprising:
(e) performing multiplex DARQ LAMP to determine the presence of SARS-CoV-2 and/or Influenza virus in the subject.

145. The method according to any of 139 through 144, wherein the LAMP reaction buffer contains dUTP for carryover prevention.

146. The method according to any of 139 through 145, wherein the container is a well in a 96 well or 384 well dish or the container is a tube.

147. The method according to any of 141 through 146, further comprising:
(f) unquenching of the fluorescent dye in the presence of a target nucleic acid to provide a fluorescent signal; and (g) detecting the fluorescent signal by determining the wavelength of emitted light for each fluorescent signal.

148. A kit for Loop-Mediated Isothermal Amplification (LAMP), comprising:
(a) a strand displacing polymerase capable of copying DNA at a temperature in the range of 50° C.-68° C.;
(b) a reversible inhibitor of the polymerase, wherein the inhibitor inhibits the strand displacing DNA polymerase at a temperature of below 50° C.;
(c) a thermolabile uracil DNA glycosylase (UDG) that is inactivated at a temperature of above 50° C.;
(d) nucleoside triphosphates comprising dATP, dGTP, dCTP, and dTTP; and dUTP; and
at least one indicator reagent that changes color or provides fluorescence if amplification occurs;
wherein any of (a) to (e) are separate or combined into one or more mixtures in the kit.

149. The kit according to 148, wherein the strand displacing polymerase is a mesophilic bacterial strand displacing polymerase and the temperature for copying the DNA is 65° C. for less than 1 hour.

150. The kit according to 148 or 149, wherein the reversible inhibitor is an oligonucleotide.

151. The kit according to any of the preceding embodiments, further comprising a receiving container for a biological sample.

152. The kit according to any of the preceding embodiments, further comprising lysis reagents for adding to or contained in the receiving container for lysing a biological sample to release any target nucleic acids therein for amplification by Loop-Mediated Isothermal Amplification (LAMP).

153. The kit according to 152, wherein the lysis reagents comprise a reducing agent and a metal chelator.

154. The kit according to 153, wherein the reducing agent is Tris (2-carboxyethyl) phosphine hydrochloride (TCEP).

155. The kit according to any of 152 to 154, wherein the lysis reagents comprise a salt of $C-(NH_2)_2NH^+$.

156. The kit according to any of 152 to 155, wherein the lysis reagents comprise a poloxamer.

157. The kit according to any of the preceding claims, further comprising: in a separate container, at least one set of LAMP primers.

158. The kit according to 157, wherein the at least one set of Loop-Mediated Isothermal Amplification (LAMP) primers further comprise a plurality of primer sets for amplifying a plurality of target nucleic acids in the biological sample.

159. The kit according to 158, wherein the at least one set of Loop-Mediated Isothermal Amplification (LAMP) primers further comprise a plurality of primer sets for amplifying a nucleic acid target from a single virus strain in the biological sample.

160. The kit according to any of claims 148-151 and 155-159, wherein any or all of the lysis reagents and/or reagents for Loop-Mediated Isothermal Amplification (LAMP) amplification except for a salt of $C-(NH_2)_2NH^+$, are lyophilized, freeze dried or in a solution.

161. The kit according to any of 148-151 and 155-160, further comprising a buffer with a buffering concentration of no more than equivalent to 5 mM Tris buffer for use with the kit components if the indicator in (e) is a pH dependent colorimetric dye.

162. The kit according to 152, further comprising instructions for use with a biological sample wherein the biological sample is selected from a body fluid or tissue, an agricultural sample, a food sample, a waste product, and a pathogen.

163. The kit according to claim 162, wherein the biological sample is a body fluid or tissue selected from the group consisting of mucous, urine, lymph, blood, saliva, feces, sputum, sweat, semen and biopsy.

164. The kit according to any of the previous claims were in the enzymes and/or oligonucleotides and/or Loop-Mediated Isothermal Amplification (LAMP) primer sets are immobilized on a substrate for reacting with a nucleic acid in the biological sample.

165. The kit according to any of 148-161 and 163-165, wherein the indicator reagent is a metallochromic dye.

166. The kit according to any of 148-164, wherein the indicator reagent is a pH sensitive colorimetric dye.

167. The kit according to any of claims 148-161 and 163-165, wherein the indicator reagent is a fluorescent dye.

168. The kit according to any of claims 148-168, further comprising a reverse transcriptase.

169. The kit according to claim 168, wherein the reverse transcriptase is selected from a virus derived reverse transcriptase, or from a Group II intron reverse transcriptase.

170. The kit according to 168-169, further comprising a reversible inhibitor of the reverse transcriptase.

171. The kit according to 152, wherein the biological sample is saliva or a nasal swab and the target nucleic acid is a single target RNA virus genome.

172. The kit according to any of 151-171, wherein the receiving container for the biological sample is a vessel with a lid, the lid containing a solution of indicator reagent for release into the reaction vessel after lysis of the biological sample or after Loop-Mediated Isothermal Amplification (LAMP).

173. The kit according to any of 148-172, suitable for use in a high sample throughput workflow that is partially or completely automated and further comprises a recording device for storing and/or reporting positive sample data after detection of a change in color or fluorescence of the indicator resulting from amplification of the target nucleic acid.

174. The kit according to any of claims 151-173, wherein the receiving container is selected from paper, a microfluidic device and a polymer surface.

175. A reaction mixture, comprising: a thermolabile uracil DNA glycosylase (UDG), a strand displacing polymerase, a reversible inhibitor of the polymerase, and a salt of C—$(NH_2)_2NH^+$.

176. A lysis mixture for releasing an RNA from a biological sample for detection by amplification and/or sequencing, comprising a poloxamer, a reducing agent and a metal chelating agent.

177. The lysis mixture of 29, further comprising a salt of C—$(NH_2)_2NH^+$.

178. A master mix comprising: a thermolabile uracil DNA glycosylase (UDG), a strand displacing polymerase, a reversible inhibitor of the polymerase, a reverse transcriptase and a reversible inhibitor of the reverse transcriptase.

179. A method for amplifying any target nucleic acid in a biological sample by Loop-Mediated Isothermal Amplification (LAMP), comprising:
    (a) combining the biological sample with a lysis reagent to form a lysis mix;
    (b) incubating the lysis mix at a temperature of at least 60° C. for a period of time in the range of 3 minutes to 45 minutes;
    (c) combining an aliquot of the heat treated mix after step (b) with amplification reagents comprising a strand displacing polymerase, a reversible inhibitor of the polymerase, a thermolabile uracil DNA glycosylase (UDG), nucleoside triphosphates, and at least one set of LAMP primers that hybridize to the target nucleic acid, to produce a reaction mix; and
    (d) incubating the reaction mix under amplification conditions for LAMP to permit inactivation of the thermolabile UDG and amplification of the target nucleic acid.

180. The method of 179, wherein the lysis reagent in (a) comprises at least one of a salt of C—$(NH_2)_2NH^+$ and a poloxamer to produce a lysis mix.

181. The method of 179 or 180, wherein the lysis reagent comprises a reducing agent and a metal chelating reagent.

182. The method of 179 or 180, wherein (b) further comprises incubating the lysis mix at 95° C. for 5 minutes.

183. The method of any of 179-182, wherein the amplification reagents include a reverse transcriptase and a reversible inhibitor of the reverse transcriptase.

184. The method according to any of 179-183, wherein any of the reagents in the lysis mix and any of the amplification reagents may be lyophilized prior to combining with the biological sample.

185. The method according to any of 179-184, wherein any of the reagents in the lysis mix and any of the amplification reagents may be immobilized on a matrix.

186. The method of any of 179-185, further comprising (c) further comprises an indicator reagent that changes color or provides fluorescence if amplification occurs.

187. The method according to 186, further comprising (e) detecting a change in color or fluorescence of the indicator reagent corresponding to the amplification of the target nucleic acid.

188. The method according to any of 179-187, wherein the biological sample is saliva.

189. The method according to any of 179-188, wherein the target nucleic acid is an RNA virus and the amplification reagents include a reverse transcriptase and a reverse transcriptase reversible inhibitor.

190. The method according to any of 179-189, wherein the RNA virus is a coronavirus and the amplification reagents include multiple sets of primers.

191. The method according to 190, wherein the multiple sets of primers include a plurality of primers sets for amplifying at least two different sequences in the coronavirus genome or cDNA copy of the coronavirus genome.

192. The method according to 191, wherein the at least two different sequences are at least a portion of Gene N and a portion of Gene E in the coronavirus.

193. A method for analyzing a biological sample to determine the presence of a target nucleic acid, comprising:
    (a) combining the biological sample with a lysis reagent comprising a reducing agent, a metal chelator and at least one of a guanidine salt and a poloxamer to produce a lysis mix; and (b) determining the presence of the target nucleic acid by selectively amplifying the target nucleic acid in a reaction mix that comprises an aliquot of the lysis mix.

194. The method of 193, wherein the reaction mix comprises an indicator reagent that changes color or provides fluorescence if amplification occurs, and the method further comprises determining whether the reaction mix contains the target nucleic acid based on a change in color or fluorescence.

195. The method of 193-194, wherein (b) further comprises: incubating the reaction mix under amplification conditions for Loop-Mediated Isothermal Amplification (LAMP) to permit amplification of the target nucleic acid.

196. A method for detecting an RNA virus in saliva or a nasal swab of a subject, comprising:
(a) collecting saliva in a receiving container that comprises:
  (i) substrate immobilized oligonucleotides for binding viral RNA and a lysis reagent mix comprising two or more reagents selected from a guanidinium salt, a poloxamer, a reducing agent, a DNase inhibitor, an RNase inhibitor, a detergent, a metal chelator and a proteolytic agent; or
  (ii) lyophilized substrate immobilized oligonucleotides for binding viral RNA, and/or one or more lyophilized reagents contained in a lysis reagent mix, wherein the lysis reagent mix comprises two or more reagents selected from a poloxamer, a reducing agent, DNase inhibitor, an RNase inhibitor, a detergent, a metal chelator and a proteolytic agent, wherein the lyophilized reagents become rehydrated when contacted by the collected saliva;
(b) incubating the receiving container after step (a) at an effective temperature and time to release nucleic acid from any coronaviruses in the saliva for binding to the immobilized oligonucleotides;
(c) removing the lysis reagent mix from the receiving vessel leaving the coronavirus genome bound to the immobilized oligonucleotides on the substrate;
(d) adding amplification reagents to the substrate after step (c), wherein amplification reagents comprise reverse transcription reagents and DNA amplification reagents, to make a reaction mix; and
(e) incubating the reaction mix under amplification conditions to amplify a cDNA copy of at least a portion of the coronavirus genome.

197. The method according to claim 196, wherein the receiving container is selected from a paper substrate, a microfluidic device or a polymer surface.

198. The method according to 196 or 197, wherein the lysis reagent mix in (i) comprises three or more reagents selected from a guanidinium salt, a poloxamer, a reducing agent, a DNase inhibitor, an RNase inhibitor, a detergent, a metal chelator and a proteolytic agent or in (ii) comprises three or more reagents where at least one reagent is lyophilized that is selected from a poloxamer, a reducing agent, DNase inhibitor, an RNase inhibitor, a detergent, a metal chelator and a proteolytic agent.

199. The method of 196 or 197, wherein the reaction mix of (d) further comprises an indicator reagent that changes color or provides fluorescence if amplification occurs, and wherein the method further comprises detecting a change in a signal that indicates the presence of coronavirus in the saliva of the subject.

200. The method according to any of 196-199, comprising amplification reagents for Loop-Mediated Isothermal Amplification (LAMP).

201. The method of any of 196-200, wherein the amplification reagents comprise the reagents in the kit according to claim 1.

202. The method according to 201, wherein the amplification reagents further comprise at least two sets of Loop-Mediated Isothermal Amplification (LAMP) primers that target different regions of a coronavirus genome.

203. The method according to 202, wherein the targeted regions comprise Gene E and Gene N on the coronavirus genome.

204. The method according to any of 196-203, wherein the amplification reagents comprise Loop-Mediated Isothermal Amplification (LAMP) primer sets targeting a second viral genome that is not a coronavirus wherein the LAMP primer sets are combined in a single reaction mix and wherein the LAMP primer set for the coronavirus is linked to a colorimetric indicator that changes color after amplification that is detectable at one wavelength and a second LAMP primer set for amplifying a second non-coronavirus nucleic acid, having a colorimetric indicator that changes color after amplification that is detectable at a second wavelength.

205. The method according to any of 196-204, wherein the amplifying step is followed by sequencing of the amplified nucleic acid.

206. A method for amplifying a target nucleic acid by Loop-Mediated Isothermal Amplification (LAMP), comprising:
(a) combining in a mixture, a biological sample from a mammalian subject with a buffer comprising a poloxamer;
(b) heating the mixture to a temperature of at least 65° C. for an effective time to denature proteins in the biological sample;
(c) allowing the sample to cool; and
(d) amplifying one or more nucleic acids from the mix by LAMP.

207. The method of 206, wherein the biological sample is saliva, a nasal swab or a buccal swab.

208. A kit for use in diagnostic detection of a target nucleic acid and variants thereof having undefined mutations, obtained from a cell or virus in a biological sample, the kit comprising:
(a) a lyophilized mixture of a strand displacing polymerase and an indicator reagent and optionally a lyophilized reverse transcriptase, wherein
  (i) the indicator reagent is characterized by its ability to change color or provide fluorescence in a nucleic acid amplification reaction; and
  (j) the strand displacing polymerase when rehydrated is capable of amplifying DNA at a temperature in the range of 50° C.-68° C.
(b) a universal primer set suitable for loop mediated amplification (LAMP) of the target nucleic acids and variants thereof having undefined mutations;
wherein any of the reagents in the kit may be combined in a mixture in a single container or provided in separate containers.

209. The kit according to 208 wherein the target nucleic acid is a target DNA that is the reverse transcription product of an RNA virus.

210. The kit according to 208 or 209, wherein the indicator reagent is a molecular beacon.

211. The kit according to any of 208-210, wherein the universal primer set suitable for LAMP is capable of hybridizing to the target DNA in the presence of a plurality of undefined mutations to provide a positive result for the target DNA in a predetermined assay time period otherwise determined for a positive sample of a target nucleic acid having a known sequence.

212. The kit according to any of 208-211, further comprising (c) a lysis reagent in a container for receiving the biological sample, wherein the lysis reagents comprise a reducing agent and a metal chelator.

213. The kit according to 212, wherein the reducing agent is Tris (2-carboxyethyl) phosphine hydrochloride (TCEP).

214. The kit according to 212, wherein the lysis reagents comprise at least one of a salt of C—$(NH_2)_2NH^+$ and a poloxamer.

215. The kit according to any of 208-214 wherein one or more of components in (a)-(b) are immobilized on a substrate.

216. The kit according to any of 208-215, wherein the indicator reagent is a metallochromic dye.

217. The kit according to any of 208-216, comprising the reverse transcriptase, wherein the reverse transcriptase is a virus encoded reverse transcriptase, or a bacteria encoded intron II reverse transcriptase.

218. A method for detecting a target nucleic acid or unknown variant thereof in a biological sample by Loop-Mediated Isothermal Amplification (LAMP), comprising:
  (a) combining the biological sample with a lysis reagent to form a lysis mix;
  (b) incubating the lysis mix at a temperature of at least 60° C. for a period of time in the range of 2 minutes to 45 minutes;
  (c) combining in a reaction mix, an aliquot of the heat treated lysis mix of step (b) with amplification reagents comprising a strand displacing polymerase, a reversible inhibitor of the polymerase, nucleoside triphosphates, and at least one set of LAMP primers that is capable of hybridizing to the target nucleic acid and to undefined variants thereof; and
  (d) incubating the reaction mix for a reaction positive period of time under amplification conditions for LAMP to detect the presence of the target nucleic acid or undefined variants thereof in the sample.

219. The method of 218, wherein the lysis reagent comprises a reducing agent and a metal chelating reagent.

220. The method of 218 or 219, wherein (b) further comprises incubating the lysis mix at 95° C. for 5 minutes.

221. The method of any of 218-220, wherein the amplification reagents include a reverse transcriptase and a reversible inhibitor of the reverse transcriptase.

222. The method according to any of 218-221, wherein any of the lysis reagents and any of the amplification reagents may be lyophilized prior to combining with the biological sample.

223. The method according to any of 218-223, wherein any of the lysis reagents and any of the amplification reagents may be immobilized on a matrix. 224. The method according to any of 218-223, wherein the biological sample is saliva. 225. The method according to any of 218-223, wherein the target nucleic acid is an RNA genome from a virus.

226. The method according to 225, wherein the virus is a coronavirus and the amplification reagents include multiple sets of primers.

227. The method according to any of 218-226, further comprising step (e) sequencing the detected target nucleic acid or variants thereof to determine the presence of novel mutations.

EXAMPLES

All reagents are commercially available and provided by New England Biolabs, Ipswich, Mass. unless otherwise specified. Although the examples are provided for the coronavirus they are also applicable to other pathogens and to the analysis of DNA and RNA.

Example 1: Identification of SARS-CoV-2 Virus RNA

SARS-CoV-2 virus RNA is analyzed directly from nasal swabs using a visual, colorimetric detection. This simple and sensitive method provides an opportunity to facilitate virus detection in the field without a requirement for complex diagnostic infrastructure. The general features of the method were reported in Tanner, et al. BioTechniques 58:59-68 (2015) and reagents for conducting the method are provided by New England Biolabs (M1800). Here the sensitivity of the method was tested for the coronavirus described as SARS-CoV-2.

LAMP Primer Design and Testing 5 sets of LAMP oligonucleotide primers targeting two fragments (Table 1) of SARS-CoV-2 sequence (GenBank accession number MN908947) were designed using the online software Primer Explorer V5 (available for free use at: https://primerexplorer.jp/e/). The two fragments corresponded to the 5' region of the ORF1a gene and Gene N. Three sets of primers were designed to target ORF1 and two for GeneN. Each set of primers was tested with synthetic DNA substrates (gBlocks®, Integrated DNA Technologies, Coralville, Iowa) and RNA (in vitro transcribed RNA from that DNA) prior to clinical use.

TABLE 1

Sequences of amplicons and LAMP primers

| LAMP primer or Amplicon | Sequence |
|---|---|
| ORF1a | CCCTATGTGTTCATCAAAC GTTCGGATGCTCGAACTGC ACCTCATGGTCATGTTATG GTTGA (SEQ ID NO: 1) |
| Fragment | GCTGGTAGCAGAACTCGAA GGCATTCAGTACGGTCGTA GTGGTGAGACACTTGGTGT CCTT (SEQ ID NO: 2) |
|  | GTCCCTCATGTGGGCGAAA TACCAGTGGCTTACCGCAA GGTTCTTCTTCGTAAGAAC GGTA (SEQ ID NO: 3) |
|  | ATAAAGGAGCTGGTGGCCA TAGTTACGGCGCCGATCTA AAGTCATTTGACTTAGGCG ACGA (SEQ ID NO: 4) |

TABLE 1-continued

Sequences of amplicons and LAMP primers

| LAMP primer or Amplicon | Sequence |
|---|---|
| | GCTTGGCACTGATCCTTAT GAAGA (SEQ ID NO: 5) |
| ORF1a-A | |
| ORF1a-A-F3 | CTGCACCTCATGGTCATGT T (SEQ ID NO: 6) |
| ORF1a-A-B3 | AGCTCGTCGCCTAAGTCA A (SEQ ID NO: 7) |
| ORF1a-A-FIP | GAGGGACAAGGACACCAAG TGTATGGTTGAGCTGGTAG CAGA (SEQ ID NO: 8) |
| ORF1a-A-BIP | CCAGTGGCTTACCGCAAGG TTTTAGATCGGCGCCGTAA C (SEQ ID NO: 9) |
| ORF1a-A-LF | CCGTACTGAATGCCTTCGA GT (SEQ ID NO: 10) |
| ORF1a-A-LB | TTCGTAAGAACGGTAATAA AGGAGC (SEQ ID NO: 11) |
| ORF1a-B | |
| ORF1a-B-F3 | TCATCAAACGTTCGGATGC T (SEQ ID NO: 12) |
| ORF1a-B-B3 | TATGGCCACCAGCTCCTT (SEQ ID NO: 13) |
| ORF1a-B-FIP | CGACCGTACTGAATGCCTT CGAGAACTGCACCTCATGG TCAT (SEQ ID NO: 14) |
| ORF1a-B-BIP | AGACACTTGGTGTCCTTGT CCCAGAAGAACCTTGCGGT AAGC (SEQ ID NO: 15) |
| ORF1a-B-LF | CTGCTACCAGCTCAACCAT AAC (SEQ ID NO: 16) |
| ORF1a-B-LB | TCATGTGGGCGAAATACCA GT (SEQ ID NO: 17) |
| ORF1a-C | |
| ORF1a-C-F3 | CTGCACCTCATGGTCATGT T (SEQ ID NO: 18) |
| ORF1a-C-B3 | GATCAGTGCCAAGCTCGTC (SEQ ID NO: 19) |
| ORF1a-C-FIP | GAGGGACAAGGACACCAAG TGTGGTAGCAGAACTCGAA GGC (SEQ ID NO: 20) |

TABLE 1-continued

Sequences of amplicons and LAMP primers

| LAMP primer or Amplicon | Sequence |
|---|---|
| ORF1a-C-BIP | CCAGTGGCTTACCGCAAGG TTTTAGATCGGCGCCGTAA C (SEQ ID NO: 21) |
| ORF1a-C-LF | ACCACTACGACCGTACTGA AT (SEQ ID NO: 22) |
| ORF1a-C-LB | TTCGTAAGAACGGTAATAA AGGAGC (SEQ ID NO: 23) |
| Gene N | ATGACCAAATTGGCTACTA CCGAAGAGCTACCAGACGA ATTCGTGGTGGTGACGGTA AAAT (SEQ ID NO: 24) |
| fragment | GAAAGATCTCAGTCCAAGA TGGTATTTCTACTACCTAG GAACTGGGCCAGAAGCTGG ACTT (SEQ ID NO: 25) |
| | CCCTATGGTGCTAACAAAG ACGGCATCATATGGGTTGC AACTGAGGGAGCCTTGAAT ACAC (SEQ ID NO: 26) |
| | CAAAAGATCACATTGGCAC CCGCAATCCTGCTAACAAT GCTGCAATCGTGCTAC (SEQ ID NO: 27) |
| Gene N-A | |
| GeneN-A-F3 | TGGCTACTACCGAAGAGCT (SEQ ID NO: 28) |
| GeneN-A-B3 | TGCAGCATTGTTAGCAGGA T (SEQ ID NO: 29) |
| GeneN-A-FIP | TCTGGCCCAGTTCCTAGGT AGTCCAGACGAATTCGTGG TGG (SEQ ID NO: 30) |
| GeneN-A-BIP | AGACGGCATCATATGGGTT GCACGGGTGCCAATGTGAT CT (SEQ ID NO: 31) |
| GeneN-A-LF | GGACTGAGATCTTTCATTT TACCGT (SEQ ID NO: 32) |
| GeneN-A-LB | ACTGAGGGAGCCTTGAATA CA (SEQ ID NO: 33) |
| Gene N-B | |
| GeneN-B-F3 | ACCGAAGAGCTACCAGACG (SEQ ID NO: 34) |
| GeneN-B-B3 | TGCAGCATTGTTAGCAGGA T (SEQ ID NO: 35) |

TABLE 1-continued

Sequences of amplicons and LAMP primers

| LAMP primer or Amplicon | Sequence |
|---|---|
| GeneN-B-FIP | TCTGGCCCAGTTCCTAGGT AGTTCGTGGTGGTGACGGT AA (SEQ ID NO: 36) |
| GeneN-B-BIP | AGACGGCATCATATGGGTT GCACGGGTGCCAATGTGAT CT (SEQ ID NO: 37) |
| GeneN-B-LF | CCATCTTGGACTGAGATCT TTCATT (SEQ ID NO: 38) |
| GeneN-B-LB | ACTGAGGGAGCCTTGAATA CA (SEQ ID NO: 39) |

These primers in a colorimetric LAMP assay were first tested on synthetic sequences corresponding to regions of the SARS-CoV-2 either as DNA or as RNA.

DNA fragments containing two SARS-CoV-2 sequences were synthesized as gBlocks. T7 RNA polymerase promoter sequences were added by PCR (M0493) (numbers indicate New England Biolabs, Inc. catalog ID numbers unless otherwise noted). The PCR reaction utilized primer pairs where one primer of the pair containing the T7 RNA promoter sequence. The PCR amplicon was then transcribed by in vitro transcription (E2050) to produce RNA with sequences that mimicked the selected portions of the SARS-CoV-2 virus. This RNA was purified using RNA clean up columns (T2040). The resulting RNAs as well as the corresponding gBlocks DNA were serially diluted in 10-fold increments using 0.1×TE buffer containing 0.01% Tween 20.

RT-LAMP reactions (for RNA) and LAMP (for DNA) using fluorescent dyes were performed using WarmStart Colorimetric LAMP 2x master mix (for DNA & RNA) (NEB product M1800) supplemented with 1 µM SYTO™-9 fluorescent double-stranded DNA binding dye (Thermo Fisher Scientific, Waltham, Mass. (S34854)) and incubated on a real-time qPCR machine (CFX96) Bio-Rad, Hercules, Calif.)) for 120 cycles with 15 seconds each cycle (total ~40 minutes). This was performed to measure amplification in real time continuously over a 40 minute time period. This was done to confirm that amplification corresponded to color change and provide correlations between input and color change.

The colorimetric LAMP assay was first described in U.S. Pat. Nos. 9,034,606, 9,580,748 and US 2019/0169683 herein incorporated by reference. A weak buffer was described for use in the assay as described.

All LAMP assays were performed in a 20 µl reaction mixture containing 2 µL of 10× primer mix of 16 µM (each) of Forward Inner Primer (FIP) and Backward Inner Primer (BIP), 2 µM (each) of F3 and B3 primers, 4 µM (each) of Forward Loop (LF) and Backward Loop (LB) primers, 10 µL of WarmStart Colorimetric Lamp 2× master mix (M1800) 5 µL of DNAse, RNase free water and 3 µl of RNA template. Individual primer pair sets that were optimal (where one set includes 6 primers) were selected for ORF1 and Gene N.

TABLE 2

| Primer | 10X concentration | 1X concentration |
|---|---|---|
| FIP | 16 µM | 1.6 µM |
| BIP | 16 µM | 1.6 µM |
| F3 | 2 µM | 0.2 µM |
| B3 | 2 µM | 0.2 µM |
| Loop F | 4 µM | 0.4 µM |
| Loop B | 4 µM | 0.4 µM |

TABLE 3

| | DNA target | RNA target detection | No Template control (NTC) |
|---|---|---|---|
| WarmStart Colorimetric LAMP 2X master mix | 12.5 µl | 12.5 µl | 12.5 µl |
| LAMP Primer Mix (10X) | 2.5 µl | 2.5 µl | 2.5 µl |
| Target DNA | 1 µl | — | — |
| Target RNA | — | 1 µl | — |
| dH$_2$O | 9 µl | 9 µl | 10 µl |
| Total volume | 25 µl | 25 µl | 25 µl |

Note:
Make primer stock in molecular biology grade H$_2$O rather than TE or other buffer in order to avoid carryover of additional buffer to the LAMP reaction. Prepare primer stocks in nuclease free water and store at −20° C. for up to 2 years.

Instructions from the New England Biolabs website (www.neb.com) were generally followed unless stated otherwise: 24 µl of the 2× master mix, plus primers and dH$_2$O were added into each desired reaction vessels and 1 µl of sample was added. After mixing, the reaction solutions were confirmed to have a bright pink color, indicating an initial high pH required for successful pH-LAMP reaction. The reaction mixture was incubated at 65° C. for 30 minutes. The tubes or vessels were then examined by eye to determine positive reactions that turned yellow or negative reactions that remained pink. Reactions can be examined earlier if desired. High copy or input reactions can exhibit full color change in as little as 10-15 minutes after incubation at 65° C. The color was visible directly on removal from the incubation temperature and could be intensified by allowing reaction to cool to room temperature. The result were photographed or scanned to record the colorimetric results, or simply kept at room temperature in the reaction vessel.

For Identification of SARS-CoV-2 virus RNA in test samples and determining the sensitivity of the assay, positive control test samples were prepared as follows: synthetic viral RNAs were spiked into Hela cells, which were then diluted and lysed using Luna Cell Ready Lysis Module (E3032). Each lysate was then diluted 10× with 0.1×TE+ 0.01% Tween 20 and 1 µL was added to standard colorimetric LAMP reactions.

For compatibility with blood recovery, the synthetic RNA described above was spiked into 200 µL whole human blood (Quadrant Health Strategies, Beverly, Mass.) and then purified the total blood RNA using Monarch Total RNA Miniprep Kit (T2010).

The results of pH dependent detection sensitivity assays showed that all five primer sets provided similar detection sensitivity and could consistently detect as low as 120 copies of the viral RNA (or 4.8 copies/pi) as determined by serial dilution of ~120 million copies down to ~120 copies (per 25 µL reaction) at 10-fold intervals in the colorimetric LAMP reactions. The relative efficiency of pH dependent colorimetric LAMP using RNA or DNA templates was determined from the real time LAMP signal using synthetic RNA with similarly diluted gBlock dsDNA. For the 2 primer sets we compared, one showed slightly slower amplification and detection with RNA template while the other appeared slightly faster, confirming the RNA is efficiently converted to cDNA by the reverse transcriptase (WarmStart RTx) and subsequently amplified via LAMP by the DNA-dependent DNA polymerase (Bst 2.0 WarmStart). This result was not adversely affected by the presence of UDP in the master mix to prevent carryover.

Example 2: Analysis of Total RNA from Crude Lysates for Identification of SARS-CoV-2 (COVID-19) Virus RNA Crude cell lysate was used in order to avoid an RNA purification step. The results indicated that about 480 copies were detected with four of the five primer sets tested in Example 1, showing a similar sensitivity as the detection sensitivity with synthetic RNA alone (FIG. 3A) with no interference by the lysate to either the amplification efficiency or visual color change. A mock experiment was set up during purification of total RNA to determine whether the synthetic RNA spiked into biological sample could be recovered. Various amounts of synthetic RNA were spiked into whole human blood and total blood RNA was purified. We were able to recover and detect the spiked RNA (FIG. 3B), indicating the total RNA did not cause detectable interference during the purification or the detection process. While the column-based approach is less compatible with the simple, field detection enabled by colorimetric LAMP, this is a typical laboratory workflow and can be used with simple isothermal amplification in a similar fashion to more expensive and involved qPCR detection workflows.

Example 3: Nucleic Acid Carryover Prevention

Using the colorimetric LAMP assay described in Example 1, the benefit of using a thermolabile UDG and a 50:50 dTTP: dUTP in addition to dCTP, dGTP and dATP was demonstrated. FIG. 6A shows that this change in reagents did not affect the sensitivity or the specificity of the assay. Moreover, these additions to the master mix were effective in removing carryover nucleic acids from one sample to the next.

More specifically: two Carryover Prevention WarmStart Colorimetric LAMP 2× master mixes (abbreviated CP-LAMP MM) were developed and evaluated in an RT-LAMP functional assay, to determine whether the carryover additives interfered with the detection reaction as follows:

Each RT-LAMP reaction contained 1×CP-LAMP MM (no UDG or with UDG), 1×LAMP primers, genomic RNA, and 1×LAMP fluorescent dye in a reaction volume of 25 µL. High-copy reactions (n=3) contained 10 ng genomic RNA; low-copy reactions (n=6) contain 0.3 ng genomic RNA; and no-template (NT) reactions (n=1) contain no RNA. The plate was incubated at 65° C. for 75 minutes in a qPCR instrument, then imaged in a flatbed fluorescence scanner. The results are shown in FIG. 6A. A control was added as shown which had neither dUTP or UDG. No difference was observed between control and samples with the carryover prevention additives.

Carryover prevention was effective as demonstrated in FIG. 6B.

Each RT-LAMP reaction contains 1×CP-LAMP MM (with UDG), 1×LAMP primers, genomic RNA, and 1×LAMP fluorescent dye in a reaction volume of 25 µL. Both rows are identical replicates. The first well in each row contains approximately 1 ng (1000 pg) of genomic RNA. From the second well onwards, 10-fold dilutions were completed, with the last well in each row serving as a no-template (NT) reaction with no RNA. The plate was incubated at 65° C. for 75 minutes in a qPCR instrument, then imaged in a flatbed fluorescence scanner. No amplified product was observed in amounts where carryover occurs.

Example 4: Nasal Sampling for Detecting SARS-CoV-2

Nasal samples are collected by swab and placed in sterile water in a microfuge tube. An aliquot of the sample is then combined with a master mix prepared as described above (see Example 3). Thermolabile UDG (New England Biolabs, Ipswich, Mass.) is added according to the manufacturer's instructions. Four primer sets from Table 1 described in Example 2 can be used here although a single set of primers for each of ORF1 and GeneN is sufficient. Modifications of the primers described in Table 1 can also be utilized. Other regions in the virus may be additionally or alternatively utilized. The reaction mixture is then heated to a temperature of about 65° C. using a temperature block for 15-60 minutes at which time the amplification is complete. The color of the reaction is then reviewed to reveal the presence or absence of the target nucleic acid. The entire reaction is amenable to substantial scaling up and can be executed in less than 1 hour from collection of sample to receiving the results.

Example 5: Colorimetric LAMP Using Lyophilized Colorimetric LAMP Mix

2× master mix (2×MM) for colorimetric LAMP was prepared using standard concentrations of LAMP reaction components described above (Bst 2.0 and RTx enzymes, aptamers to both, nucleotides, pH dependent dye, salt, detergent in a weakly buffered solution) together with 150 mM Trehalose, glycerol-free WarmStart RTx and high concentrations of WarmStart Bst 2.0. Extra KOH was added to half of the mix to increase the pH of the 2×MM to pH 8.2 from pH 8.0. To determine whether LAMP activity of the 2×MM were the same at both pHs for lyophilized samples stored at room temperature and aqueous samples stored at −20° C., 12.5 µl of 2×MM at pH 8.0 and 12.5 µl of the 2×MM at pH 8.2 were lyophilized and an equal volume of 2×MM at the different pHs in liquid form were stored at −20° C. Lyophilization (freeze drying) was performed under standard conditions (see for example, Millrock Technologies, NY, Labogene Denmark). The lyophilized 2×MMs were reconstituted with 12.5 µl H$_2$O and the pH was measured. The pH in the reconstituted 2×MM was found to have decreased by about 0.25 units. The reconstituted 2×MM and the 2×MM previously stored at −20° C. were then added to 12.5 µl of primer/template mix and 1 µM dsDNA binding fluorescent dye (Syto-9). The primer set for HMBS2 was used for RT-LAMP and the template was Jurkat total RNA at 10 ng or 0.3 ng. The reaction was incubated in a Bio-Rad IQ™5 Real Time PCR machine (Bio-Rad, Hercules, Calif.) to monitor the speed of the reaction and colorimetric or fluorometric detection of amplicons at the end of a 45 minute incubation at 65° C.

Results: both batches (initial pH 8.0 or pH 8.2, only the data from the pH 8.2 batch is shown) worked well after lyophilization. There was no difference in colorimetric detection (FIG. 7, and FIG. 9A-9B) or real time detection (FIGS. 8A-8C and FIG. 9C) with either high or low amount of template in the RT-LAMP.

Example 6: PAR-Based Colorimetric Detection of Nucleic Acid Amplification is an Effective Alternative to pH Dependent Colorimetric LAMP A standard 2×LAMP master mix was prepared (see Example 1) and added to DNA so that the reaction mix contained using the following DNA polymerases in separate reactions: Bst LF, Bst 3.0, Bst 2.0 or WarmStart Bst 2.0 (all products from New England Biolabs, Ipswich, Mass.) in standard amplification buffer containing Tris-HCl, pH 8.8 at 25° C.; $(NH_4)_2SO_4$; KCl; $MgSO_4$. The buffer was varied from 0-4% Triton X-100. PAR concentration was varied from 250 µM to 50 µM PAR with results shown for 150 µM, 100 µM, 75 µM and 50 µM (FIG. 13A-13D). $MnCl_2$ was used throughout at concentrations in the range of 0.4 mM-1.6 mM. In FIG. 13A-13D, the reactions shown contained 0.5 µM $MnCl_2$. The LAMP primer set was BRCA2b including FIP/BIP/F3/B3/LF/LB (see below). 1 µl Hela genomic DNA (100 ng/µl) was used in the positive samples and no DNA in the controls. The reaction was performed at 65° C. for 1 hour. A positive endpoint was yellow corresponding to the reaction of manganese with pyrophosphate. The negative control was orange corresponding to the reaction of manganese with PAR.

TABLE 4

| Primers for PAR-based colorimetric test | |
|---|---|
| BRCAb_F3 | TCCTTGAACTTTGGTCTCC (SEQ ID NO: 40) |
| BRCAb_B3 | CAGTTCATAAAGGAATTGA TAGC (SEQ ID NO: 41) |
| BRCAb_FIP | ATCCCCAGTCTGTGAAATT GGGCAAAATGCTGGGATTA TAGATGT (SEQ ID NO: 42) |
| BRCAb_BIP | GCAGCAGAAAGATTATTAA CTTGGGCAGTTGGTAAGTA AATGGAAGA (SEQ ID NO: 43) |
| BRCAb_LF | AGAACCAGAGGCCAGGCGAG (SEQ ID NO: 44) |
| BRCAb_LB | AGGCAGATAGGCTTAGACTC AA (SEQ ID NO: 45) |

Example 7: Non-Ionic Detergent Increases the Positive Signal in a LAMP Reaction Using PAR to Detect Sample An example of a non-ionic detergent (Triton X-100) was added to the LAMP 2× master mix containing PAR. In this example, the reaction mix contained Bst 2.0, PAR (200 µM), Manganese (0.8 mM), Isothermal amplification buffer with 2% Triton X-100, the BRCA 2b primer set as used in Example 5 and 1 µl Hela gDNA. Although the beneficial effect of adding Triton X-100 to the colorimetric PAR LAMP reaction is shown here, any non-ionic detergent from the Triton series or from the Brij series is expected to show similar benefits. The results are shown in FIG. 11A-11B. 2% Triton X-100 was used in FIG. 14 to provide enhanced signal without adversely affecting polymerase activity although 1%-3% Triton X-100 also showed enhanced signal in visible wave lengths in FIG. 13A-13D.

Example 8: Guanidine Hydrochloride Significantly Increases the Rate of Isothermal Amplification Reactions (a) LAMP Guanidine hydrochloride (10 mM-60 mM) not only increased the rate of the LAMP reaction performed according to Example 1, but also improved the limit of detection sensitivity (see FIG. 16, FIGS. 17A-17C and FIG. 18A-18D).

(i) BRCA and CFTR detection: Standard LAMP amplification was performed in 1× ThermoPol buffer and Bst 2.0 DNA polymerase at 65° C. using 10 ng of genomic DNA isolated from Hela cells as template. Two amplification targets were tested: BRCA gene fragment and CFTR gene fragment. Guanidine hydrochloride at a final concentration of 0 mM-60 mM were added to the reactions. The amplification reactions contained 1 µM dsDNA binding dye-Syto9 and the reaction was performed and the reaction speed was monitored on a Bio-Rad IQ5 Real Time PCR machine.

(ii) SARS-CoV-2 detection: single primer set in a single LAMP assay: As shown in FIG. 16, guanidine significantly increased the LAMP reaction speed for both primer sets with optimal concentration range between 20 mM-40 mM for primer sets 3 and 4 for coronavirus detection. The primer sets were tested against an AccuPlex™ SARS-CoV-2 Verification Panel (SeraCare Milford, Mass.) where the viral RNA is contained in a noninfectious viral protein coat.

(iii) SARS-CoV-2 detection: multiple primer sets in a single LAMP assay

Multiple primers used in a single LAMP reaction improved the sensitivity of colorimetric LAMP reactions. For example, when primer set 3 and 4 were used together, sensitivity of the LAMP assay increased (see FIG. 19A-19C).

Primer Set 1 or 5: As1e/Orf1a (5'-3'):

| As1e_F3 | CGGTGGACAAATTGTCAC (SEQ ID NO: 46) |
|---|---|
| As1e_B3 | CTTCTCTGGATTTAACACA CTT (SEQ ID NO: 47) |
| As1e_LF CTGAACACT | TTACAAGCTTAAAGAATGT (SEQ ID NO :48) |
| As1e_LB | TTGAATTTAGGTGAAACAT TTGTCACG (SEQ ID NO: 49) |
| As1e_FIP | TCAGCACACAAAGCCAAAA ATTTATTTTTCTGTGCA AAGGAAATTAAGGAG (SEQ ID NO: 50) |
| As1e_BIP | TATTGGTGGAGCTAAACTT AAAGCCTTTTCTGTAC AATCCCTTTGAGTG (SEQ ID NO: 51) |

Primer Set 2: Gene N-A (5'-3'):

| GeneN-F3 | TGGCTACTACCGAAGAGCT (SEQ ID NO: 28) |
|---|---|
| GeneN-B3 | TGCAGCATTGTTAGCAGGAT (SEQ ID NO: 29) |
| GeneN-FIP | TCTGGCCCAGTTCCTAGGTAGTCCAGACGAATTCGTGGTGG (SEQ ID NO: 30) |
| GeneN-BIP | AGACGGCATCATATGGGTTGCACGGGTGCCAATGTGATCT (SEQ ID NO: 31) |
| GeneN-LoopF | GGACTGAGATCTTTCATTTTACCGT (SEQ ID NO: 32) |
| GeneN-LoopB | ACTGAGGGAGCCTTGAATACA (SEQ ID NO: 33) |

Primer Set 3

| Gene N-2 | |
|---|---|
| N2-F3 | ACCAGGAACTAATCAGACAAG (SEQ ID NO: 52) |
| N2-B3 | GACTTGATCTTTGAAATTTGGATCT (SEQ ID NO: 53) |
| N2-FIP | TTCCGAAGAACGCTGAAGCG-GAACTGATTACAAACATTGGCC (SEQ ID NO: 54) |
| N2-BIP | CGCATTGGCATGGAAGTCAC-AATTTGATGGCACCTGTGTA (SEQ ID NO: 55) |
| N2-LF | GGGGGCAAATTGTGCAATTTG (SEQ ID NO: 56) |
| N2-LB | CTTCGGGAACGTGGTTGACC (SEQ ID NO: 57) |

Primer Set 4

| Gene E | |
|---|---|
| E1-F3 | TGAGTACGAACTTATGTACTCAT (SEQ ID NO: 58) |
| E1-B3 | TTCAGATTTTTAACACGAGAGT (SEQ ID NO: 59) |
| E1-FIP | ACCACGAAAGCAAGAAAAAGAAGTTCGTTTCGGAAGAGACAG (SEQ ID NO: 60) |
| E1-BIP | TTGCTAGTTACACTAGCCATCCTTAGGTTTTACAAGACTCACGT (SEQ ID NO: 61) |

| Gene E | |
|---|---|
| E1-LB | GCGCTTCGATTGTGTGCGT (SEQ ID NO: 62) |
| E1-LF | CGCTATTAACTATTAACG (SEQ ID NO: 63) |

Primer Set 1 or 5: As1e/Orf1a (5'-3') SEQ ID NO: 46-51:

| As1e_F3 | CGGTGGACAAATTGTCAC (SEQ ID NO: 46) |
|---|---|
| As1e_B3 | CTTCTCTGGATTTAACACACTT (SEQ ID NO: 47) |
| As1e_LF | TTACAAGCTTAAAGAATGTCTGAACACT (SEQ ID NO :48) |
| As1e_LB | TTGAATTTAGGTGAAACATTTGTCACG (SEQ ID NO: 49) |
| As1e_FIP | TCAGCACACAAAGCCAAAAATTTATTTTCTGTGCAAAGGAAATTAAGGAG (SEQ ID NO: 50) |
| As1e_BIP | TATTGGTGGAGCTAAACTTAAAGCCTTTTCTGTACAATCCCTTTGAGTG (SEQ ID NO: 51) |

In addition, similar effect was observed with Bst DNA polymerase, large fragment, Bst 3.0, and in a RT-LAMP with RTx or AMV reverse transcriptase.

We also tested several related compounds containing the guanidine moiety (guanidinium compounds) and found that they also increased the rate of LAMP. The compounds tested included Guanidine thiocyanate, Guanidine chloride and Guanidine sulfate (see FIG. 15).

The observed increase in rate of a LAMP reaction could be further enhanced in the presence of varying amounts of salt concentrations. LAMP reactions were set up in ThermoPol buffer (10 mM KCl) for Bst2.0 (see FIG. 17B or in isothermal amplification buffer (50 mM KCl) for Bst 3.0 (see FIG. 17C) using a lambda2 primer set with 0.5 ng lambda DNA with or without 30 mM guanidine hydrochloride. Addition of guanidine stimulated the LAMP amplification rate significantly at the lower end of the KCl concentration both with Bst 2.0 and Bst 3.0.

(b) Helicase-Dependent Amplification (HDA)

Standard HDA in IsoAmp II kit (H0110) was performed using 0.1 ng plasmid provided in the kit but added guanidine hydrochloride at a final concentration of 0 mM-60 mM. The reactions were performed at 65° C. and EvaGreen dye was included to monitor the progression of amplification. The Tt (time to threshold) was used to estimate the rate of amplification. Tt was shown to be 5 minutes shorter than standard HDA reactions. It was concluded that guanidine HCl increase melt temp for 0.5° C. per 10 mM up to 60 mM guanidine hydrochloride. Isothermal reactions were monitored in the presence of reduced NaCl in the buffer. Increased rates were observed when NaCl was reduced from the standard amount of 40 mM to 10 mM NaCl. Less NaCl gave a higher RFU signal (see FIG. 17A).

Example 9: Detection of Polynucleotides in Saliva Samples Using pH-Dependent Colorimetric LAMP Below is an example of the use of a lysis buffer suitable for directly assaying saliva samples in a pH dependent colorimetric LAMP. The workflow from saliva collection to LAMP analysis is shown in FIG. 20.

The lysis buffer was tested to determine an optimal formula for enhanced sensitivity of a LAMP assay for SARS-CoV-2.

(a) A lysis buffer containing guanidine hydrochloride (GnHCL) (Millipore Sigma, Burlington, Mass.) was tested at various concentrations in the range of 10 mM-400 mM (1×) in combination with 1 mM, 4 mM and 8 mM Tris(2-carboxyethyl)phosphine hydrochloride (TCEP)(Millipore Sigma, Burlington, Mass.) (1×) with or without 75 mM LiCl (NEB product 620151) (1×) against a SARS-CoV-2 virus titer that was varied for different samples containing 5,000 cps/ml, 10,000 cps/ml, 20,000 cps/ml or 40,000 cps/ml (from a stock solution of 100,000 cps/ml from SeraCare, Milford, Mass.). The virus was spiked into saliva of 20 μl, 30 μl, 35 μl and 37.5 μl volumes with TCEP and GnHCL. Copies of actin RNA at 100 copies/μl saliva was used as a control. Lysis of the virus in saliva added to the saliva lysis mix occurred at 95° C. for 5 minutes (the 10× lysis buffer contained 100 mM-4 M GnHCL, 10 mM-80 mM TCEP and 750 mM LiCl)

N2+E1 primer sets were added to a LAMP master mix (New England Biolabs, Ipswich, Mass.) containing reverse transcriptase to amplify SARS-CoV-2 virus derived RNA.

Some of the results are shown in FIG. 21A and FIG. 21B (400 mM GnHCL and varying TCEP concentration, pH and LiCl concentration for 20,000 cps/ml where final concentrations are given), FIG. 22 showing the effect of increasing the concentration of TCEP, and FIG. 23A-FIG. 23D where the LAMP reaction time was varied from 35 minutes to 60 minutes with and without LiCl.

The following conditions provided 100% detection from 16 samples (16/16) containing 40 virus particles/sample under the following conditions for 10× lysis buffer: 4M GnHCL, 40 mM TCEP and 750 mM LiCl pH 8. 5 μl of buffer was combined with 45 μl of sample (35 μl saliva spiked with 10 μl of SeraCare). After a heating step at 95° C. for 5 minutes, 2 μl of the treated saliva sample was then added to 18 μl of a LAMP master mix (10 μl of 2× stock from NEB product M1800, 0.8 μl 25× primer set N2 and 0.8 μl 25× primer set E1, 0.4 μl 50× dye and 6 μl water to a total of 18 μl) and incubated at 65° C. for 35 minutes. The lysis buffer was found to be compatible with colorimetric LAMP (FIG. 21A-21D to FIG. 23A-23D), fluorescent LAMP and RT-qPCR (FIG. 24). It should be noted that where a lysis buffer is used that contained guanidine salt, it was not necessary to add the guanidine salt to the master mix because of the carryover of this salt from the lysis buffer.
Control Primer Sequences: hActin (5'-3')

| ACTB-F3 | AGTACCCCATCGAGCACG (SEQ ID NO: 96) |
| ACTB-B3 | AGCCTGGATAGCAACGTACA (SEQ ID NO: 97) |
| ACTB-FIP | GAGCCACACGCAGCTCATT GTATCACCAACTGGG ACGACA (SEQ ID NO: 98) |
| ACTB-BIP | CTGAACCCCAAGGCCAACCG GCTGGGGTGTTGAAGG TC (SEQ ID NO: 99) |
| ACTB-LoopF | TGTGGTGCCAGATTTTCTC CA (SEQ ID NO: 100) |
| ACTB-LoopB | CGAGAAGATGACCCAGATCAT GT (SEQ ID NO: 102) |

Example 10: Detection of Polynucleotides in Saliva Samples Using RT-qPCR

The RT-QPCR reaction was set up as follows:

| COMPONENT | 20 μl REACTION | FINAL CONCENTRATION |
|---|---|---|
| Luna Universal Probe One-Step Reaction Mix (2X) | 10 μl | 1X |
| Luna WarmStart ® RT Enzyme Mix (20X) | 1 μl | 1X |
| Forward primer (10 μM) | 0.8 μl | 0.4 μM |
| Reverse primer (10 μM) | 0.8 μl | 0.4 μM |
| Probe (10 μM) | 0.4 μl | 0.2 μM |
| Template RNA | 2 μl | |
| Nuclease-free Water | 5 μl | |

The thermal cycler was set up as follows:

| CYCLE STEP | TEMPERATURE | TIME | CYCLES |
|---|---|---|---|
| Reverse Transcription | 55° C.* | 10 minutes | 1 |
| Initial Denaturation | 95° C. | 1 minute | 1 |
| Denaturation | 95° C. | 10 seconds | 45 |
| Extension | 60° C. | CV seconds** (+plate read) | |

SARS-CoV-2 RNA (Twist Biosciences, San Francisco, Calif.) and virus (SeraCare, Milford, Mass.) were spiked separately into different tubes of 2× saliva lysis buffer. The virus was previously spiked into saliva. A positive control contained purified RNA and a negative control contained water only. The results are consisted with those reported for RT QPCR from saliva or nasopharyngeal swabs where detection limits were ascertained from 10 copies/sample (5000 cps/ml) up to 100,000 cps/ml.

Example 11: Lysis Buffer has Minimal or No Adverse Effects on RT-qPCR or on LAMP The lysis buffer as a whole had no adverse effects on the sensitivity of RT-QPCR or pH-dependent colorimetric LAMP. The results are shown in FIG. 24.

Example 12: Automation of a Workflow to Achieve a Throughput of 100,000 Reactions in about 20 Hours A workflow that is capable of delivering high volume throughput is illustrated in FIG. 28A-FIG. 28F and may include the following instruments: RNA collection tubes from Ora (Ottawa, Canada) (ORE-100), 96-384 tube to plate sample transfer (Bravo with 96 or 384 ST Head from Agilent, Santa Clara, Calif.), 384 well plate consumables (Corning, N.Y.), 384 well filling LAMP master mix into detection plates (BioTek, Winooski, Vt.), heat sealing of plates (Thermo Fisher, Waltham, Mass.), Automated 65° C. timed incubation (StoreX-Liconic Instruments) or Intek conveyer (Intek WA), Endpoint fluorescence (BioTek, Winooski, Vt.) or SpectraMax. Although any of these instruments can be switched out for other comparable devices, the workflow illustrates the suitability of colorimetric LAMP for high throughput workflows that are relatively simple, cost effective, efficient, and sensitive.

Example 13: A Surfactant Containing Buffer for Use in a Sensitive Nucleic Acid Assay for Detecting SARS-CoV-2 in Saliva A buffer was formulated at a concentration that was a suitable multiple of the final concentration for adding to a volume of sample. Although the buffer may be formulated in high concentrations such as 10× or 5×, a concentration of 2× sample buffer was used here as this offered ease of mixing with the relatively viscous saliva sample.

The NEB sample 2× buffer (2× contains 8 mM TCEP/NaOH (pH 8.2) 800 mM GuHCl, 150 mM LiCl, 0.2 mM EDTA, 0.4% PF68) was found to be stable over months at 2× concentration. The final concentration of the sample buffer (NEB buffer) combined with saliva was: 4 mM TCEP (pH 8.2) 400 mM GuHCl, 75 mM LiCl, 0.1 mM EDTA, 0.2% PF68.

The CEPKO buffer (1× contains 2.5 mM TCEP, 11 mM NaOH, 1 mM EDTA) was found to be stable at a 100× concentration but was not stable at 2× or 5× concentration and 100× Cepko buffer was made freshly for each experiment.

Experimentation showed that a reducing agent in the buffer (TCEP) could be used within the range of 1 mM-8 mM and pH adjusted to pH 8 with NaOH. Guanidinium hydrochloride was preferably included in the sample buffer for testing using pH colorimetric LAMP. The surfactant used in this example was the poloxamer PF68. Although used here at 0.2%, the concentration can be anywhere in the range of 0.1%-1%. In the above formulation, EDTA was used at 0.1 mM but the concentration of EDTA can be in the range of 0.1%-1%.

The Effect of Saliva on the Sensitivity of LAMP

In this example, heat inactivated SARS-CoV-2 ($3.75 \times 10^8$/cps/ml) or gamma irradiated SARS-CoV-2 ($1.75 \times 10^9$ cps/ml) supplied by BEI Resources or from ATCC was serially diluted to determine whether the presence of saliva could adversely affect the sensitivity of the assay. The assay was carried out as follows:

16 μL virus either in saliva or combined with 4 μL 5×NEB sample buffer was serially diluted 1:10 in 1× buffer. All samples were heated at 95° C. for 5 minutes and 2 μL was added to each LAMP reaction using E1 and N2 sets of primers as provided in Example 3 and WarmStart® Colorimetric LAMP 2× Master Mix with UDG (M1804 from New England Biolabs) or WarmStart® Colorimetric LAMP 2× Master Mix (DNA & RNA) (M1800 from New England Biolabs).

(a) Virus was heat inactivated SARS-CoV-2 (not in saliva). 60 copies of virus could be detected in 100% of the samples and 6 copies of virus could be detected in about 85% of the samples tested using colorimetric LAMP (observing pH dependent color change) and also using fluorescence based LAMP (measuring Cq).

(b) Virus was Gamma irradiated SARS-CoV-2 (not in saliva). 28 copies of virus at 100% and 3 copies of virus could be detected in 50% of samples.

(c) The sensitivity of the assay was determined as performed in (a) and (b) but this time virus was added to saliva before the serial dilution in the sample buffer and heat treatment prior to performing LAMP. The sensitivity of the assay was found to vary in the presence of saliva resulting in some inhibition depending on the source of the saliva. However, the use of PF68 prior and during the first heating step significantly improved the sensitivity of the assays for virus in saliva.

Example 14: Improvements in Isothermal Amplification of Nucleic Acids from RNA Viruses in Saliva We observed that RNase activity is very high in saliva and although a detergent such as Tween and Triton X is effective at solubilizing virus capsids at room temperature and efficiently releasing RNA, these detergents also make the target RNA more susceptible to RNase degradation.

We selected a different detergent, namely an alkoxylated alcohol that does not appear to solubilize the virus at room temperature or rather solubilized virions very slowly at room temperature but rather it acts at the high temperatures used to inactivate RNases so the result was that the yield of viral RNA was improved.

When saliva spiked with a known amount of virus was (1) treated with heat (95° C. for 5 minutes); (2) treated with buffer containing Pluronic F68 (PF68); (3) treated with heat and buffer containing Pluronic F68, and tested for RNase activity, only the combination of heat and buffer (PF68) was found to sufficiently inactivate RNase activity in fresh saliva to protect the RNA from degradation.

This result is important as it means that saliva samples combined with a buffer containing an alkoxylated alcohol can provide greater sensitivity.

The following methods of collection of saliva were used:
A. Collection of saliva for storage of samples until analysis.
  (a) A container with sample saliva was heated for 30 minutes at 65° C. to inactivate virus. Samples can be treated immediately or stored at 4° C. or −20° C. for several days.
  (b) NEB buffer containing an alkoxylated alcohol e.g. PF68 was added to the sample at the start of analysis. The sample was found to be stable at room temperature for up to 6 hours. This is helpful when large numbers of samples are being processed so that the samples may be maintained on the bench until ready to perform the LAMP reaction.

The samples were then heated to 95° C. for 5 minutes. This step releases RNA from inactivated virus while the alkoxylated alcohol in the buffer substantially reduced RNase activity. In contrast, RNase activity remained very high after the samples were heated at 95° C. for 5 minutes in the absence of buffer. This corresponded to an absence of detection using LAMP. If other detergents such as Triton X-100 or Tween-20 were used in buffer, even though after the heating step, the remaining RNase activity requires the samples to be stored on ice to prevent the virus RNA degradation.

NEB 1× buffer formulation in the saliva sample in this example was 400 mM GnHCL, 4.5 mM TCEP pH 8.2, 75 mM LiCl and 0.2% PF68. The reagent buffer was prepared as a 2× formulation containing 800 mM GnHCL, 9 mM TCEP pH 8.2, 150 mM LiCl, and 0.4% PF68.

B. Collection of saliva in container in which the NEB buffer is released from a capsule in the lid. No 65° C./30 minutes heating step is required to inactivate virus. Sample was good at room temperature for up to 6 hours.

Heat saliva sample to 95° C. for 5 minutes to release RNA from the capsids in the saliva.

After heat treatment, the sample should be used in LAMP detected as soon as possible. If samples have to be stored, they should be stored at −20° C. or preferably −80 C. Store 1A or 1B on ice for up to a couple of days as needed, longer at −20° C.

An aliquot of saliva sample was removed and diluted 10 fold into LAMP reaction kit (e.g. 2 μl of saliva sample into 18 μl of LAMP reaction mix).

Results: 20 cps of virus mixed with saliva could be detected 100% sensitivity for 12/12 samples tested using saliva from a single source.

Saliva samples were collected from multiple donors and spiked with attenuated RNA virus particles. 5 μL of Sera-Care (mock virus with 100 cps/μL) was added to 30 μL of Saliva, 5 μL of water and 10 μL of 5×NEB buffer. Therefore, the original titer in mixed SeraCare-Saliva sample was 14.3 copies/μL and after adding buffer and water, the titer was 10 copies/μL.

NEBuffer (2×NEB inactivation buffer formulation as a reagent: 800 mM GnHCL, 9 mM TCEP pH 8.2.150 mM LiCl and 0.4% PF68 (no Proteinase K included here)) was added to the saliva. Samples were stable with no observable decrease in detectable copies of viral RNA even when stored at room temperature for at least 6 hours. Samples were then heat at 95° C. for 5 minutes and stored on ice. Aliquots were then used for LAMP detection or RT-qPCR as described in previous examples.

PF68 improved the sensitivity of the LAMP reaction where 20 copies of virus mixed with saliva from different donors could be detected with 100% sensitivity.

1A) Collection of saliva for storage of samples until analysis.

When ready to analyze, add buffer (should contain preferred non-ionic detergent e.g. PF68) (Sample is good at RT for up to 6 hours) and heat to 95° C. for 5 minutes. This step releases RNA from inactivated virus and detergent in buffer with detergent substantially reduces RNase activity. In contrast, RNase activity remains very high after the samples were heated at 95° C. for 5 minutes in the absence of buffer, therefore no SARS-CoV-2 signal can be detected. If other detergents such as Triton X-100 or Tween-20 were used in buffer, even though after the heating step RNase activity was significantly reduced, the remaining RNase activity requires the samples to be stored on ice to prevent the virus RNA degradation.

1B) Collection of saliva in container in which the buffer is released from a capsule in the lid. No 65° C./30 minutes heating step required to inactivate virus. Sample is good at RT for up to 6 hours.

Heat 95° C. for 5 minutes.

After heat treatment, sample should be used in LAMP detected as soon as possible. If samples have to be stored, they should be stored at −20° C. or preferably −80° C. Store 1A or 1B on ice for up to a couple of days as needed, longer at −20° C.

Take an aliquot of saliva sample and dilute 10 fold into LAMP reaction kit (e.g. 2 ul of saliva sample into 18 μl of LAMP reaction mix).

Results: 20 cps of virus mixed with saliva can be detected 100% sensitivity for 12/12 samples tested using saliva from 1 person.

Example 15: An Alternate Protocol for SARS-CoV-2 Screening

Saliva was collected in 1.5 ml barcoded tubes and heated to 65° C. for 30 minutes at the collection site in a buffer that contained 0.2% PF68 or Triton X-100 or no detergent. In this example, the sample was spiked with non-infectious heat inactivated SARS-CoV-2 virus grown in cell culture (ATCC).

25 μL of saliva was mixed with 25 μL of 2× inactivation buffer (1× Cepko inactivation buffer: 2.5 mM TCEP, 11 mM NaOH and 1 mM EDTA)—see Apr. 28, 2020 (https://doi.org/10.1101/2020.04.23.20076877) or NEBuffer (1× inactivation buffer: 4 mM TCEP, 1 mM EDTA, 25 mM LiCl and 400 mM GnCl). When Triton X-100 was added to the Cepko buffer, it was found that the RNA was not preserved at room temperature.

A space change multichannel pipette was used to transfer saliva into 96-well plate with buffer and mixed samples were heated at 95° C. for 5 minutes. 2 μL of sample was transferred into a LAMP reaction followed by a 65° C. 30 minutes amplification and data collection by observing a color change in a tube. The protocol is described in FIG. 30. Examples of the results obtained are shown in FIG. 31A-31C.

Sample in buffer that did not contain detergent could be stored on ice to preserve viral RNA prior to the 95° C. heat step. If Triton X-100 was added to the buffer, it was found that the RNA was not preserved even at room temperature. However, when Pf68 was added to either CepKo buffer and NEBuffer, the sensitivity of both assays were increased compared to the use of Triton-100 despite some variability associated with saliva samples from different human subjects.

Example 16: Immobilization of Oligonucleotide Reagents to Enhance Sensitivity and/or Improve Efficiency of Workflow for Diagnosis of SARS-CoV-2

Immobilized reagents provide an opportunity to achieve enrichment of target nucleic acid from a biological sample and/or reduce the number of steps in a workflow.

This example describes the application of bead immobilized reagents to improve a coronavirus testing workflow that utilizes saliva as a starting material to test for the presence of SARS-CoV-2 virus. and uses LAMP to amplify cDNA derived from any SARS-CoV-2 RNA from virus present in the saliva to determine whether an individual is infected. Human saliva is used and an attenuated SARS-CoV-2 is spiked into the saliva at known concentrations.

The saliva is collected in a first receiving vessel containing a buffer that includes a surfactant/detergent. Enrichment of the SARS-CoV-2 RNA is initiated by the release of viral nucleic acid from virus followed by hybridization of the released RNA to biotinylated oligonucleotides immobilized on streptavidin coated magnetic beads or oligonucleotide coated glass beads. In this test, we use a non-ionic detergent-Pluronic F-68 as the surfactant in the receiving vessel. The contents of the receiving tube is varied as described below and may additionally contain one or more RNase inhibitors and a proteolytic agent.

1. Buffer contains PF-68, magnetic beads coated with a DNA oligonucleotide primer for initiating reverse transcription plus heat labile Proteinase K.
2. Buffer contains the Pf-68, magnetic beads coated with a DNA oligonucleotide primer for initiating reverse transcription absent heat labile Proteinase K, plus guanidinium chloride.
3. Buffer contains PF-68, glass (or any silica-derived) beads of at least 1 mm diameter optionally coated with a DNA oligonucleotide primer for initiating reverse transcription plus heat labile Proteinase K.
4. Buffer contains PF-68, glass (or any silica-derived) beads of at least 1 mm diameter optionally coated with a DNA oligonucleotide primer for initiating reverse transcription absent heat labile Proteinase K, plus guanidinium chloride.
5. Buffer contains PF-68, magnetic beads coated with an RNA or DNA oligonucleotide primer for binding the viral RNA at a predetermined location (e.g. EIA) plus heat labile Proteinase K.
6. Buffer contains PF-68, magnetic beads coated with coated with an RNA or DNA oligonucleotide primer for binding the viral RNA at a predetermined location (e.g. EIA) absent heat labile Proteinase K, plus guanidinium chloride.
7. Buffer contains PF-68, glass (or any silica-derived) beads of at least 1 mm diameter optionally coated with an RNA or DNA oligonucleotide primer for binding the viral RNA at a predetermined location (e.g. EIA) plus heat labile Proteinase K.
8. Buffer contains PF-68, glass beads (or any silica-derived) of at least 1 mm diameter optionally coated with an RNA or DNA oligonucleotide primer for binding the viral RNA at a predetermined location (e.g. EIA) absent heat labile Proteinase K, plus guanidinium chloride.

Workflow Details

Following the binding step, the magnetic beads containing the hybridized viral genome are separated from the buffer by means of a magnet, where the buffer containing unwanted biological material is discarded and the beads suspended in a buffer containing reagents for reverse transcription and amplification by LAMP (see RT-LAMP from New England Biolabs, Ipswich, Mass.).

For the glass beads containing the hybridized viral genome or target(s), a filter with a pore size less than the diameter of the beads is placed in a sleeve within a second receiving vessel (see U.S. patent application Ser. No. 16/547,844 and New England Biolabs, Ipswich, Mass.) In this case, the receiving vessel has an exit that has an open and shut position. In the open position, the buffer containing the unwanted biological material is drained away and the sleeve placed into a second tube containing a buffer suitable for amplification (e.g., RT-LAMP, RT-qPCR, etc.).

Hypothesized Results

Where magnetic beads were used, enrichment of viral RNA only was achieved and hence cDNA was also specific for the target viral RNA. In contrast, use of glass beads would result in adsorption of some non-target viral RNA and hence cDNA would include non-viral cDNA. Nonetheless this contamination would have negligible impact since the plurality of sets of probes for LAMP are highly specific for the target viral genome.

If a person is infected with SARS-CoV-2, the saliva is expected to contain between 10,000-20,000 viral particles. For a positive result to be obtained using LAMP, it is desirable to be able to detect the presence of at least 25 viral genomes. The immobilization of oligonucleotide probes and enrichment of target nucleic acids from saliva is expected to deliver this degree of sensitivity even if hybridization of target viral RNA to immobilized probes is not 100% efficient. In fact, even if this were less than 5% efficient, the sensitivity and reproducibility of the LAMP based test would be expected to increase besides any loss of efficiency in handling large numbers of samples or significant increase in workflow complexity.

Example 17: Detection of Influenza and SARS-CoV-2 in a Multiplex Reaction

Multiplex Reaction-Selection of Primer Sets

For Influenza detection, a variety of LAMP primer sets reported by others (Parida et al. J Mol Diagn 13(1), 100-107 (2011), Mahony et al. J Clin Virol 58(1), 127-131 (2013), Ahn et al. BMC Infect Dis 19(1), 676 (2019) and Takayama et al. J Virol Methods 267 53-58 (2019)) were synthesized, tested and compared with respect to compatibility and utility in DARQ LAMP. These primer sets were also evaluated for speed, sensitivity, and ability to multiplex with the SARS-CoV-2 sets. From this comparison we selected the IAV and IBV primer sets from Takayama et al. as they were found to be the most sensitive primer sets for DARQ LAMP. The multiplex LAMP tested contained the IAV and IAB primer sets for Influenza, the E1 primer set for SARS-CoV-2 and ACTB for an internal control.

Materials and Methods

DARQ LAMP primer sets (F3, B3, FIP, BIP, LF and LB) plus a duplex oligo consisting of the FIP modified at its 5'-end with a dark quencher (Q-FIP) annealed to a complementary F1c oligo with 3' fluorophore (Fd) (Table 1) were selected for target RNAs. The E1 LAMP primers targeting SARS-CoV-2 sequence (GenBank accession number MN908947) and IAV and IBV primer sets (Takayama, et al). were synthesized at Integrated DNA Technologies (Coralville, Iowa) with standard desalting for conventional LAMP primers and HPLC purification for QFIP and Fd oligos. Synthetic SARS-CoV-2 RNA containing equal ratio of the viral genome regions was purchased from Twist Bioscience, California (Twist Synthetic SARS-CoV-2 RNA Control 2 #102024, MN908947.3). RNAs for Influenza A (H1N1) (VR-1737D, Strain A/Virginia/ATCC/2009), A (H3N2) (VR-1811D, Strain A/Virginia/ATCC6/2012) and B (VR-1885DQ, Strain B/Wisconsin/1/2010 BX-41A) were purchased from ATCC. Viral RNA was diluted to lower concentrations in 10 ng/μl Jurkat total RNA (BioChain) based on quantification provided by the manufacturers. For the 24 repeat reactions, the amount of RNA used was 50 copies of SARS-CoV-2 RNA, 1 ul of 1:1000 diluted Influenza A RNA and approximately 21 copies for Influenza B RNA. This amount of viral RNAs was sufficient for more than half but not all the 24 repeats to show positive amplification thus allowing detection of sensitivity change under different conditions.

Primer sets are shown in Table 3:

TABLE 3

| Primer set | Sequence |
|---|---|
| E1[11] | |
| E1-F3 | TGAGTACGAACTTATGTACTCAT (SEQ ID NO: 70) |
| E1-B3 | TTCAGATTTTTAACACGAGAGT (SEQ ID NO: 71) |
| E1-FIP | ACCACGAAAGCAAGAAAAAGAAG TTCGTTTCGGAAGAGACAG (SEQ ID NO: 72 |
| E1-BIP | TTGCTAGTTACACTAGCCATCCT TAGGTTTTACAAGACTCACGT (SEQ ID NO: 73) |
| E1-LF | CGCTATTAACTATTAACG (SEQ ID NO: 74) |
| E1-LB | GCGCTTCGATTGTGTGCGT (SEQ ID NO: 75) |
| E1-QFIP | /5IABkFQ/ACCACGAAAGCAAG AAAAAGAAGTTCGTTTCGGAAGA GACAG (SEQ ID NO: 76) |
| E1-FD | ACTTCTTTTTCTTGCTTTCGTGG T/3Joe_N/ (SEQ ID NO: 77) |
| IAV | |
| IAV-F3-1 | GACTTGAAGATGTCTTTGC (SEQ ID NO: 78) |
| IAV-F3-2 | GACTGGAAAGTGTCTTTGC (SEQ ID NO: 79) |
| IAV-B3-1 | TRTTATTTGGGTCTCCATT (SEQ ID NO: 80) |
| IAV-B3-2 | TRTTGTTTGGGTCCCCATT (SEQ ID NO: 81) |
| IAV-FIP | TTAGTCAGAGGTGACARRATTGC AGATCTTGAGGCTCTC (SEQ ID NO: 82) |
| IAV-BIP | TTGTKTTCACGCTCACCGTGTTT GGACAAAGCGTCTACG (SEQ ID NO: 83) |
| IAV-LF | GTCTTGTCTTTAGCCA (SEQ ID NO: 84) |
| IAV-LB | CMAGTGAGCGAGGACTG (SEQ ID NO: 85) |
| IAV-QFIP | /5IAbRQ/TTAGTCAGAGGTGAC ARRATTGCAGATCTTGAGGCTCT C (SEQ ID NO: 86) |
| IAV-Fd | CAATYYTGTCACCTCTGACTAA/ 3Cy5Sp/ (SEQ ID NO: 87) |
| IBV | |
| IBV-F3 | GCAACCAATGCCACCATA (SEQ ID NO: 88) |
| IBV-B3 | TTCTCTCTTCAAGRGACATC (SEQ ID NO: 89) |
| IBV-FIP | TAGTCAAGGGCYCTTTGCCACTT TGAAGCAGGAATTCTGGA (SEQ ID NO: 90) |
| IBV-BIP | CAAGACCGCCTAAACAGACTAAA CTTTTACTTTCAGGCTCACTT (SEQ ID NO: 91) |
| IBV-LF | TGAAAGYCTTTCATAGCAC (SEQ ID NO: 92) |
| IBV-LB | CAAGAATAAAGACTCACAAC (SEQ ID NO: 93) |
| IBV-QFIP | /5IABkFQ/TAGTCAAGGGCYC TTTGCCACTTTGAAGCAGGAAT TCTGGA (SEQ ID NO: 94) |
| IBV-Fd | TGGCAAAGRGCCCTTGACTA/ 36-FAM/ (SEQ ID NO: 95) |
| ACTB | |
| ACTB-F3 | AGTACCCCATCGAGCACG (SEQ ID NO: 96) |
| ACTB-B3 | AGCCTGGATAGCAACGTACA (SEQ ID NO: 97) |
| ACTB-FIP | GAGCCACACGCAGCTCATTGT ATCACCAACTGGGACGACA (SEQ ID NO: 98) |
| ACTB-BIP | CTGAACCCCAAGGCCAACCGG CTGGGGTGTTGAAGGTC (SEQ ID NO: 99) |
| ACTB-LF | TGTGGTGCCAGATTTTCTCCA (SEQ ID NO: 100) |
| ACTB-LB | CGAGAAGATGACCCAGATCAT GT (SEQ ID NO: 102) |
| ACTB-QFIP | /5IAbRQ/GAGCCACACGCAG CTCATTGTATCACCAACTGGG ACGACA (SEQ ID NO: 103) |
| ACTB-Fd | TACAATGAGCTGCGTGTGGCT C/3Rox_N/ (SEQ ID NO: 104) |

All Influenza primers were initially screened for performance using WarmStart® Colorimetric LAMP 2× Master Mix (DNA & RNA) (New England Biolabs, M1800) and with WarmStart LAMP Kit (DNA & RNA) (New England Biolabs, E1700) supplemented with 1 μM SYTO®-9 double-stranded DNA binding dye (ThermoFisher, S34854). DARQ LAMP reactions contained 1×E1700 (New England Biolabs), with an additional 0.32 U/μL Bst 2.0 WarmStart DNA Polymerase (New England Biolabs, M0538), 40 mM guanidine chloride (Sigma, RDD001) and standard concentrations of LAMP primers (0.2 μM F3, 0.2 μM B3, 1.6 μM FIP, 1.6 μM BIP, 0.4 μM LoopF, 0.4 μM Loop B) supplemented with DARQ FIP duplex (0.22 μM QFIP: 0.18 μM Fd, pre-annealed as 55 μM QFIP: 45 μM Fd by heating to 95° C. and slowly cooling to room temperature). The concentration for ACTB primers was reduced to 0.25× the standard concentrations for LAMP primers (0.05 μM F3, 0.05 µM B3, 0.4 µM FIP, 0.4 µM BIP, 0.1 µM LoopF, 0.1 µM Loop B) with DARQ FIP duplex added as 0.066 µM QFIP and 0.054 µM Fd. The reactions were incubated at 60° C. in half-skirted plates (BioRad, HSP9601) on a real-time qPCR machine (Bio-Rad CFX96). Real time LAMP signal was acquired every 15 seconds for 108 cycles (total incubation time ~40 minutes for single channel or 49 minutes for 4-channel acquisition). Completed LAMP reactions were then scanned on BioTek Synergy NEO 2 microplate reader for fluorescence signal for 5-FAM (Excitation, 484/20, Emission 530/25, Signal Gain 75), HEX (524/20, 565/20, 75), 5-ROX (569/20, 615/25, 85) and Cy5 (640/20, 682/20, 75). The threshold for the positive signal was set as above the sum of average raw fluorescence units (RFU) of 8 NTC reactions plus 10× of their standard deviation.

The results showed that the amplification speed (determined from Cq) and detection sensitivity (plots of RFU from endpoint scanning) was similar for conventional LAMP monitored using Syto-9 and for DARQ-LAMP. 24 repeats with 50 copies of SARS-CoV-2 RNA or 8 repeats of NTC were tested using E1 or E1 and ACTB. Sensitivity was also tested for SARS-CoV-2 in the presence of (E1+ACTB) (E1+ACTB+IAV) and (E1+ACTB+IAV+IBV) primer sets by DARQ LAMP (see for example FIG. 31A-31C).

Example 18: SARS-Cov-2 RT LAMP Assay Validation for Saliva Samples

The conditions for performing a LAMP reaction on saliva samples to detect SARS-Cov-2 were stringently tested to provide a method that was accurate and reproducible not just for a single operator or technician but for multiple operators and technicians. The results below show that this was achieved successfully. Moreover, this approach has been tested successfully on another RNA virus, namely Eastern equine encephalitis using crushed mosquitos that contain virus infected blood from mammalian hosts using a single set of LAMP primers. RT-LAMP detects the genetic material present in the SARS-CoV-2 virus. The RNA genome is first reverse transcribed to create a complementary DNA (cDNA) strand. Specific cDNA primers then amplify conserved SARS-CoV-2 regions within two targets, the N and E genes. Amplification is detected by increased fluorescence as the included dye intercalates in the newly created cDNA. In addition, a pH indicator dye signals a change in pH resulting from the release of H+ as nucleotide triphosphates are incorporated into the cDNA amplification product. In the absence of the target N and E regions no cDNA amplification occurs, and hence no fluorescent signal increase or pH indicator change is noted. An analogous reaction targeting human actin RNA is run separately on each sample to ensure the sample is devoid of reaction inhibitors and contains sufficient material for baseline detection.

Cq refers to the cycle number in which the fluorescence signal passes a threshold. If no signal above threshold can be detected, Cq is reported as N/A (not available). The more target RNA present, the smaller the Cq value obtained. In the current protocol, the fluorescence signal is read at 15 second intervals throughout the reaction period of 36 minutes.

Color change indicates the presence of a target nucleic acid. Color tone of LAMP without target is pink and with detectable target is yellow. Amplification is determined visually and recorded using a scanner where yellow indicates virus is present and pink indicates that the virus is absent. Sometimes the color is orange if the reaction contains an inhibitory substance or a very low copy number of virus.

A. Reagents/Solutions

Primer sets for both SARS-CoV-2 and actin RNA detection, TCEP, Hydrochloride solid (Millipore Sigma), Sodium hydroxide (NaOH) solution, EDTA solution, Pluronic F-68 (PF68) Non-ionic Surfactant (ThermoFisher Scientific), Nuclease-free water (New England Biolabs)

B. Controls: Inactivated SARS-CoV-2 Positive Control (BEI Resources), Human Total RNA Positive Control (ThermoFisher)

C. Equipment: Bio-Rad CFX96 qPCR instrument, Bio-Rad Thermal Cycler. Eppendorf Xplorer® plus, single-channel, 5-100 µL electronic pipette, 8-channel, 15-300 µL electronic pipette, 12-channel, 5-100 µL electronic pipette.

D. Buffers 1. 100× Stock Buffer (10 mL)

TABLE 4

| Component | Stock Concentration | Final Concentration (100x) | 10 mL |
|---|---|---|---|
| TCEP | 0.5M | 0.25M | 5 mL |
| NaOH | 10M | 1.1M | 1.1 mL |
| EDTA | 0.5M | 0.1M | 2 mL |
| Nuclease free H$_2$O | | | 1.1 mL |
| Total | | | 10 mL |

2. 2× Saliva Lysis Buffer (SLB) Buffer (100 mL)

TABLE 5

| Component | Stock Concentration | 100 mL 2X |
|---|---|---|
| Stock buffer | 100X | 2 mL |
| 10% Pluronic F-68 | 50X | 4 mL |
| Nuclease free H$_2$O | | 94 mL |
| Total | | 100 mL |

Method of Analysis of the Saliva Sample

An inactivated SARS-CoV-2 Positive Control was obtained from BEI resources (Manassas, Va.) Pooled human saliva samples negative for SARS-CoV-2 (from NEB research study) were also tested. Human total RNA was monitored with a sample extraction and inhibition control using detection of actin mRNA where actin mRNA was obtained from ThermoFisher (MA). SARS-CoV-2 positive and negative clinical saliva samples provide by Mirimus Clinical Labs, a CLIA-certified facility where SARS-CoV-2 sample status was classified by Mirimus following RNA extraction using ThermoFisher TaqPath. 30 positive and 30 negative samples were analyzed in this example. The primers used in LAMP targeting gene N, Orf1ab, and S genes.

Saliva samples were heated in 1.5 mL labelled tubes at 65° C. for 30 min to inactivate any SARS-CoV2, and subsequently stored on ice or in the refrigerator for up to 72 hours. 154 of individual heat-inactivated test samples were transferred into 94 of the individual wells of a 96 well SLB plate. Up to 94 test samples were added into each 96 well SLB plate. One well was reserved for the negative control (NC) and one for the positive control (PC). See an example plate in FIG. 33.

1. Controls
   a. 15 µl of H$_2$O was added to each of the two plates, in negative control well
   b. 15 µL of H$_2$O containing 50 copies of heat inactivated virus was dispensed into the positive control well in the SARS-CoV-2 test plate.

2. Sample plates were heated for 95° C. for 5 minutes then held at 4° C. The samples were stored at 0-4° C. for up to 24 hours prior to performing the LAMP detection reaction.

A. Preparation of SARS-CoV-2 LAMP reaction plate and actin LAMP reaction plate in AirClean PCR Workstation 1. A 2 mL Eppendorf tube was labelled for SARS-CoV-2 reaction mix and another for human actin reaction mix and both were placed on ice.
2. The following SARS-CoV-2 RT-LAMP reaction mix was prepared for one 96-well plate:

TABLE 6

| Component | Volume/reaction | Volume/100 reactions |
|---|---|---|
| 2x Master Mix, (NEB: E2019) | 10 μl | 1000 μl |
| 10X SARS-CoV-2 primer mix (NEB: S1883*) | 2 μl | 200 μl |
| 10X GuHCl solution | 2 μl | 200 μl |
| 50X Syto 9 dye | 0.4 μl | 40 μl |
| Nuclease free H$_2$O | 3.6 μl | 360 μl |
| Total | 18 μl | 1800 μl |

3. Prepare actin RT-LAMP reaction mix for one 96-well plate:

TABLE 7

| Component | Volume/reaction | Volume/100 reactions |
|---|---|---|
| 2x Master Mix, (NEB: E2019) | 10 μl | 1000 μl |
| 10X actin primer mix (NEB: S0164*) | 2 μl | 200 μl |
| 10X GuHCl solution | 2 μl | 200 μl |
| 50X Syto 9 dye | 0.4 μl | 40 μl |
| Nuclease free H$_2$O | 3.6 μl | 360 μl |
| Total | 18 μl | 1800 μl |

*NEB: E2019 RT-LAMP kit contains two 10X Primer mixes. The SARS-CoV-2 LAMP reaction uses primer mix S1883, and the actin LAMP reaction uses primer mix S0164.

18 μL SARS-CoV-2 LAMP reaction mix was distributed to each well of the SARS-CoV-2 reaction plate. 18 μL actin LAMP reaction mix was distributed to each well of the actin reaction plate.

An inactivated SARS-CoV-2 Positive Control was obtained from BEI resources (Manassas, Va.) Pooled human saliva samples negative for SARS-CoV-2 (from NEB research study) were also tested. Human total RNA was monitored with a sample extraction and inhibition control using detection of actin mRNA where actin mRNA was obtained from ThermoFisher (MA). SARS-CoV-2 positive and negative clinical saliva samples provide by Mirimus Clinical Labs, a CLIA-certified facility where SARS-CoV-2 sample status was classified by Mirimus following RNA extraction using ThermoFisher TaqPath. 30 positive and 30 negative samples were analyzed in this example. The primers used in LAMP targeting gene N, Orf1ab, and S genes.

2 μL prepared sample and the actin control were transferred from the SLB plate to the SARS-CoV-2 LAMP reaction plate containing 18 ul of LAMP reaction mi. 2 μL of 1 ng/μL human RNA was transferred into the positive control well. The thermal cycler was set to 97 cycles, each at 65° C. for 15 seconds (total time approximately 36 minutes), followed by a hold at 10° C. and fluorescence recorded during the 97 cycles. A 'post-amplification' image of the plate was generated for visual confirmation of results.

Using the method described above, the saliva assay was tested using negative saliva samples spiked with inactivated SARS-CoV-2 (contingent samples) and clinical samples. No RNA purification was performed.

10 different negative saliva were pooled.

320 copies/uL inactivated virus (BEI) were added to negative pooled saliva.

This spiked saliva was then diluted by a 1:2 serial dilution: 7 fold) in negative saliva. Triplicate saliva samples were prepared for each dilution. 15 uL of saliva was combined with 15 uL of 2× sample buffer and incubated at 95° C. for 5 minutes. 2 uL of sample was added to 20 uL of a LAMP reaction mix for triplicate LAMP reactions at each dilution. Cq values were obtained. The LOD of SARS-Cov-2 detection was 40 copies/ul.

Every positive SARS-CoV-2 saliva sample was retested in triplicate. If repeat testing showed more than 2 positive SARS-CoV-2 results, a "Positive" determination was recorded. Otherwise, the test was deemed inconclusive. For initially inconclusive saliva samples, the assay was repeated using original saliva sample with triplicate LAMP reactions to confirm the result.

Results
Clinical Sample Validation

TABLE 8

| Plate ID | Mirimus positive | Mirimus negative | Li_2/24/2021 Covid | Li_2/24/2021 Actin | Zhang_3/4/2021 Covid | Zhang_3/4/2021 Actin | Li_3/5/2021 Covid | Li_3/5/2021 Actin |
|---|---|---|---|---|---|---|---|---|
| F7 | 1 | | 27.51 | 28.07 | 25.44 | 29.42 | 25.62 | 29.39 |
| F4 | 2 | | 26.6 | 25.95 | 24.28 | 28.47 | 25.39 | 27.16 |
| E2 | 3 | | 27.39 | 28.05 | 24.92 | 30.86 | 25.51 | 29.6 |
| D8 | 4 | | 27.33 | 30.14 | 23.32 | 30.9 | 25.31 | 29.76 |
| B5 | 5 | | 27.36 | 26.15 | 24.53 | 33.74 | 25.35 | 31.45 |
| F1 | 6 | | 26.49 | 26.24 | 26.18 | 28.24 | 25.23 | 28.02 |
| E3 | 7 | | 26.24 | 26.54 | 24.92 | 32.42 | 25.21 | 27.9 |
| D1 | 8 | | 25.8 | 29.33 | 25.21 | 28.48 | 25.62 | 29.52 |
| E5 | 9 | | 26.61 | 26.16 | 24.25 | 29.79 | 25.74 | 28.83 |
| F3 | 10 | | 26.9 | 30.44 | 25.85 | 30.37 | 24.57 | 29.13 |
| E4 | 11 | | 25.06 | 26.5 | 25.28 | 47.64 | 25.24 | 31.4 |
| H7 | 12 | | 26.58 | 26.3 | 24.02 | 28.82 | 26.07 | 29.8 |
| C8 | 13 | | 27.17 | 26.94 | 25.57 | 33.12 | 25.22 | 28.53 |
| A7 | 14 | | 26.39 | 34.69 | 26.21 | 30.54 | 25.31 | 32.15 |
| A3 | 15 | | 26.72 | 25.6 | 24.83 | 33.87 | 27.19 | 29.19 |
| H3 | 16 | | 26.8 | 29.57 | 26.47 | 32.19 | 24.51 | 29.1 |
| C4 | 17 | | 36.36 | 29.45 | 29.51 | 39.22 | 28.98 | 33.44 |
| A4 | 20 | | 40.18 | 63.07 | 29.67 | 77.04 | 29.06 | 30.54 |

TABLE 8-continued

| Plate ID | Mirimus positive | Mirimus negative | Li_2/24/2021 Covid | Actin | Zhang_3/4/2021 Covid | Actin | Li_3/5/2021 Covid | Actin |
|---|---|---|---|---|---|---|---|---|
| C3 | 21 | | 32.64 | 28.54 | 27.21 | 38.6 | N/A | 30.25 |
| B7 | 22 | | 29.57 | 28.77 | 26.74 | 31.22 | 31.02 | 29.88 |
| H2 | 23 | | 36.87 | 28.73 | 25.72 | 43.93 | 29.33 | 30.96 |
| D6 | 24 | | 31.05 | 32.76 | 33.02 | 56.05 | 28.63 | 30.3 |
| F6 | 25 | | 33.44 | 28.04 | 27.3 | 34.6 | 31.34 | 31.68 |
| A8 | 27 | | 35.55 | 27.02 | 27.2 | 32.27 | 28.98 | 31.65 |
| B4 | 28 | | 84.32 | 27.84 | 90.39 | 36.61 | 29.15 | 28.37 |
| F2 | 29 | | 31.6 | 26.83 | 27.82 | 30.18 | 27.67 | 29.18 |
| C6 | 30 | | 30.87 | 25.35 | 30.17 | 29.76 | 62.49 | 28.02 |
| B6 | 33 | | 29.83 | 26.9 | 28.72 | 27.68 | 28.58 | 29 |
| H5 | 37 | | 31.13 | 27.52 | 62.39 | 36.12 | 32.04 | 28.38 |
| G1 | 39 | | 30.48 | 25.88 | 28.45 | 29.86 | 27.94 | 28.91 |
| H4 | | 1 | N/A | 30.57 | N/A | 34.07 | N/A | 33.17 |
| D7 | | 2 | N/A | 28.85 | N/A | 29.15 | N/A | 30.55 |
| D2 | | 3 | N/A | 33.15 | N/A | 33.99 | N/A | 34.53 |
| E6 | | 5 | N/A | 29.34 | N/A | 31.18 | N/A | 30.19 |
| B1 | | 6 | N/A | 27.26 | N/A | 31.34 | N/A | 29.49 |
| G3 | | 7 | N/A | 31.03 | N/A | 33.54 | N/A | 34.47 |
| G7 | | 8 | N/A | 28.77 | N/A | 33.03 | N/A | 30.21 |
| E1 | | 9 | N/A | 28.55 | 88.79 | 31.07 | 86.9 | 29.6 |
| D3 | | 10 | N/A | 34.38 | N/A | 35.32 | N/A | 37.07 |
| A5 | | 11 | N/A | 27.79 | N/A | 30.76 | N/A | 29.34 |
| G2 | | 12 | N/A | 30.74 | N/A | 33.17 | N/A | 30.47 |
| E7 | | 13 | N/A | 36.25 | N/A | 36.37 | N/A | 38.04 |
| C2 | | 14 | N/A | 29.75 | N/A | 30.95 | N/A | 32.25 |
| C5 | | 15 | N/A | 29.13 | 96.05 | 29.59 | 95.09 | 29.66 |
| G4 | | 16 | N/A | 31.07 | N/A | 32.52 | N/A | 32.57 |
| D5 | | 17 | N/A | 27.87 | N/A | 30.77 | N/A | 29.91 |
| D4 | | 18 | N/A | 29 | N/A | 29.6 | N/A | 29.18 |
| C7 | | 19 | N/A | 28.59 | N/A | 31.17 | 86.94 | 32.64 |
| B3 | | 20 | N/A | 29.16 | N/A | 30.5 | N/A | 30.49 |
| A1 | | 21 | N/A | 28.53 | N/A | 33.76 | 96.03 | 31.5 |
| A2 | | 22 | N/A | 34.17 | N/A | 34.19 | N/A | 37.21 |
| G6 | | 23 | N/A | 28.71 | N/A | 30.67 | N/A | 31.23 |
| H6 | | 24 | N/A | 27.15 | N/A | 29.76 | N/A | 30.34 |
| H1 | | 25 | N/A | 30.1 | 81.5 | 32.02 | N/A | 35.03 |
| F5 | | 26 | N/A | 29.15 | N/A | 31.28 | N/A | 31.3 |
| B2 | | 27 | N/A | 29.39 | N/A | 32.34 | N/A | 32.23 |
| C1 | | 28 | N/A | 29.29 | N/A | 30.94 | 82.82 | 30.43 |
| A6 | | 29 | N/A | 28.1 | 81.26 | 30.94 | N/A | 30.66 |
| G5 | | 30 | N/A | 26.19 | N/A | 28.66 | N/A | 27.68 |
| B8 | | 31 | N/A | 32 | N/A | 33.34 | N/A | 33.57 |
| E8 | H2O | H2O | N/A | N/A | N/A | 91.06 | N/A | 83.94 |
| F8 | H2O | H2O | N/A | N/A | N/A | 90.91 | N/A | 83.98 |
| G8 | Virus | hRNA | 24.54 | 20.92 | 23.3 | 20.88 | 23.47 | 22.42 |
| H8 | Virus | hRNA | 25.08 | 20.62 | 23.89 | 21.02 | 24.03 | 22.39 |
| | | total | 59/60 | 60/60 | 59/60 | 59/60 | 59/60 | 60/60 |
| | | % | 98% | 100% | 98% | 98% | 98% | 100% |

Cq values for the individual assays are given above. Samples were anonymized on the plate but sorted for the table.
H₂O indicates a water negative control.
Virus indicates 50 copies of SARS-CoV-2 positive control.
hRNA indicates 2 ng human total RNA positive control for actin mRNA.
Orange box indicates sample not meeting Mirimus assay expectation.
The following parameters were provided.

1. Accuracy
   A. Concordance with expected positive results
      i. Contrived samples (virus-negative saliva spiked with known amounts of virus)
         1. All 96 samples with at least 40 copies/assay were correctly identified using the assay.
         2. All 30 samples lacking added virus were correctly identified as negative and 30 Mirimus positive samples were identified as positive.
      ii. Clinical samples
         1. Each run showed either 59/60 or 60/60 concordance with Mirimus results
         2. Minimally 98% accuracy for one operator and for multiple operators at least 97% accuracy (58/60 samples)
   B. Reproducibility of the assay
      i. Contrived samples
         1. All 20 virus-containing samples, each in triplicate, were found to be positive (60 samples)
         2. All 6 saliva samples without virus were found to be negative
      ii Clinical samples
         1. In the hands of two different technicians on three separate days at least 59 Of 60 samples matched the assay results provided by Mirimus (98%)
         2. Pairwise comparison of individual runs showed agreement between runs. Testing results were consistent (within 95%) on two separate days with two independent technicians, using identical samples 3. Sensitivity: (True positives)/(True positives+False negatives)

A. Determination of Limit of Detection (LOD) using contrived samples

Samples with Cq values below 70 were scored as positive for SARS-CoV-2 as per assay protocol. All nine samples with at least 40 viral copies/pi were found to be positive by the assay criteria. Samples with 20 or 10 viral copies/pi were found to be positive in 8/9 or 7/9 samples, respectively. No samples in the negative controls were found to be positive. LOD was set at 40 viral copies/pi, with reliability dropping off below that level. The following LOD values were obtained: From contrived samples, 40 copies/pi: 9/(9+0)=100%; 20 copies/pi: 8/(8+1)=89%; 10 copies/pi: 7/(7+2)=78%. From Clinical samples, Feb. 24, 2021: 29/(29+1)=97%, 3/4/21: 29/(29+1)=97% and 3/5/21: 29/(29+1)=97%

4. Specificity: (True negatives)/(True negatives+False positives)

A. from LOD determinations
  i. At 40 copies/pi: 9/(9+0)=100%
  ii. At 20 copies/pi: 9/(9+0)=1 00%
  iii. At 10 copies/pi: 9/(9+0)=100%

B. From clinical samples
  i. 2/24/21 30/(30+0)=100%
  ii. 3/4/21 30/(30+0)=100%
  iii. 3/5/21 30/(30+0)=100%

5. Reportable values

A. Values reported as detected or undetected.

B. Reproducibility suffered at virus concentrations less than 40 copies/pi.

C. Detection occurred at all tested virus concentrations above 40 copies/μL.

6. Reference range:

As can be seen in the accompanying figure, the anticipated viral load in saliva ranged between $10^4$-$10^{10}$ copies/mL in patients, with decreasing viral loads as infection progresses. The LOD for this method was 40 copies/pi, or $4×10^4$ copies/mL, covering the vast majority of expected infection viral titers, particularly in the early stages of infection.

Example 19: Universal Assay for a Pathogen and its Known and Unknown Variants

In order to provide solutions for distinguishing sequence variants rather than just tolerating them, we designed a variant-specific LAMP detection method based on molecular beacons targeting a 9-base deletion in Orf1a that is more widely observed (SGF deletion), enabling the detection of multiple variants of concern including B.1.1.7, B.1.351, and P.1.

The phrase "Target nucleic acids with (i) a known sequence or (ii) a known sequence with a plurality of undefined mutations therein" refers to variants of a target nucleic acid in a cell or virus that have "undefined mutations". Undefined mutations may arise in a cell or virus pathogen to evade host immune mechanisms or medications or for other reasons. The mutations that arise may result in changed properties relating to virulence and pathogenicity usually by increasing one or both. Often these variants coexist with other mutants or variants. It is beneficial to an animal population such as humans if the appearance of a new variant is rapidly detected before extensive spreading.

PCR is an established, sensitive method of detecting specific target nucleic acids. that require two primers only and a thermocycling protocol. If novel mutations arise in a target nucleic particularly at the 3' end of the primer binding site, PCR will take longer to amplify the nucleic acid to the point that a positive sample will register as negative. A negative PCR result is one that does not yield a positive signal after a predetermined number of thermocycles. This can have negative repercussions for detecting infected individuals in a population in which multiple variants coexist where an infected person may receive a negative result on the basis of less than ideal PCR primers. Efficiency of primer annealing is therefore a factor in considering sensitivity of a PCR reaction.

PCR differs from LAMP amplification in ways that include the nature of the amplification itself. Without being limited by theory it is proposed here that the inefficiencies in primer hybridization for PCR are amplified by the protocol compared with LAMP. In PCR, amplification is a series of discrete events in which primers are required to bind to each molecule in the population and then to bind to each of the amplicons in every cycle. Therefore any inefficiency in binding due to mutations is itself amplified. In contrast, LAMP uses 4, 5 or 6 primers which create intermediate species that are then amplified from multiple primer binding events and locations, These multiple binding and amplification sites reduce the impact of primer binding efficiencies.

The use of the term "universal primer set" is intended to refer to a primer set used in LAMP to detect a specific gene or specific sequence in a target nucleic acid or the entire nucleic acid. The specific gene, sequence or the entire target nucleic acid may contain mutations including one or more, or a plurality of previously unknown mutations. The presence of mutations in the target nucleic acid is referred to here as target nucleic acid variants. These mutations may be additions, deletions or point mutations that occur at primer binding sites for primers used in nucleic acid amplification assays to determine the presence of a pathogenic cell or virus. The universal primer set is so named because the primers can initiate amplification reactions to detect a specific target with a similar sensitivity and specificity regardless of known or unknown mutations in the primer binding sites of that target. However, it is expected that the deletions or additions will not exceed 10 nucleotides or more particularly will not exceed 9 nucleotides for example, will not exceed 8 nucleotides for example, will not exceed 6 nucleotides within primer binding regions. In some embodiments, it was found that deletions of 9 nucleotides and 6 nucleotides in the FIP and BIP primer binding sites could be detected by LAMP using the universal LAMP primer set although it was noted that a deletion of 9 nucleotides could reduce sensitivity of a diagnostic test. The universal primer set is also able to detect a mixture of nucleic acids where some nucleic acids may have a particular target sequence and others are variants thereof. The universal primer set may include 4, 5 or 6 primers. In some circumstances, a plurality of universal primer sets will be used to detect a target nucleic acid for amplifying different regions of the target nucleic acid.

LAMP is characterized by the use of 4 different primers specifically designed to recognize 6 distinct regions of the target gene. The four primers include 2 inner primers (Forward inner primer (FIP) and Backward inner primer) and 2 outer primers (Forward outer primer (F3) and Backward outer primer (B3). A universal primer set may also include 2 additional primers-Loop primers (Loop forward (LF) and Loop backward (LB) primers. Although the loop primers are optional, they can increase sensitivity and specificity of the amplification reaction.

The term "reaction positive period of time" refers to the reaction time for amplification prior to an established cut-off time in which a sample is determined to be positive. The cut-off time for amplification to occur has been established by diagnostic laboratories to determine if a sample is positive or negative.

Materials and Methods

Single point mutation LAMP primers: Three previously described LAMP primer sets for SARS-CoV-2 were chosen to profile mutational position effects: As1e [20], E1, and N2 [4] (Table 9). A point mutation that appeared within GISAID sequences as monitored by NEB Primer Monitor (primer-montor.neb.com) was introduced at every base position for each of the primers changing: C→T, T→C, G→T, or A→C. The resulting 572 primers were synthesized in 96-well plates at 10× concentration (2 μM F3, B3; 16 μM FIP, BIP; 4 μM LoopF, LoopB) by Integrated DNA Technologies (IDT) and spot-checked for concentration using 90 of the provided oligos.

TABLE 9

LAMP Primers*

| Assay | Primer | Sequence |
|---|---|---|
| SFG | | |
| | F3 | GCTTTTGCAATGATGTTTGTC (SEQ ID NO: 1105) |
| | B3 | AGTGTCCACACTCTCCTAG (SEQ ID NO: 106) |
| | FIP | CCAACTAGCAGGCATATAGAC CATACATTTCTCTGTTTGTTT TTGTTACC (SEQ ID NO: 107) |
| | BIP | ATGACATGGTTGGATATGGTT GGTTCTTGCTGTCATAAGGAT T (SEQ ID NO: 108) |
| | LF | AAGCTACAGTGGCAAGAGAA (SEQ ID NO: 109) |
| | FB | ATGCATCAGCTGTAGTGTTA CT (SEQ ID NO: 110) |
| | MB-WT | /5Cy3/GGAGCTT + T GT + CTGGTTT + TA AG + CTCC/3IAbRQSp/ (SEQ ID NO: 111) |
| | MB-DEL | /56-FAM/CGCAGTT + T GAAG + CTAAA + A + G A + CTGCG/3IABkFQ/ (SEQ ID NO: 112) |
| As1e | | SEQ ID NOs: 46-51 |
| E1 | | SEQ ID NOs: 70-75 |
| N2 | | SEQ ID NOs: 52-57 |

LAMP primers and molecular beacons: LAMP primers were designed with the SGF deletion located between B1c and LB (FIGS. 37A and 37B) using LAMP Primer Design Tool at NEB https://lamp.neb.com/#!/) and with enough length between B1c and LB to accommodate the location of molecular beacons in this region. Molecular beacons targeting either wild-type or the SGF deletion sequence were designed using principles according to Sherrill-Mix et al., Genome Biol, 22(1), 169 (2021). As the deletion is located in a relatively AT-rich region, the annealing temperatures for these beacons are lower: the calculated Tm of the annealed beacon-target for wt MB and SGFdel MB is 63.9° C. and 62.5° C., and the stem is 55.1° C. and 54.7° C., respectively.

These beacons were synthesized as Affinity Plus qPCR Probes by IDT with sequences shown in Table 9.

RT-LAMP reactions: RT-LAMP reactions were performed using WarmStart® LAMP Kit (DNA & RNA) (E1700) with standard primer concentrations (0.2 μM F3, 0.2 μM B3, 1.6 μM FIP, 1.6 μM BIP, 0.4 μM Loop F, 0.4 μM Loop B) in the presence of 40 mM guanidine hydrochloride in 25 μl on 96-well plates at 65° C. in a Bio-Rad CFX96 instrument. LAMP amplification was measured by including 1 uM SYTO™-9 fluorescent dye (ThermoFisher S34854), 0.5 μM SGFdel or 1.0 μM wt beacon and signal was acquired at 15 second intervals. Synthetic SARS-CoV-2 RNAs were obtained from Twist Bioscience (Control 2 for WT MN908947.3, Control 14 for B.1.1.7, Control 16 for B.1.351 and Control 17 for P.1) and diluted in 10 ng/μl Jurkat total RNA based on the copy number provided by the manufacturer.

Results

Positional Mutation Effects

To mimic the effect of a potential SARS-CoV-2 variant in an RT-LAMP assay, we focused on single point mutations at each primer base position and the SGF deletion that is found in several variants of concern. For the single point mutation primers, each of the 527 variant primers from the 3 assays (As1e, N2, E1) was tested in RT-LAMP reactions with three different SARS-CoV-2 RNA copy number concentrations: 100, 200, and 10,000 copies in order to gain a sense of the mutation effect on reaction speed and sensitivity. Both lower concentrations allowed for amplification effects to be confidently determined outside of stochastic performance when close to the limit of detection in the 100 copy reactions, particularly for the As1e primer set which displays slightly lower sensitivity in our testing. The reaction output speed was measured relative to the fully-complementary wild-type primer, and relative effect plotted against the position in the primer sequence (FIG. 36A-36F). Overall, evaluating the 4,500 RT-LAMP assays with single point mutations within any of the six primers, regardless of gene, resulted in minimal to no effect on the ability to amplify the target at any of the copy numbers used.

The most common result across the primers was a 5%-10% reduction in amplification speed in the presence of a mismatch. The B3 primers showed remarkably little impact in any of the 69 variant primer sets for the 3 amplicons, though the F3 primer did see some slowing when mismatches were present away from the 5' end in the E1 and As1e sets (FIG. 36A, 36B). These primers are the least critical to the reaction, but the difference between the two may indicate differential tolerances to mismatches by the reaction initiation (B3 annealing to single-stranded RNA and extension by RTx reverse transcriptase) vs. the strand invasion and displacement via est 2.0 polymerase that occurs at the F3 primer. With the more critical FIP and BIP primers, the 3' half of the primer (F2/B2) serves to invade and primer double-stranded DNA, with the 5' half annealing to displaced product strands to form the 'loop' dumbbell shapes for amplification. The results in FIG. 36C-D clearly indicate more impact of mutations on the F2/B2 regions, with more variant oligos causing amplification delays relative to fully base-paired control toward the 3' end of the FIP and BIP in all 3 gene assays. The extreme 5' end was more likely to display sensitivity to mismatch, likely indicating an impact on extension from a mismatch in the looped-back LAMP hairpin structure, but sensitivity was not impacted in these tests.

As a summary of the effects Table 10 lists the number of positions from each primer that resulted in a detection cycle change of more than 10% from the WT primer. Though overall effects on amplification were minimal, the greater impact of 3' mutations is clear from the trends in FIG. 36A-F. And while a significant number of variant primers resulted in slowing of the reaction, in all 527 variant primers tested no mutation position prevented amplification in the RT-LAMP reaction with SARS-CoV-2 RNA even with lower RNA copy numbers.

TABLE 10

Effect of Single Point Mutations

| Primer | No. Bases with >10% LAMP Time Change | Total Bases |
|---|---|---|
| F3 | 22 | 62 |
| B3 | 0 | 69 |
| FIP | 27 | 131 |
| BIP | 21 | 128 |
| LF | 18 | 68 |
| LB | 13 | 66 |

Deletion Detection with Molecular Beacons

To investigate the effect of a deletion on an RT-LAMP assay, we designed a primer set targeting the SGF deletion region (Orf1a 3675-3677) with two molecular beacons targeting either the WT or the variant target region (FIG. 37A). We initially checked this primer set for specificity and sensitivity and found it was able to detect both WT and variants RNA with similar sensitivity of approximately 50 copies and with no apparent non-template amplification signal in 40 minute reactions (data not shown). We then evaluated detection using the molecular beacons with 10-fold dilutions of WT or B.1.1.7 synthetic RNA and compared them with conventional intercalating fluorescence detection. Both molecular beacons detected their intended targets as designed with robust specificity and even at 10,000 copies of target RNA they only recognized only their intended amplification products (FIG. 37. B). This is in contrast to another strategy where the deletion was placed at the ends of the FIP and BIP [16] and detected with intercalating dye. With this design, WT vs. B.1.1.7 discrimination was efficient at low (≤1,000 copies RNA) inputs but the two variant sequences could only be distinguished by their amplification speed at higher copy numbers.

We then assessed the sensitivity of the SGFdel beacon to detect variant RNA containing the SGF deletion. We performed 24 repeats of LAMP reactions each with 50 copies of synthetic RNAs from B.1.1.7, B.1.351, or P.1 and the reactions were detected by either the molecular beacons or by dsDNA binding dye SYTO-9. The results indicated SGFdel MB was able to detect all the variant RNAs with efficiency similar to that with ds DNA binding dye (Table 11). We further tested combining both molecular beacons so that the identity of the input viral RNA could be determined in the same LAMP reaction. We tested 24 repeat reactions in the presence of both SGFwt or SGFdel molecular beacons and compared to the detection with single beacons. We found that target RNAs were reliably detected with the same level of sensitivity when both beacons were present and no cross interaction between the two beacons was observed (Table 12).

TABLE 11

Specific Detection of Variant RNA with LAMP and Molecular Beacons

| | RNA | | | |
|---|---|---|---|---|
| | WT | B.1.1.7 | B.1.351 | P.1 |
| SYTO-9 | 21 | 21 | 23 | 24 |
| Beacon | 18 | 17 | 24 | 23 | positives from 24 repeats, 50 copies/reaction

TABLE 12

Dual-beacon RT-LAMP for Variant RNA Detection

| | | Single Beacon | | Duplex | |
|---|---|---|---|---|---|
| | | Cy3 (WT) | FAM (Del) | Cy3 (WT) | FAM (Del) |
| RNA | WT | 20 | — | 20 | 0 |
| | P1 | — | 18 | 0 | 22 | positives from 24 repeats, 50 copies/reaction

Here we established the first comprehensive screen of LAMP primer tolerance to mutation in target nucleic acids with (i) a known sequence or (ii) a known sequence with a plurality of undefined mutations therein.

We investigated a single base mutation at every position of every primer in three prominent SARS-CoV-2 RT-LAMP assays. Remarkably, we find very little impact of the single base changes, with only marginal effect on speed in most positions. The robustness of RT-LAMP to sequence variation is a significant benefit to its adoption, with reduced worry about deleterious effects from the commonly emerging single-base changes that could occur with some frequency in the regions targeted by the LAMP primers. Additionally, many RT-LAMP assays combine primer sets for added speed and sensitivity [4], adding an additional layer of protection against possible sequence variation.

The converse of this assay robustness however is an inherent difficulty in identifying variants during the amplification reaction. While sequencing offers greater confidence and detail for variant calling the ability to utilize the diagnostic amplification for prospective variant identification as with the TaqPath S-gene dropout is a valuable feature of a potential diagnostic method. We observed difficulty targeting even a large 9-base deletions by typical LAMP primer design alone, but by utilizing a molecular beacon approach as first described by [19] we were able to accurately amplify and identify RNA from the three SARS-CoV-2 variant sequences containing the SGF deletion. By combining the beacons for the wild-type and deletion sequence, we could call wild-type or variant based on the detected sequence, indicating the potential ability for variant calling in the RT-LAMP assay by multiplexed beacon design.

Taken together these data position RT-LAMP as an attractive diagnostic method with a high level of tolerance to common sequence mutations. Recent FDA guidance described a need for understanding this tolerance for any molecular diagnostic test and use of RT-LAMP provides increased confidence in a diagnostic test that detects evolving pathogens with consistent performance. In situations where variant identification is desired, use of molecular beacons provides a sensitive addition to specific sequence detection with fluorescence detection.

What is claimed is:

1. A kit for use in diagnostic detection of a target nucleic acid and variants thereof having undefined mutations, obtained from a cell or virus in a biological sample, the kit comprising:
   (a) a lyophilized mixture of a strand displacing polymerase and an indicator reagent and optionally a lyophilized reverse transcriptase, wherein:
      (i) the indicator reagent is characterized by its ability to change color or provide fluorescence in a nucleic acid amplification reaction; and
      (ii) the strand displacing polymerase when rehydrated is capable of amplifying DNA at a temperature in the range of 50° C.-68° C.;
   (b) a universal primer set suitable for loop mediated amplification (LAMP) of the target nucleic acids and variants thereof containing undefined mutations within one or more of the primer binding sites;
   wherein the universal primer set suitable for LAMP is capable of hybridizing to the target DNA in the presence of a plurality of undefined mutations, and is configured to provide a positive result for the target DNA in a predetermined assay time period otherwise determined for a positive sample of a target nucleic acid having a known sequence;
   wherein any of the reagents in the kit may be combined in a mixture in a single container or provided in separate containers.

2. The kit according to claim 1, wherein the universal primer set suitable for loop mediated amplification (LAMP) are similarly diagnostic for the target nucleic acids and variants thereof where the any deletions and additions in the BIF and FIP primer binding sites of the variants do not exceed 6-9 nucleotides.

3. The kit according to claim 1, wherein the target DNA is the reverse transcription product of an RNA virus.

4. The kit according to claim 3, wherein the RNA virus is a coronavirus.

5. The kit according to claim 1, wherein the indicator reagent is a molecular beacon or a metallochromic dye.

6. The kit according to claim 1, further comprising (c) a lysis reagent in a container for receiving the biological sample, wherein the lysis reagents comprise a reducing agent and a metal chelator.

7. The kit according to claim 6, wherein the reducing agent is Tris (2-carboxyethyl) phosphine hydrochloride (TCEP).

8. The kit according to any of claim 1, wherein the lysis reagents comprise at least one of a salt of $C-(NH_2)_2NH^+$ and a poloxamer.

9. The kit according to claim 1, wherein one or more of components in (a)-(b) are immobilized on a substrate.

10. The kit according to claim 1, comprising the reverse transcriptase, wherein the reverse transcriptase is a virus encoded reverse transcriptase, or a bacteria encoded intron II reverse transcriptase.

11. A method for detecting a target nucleic acid or unknown variant thereof in a biological sample by Loop-Mediated Isothermal Amplification (LAMP), comprising:
   (a) combining the biological sample with a lysis reagent to form a lysis mix;
   (b) incubating the lysis mix at a temperature of at least 60° C. for a period of time in the range of 2 minutes to 45 minutes;
   (c) combining in a reaction mix, an aliquot of the heat treated lysis mix of step (b) with amplification reagents comprising a strand displacing polymerase, a reversible inhibitor of the polymerase, nucleoside triphosphates, and at least one set of LAMP primers that is capable of hybridizing to the target nucleic acid and to undefined variants of the target nucleic acid; and
   (d) incubating the reaction mix for a reaction positive period of time under amplification conditions for LAMP to detect the presence of the target nucleic acid or undefined variants thereof in the sample.

12. The method of claim 11, wherein the lysis reagent comprises a reducing agent and a metal chelating reagent.

13. The method of claim 11, wherein (b) further comprises incubating the lysis mix at 95° C. for 5 minutes.

14. The method of claim 11, wherein the amplification reagents include a reverse transcriptase and a reversible inhibitor of the reverse transcriptase.

15. The method according to claim 11, wherein any of the reagents in the lysis mix and any of the amplification reagents may be lyophilized prior to combining with the biological sample.

16. The method according to claim 11, wherein any of the reagents in the lysis mix and any of the amplification reagents may be immobilized on a matrix.

17. The method according to claim 11, wherein the biological sample is saliva.

18. The method according to claim 11, wherein the target nucleic acid is an RNA virus.

19. The method according to claim 18, wherein the RNA virus is a coronavirus and the amplification reagents include multiple sets of universal primers.

20. The method according to claim 11, further comprising step (e) sequencing the detected target nucleic acid or variants thereof to determine the presence of a novel mutations.

* * * * *